US009815890B2

(12) United States Patent
Holers et al.

(10) Patent No.: US 9,815,890 B2
(45) Date of Patent: *Nov. 14, 2017

(54) ANTIBODIES TO THE C3D FRAGMENT OF COMPLEMENT COMPONENT 3

(75) Inventors: V. Michael Holers, Denver, CO (US); Joshua M. Thurman, Greenwood Village, CO (US); Liudmila Kulik, Aurora, CO (US); Stephen Tomlinson, Charleston, SC (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/805,522

(22) PCT Filed: Jun. 22, 2011

(86) PCT No.: PCT/US2011/041517
§ 371 (c)(1),
(2), (4) Date: Jan. 31, 2013

(87) PCT Pub. No.: WO2011/163412
PCT Pub. Date: Dec. 29, 2011

(65) Prior Publication Data
US 2013/0129728 A1    May 23, 2013

Related U.S. Application Data

(60) Provisional application No. 61/357,499, filed on Jun. 22, 2010.

(51) Int. Cl.
*C07K 16/28* (2006.01)
*A61K 39/395* (2006.01)
*C07K 16/18* (2006.01)
*C07K 14/47* (2006.01)

(52) U.S. Cl.
CPC ............ *C07K 16/18* (2013.01); *C07K 14/472* (2013.01); *C07K 2317/33* (2013.01); *C07K 2317/76* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| 3,710,795 | A | 1/1973 | Higuchi et al. |
| 4,454,151 | A | 6/1984 | Waterbury |
| 4,634,666 | A | 1/1987 | Engleman et al. |
| 4,676,980 | A | 6/1987 | Segal et al. |
| 4,797,368 | A | 1/1989 | Carter et al. |
| 4,816,567 | A | 3/1989 | Cabilly et al. |
| 4,863,457 | A | 9/1989 | Lee |
| 4,883,784 | A | 11/1989 | Kaneko |
| 5,139,941 | A | 8/1992 | Muzyczka et al. |
| 5,212,071 | A | 5/1993 | Fearon et al. |
| 5,260,203 | A | 11/1993 | Ladner et al. |
| 5,308,341 | A | 5/1994 | Chanoch |
| 5,310,729 | A | 5/1994 | Lernhardt |
| 5,328,470 | A | 7/1994 | Nabel et al. |
| 5,331,090 | A | 7/1994 | Lernhardt |
| 5,447,150 | A | 9/1995 | Bacon |
| 5,472,939 | A | 12/1995 | Fearon et al. |
| 5,476,511 | A | 12/1995 | Gwon et al. |
| 5,501,856 | A | 3/1996 | Ohtori et al. |
| 5,545,806 | A | 8/1996 | Longberg et al. |

(Continued)

FOREIGN PATENT DOCUMENTS

| EP | 0358130 A2 | 3/1990 |
| EP | 430539 A2 | 11/1990 |

(Continued)

OTHER PUBLICATIONS

"Monoclonal antibody to human C3(C3d), Catalog No. A207," Quidel Corporation Product Catalog, <http://www.quidel.com/products/product_detail.php?prod=73&group=2>, retrieved on Apr. 25, 2013 (2 pages).
Dobbie et al., "Epitope specificities and quantitative and serologic aspects of monoclonal complement (C3c and C3d) antibodies," Transfusion. 27(6):453-459 (1987).
Kovacs et al., "Mapping of the C3d ligand binding site on complement receptor 2 (CR2/CD21) using nuclear magnetic resonance and chemical shift analysis," J Biol Chem. 284(14):9513-9520 (2009).
Tamerius et al., "Detection of a neoantigen on human C3bi and C3d by monoclonal antibody," J Immunol. 135(3):2015-2019 (1985).
International Preliminary Report on Patentability and Written Opinion for International Application No. PCT/US2011/041517, dated Dec. 28, 2012 (11 pages).

(Continued)

*Primary Examiner* — Phillip Gambel
(74) *Attorney, Agent, or Firm* — Cooley LLP; Ivor R. Elrifi; Katherine Miller

(57) ABSTRACT

The present invention relates to methods and materials for modulating the complement alternative pathway (CAP), the complement classical pathway (CCP), the complement lectin/mannose pathway (CMP), or combinations thereof, as well as methods and materials for targeting diagnostic, prophylactic and therapeutic agents to localized areas of tissue within the body where they may more directly exert their effects upon the intended target cells or tissue, with reduced, associated systemic effects compared with administration of the same or similar agents in an untargeted, systemic manner. The methods and materials of the present invention may therefore allow for increased efficacy, lower threshold effective dosages and/or lower effective maintenance doses, and/or reduced associated undesired or adverse effects in terms of frequency or severity of occurrence, or both. The present invention also relates to methods and materials for modulating a host humoral immune response, especially reducing, inhibiting, or preventing a host humoral immune response.

18 Claims, 12 Drawing Sheets

(56) References Cited

U.S. PATENT DOCUMENTS

| | | |
|---|---|---|
| 5,545,807 A | 8/1996 | Surani et al. |
| 5,569,825 A | 10/1996 | Lonberg et al. |
| 5,591,669 A | 1/1997 | Krimpernfort et al. |
| 5,612,205 A | 3/1997 | Kay et al. |
| 5,624,821 A | 4/1997 | Winter et al. |
| 5,625,126 A | 4/1997 | Longberg et al. |
| 5,625,825 A | 4/1997 | Rostoker et al. |
| 5,633,425 A | 5/1997 | Longberg et al. |
| 5,643,763 A | 7/1997 | Dunn et al. |
| 5,648,260 A | 7/1997 | Winter et al. |
| 5,661,016 A | 8/1997 | Longberg et al. |
| 5,679,345 A | 10/1997 | Sanfilippo et al. |
| 5,679,546 A | 10/1997 | Ko et al. |
| 5,721,367 A | 2/1998 | Kay et al. |
| 5,733,254 A | 3/1998 | Jones et al. |
| 5,759,808 A | 6/1998 | Casterman et al. |
| 5,770,429 A | 6/1998 | Longberg et al. |
| 5,789,215 A | 8/1998 | Berns et al. |
| 5,789,650 A | 8/1998 | Longberg et al. |
| 5,814,318 A | 9/1998 | Longberg et al. |
| 5,851,528 A | 12/1998 | Ko et al. |
| 5,874,299 A | 2/1999 | Longberg et al. |
| 5,877,397 A | 3/1999 | Longberg et al. |
| 5,939,598 A | 8/1999 | Kucherlapati et al. |
| 5,981,481 A | 11/1999 | Fearon et al. |
| 6,075,181 A | 6/2000 | Kucherlapati et al. |
| 6,095,141 A | 8/2000 | Armer et al. |
| 6,114,598 A | 9/2000 | Kucherlapati et al. |
| 6,140,472 A | 10/2000 | Rosengard et al. |
| 6,146,361 A | 11/2000 | Dibiasi et al. |
| 6,150,584 A | 11/2000 | Kucherlaptai et al. |
| 6,162,963 A | 12/2000 | Kucherlaptai et al. |
| 6,170,717 B1 | 1/2001 | DiGiovanni et al. |
| 6,192,891 B1 | 2/2001 | Gravel et al. |
| 6,200,296 B1 | 3/2001 | Dibiasi et al. |
| 6,214,966 B1 | 4/2001 | Harris |
| 6,224,866 B1 | 5/2001 | Barbera-Guillem |
| 6,248,365 B1 | 6/2001 | Romisch et al. |
| 6,255,458 B1 | 7/2001 | Longberg et al. |
| 6,277,099 B1 | 8/2001 | Strowe et al. |
| 6,291,239 B1 | 9/2001 | Prodinger et al. |
| 6,300,129 B1 | 10/2001 | Longberg et al. |
| 6,302,855 B1 | 10/2001 | Lav et al. |
| 6,331,313 B1 | 12/2001 | Wong et al. |
| 6,355,245 B1 | 3/2002 | Evans et al. |
| 6,368,596 B1 | 4/2002 | Ghetie et al. |
| 6,432,679 B1 | 8/2002 | Mond et al. |
| 6,458,360 B1 | 10/2002 | Fearon et al. |
| 6,503,947 B1 | 1/2003 | Lipton et al. |
| 6,521,450 B1 | 2/2003 | Atkinson et al. |
| 6,572,856 B1 | 6/2003 | Taylor et al. |
| 6,657,103 B1 | 12/2003 | Kucherlaptai et al. |
| 6,673,986 B1 | 1/2004 | Kucherlaptai et al. |
| 6,680,209 B1 | 1/2004 | Buechler et al. |
| 6,713,610 B1 | 3/2004 | Kucherlaptai et al. |
| 6,794,132 B2 | 9/2004 | Buechler et al. |
| 6,820,011 B2 | 11/2004 | Chen et al. |
| 6,897,290 B1 | 5/2005 | Atkinson et al. |
| 6,933,368 B2 | 8/2005 | Co et al. |
| 6,962,903 B2 | 11/2005 | Allison |
| 7,041,871 B1 | 5/2006 | Lonberg et al. |
| 7,045,676 B1 | 5/2006 | Gordon et al. |
| 7,390,786 B2 | 6/2008 | Warne et al. |
| 7,407,475 B2 | 8/2008 | Allison |
| 7,423,128 B2 | 9/2008 | Gazit-Bornstein et al. |
| 7,439,331 B2 | 10/2008 | Fung et al. |
| 7,556,615 B2 | 7/2009 | Pettis et al. |
| 7,576,182 B1 | 8/2009 | Goddard et al. |
| 7,635,676 B2 | 12/2009 | Allison |
| 7,635,678 B2 | 12/2009 | Allison |
| 7,635,679 B2 | 12/2009 | Fumero et al. |
| 7,635,680 B2 | 12/2009 | Allison |
| 7,645,739 B2 | 1/2010 | Allison |
| 7,704,497 B2 | 4/2010 | Dall'Acqua et al. |
| 7,759,304 B2 | 7/2010 | Gilkeson et al. |
| 7,964,705 B2 | 6/2011 | Emlen et al. |
| 7,999,082 B2 | 8/2011 | Holers et al. |
| 8,007,804 B2 | 8/2011 | Tomlinson et al. |
| 9,259,488 B2 * | 2/2016 | Holers ............... A61K 49/1875 |
| 2002/0103346 A1 | 8/2002 | Vogel et al. |
| 2003/0077273 A1 | 4/2003 | Linnik et al. |
| 2003/0165509 A1 | 9/2003 | Ghetie et al. |
| 2003/0180292 A1 | 9/2003 | Hanna et al. |
| 2003/0181531 A1 | 9/2003 | Sherris et al. |
| 2003/0229905 A1 | 12/2003 | Kucherlaptai et al. |
| 2004/0005538 A1 | 1/2004 | Chen et al. |
| 2004/0006776 A1 | 1/2004 | Meade et al. |
| 2004/0010810 A1 | 1/2004 | Kucherlaptai et al. |
| 2004/0058313 A1 | 3/2004 | Abreu |
| 2004/0093622 A1 | 5/2004 | Kucherlaptai et al. |
| 2004/0191252 A1 | 9/2004 | Taylor et al. |
| 2004/0219156 A1 | 11/2004 | Goldenberg et al. |
| 2004/0229827 A1 * | 11/2004 | Steward et al. ............... 514/44 |
| 2005/0002128 A1 | 1/2005 | Ito et al. |
| 2005/0032128 A1 | 2/2005 | Halperin |
| 2005/0054055 A1 | 3/2005 | Kucherlaptai et al. |
| 2005/0076395 A1 | 4/2005 | Kucherlaptai et al. |
| 2005/0232920 A1 | 10/2005 | Fung et al. |
| 2005/0260198 A1 | 11/2005 | Holers et al. |
| 2005/0265995 A1 | 12/2005 | Tomlinson et al. |
| 2005/0271660 A1 | 12/2005 | Wang |
| 2005/0287630 A1 | 12/2005 | Kucherlaptai et al. |
| 2006/0002944 A1 | 1/2006 | Ashkenazi et al. |
| 2006/0014681 A1 | 1/2006 | Chen et al. |
| 2006/0040363 A1 | 2/2006 | Kucherlaptai et al. |
| 2006/0105347 A1 | 5/2006 | Meade et al. |
| 2006/0178308 A1 | 8/2006 | Schwaeble et al. |
| 2006/0263819 A1 | 11/2006 | Hageman et al. |
| 2006/0276388 A1 | 12/2006 | Christa et al. |
| 2006/0292141 A1 | 12/2006 | Holers et al. |
| 2007/0003544 A1 | 1/2007 | Hanna |
| 2007/0020647 A1 | 1/2007 | Hageman et al. |
| 2007/0134260 A1 | 6/2007 | Feger et al. |
| 2007/0172483 A1 | 7/2007 | Schwaeble et al. |
| 2007/0224197 A1 | 9/2007 | Chen et al. |
| 2008/0029911 A1 | 2/2008 | Jeon et al. |
| 2008/0118506 A1 | 5/2008 | An et al. |
| 2008/0221011 A1 | 9/2008 | Gilkeson et al. |
| 2008/0241223 A1 | 10/2008 | Nivaggioli et al. |
| 2008/0267980 A1 | 10/2008 | Tomlinson et al. |
| 2008/0299114 A1 | 12/2008 | Emlen et al. |
| 2009/0081211 A1 | 3/2009 | Campagne |
| 2009/0087907 A1 | 4/2009 | Pebay et al. |
| 2009/0110679 A1 | 4/2009 | Li et al. |
| 2009/0175875 A1 | 7/2009 | Etemad-Gilbertson et al. |
| 2009/0304706 A1 | 12/2009 | Lu et al. |
| 2011/0014614 A1 | 1/2011 | Liew |
| 2011/0015127 A1 | 1/2011 | Gilkeson et al. |
| 2011/0286938 A1 * | 11/2011 | Thurman et al. .......... 424/9.323 |
| 2011/0293605 A1 * | 12/2011 | Sathish et al. ............. 424/133.1 |
| 2012/0015871 A1 | 1/2012 | Tomlinson et al. |
| 2012/0015872 A1 | 1/2012 | Tomlinson et al. |
| 2012/0135430 A1 * | 5/2012 | Zhang et al. ................ 435/7.92 |
| 2012/0171206 A1 | 7/2012 | Tomlinson et al. |
| 2013/0029912 A1 | 1/2013 | Holers et al. |
| 2013/0129728 A1 | 5/2013 | Holers et al. |
| 2013/0190477 A1 | 7/2013 | Kovacs et al. |

FOREIGN PATENT DOCUMENTS

| | | |
|---|---|---|
| EP | 0402226 A1 | 12/1990 |
| EP | 0402266 A2 | 12/1990 |
| EP | 0546073 B1 | 8/1991 |
| EP | 0463151 B1 | 11/1991 |
| EP | 488401 | 11/1991 |
| JP | 05507197 A | 10/1993 |
| JP | 09502985 A | 3/1997 |
| JP | 2002-534959 A | 10/2002 |
| WO | WO-91/16437 A1 | 10/1991 |
| WO | WO 92/03918 | 3/1992 |
| WO | WO 92/22645 | 12/1992 |
| WO | WO 92/22647 | 12/1992 |
| WO | WO 92/22670 | 12/1992 |
| WO | WO 93/12227 | 6/1993 |

(56) References Cited

FOREIGN PATENT DOCUMENTS

| WO | WO 94/00569 | 1/1994 |
|---|---|---|
| WO | WO 94/02602 | 2/1994 |
| WO | WO 94/25585 | 11/1994 |
| WO | WO 94/28027 | 12/1994 |
| WO | WO 94/29351 | 12/1994 |
| WO | WO-96/12742 A1 | 5/1996 |
| WO | WO 96/27011 | 9/1996 |
| WO | WO 96/34096 | 10/1996 |
| WO | WO 97/13852 | 4/1997 |
| WO | WO-98/07835 A2 | 2/1998 |
| WO | WO 98/24884 | 6/1998 |
| WO | WO 98/24893 | 6/1998 |
| WO | WO 98/47531 | 10/1998 |
| WO | WO-99/44625 A1 | 9/1999 |
| WO | WO 99/51642 | 10/1999 |
| WO | WO 00/34317 | 6/2000 |
| WO | WO-00/34317 A2 | 6/2000 |
| WO | WO-00/34317 A3 | 8/2000 |
| WO | WO-00/67796 A1 | 11/2000 |
| WO | WO-02/068579 A2 | 9/2002 |
| WO | WO 02/069232 A2 | 9/2002 |
| WO | WO 2004/024156 A1 | 3/2004 |
| WO | WO 04/026380 A2 | 4/2004 |
| WO | WO-2004/045520 A2 | 6/2004 |
| WO | WO-2004/103288 A2 | 12/2004 |
| WO | WO 2004/108158 A1 | 12/2004 |
| WO | WO 2005/011735 A2 | 2/2005 |
| WO | WO-2005/014618 A2 | 2/2005 |
| WO | WO-2005/044998 A2 | 5/2005 |
| WO | WO-2005/072479 A2 | 8/2005 |
| WO | WO-2005/077417 A1 | 8/2005 |
| WO | WO-2006/030220 A1 | 3/2006 |
| WO | WO 2006/53301 A2 | 5/2006 |
| WO | WO-2006/062716 A2 | 6/2006 |
| WO | WO-2006/083533 A2 | 8/2006 |
| WO | WO-2006/088950 A2 | 8/2006 |
| WO | WO-2006/128006 A1 | 11/2006 |
| WO | WO 2007/024715 A2 | 3/2007 |
| WO | WO-2007/029008 A2 | 3/2007 |
| WO | WO-2007/035857 A2 | 3/2007 |
| WO | WO-2007/056227 A2 | 5/2007 |
| WO | WO-2007/112403 A2 | 10/2007 |
| WO | WO-2007/129895 A2 | 11/2007 |
| WO | WO-2007/149567 A2 | 12/2007 |
| WO | WO 2008/024188 A2 | 2/2008 |
| WO | WO-2008/154251 A2 | 12/2008 |
| WO | WO-2009/029669 A1 | 3/2009 |
| WO | WO-2009/056631 A2 | 5/2009 |
| WO | WO-2009/110918 A1 | 9/2009 |
| WO | WO-2010/015608 A1 | 2/2010 |
| WO | WO-2010/091183 A2 | 8/2010 |
| WO | WO-2010/136311 A2 | 12/2010 |
| WO | WO-2011/057158 A1 | 5/2011 |
| WO | WO-2011/143637 A1 | 11/2011 |
| WO | WO-2011/163412 A1 | 12/2011 |
| WO | WO-2013/117035 A1 | 8/2013 |
| WO | WO-2013/177035 A2 | 11/2013 |

OTHER PUBLICATIONS

"Monoclonal antibody to human C3d (neo), Catalog No. A250," Quidel Corporation Product Catalog, <http://www.quidel.com/products/product_detail.php?prod=160&group=2>, retrieved on Dec. 26, 2013 (2 pages).

Aguado et al., "Monoclonal antibodies against complement 3 neoantigens for detection of immune complexes and complement activation. Relationship between immune complex levels, state of C3, and numbers of receptors for C3b," J Clin Invest. 76:1418-26 (1985).

Amsterdam et al., "Limitation of reperfusion injury by a monoclonal antibody to C5a during myocardial infarction in pigs," Am J Physiol. 268(1):H448-57 (1995).

Atkinson et al., "Targeted complement inhibitors protect against posttransplant cardiac ischemia and reperfusion injury and reveal an important role for the alternative pathway of complement activation," J Immunol. 185:7007-13 (2010).

Brauer et al., "Functional activity of anti-C6 antibodies elicited in C6-deficient rats reconstituted by liver allografts. Ability to inhibit hyperacute rejection of discordant cardiac xenografts," Transplantation 61(4):588-94 (1996).

Cardarelli et al., "A nonfucosylated human antibody to CD19 with potent B-cell depletive activity for therapy of B-cell malignancies," Cancer Immunol Immunother. 59(2):257-65 (2010).

Colvin, "Antibody-mediated renal allograft rejection: diagnosis and pathogenesis," J Am Soc Nephrol. 18(4):1046-56 (2007).

Dilillo et al., "Selective and efficient inhibition of the alternative pathway of complement by a mAb that recognizes C3b/iC3b," Mol Immunol. 43:1010-9 (2006).

Edberg et al., "Quantitative analyses of the binding of soluble complement-fixing antibody/dsDNA immune complexes to CR1 on human red blood cells," J Immunol. 139:3739-47 (1987).

Fritzinger et al., "Functional characterization of human C3/cobra venom factor hybrid proteins for therapeutic complement depletion," Develop Comp Immunol. 33(1):105-16 (2009).

Fritzinger et al., "Molecular cloning and derived primary structure of cobra venom factor," Proc Natl Acad Sci USA. 91:12775-12779 (1994); correction 92: 7065 (1995).

Girardi et al., "Complement C5a receptors and neutrophils mediate fetal injury in the antiphospholipid syndrome," J Clin Invest. 112(11):1644-54 (2003).

Hannan et al., "Mutational analysis of the complement receptor type 2 (CR2/CD21)-C3d interaction reveals a putative charged SCR1 binding site for C3d," J Mol Biol. 346(3):845-58 (2005).

Heinen et al., "Factor H-related protein 1 (CFHR-1) inhibits complement C5 convertase activity and terminal complex formation," Blood. 114(12):2439-47 (2009).

Hill, "Eculizumab for the treatment of paroxysmal nocturnal hemoglobinuria," Clin Adv Hematol Oncol. 3(1 1):849-50 (2005).

Holers et al., "The alternative pathway of complement in disease: Opportunities for therapeutic targeting," Mol. Immunol. 41:147-152 (2004).

Holers, "The spectrum of complement alternative pathway-mediated diseases," Immunol Rev. 223:300-316 (2008).

Homeister et al., "Soluble complement receptor type 1 prevents human complement-mediated damage of the rabbit isolated heart," J Immunol. 150(3):1055-1064 (1993).

Author manuscript of Huang et al., "A novel targeted inhibitor of the alternative pathway of complement and its therapeutic application in ischemia/reperfusion injury," available in PMC Nov. 25, 2009, published in final edited form as: J Immunol. 181(11): 8068-8076 (2008) (19 pages).

Janssen et al., "Structure of C3b reveals conformational changes that underlie complement activity," Nature. 444:213-216 (2006).

Jozsi et al., "Attachment of the soluble complement regulator factor H to cell and tissue surfaces: relevance for pathology," Histol Hitopathol. 19:251-8 (2004).

Kaplan, "Eculizumab Alexion," Curr Opin Investig Drugs. 3(7):1017-23 (2002).

Kroshus et al., "Complement inhibition with an anti-05 monoclonal antibody prevents acute cardiac tissue injury in an ex vivo model of pig-to-human xenotransplantation," Transplantation. 60(11):1194-202 (1995).

Lemoli et al., "Immunological effects of omalizumab in chronic urticaria: a case report," J Invest Allergol Clin Immunol. 20(3):252-4 (2010).

Liszewski et al., "Complement inhibitors as therapeutic agents," Clin Immunol Newsletter. 17(12):168-73 (1997).

Luqman et al., "The antileukemia activity of a human anti-CD40 antagonist antibody, HCD122, on human chronic lymphocytic leukemia cells," Blood. 112(3):711-20 (2008).

Lyubarsky et al., "Recovery phase of the murine rod photoresponse reconstructed from electroretinographic recordings," J Neurosci. 16(2):563-571 (1996).

Mastellos et al., "Novel monoclonal antibodies against mouse C3 interfering with complement activation: description of fine specificity and applications to various immunoassays," Mol Immunol. 40(16):1213-21 (2004).

(56) References Cited

OTHER PUBLICATIONS

Meri et al., "Structural composition and functional characterization of soluble CD59: heterogeneity of the oligosaccharide and glycophosphoinositol (GPI) anchor revealed by laser-desorption mass spectrometric analysis," Biochem J. 316(3):923-35 (1996).
Mollnes et al., "Identification of a human C5 beta-chain epitope exposed in the native complement component but concealed in the SCSb-9 complex," Scand J Immunol. 28:307-12 (1988).
Moongkarndi et al., "Immunological and functional properties of two monoclonal antibodies against human C5," Immunobiol. 165:323 (1983).
Moongkarndi et al., "Monoclonal antibodies against the fifth component of human complement," Immunobiol. 162:397 (1982).
Moore et al., "Molecular cloning of the cDNA encoding the Epstein-Barr virus/C3d receptor (complement receptor type 2) of human B lymphocytes," Proc Natl Acad Sci USA. 84:9194-8 (1987).
Morgan, "Clinical complementology: recent progress and future trends," Eur J Clin Invest. 24(4):219-28 (1994).
Müller-Eberhard, "Molecular organization and function of the complement system," Ann Rev Biochem. 57:321-47 (1988).
NCBI Blast for Accession No. NP_001006659.1. Retrieved on Dec. 26, 2013 (5 pages).
NCBI Blast for Accession No. NP_031784.1. Retrieved on Dec. 26, 2013 (4 pages).
NCBI Blast for GenBank Accession No. U09969. Retrieved on Nov. 15, 2013 (3 pages).
NCBI Blast for UniProtKB/Swiss-Prot Accession No. O55186. Retrieved on Nov. 13, 2013 (5 pages).
NCBI Blast for UniProtKB/Swiss-Prot Accession No. P06909. Retrieved on Nov. 13, 2013 (19 pages).
NCBI Blast for UniProtKB/Swiss-Prot Accession No. P08173. Retrieved on Nov. 13, 2013 (4 pages).
NCBI Blast for UniProtKB/Swiss-Prot Accession No. P08603. Retrieved on Nov. 13, 2013 (1 page).
NCBI Blast for UniProtKB/Swiss-Prot Accession No. P13987. Retrieved on Nov. 13, 2013 (16 pages).
NCBI Blast for UniProtKB/Swiss-Prot Accession No. P15529. Retrieved on Nov. 13, 2013 (30 pages).
NCBI Blast for UniProtKB/Swiss-Prot Accession No. P17927. Retrieved on Nov. 13, 2013 (1 page).
NCBI Blast for UniProtKB/Swiss-Prot Accession No. Q61475. Retrieved on Nov. 13, 2013 (11 pages).
Niemann et al., "The use of monoclonal antibodies as probes of the three-dimensional structure of human complement factor D," J Immunol. 132(2):809-15 (1984).
Nozaki et al., "Drusen complement components C3a and C5a promote choroidal neovascularization," Proc Natl Acad Sci USA. 103(7):2328-2333 (2006).
Oglesby et al., "Membrane cofactor protein (CD46) protects cells from complement-mediated attack by an intrinsic mechanism," J Exp Med. 175:1547-51 (1992).
Paixao-Cavalcante et al., "Factor H facilitates the clearance of GBM bound iC3b by controlling C3 activation in fluid phase," Mol Immunol. 46:1942-50 (2009).
Pascual et al., "A monoclonal antibody which blocks the function of factor D of human complement," J Immunol Methods. 127:263-9 (1990).
Pascual et al., "Inhibition of complement alternative pathway in mice with Fab antibody to recombinant adipsin/factor D," Eur J Immunol. 23:1389-92 (1993).
Patel et al., "Pexelizumab: a novel therapy for myocardial ischemia-reperfusion," Drugs Today (Barc). 41(3):165-70 (2005).
Prota et al., "The crystal structure of human CD21: Implications for Epstein-Barr virus and C3d binding," Proc Natl Acad Sci USA. 99:10641-6 (2002).
Quigg et al., "Blockade of antibody-induced glomerulonephritis with Crry-Ig, a soluble murine complement inhibitor," J Immunol. 160(9):4553-60 (1998).
Rabinovici et al., "Role of complement in endotoxin/platelet-activating factor-induced lung injury," J Immunol. 149(5):1744-50 (1992).
Rao et al., "OKB7, a monoclonal antibody that reacts at or near the C3d binding site of human CR2," Cell Immunol. 93(2):549-555 (1985).
Rehrig et al., "Complement inhibitor, complement receptor 1-related gene/protein y-Ig attenuates intestinal damage after the onset of mesenteric ischemia/reperfusion injury in mice," J Immunol. 167:5921-7 (2001).
Rinder et al., "Blockade of C5a and C5b-9 generation inhibits leukocyte and platelet activation during extracorporeal circulation," J Clin Invest. 96(3):1564-72 (1995).
Rohrer et al., "A targeted inhibitor of the alternative complement pathway reduces angiogenesis in a mouse model of age-related macular degeneration," Invest Ophthalmol Vis Sci. 50(7):3056-3064 (2009).
Rohrer et al., "Eliminating complement factor D reduces photoreceptor susceptibility to light-induced damage," Invest Ophthalmol Vis Sci. 48(11):5282-9 (2007).
Rohrer et al., "Role of neurotrophin receptor TrkB in the maturation of rod photoreceptors and establishment of synaptic transmission to the inner retina," J Neurosci. 19(20):8919-8930 (1999).
Rother et al., "Discovery and development of the complement inhibitor eculizumab for the treatment of paroxysmal nocturnal hemoglobinuria," Nat Biotechnol. 25(11):1256-64, 1488 (2007).
Sahu et al., "Identification of multiple sites of interaction between heparin and the complement system," Mol Immunol. 30(7):679-84 (1993).
Sokoloff et al., "Targeting of cancer cells with monoclonal antibodies specific for C3b(ii)," Cancer Immunol and Immunother. 49(10):551-62 (2000).
Tanhehco et al., "The anti-factor D antibody, MAb 166-32, inhibits the alternative pathway of the human complement system," Transplant Proc. 31(55):2168-71 (1999).
Thomas et al., "Inhibition of complement activity by humanized anti-05 antibody and single-chain Fv," Mol Immunol. 33(17-18):1389-401 (1996).
Thurman et al., "Lack of a functional alternative complement pathway ameliorates ischemic acute renal failure in mice," J. Immunol. 170(3):1517-1523(2003).
Tosic et al., "Preparation of monoclonal antibodies to C3b by immunization with C3b(i)-sepharose," J Immunol Methods. 120:241-9 (1989).
Ueda et al., "Probing Functional Sites on Complement Protein B with Monoclonal Antibodies," J. Immunol. 138(4):1143-1149(1987).
van der Elsen et al., "A crystal structure of the complex between human complement receptor 2 and its ligand C3d," Science. 332:608-611 (2011).
Wang et al., "Amelioration of Lupus-like autoimmune disease in NZB/W $F_1$ mice after treatment with a blocking monoclonal antibody specific for complement component C5," Proc Natl Acad Sci USA. 93(16):8563-8 (1996).
Wang et al., "Anti-C5 monoclonal antibody therapy prevents collagen-induced arthritis and ameoliorates established disease," Proc Natl Acad Sci USA. 92(19):8955-9 (1995).
Weis et al., "Identification of a 145,000 Mr membrane protein as the C3d receptor (CR2) of human B lymphocytes," Proc Natl Acad Sci USA. 81:881-5 (1984).
Weisman et al., "Soluble human complement receptor type 1: in vivo inhibitor of complement suppressing post-ischemic myocardial inflammation and necrosis," Science. 249(4965):146-151 (1990).
Whiss, "Pexelizumab Alexion," Curr Opin Investig Drugs. 3(6):870-7 (2002).
Supplementary European Search Report for European Patent Application No. EP11798880.8, dated Jan. 7, 2014 (13 pages).
Abrahmsén et al., "Engineering subtilisin and its substrates for efficient ligation of peptide bonds in aqueous solution," Biochemistry. 30:4151-4159 (1991).
Ahearn et al., "Disruption of the Cr2 locus results in a reduction in B-1a cells and in an imparied B cell response to T-dependent antigen," Immunity. 4(3):251-262 (1996).

(56) References Cited

OTHER PUBLICATIONS

Ahearn et al., "Epstein-Barr virus (EBV) infection of murine L cells expressing recombinant human EBV/C3d receptor," Proc Natl Acad Sci USA. 85:9307-11 (1988).
Ahearn et al., "Structure and function of the complement receptors, CR1 (CD35) and CR2 (CD21)," Adv Immunol. 46:183-219 (1989).
Andrews et al., "Spontaneous murine Lupus-like syndromes. Clinical and immunopathological manifestations in several strains," J Exp Med. 148:1198-215 (1978).
Arumugam et al., "Complement mediators in ischemia-reperfusion injury," Clin Chim Acta. 374:33-45 (2006).
Arumugam et al., "Protective effect of a human C5a receptor antagonist against hepatic ischaemia-reperfusion injury to rats," J Hepatol. 40:934-41 (2004).
Aslam et al., "Folded-back solution structure of monomeric factor H of human complement by synchrotron X-ray and neutron scattering, analytical ultracentrifugation and constrained molecular modelling," J Mol Biol. 309(5):1117-1138 (2001).
Asokan et al., "Characterization of human complement receptor type 2 (CR2/CD21) as a receptor for IFN-alpha: a potential role in systemic lupus erythematosus," J Immunol. 177:383-94 (2006).
Atkinson et al., "Complement-dependent P-selectin expression and injury following ischemic stroke," J Immunol. 177:7266-74 (2006).
Atkinson et al., "Targeted complement inhibition by C3d recognition ameliorates tissue injury without apparent increase in susceptibility to infection," J Clin Invest. 115(9):2444-53 (2005).
Atkinson et al., "Targeted inhibition of the alternative complement pathway delays the onset of antibody-mediated rejection in a mouse heterotopic heart transplant model," Mol Immunol. 44:3944, Abstract No. P24 (2007).
Aubry et al., "CD21 is a ligand for CD23 and regulates IgE production," Nature. 358(6386):505-507 (1992).
Aubry et al., "CD23 interacts with a new functional extracytoplasmic domain involving N-linked oligosaccharides on CD21," J Immunol. 152:5806-13 (1994).
Author manuscript of Clark et al., "Evidence for non-traditional activation of complement factor C3 during murine liver regeneration," available in PMC Jun. 1, 2009, published in final edited form as: Mol Immunol. 45(11):3125-32 (2008) (15 pages).
Author manuscript of Habermann et al., "Increased serum levels of complement C3a anaphylatoxin indicate the presence of colorectal tumors," available in PMC Sep. 8, 2008, published in final edited form as: Gastroenterol. 131(4):1020-9 (2006) (17 pages).
Baechler et al., "Interferon-inducible gene expression signature in peripheral blood cells of patients with severe lupus," Proc Natl Acad Sci USA. 100:2610-5 (2003).
Bagshawe et al., "A cytotoxic agent can be generated selectively at cancer sites," Br J Cancer. 58:700-703 (1988).
Bagshawe, "Towards generating cytotoxic agents at cancer sites," Br J Cancer. 60:275-281(1989).
Baldo et al., "The adipsin-acylation stimulating protein system and regulation of intracellular triglyceride synthesis," J Clin Invest. 92:1543-47 (1993).
Banda et al., "Targeted inhibition of the complement alternative pathway with complement receptor 2 and factor H attenuates collagen antibody-induced arthritis in mice," J Immunol. 183:5928-37 (2009).
Baranyi et al., "Cell-surface bound complement regulatory activity is necessary for the in vivo survival of KDH-8 rat hepatoma," Immunology. 82(4):522-8 (1994).
Barlow et al., "Solution structure of a pair of complement modules by nuclear magnetic resonance," J Mol Biol. 232:268-284 (1993).
Battelli et al., "T lymphocyte killing by a xanthine-oxidase-containing immunotoxin," Cancer Immunol Immunother. 35:421-425 (1992).
Benvenuti et al., "Crystallization of soluble proteins in vapor diffusion for X-ray crystallography," Nat Protoc. 2(7):1633-1651 (2007).

Bergelson et al., "Decay-accelerating factor (CD55), a glycosylphosphatidylinositol-anchored complement regulatory protein, is a receptor for several echoviruses," Proc Nat Aced Sci USA. 91(13):6245-9 (1994).
Blank et al., "Hemoglobin interference from in vivo hemolysis," Clin Chem. 31(9):1566-9 (1985).
Bohnsack et al., "CR2 ligands modulate human B cell activation," J Immunol. 141:2569-76 (1988).
Boross et al., "Boosting antibody therapy with complement," Blood. 119(25):5945-5947 (2012).
Brodsky, "How I treat paroxysmal nocturnal hemoglobinuria," Blood. 113(26):6522-7 (2009).
Brown et al., "Molecular and cellular mechanisms of receptor-mediated endocytosis," DNA Cell Biol. 10:399-409 (1991).
Bykov, "Complement system and alcoholic liver disease," University of Helsinki 1-69 (2008).
Camargo et al., "Interleukin-6 protects liver against warm ischemia/reperfusion injury and promotes hepatocyte proliferation in the rodent," Hepatology. 26:1513-20 (1997).
Cambier, "Signalling processes in haematopoietic cells: positive and negative signal co-operativity in the immune system: the BCR, Fc gamma RIIB, CR2 paradigm," Biochem Soc Trans. 25(2):441-445 (1997).
Caragine et al., "A tumor-expressed inhibitor of the early but not late complement lytic pathway enhances tumor growth in a rat model of human breast cancer," Cancer Res. 62(4):1110-5 (2002).
Carel et al., "Structural requirements for C3d,g/Epstein-Barr virus receptor (CR2/CD21) ligand binding, internalization, and viral infection," J Biol Chem. 265(21):12293-9 (1990).
Carroll, "The role of complement and complement receptors in induction and regulation of immunity," Annu Rev Immunol. 16:545-568 (1998).
Carroll, The role of complement in B cell activation and tolerance. *Advances in Immunology*. Dixon,74:61-88 (2000).
Carter et al., "CD19: lowering the threshold for antigen receptor stimulation of B lymphocytes," Science. 256:105-7 (1992).
Carter et al., "Polymeric C3dg primes human B lymphocytes for proliferation induced by anti-IgM," J Immunol. 143(6):1755-60 (1989).
Carter et al., "Synergistic interaction between complement receptor type 2 and membrane IgM on B lymphocytes," J Immunol. 141:457-63 (1988).
Casasnovas et al., "Crystal structure of two CD46 domains reveals an extended measles virus-binding surface," EMBO J. 18(11):2911-2922 (1999).
Chavez-Cartaya et al., "Regulation of the complement cascade by soluble complement receptor type 1. Protective effect in experimental liver ischemia and reperfusion," Transplantation. 59:1047-52 (1995).
Chen et al., "CD59 expressed on a tumor cell surface modulates decay-accelerating factor expression and enhances tumor growth in a rat model of human neuroblastoma," Cancer Res. 60(11):3013-8 (2000).
Chen et al., "Gene therapy for brain tumors: regression of experimental gliomas by adenovirus-mediated gene transfer in vivo," Proc Natl Acad Sci USA. 91:3054-3057 (1994).
Christiansen et al., "A functional analysis of recombinant soluble CD46 in vivo and a comparison with recombinant soluble forms of CD55 and CD35 in vitro," Eur J Immunol. 26(3):578-85 (1996).
Clavien et al., "Strategies for safer liver surgery and partial liver transplantation," N Engl J Med. 356:1545-59 (2007).
Clemenza et al., "Structure-guided identification of C3d residues essential for its binding to complement receptor 2 (CD21)," J Immunol. 165:3839-3848 (2000).
Cooper et al., "Immunobiology of CR2, the B lymphocyte receptor for Epstein-Barr virus and the C3d complement fragment," Ann Rev Immunol. 6:85-113 (1988).
Crumm et al., "Adenine necleotide changes in the remnant liver: an early signal for regeneration after partial hepatectomy," Hepatology. 48:898-908 (2008).
Cudney, "Protein crystallization and dumb luck," The Rigaku Journal. 16(1):1-7 (1999).

(56) References Cited

OTHER PUBLICATIONS

Dahm et al., "Small-for-size syndrome after partial liver transplantation: definition, mechanisms of disease and clinical implications," Am J Transplant. 5:2605-10 (2005).
Davies et al., "CD59, a Ly-6-Like protein expressed in human lymphoid cells, regulates the action of the complement membrane attack complex on homologous cells," J Exp Med. 170(3):637-54 (1989).
De Córdoba et al., "The human complement factor H: functional roles, genetic variations and disease associations," Molec Immunol. 41:355-67 (2004).
Delaglio et al., "NMRPipe: a multidimensional spectral processing system based on UNIX pipes," J Biomol NMR. 6:277-93 (1995).
Delcayre et al., "Epstein Barr virus/complement C3d receptor is an interferon alpha receptor," EMBO J. 10:919-26 (1991).
Delcayre et al., "Inhibition of Epstein-Barr virus-mediated capping of CD21/CR2 by alpha interferon (IFN-alpha): immediate antiviral activity of IFN-alpha during the early phase of infection," J Virol. 67:2918-21 (1993).
Dempsey et al., "C3d of complement as a molecular adjuvant: bridging innate and acquired immunity," Science. 271:348-350 (1996).
Dev et al., "Electrochemotherapy—A novel method of cancer treatment," Cancer Treat Rev. 20:105-115 (1994).
Diefenbach et al., "Mutation of residues in the C3dg region of human complement component C3 corresponding to a proposed binding site for complement receptor type 2 (CR2, CD21) does not abolish binding of iC3b or C3dg to CR2," J Immunol. 154(5):2303-2320 (1995).
Dierich et al., "Structural and functional relationships among receptors and regulators of the complement system," Mol Immunol. 25(11):1043-1051 (1988).
Dominguez et al., "Haddock: a protein-protein docking approach based on biochemical or biophysical information," J Am Chem Soc. 125:1731-7 (2003).
Drenth, Crystalling a Protein. *Principles of Protein X-Ray Crystallography*. Springer-Verlag, 1-21 (1999).
Duits et al., "Selective enhancement of Leu-Cam expression by Interleukin 6 during differentiation of human promonocytic U937 cells," Scand J Immunol. 33(2):151-9 (1991).
Duranski et al., "Cytoprotective effects of nitrite during in vivo ischemia-reperfusion of the heart and liver," J Clin Invest. 115(5):1232-40 (2005).
Dutkowski et al., "Novel short-term hypothermic oxygenated perfusion (HOPE) system prevents injury in rat liver graft from non-heart beating donor," Ann Surg. 244(6):968-76, discussion 976-7 (2006).
Dörig et al., "The human CD46 molecule is a receptor for measles virus (Edmonston strain)," Cell. 75(2):295-305 (1993).
EBI Accession No. CQ729676, <http://ibis/IBIS/exam/dbfetch.jsp?id=EM_PAT:CQ729676>retrieved on Jan. 3, 2011(1 page).
Edwards et al., "Complement factor H polymorphism and age-related macular degeneration," Science. 308:421-4 (2005).
Elvington et al., "A targeted complement-dependent strategy to improve the outcome of mAb therapy, and characterization in a murine model of metastatic cancer," Blood. 119(25):6043-6051 (2012).
Extended European Search Report and Written Opinion for European Application No. 11781394.9, dated Sep. 19, 2013 (11 pages).
Extended European Search Report for European Application No. 10829204.6, dated Mar. 5, 2013 (9 pages).
Fabrikant, "The kinetics of cellular proliferation in regenerating liver," J Cell Biol. 36(3):551-65 (1968).
Fausto, "Involvement of the innate immune system in liver regeneration and injury," J Hepatol. 45:347-9 (2006).
Fearon et al., "The CD19/CR2/TAPA-1 complex of B lymphocytes: Linking natural to acquired immunity," Annu Rev Immunol. 13:127-149 (1995).
Fearon, "The complement system and adaptive immunity," Semin Immunol. 10(5):355-361 (1998).

Ferreira et al., "Factor H-mediated cell surface protection from complement is critical for the survival of PNH erythrocytes," Blood. 110(6):2190-2 (2007).
Fingeroth et al., "Characterization of a T-lymphocyte Epstein-Barr virus/C3d receptor (CD21)," J Virol. 62:1442-7 (1988).
Fingeroth et al., "Epstein-Barr virus receptor of human B lymphocytes is the C3d receptor CR2," Proc Natl Acad Sci USA. 81(14):4510-4514 (1984).
Fingeroth et al., "Identification of murine complement receptor type 2," Proc Natl Acad Sci USA. 86(1):242-246 (1989).
Fiorini et al., "Development of an unbiased method for the estimation of liver steatosis," Clin Transplant. 18:700-6 (2004).
Fishelson et al., "Regulation of the alternative pathway of complement by pH," J Immunol. 138(10):3392-5 (1987).
Fondevila et al., "The membrane attack complex (C5b-9) in liver cold ischemia and reperfusion injury," Liver Transpl. 14:1133-41 (2008).
Franco-Gou et al., "Protection of reduced-size liver for transplantation," Am J Transplant. 4(9):1408-20 (2004).
Frémeaux-Bacchi et al., "Soluble CD21 induces activation and differentiation of human monocytes through binding to membrane CD23," Eur J Immunol. 28:4268-4274 (1998).
Fujisaku et al., "Genomic organization and polymorphisms of the human C3d/Epstein-Barr virus receptor," J Biol Chem. 264:2118-25 (1989).
Fukuoka et al., "Molecular cloning of murine decay accelerating factor by immunoscreening," International Immunology. 8:379-385 (1996).
Gomez et al., "Role of ischaemic preconditioning in liver regeneration following major liver resection and transplantation," World J Gastroenterol. 13(5):657-70 (2007).
Goodford, "A computational procedure for determining energetically favorable binding sites on biologically important macromolecules," *J. Med. Chem.* 28: 849-857, 1985.
Gordon, "B-cell signalling via the C-type lectins CD23 and CD72," Immunol Today. 15(9):411-417 (1994).
Greene et al., "Partial hepatectomy in the mouse: technique and perioperative management," J Invest Surg. 16:99-102 (2003).
Greenspan et al., "Defining epitopes: Its not as easy as it seems," Nat Biotechnol. 17:936-937 (1999).
Grzesiek et al., "Improved 3D triple-resonance NMR techniques applied to a 31-kDa protein," J Magn Reson. 96:432-40 (1992).
Guthridge et al., "Epitope mapping using the X-ray crystallographic structure of complement receptor type 2 (CR2)/CD21: Identification of a highly inhibitory monoclonal antibody that directly recognizes the CR2-C3d interface," J Immunol. 167:5758-5766 (2001).
Guthridge et al., "Structural studies in solution of the recombinant N-terminal pair of short consensus/complement repeat domains of complement receptor type 2 (CR2/CD21) and interactions with its ligand C3dg," Biochemistry. 40:5931-5941 (2001).
Haan et al., "Different functional domains in the cytoplasmic tail of glycoprotein B are involved in Epstein-Barr virus-induced membrane fusion," Virology. 290:106-14 (2001).
Haddad et al., "Depletion of glycoprotein gp85 from virosomes made with Epstein-Barr virus proteins abolishes their ability to fuse with virus receptor-bearing cells," J Virol. 63:4998-5005 (1989).
Hageman et al., "A common haplotype in the complement regulatory gene factor H (HF1/CFH) predisposes individuals to age-related macular degeneration," Proc Natl Aced Sci USA. 102(20):7227-32 (2005).
Haines et al., "Complement factor H variant increases the risk of age-related macular degeneration," Science. 308(5720):419-21 (2005).
Ham et al., "Studies on destruction of red blood cells. II. Chronic hemolytic anemia with paroxysmal nocturnal hemoglobinuria: certain immunological aspects of the hemolytic mechanism with special reference to serum complement," J Clin Invest. 18:657-72 (1939).
Hampton Research, Catalog, 5 & 7 (2001).
Hampton Research, Crystal Screen User Guide, 27632 El Lazo Road, Laguna Niguel, California, 1991 (4 pages).
Hannan et al., "Structure of complement receptor (CR) 2 and CR2-C3d complexes," Biochem Soc Trans. 30:983-9 (2002).

(56) References Cited

OTHER PUBLICATIONS

Harada et al., "Antithrombin reduces ischemia/reperfusion injury of rat liver by increasing the hepatic level of prostacyclin," Blood. 93:157-64 (1999).
Harlow et al., Proteolytic Fragments of Antibodies. *Antibodies: A Laboratory Manuel*. 626-629 (1988).
Harris et al., "Tailoring anti-complement therapeutics," Biochem Soc Trans. 30(6):1019-26 (2002).
Hautekeete et al., "Microvesicular steatosis of the liver," Acta Clin Belg. 45(5):311-326 (1990). Abstract Only.
He et al., "Delivery of antioxidative enzyme genes protects against ischemia/reperfusion-induced liver injury in mice," Liver Transpl. 12:1869-79 (2006).
Hebell et al., "Suppression of the immune response by a soluble complement receptor of B lymphocytes," Science. 254:102-105 (1991).
Helling et al., "Partial hepatectomy with or without endotoxin does not promote apoptosis in the rat liver," J Surg Res. 116:1-10 (2004).
Helling, "Liver failure following partial hepatectomyn" HPB (Oxford). 8:165-74 (2006).
Heyman, "Regulation of antibody responses via antibodies, complement, and Fc receptors," Ann Rev Immunol. 18:709-737 (2000).
Higgins et al., "A soluble chimeric complement inhibitory protein that possesses both decay-accelerating and factor I cofactor activities," J Immunol. 158(6):2872-81 (1997).
Higgins et al., "Experimental pathology of the liver. 1. Restoration of the liver of the white rat following partial surgical removal," Arch Pathol. 12:186-202 (1931).
Hill et al., "Sustained response and long-term safety of eculizumab in paroxysmal nocturnal hemoglobinuria," Blood. 106:2559-65 (2005).
Hillmen et al., "Effect of eculizumab on hemolysis and transfusion requirements in patients with paroxysmal nocturnal hemoglobinuria," N Engl J Med. 350(6):552-9 (2004).
Holers, Complement Receptors. *The Year in Immunology 1988. Cellular, Molecular and Clinical Aspects*. Cruse et al., 4:231-240 (1989).
Holers, Complement. *Clinical Immunology, Principles and Practice*. Mosby ed. 363-91 (1996).
Hori et al., "Crry, a complement regulatory protein, modulates renal interstitial disease induced by proteinuria," Kidney Int. 56:2096-2106 (1999).
Hsu et al., "Chronic progression of tubulointerstitial damage in proteinuric renal disease is mediated by complement activation: a therapeutic role for complement inhibitors?" J Am Soc Nephrol. 14:S186-91 (2003).
Huang et al., "Insights into the human CD59 complement binding interface toward engineering new therapeutics," J Biol Chem. 280(40):34073-9 (2005).
Hughes et al., "Monoclonal antibody targeting of liposomes to mouse lung in vivo," Cancer Res. 49(22):6214-20 (1989).
Humor et al., "Liver regeneration after adult living donor and deceased donor split-liver transplants," Liver Transpl. 10(3):374-8 (2004).
Humblet et al., "3D database searching and docking strategies," Topics in Drug Design and Discovery. *Annual Reports in Medicinal Chemistry*. Bristol et al., 28:275-284 (1993).
Iida et al., "Identification of the membrane receptor for the complement fragment C3d by means of a monoclonal antibody," J Exp Med. 158:1021-33 (1983).
Iimuro et al., "NFkappaB prevents apoptosis and liver dysfunction during liver regeneration," J Clin Invest. 101(4):802-11 (1998).
Imai et al., "Enhancement of antibody-dependent mechanisms of tumor cell lysis by a targeted activator of complement," Cancer Res. 67(19):9535-9541 (2007).
International Search Report for International Application No. PCT/US2011/036552, mailed Jul. 26, 2011 (7 pages).
International Search Report for International Application No. PCT/US2003/36459, mailed Sep. 15, 2004 (2 pages).
International Search Report for International Application No. PCT/US2007/014602, mailed on Mar. 6, 2008 (5 pages).
International Search Report for International Application No. PCT/US2010/040973, mailed Oct. 14, 2010 (5 pages).
International Search Report for International Application No. PCT/US2010/055745, mailed Feb. 4, 2011 (3 pages).
Jackson et al., "Pl3K/Akt activation is critical for early hepatic regeneration after partial hepatectomy," Am J Physiol Gastrointest Liver Physiol. 294:G1401-10 (2008).
Jacobson et al., "Clinical and immunologic features of transient cold agglutinin-hemolytic anemia," Am J Med. 54:514-21 (1973).
Janssen et al., "Structure of compstatin in complex with complement component C3c reveals a new mechanism of complement inhibition," J Biol Chem. 282:29241-7 (2007).
Janzi et al., "Serum microarrays for large scale screening of protein levels," Mol Cell Proteomics. 4(12):1942-7 (2005).
Jin et al., "Interleukin-6 inhibits oxidative injury and necrosis after extreme liver resection," Hepatology. 46:802-12 (2007).
Jin et al., "Paradoxical effects of short- and long-term interleukin-6 exposure on liver injury and repair," Hepatology. 43:474-84 (2006).
Johswich et al., "Ligand specificity of the anaphylatoxin C5L2 receptor and its regulation on myeloid and epithelial cell lines," J Biol Chem. 281(51):39088-95 (2006).
Juhl et al., "Complement killing of human neuroblastoma cells: A cytotoxic monoclonal antibody and its F(ab')2-cobra venom factor conjugate are equally cytotoxic," *Mol Immunol.* 27(10):957-964 (1990).
Kadry et al., "Liver regeneration after adult living donor and deceased donor split-liver transplants," Liver Transpl. 10(8):1078 (2004).
Kalant et al., "C5L2 is a functional receptor for acylation-stimulating protein," J Biol Chem 208(25):23936-44 (2005).
Kalant et al., "The chemoattractant receptor-like protein C5L2 binds the C3a des-Arg77/acylation-stimulating protein," J Biol Chem 278(13):11123-9 (2003).
Kalli et al., "Interaction of iC3b with recombinant isotypic and chimeric forms of CR2," J Immunol. 147(2):590-594 (1991).
Khurana et al., "Crystal structure of 2,5-diketo-D-gluconic acid reductase A complexed with NADPH at 2.1-A resolution," Proc Natl Acad Sci 95:6768-6773 (1998).
Kildsgaard et al., "A critical evaluation of the putative role of C3adesArg (ASP) in lipid metabolism and hyperapobetalipoproteinemia," Mol Immunol. 36:869-76 (1999).
Klein et al., "Complement factor H polymorphism in age-related macular degeneration," Science. 308(5720):385-9 (2005).
Koski et al., "Cytolysis of nucleated cells by complement: cell death displays multi-hit characteristics," Proc Natl Acad Sci USA. 80:3816-3820 (1983).
Kovacs et al., "Biophysical investigations of complement receptor 2 (CD21 and CR2)-ligand interactions reveal amino acid contacts unique to each receptor-ligand pair," J Biol Chem. 285:27251-8 (2010).
Kroshus et al., "A recombinant soluble chimeric complement inhibitor composed of human CD46 and CD55 reduces acute cardiac tissue injury in models of pig-to-human heart transplantation," Transplantation. 69(11):2282-9 (2000).
Krushkal et al., "Evolutionary relationships among proteins encoded by the regulator of complement activation gene cluster," Mol Biol Evol. 17(11):1718-30 (2000).
Kuby et al., Antigens. *Immunology (2nd edition)*. W H Freeman and Company, 85-96 (1994).
Kundrot, "Which strategy for a protein crystallization project?" Cell Mol Life Science. 61(5):525-536 (2004).
Kuraya et al., "Expression of the complement regulatory proteins CD21, CD55, and CD59 on Burkitt lymphoma lines: Their role in sensitivity to human serum-meidated lysis," Eur J Immunol. 22(7):1871-1876 (1992).
La Flamme et al., "Lack of C3 affects Th2 response development and the sequelae of chemotherapy in schistosomiasis," J Immunol. 170:470-6 (2003).

(56) References Cited

OTHER PUBLICATIONS

Lambris et al., "Mapping of the C3d receptor (CR2)-binding site and a neoantigenic site in the C3d domain of the third component of complement," Proc Natl Aced Sci USA. 82(12):4235-4239 (1985).
Law et al., "Action of the C3b-inactivator of the cell-bound C3b," J Immunol. 122(3):759-65 (1979).
Law et al., Complement. *In Focus*. Male, vii-ix (1995).
Lehmann et al., "Complement inhibition by soluble complement receptor type 1 improves microcirculation after rat liver transplantation," Transplantation. 66:717-22 (1998).
Lehmann et al., "Impact of inhibition of complement by sCR1 on hepatic microcirculation after warm ischemia," Microvasc Res. 62:284-92 (2001).
Leivo et al., "C3d fragment of complement interacts with laminin and binds to basement membranes of glomerulus and trophoblast," J Cell Biol. 103:1091-100 (1986).
Leu et al., "Triggering of interferon γ-primed macrophages by various known complement activators for nonspecific tumor cytotoxicity," Cell Immunol. 106:114-121 (1987).
Linton et al., "therapeutic efficacy of a novel membrane-targeted complement regulator in antigen-induced arthritis in the rat," Arthritis Rheum. 43(11):2590-7 (2000).
Litzinger et al., "Biodistribution and immunotargetability of ganglioside-stabilized dioleoylphosphatidylethanolamine liposomes," Biochimica et Biophysica Acta. 1104:179-87 (1992).
Lowell et al., "Mapping of the Epstein-Barr virus and C3dg binding sites to a common domain on complement receptor type 2," J Exp Med. 170(6):1931-1946 (1989).
Luxembourg et al., "Modulation of signaling via the B cell antigen receptor by CD21, the receptor for C3dg and EBV," J Immunol. 153:4448-57 (1994).
Lyubchenko et al., "Coligation of the B cell receptor with complement receptor type 2 (CR2/CD21) using its natural ligand C3dg: activation without engagement of an inhibitory signaling pathway," J Immunol. 174:3264-72 (2005).
Mache et al., "Complement inhibitor eculizumab in atypical hemolytic uremic syndrome," Clin J Am Soc Nephrol. 4(8):1312-6 (2009).
MacLaren et al., "Adipokines and the immune system: an adipocentric view," Adv Exp Med Biol. 632:1-21 (2008).
Markiewski et al., "C3a and C3b activation products of the third component of complement (C3) are critical for normal liver recovery after toxic injury," J Immunol. 173:747-754 (2004).
Martin et al., "Determination of the role for CD21 during Epstein-Barr virus infection of B-lymphoblastoid cells," J Virol. 68(8):4716-4726 (1994).
Martin et al., "Determination of the structural basis for selective binding of Epstein-Barr virus to human complement receptor type 2," J Exp Med. 174:1299-1311 (1991).
Maslowska et al., "Novel roles for acylation stimulating protein/C3adesArg: a review of recent in vitro and in vivo evidence," Vitam Horm. 70:309-32 (2005).
Mastellos et al., "A novel role of complement: mice deficient in the fifth component of complement (C5) exhibit impaired liver regeneration," J Immunol. 166(4):2479-86 (2001).
Matsumoto et al., "Intersection of the complement and immune systems: A signal transduction complex of the B lymphocyte-containing complement receptor type 2 and CD19," J Exp Med. 173(1):55-64 (1991).
Matsuo et al., "Complement in renal tubulointerstitial injuries," Proceedings of the 35th Complement Symposium 21-22 (1998).
McPherson, "Current approaches to macromolecular crystallization," Eur J Biochem. 189(1):1-23 (1990).
Mendrick et al., "I. induction of proteinuria in the rat by a monoclonal antibody against SGP-115/107," Kidney Int. 33:818-30 (1988).
Mendrick et al., "Monoclonal antibodies against rat glomerular antigens: production and specificity," Lab Invest. 49(1):107-17 (1983).
Moir et al., "B cells of HIV-1-infected patients bind virions through CD21-complement interactions and transmit infectious virus to activated T cells," J Exp Med. 192(5):637-646 (2000).

Mold et al., "Activation of the alternative complement pathway by EBV and the viral envelope glycoprotein, gp350," J Immunol. 140(11):3867-3874 (1988).
Molesworth et al., "Epstein-Barr virus gH is essential for penetration of B cells but also plays a role in attachment of virus to epithelial cells," J Virol. 74(14):6324-32 (2000).
Molina et al., "Analysis of C3b/C3d binding sites and factor I cofactor regions within mouse complement receptor 1 and 2," J Immunol. 153(2):789-795 (1994).
Molina et al., "Analysis of Epstein-Barr virus-binding sites on complement receptor 2 (CR2/CD21) using human-mouse chimeras and peptides," J Biol Chem. 266(19-20):12173-9 (1991).
Molina et al., "Characterization of a complement receptor 2 (CR2, CD21) ligand binding site for C3. An initial model of ligand interaction with two linked short consensus repeat modules," J Immunol. 154:5426-5435 (1995).
Molina et al., "Markedly impaired humoral immune response in mice deficient in complement receptors 1 and 2," Proc Natl Acad Sci USA. 93:3357-3361 (1996).
Moore et al., "Hydrodynamic, electron microscopic, and ligand-binding analysis of the Epstein-Barr virus/C3dg receptor (CR2)," J Biol Chem. 264:20576-82 (1989).
Moore et al., "Inhibition of Epstein-Barr virus infection In Vitro and In Vivo by soluble CR2 (CD21) containing two short consensus repeats," J Virol. 65(7):3559-3565 (1991).
Moran et al., "Human recombinant soluble decay accelerating factor inhibits complement activation in vitro and in vivo," J Immunol. 149:1736-1743 (1992).
Morikis et al., "The electrostatic nature of C3d-complement receptor 2 association," J Immunol. 172:7537-47 (2004).
Mullen et al., "Structure of the Epstein-Barr virus gp42 protein bound to the MHC class II receptor HLA-DR1," Mol Cell. 9:375-85 (2002).
Mulligan et al., "Endothelial targeting and enhanced antiinflammatory effects of complement inhibitors possessing sialyl Lewisx moieties," J Immunol 162(8):4952-9 (1999).
Murray et al., "Functional bioactive recombinant acylation stimulating protein is distinct from C3a anaphylatoxin," J Lipid Res. 38:2492-501 (1997).
Murray et al., "Mice lacking acylation stimulating protein (ASP) have delayed postprandial triglyceride clearance," J Lipid Res. 40:1671-6 (1999).
Murray et al., "Reduced body weight, adipose tissue, and leptin levels despite increased energy intake in female mice lacking acylation-stimulating protein," Endocrinology. 141(3):1041-9 (2000).
Nagar et al., "X-ray crystal structure of C3d: A C3 fragment and ligand for complement receptor 2," Science. 280(5367):1277-81 (1998).
NCBI Blast for UniProtKB/Swiss-Prot Accession No. P00746. Retrieved on Nov. 13, 2013 (14 pages).
NCBI Blast for UniProtKB/Swiss-Prot Accession No. P00751. Retrieved on Nov. 13, 2013 (1 page).
NCBI Blast for UniProtKB/Swiss-Prot Accession No. P01024. Retrieved on Nov. 13, 2013 (29 pages).
NCBI Blast for UniProtKB/Swiss-Prot Accession No. P01027. Retrieved on Nov. 13, 2013 (13 pages).
NCBI Blast for UniProtKB/Swiss-Prot Accession No. P03953. Retrieved on Nov. 13, 2013 (6 pages).
NCBI Blast for UniProtKB/Swiss-Prot Accession No. P04004. Retrieved on Nov. 13, 2013 (14 pages).
NCBI Blast for UniProtKB/Swiss-Prot Accession No. P04186. Retrieved on Nov. 13, 2013 (9 pages).
NCBI Blast for UniProtKB/Swiss-Prot Accession No. P05155. Retrieved on Nov. 13, 2013 (29 pages).
NCBI Blast for UniProtKB/Swiss-Prot Accession No. P10909. Retrieved on Nov. 13, 2013 (21 pages).
NCBI Blast for UniProtKB/Swiss-Prot Accession No. P11680. Retrieved on Nov. 13, 2013 (5 pages).
NCBI Blast for UniProtKB/Swiss-Prot Accession No. P27918. Retrieved on Nov. 13, 2013 (13 pages).
NCBI Blast for UniProtKB/Swiss-Prot Accession No. P29788. Retrieved on Nov. 13, 2013 (10 pages).

(56) References Cited

OTHER PUBLICATIONS

NCBI Blast for UniProtKB/Swiss-Prot Accession No. P58019. Retrieved on Nov. 13, 2013 (5 pages).
NCBI Blast for UniProtKB/Swiss-Prot Accession No. P97290. Retrieved on Nov. 13, 2013 (6 pages).
NCBI Blast for UniProtKB/Swiss-Prot Accession No. Q06890. Retrieved on Nov. 13, 2013 (9 pages).
NCBI Blast for UniProtKB/Swiss-Prot Accession No. Q9P296. Retrieved on Nov. 13, 2013 (9 pages).
NCBI Protein Database Accession No. P08173. Retrieved Feb. 18, 2014 (4 pages).
NCBI Protein Database Accession No. P13987. Retrieved Feb. 18, 2014 (12 pages).
NCBI Protein Database Accession No. P15529. Retrieved Feb. 18, 2014 (21 pages).
NCBI Protein Database Accession No. P58019. Retrieved Feb. 18, 2014 (4 pages).
Nemerow et al., "Identification and characterization of the Epstein-Barr virus receptor on human B lymphocytes and its relationship to the C3d complement receptor (CR2)," J Virol. 55(2):347-51 (1985).
Nemerow et al., "Identification of an epitope in the major envelope protein of Epstein-Barr virus that mediates viral binding to the B lymphocyte EBV receptor (CR2)," Cell. 56:369-77 (1989).
Nemerow et al., "Identification of gp350 as the viral glycoprotein mediating attachment of Epstein-Barr virus (EBV) to the EBV/C3d receptor of B cells: sequence homology of gp350 and C3 complement fragment C3d," J Virol. 61(5):1416-20 (1987).
Ngo et al., Computational Complexity, Protein Structure Prediction, and the Levinthal Paradox. *The Protein Folding Problem and Tertiary Structure Prediction*. Merz et al., 491-495 (1994).
Okano, "Epstein-Barr virus infection and its role in the expanding spectrum of human diseases," Acta Paediatr. 87:11-18 (1998).
Paglialunga et al., "Reduced adipose tissue triglyceride synthesis and increased muscle fatty acid oxidation in C5L2 knockout mice," J Endocrinol. 194:293-304 (2007).
Pervushin et al., "Attenuated T2 relaxation by mutual cancellation of dipole-dipole coupling and chemical shift anisotropy indicates an avenue to NMR structures of very large biological macromolecules in solution," Proc Natl Acad Sci USA. 94:12366-71 (1997).
Petersen et al., "The mannan-binding lectin pathway of complement activation: biology and disease association," Mol Immunol. 38:133-49 (2001).
Piatesi et al., "Immunological optimization of a generic hydrophobic pocket for high affinity hapten binding and Diels-Alder activity," Chembiochem. 5(4):460-466 (2004).
Pietersz et al., "Antibody conjugates for the treatment of cancer," Immunolog Reviews. 129:57-80 (1992).
Poznansky et al., "The difference between human C3F and C3S results from a single amino acid change from an asparagine to an aspartate residue at position 1216 on the α-chain of the complement component C3," J Immunol. 143(4):1254-1258 (1989).
Preissner, "Structure and biological role of vitronectin," Annu Rev Cell Biol. 7:275-310 (1991).
Prodeus et al., "A critical role for complement in maintenance of self-tolerance," Immunity. 9(5):721-731 (1998).
Prodinger et al., "Characterization of C3dg binding to to a recess formed between short consensus repeats 1 and 2 of complement receptor type 2 (CR2; CD21)," J Immunol. 161:4604-4610 (1998).
Quigg et al., "Production and fuctional analysis of rat CD59 and chimeric CD59-Crry as active soluble proteins in Pichia pastoris," Immunol. 99(1):46-53 (2000).
Ramm et al., "Transmembrane channel formation by complement: functional analysis of the number of C5b6, C7, C8, and C9 molecules required for a single channel," Pro Natl Aced Sci. 79(15):4751-5 (1982).
Reeck et al., "Homology in proteins and nucleic acids: A terminology muddle and a way out of it," Cell. 50:667 (1987).
Ricklin et al., "Complement-targeted therapeutics," Nat Biotechnol. 25(11):1265-75 (2007).
Rioux, "TP-10 AVANT immunotherapeutics," Curr Opin Invest Drugs 2(3):364-71 (2001).
Risitano et al., "Complement fraction 3 binding on erythrocytes as additional mechanism of disease in paroxysmal nocturnal hemoglobinuria patients treated by eculizumab," Blood. 113(17):4094-4100 (2009) (25 pages).
Risitano et al., "Paroxysmal nocturnal hemoglobinuria: pathophysiology, natural history and treatment options in the era of biological agents," Biologics. 2(2):205-222 (2008).
Risitano et al., "The complement receptor 2/factor H fusion protein TT30 protects paroxysmal nocturnal hemoglobinuria erythroctyes from complement-mediated hemolysis and C3 fragment opsonization," Blood. 119(26):6307-6316 (2012).
Risitano et al., "TT30, a novel regulator of the complement alternative pathway (CAP), inhibits hemolysis of paroxysmal nocturnal hemoglobinuria (PNH) erythrocytes and prevents upstream C3 binding on their surface in an in vitro model," <https://ash.confex.com/ash/2009/webprogram/Paper19102.html>, retrieved on Dec. 26, 2013 (2 pages).
Rittershaus et al., "Recombinant glycoproteins that inhibit complement activation and also bind the selectin adhesion molecules," J Biol Chem. 274(16):11237-44 (1999).
Roffler et al., "Anti-neoplastic glucuronide prodrug treatment of human tumor cells targeted with a monoclonal antibody-enzyme conjugate," Biochem Pharmacol. 42:2062-2065 (1991).
Ross et al., "Macrophage cytoskeleton association with CR3 and CR4 regulates receptor mobility and phagocytosis of iC3b-opsonized erythrocytes," J Leukoc Biol. 51(20):109-117 (1992).
Rothlein et al., "The requirement for lymphocyte function-associated antigen 1 in homotypic leukocyte adhesion stimulated by phorbol ester," J Exp Med. 163(5):1132-49 (1986).
Rudikoff et al., "Single amino acid subsitution altering antigen-binding specificity," Proc Natl Acad Sci USA. 79(6):1979-19783 (1982).
Rushmere et al., "Production and functional characterization of a soluble recombinant form of mouse CD59," Immunol. 99(2):326-32 (2000).
Salerno et al., "A soluble chimeric inhibitor of C3 and C5 convertases, complement activation blocker-2, prolongs graft survival in pig-to-rhesus monkey heart transplantation," Xenotransplantation. 9(2):125-34 (2002).
Santiago-Raber et al., "Type-I interferon receptor deficiency reduces lupus-like disease in NZB mice," J Exp Med. 197:777-88 (2003).
Sarnaik et al., "Periodic transfusions for sickle cell anemia and CNS infarction," Am J Dis Child. 133(12):1254-7 (1979).
Satoh et al., "Energy metabolism regeneration in transgenic mouse liver expressing creatine kinase after major hepatectomy," Gastroenterology. 101:1166-74 (1996).
Schwarzenbacher et al., "Crystal structure of human b2-glycoprotein I: implications for phospholipid binding and the antiphospholipid syndrome," EMBO J. 18:6228-39 (1999).
Scola et al., "The human complement fragment receptor, C5L2, is a recycling decoy receptor," Mol Immunol. 46:1149-62 (2009).
Selzner et al., "Failure of regeneration of the steatotic rat liver: disruption at two different levels in the regeneration pathway," Hepatology. 31:35-42 (2000).
Senter et al., "Generation of 5-fluorouracil from 5-fluorocytosine by monoclonal antibody-cytosine deaminase conjugates," Bioconjugate Chem. 2:447-451 (1991).
Senter et al., "Generation of cytotoxic agents by targeted enzymes," Bioconjugate Chem. 4:3-9 (1993).
Seya et al., "Limited proteolysis of complement protein C3b by regulatory enzyme C3b inactivator: Isolation and characterization of a biologically active fragment, C3d,g," J Biochem. 97(1):373-382 (1985).
Sharkey et al., "Biodistribution and radiation dose estimates for yttrium- and iodine-labeled monoclonal antibody IgG and fragments in nude mice bearing human colonic tumor xenografts," Cancer Res. 50:2330-2336 (1990).
Sharkey et al., "Rapid blood clearance of immunoglobulin G2a and immunoglobulin G2b in nude mice," Cancer Res. 51:3102-3107 (1991).

(56) References Cited

OTHER PUBLICATIONS

Sharma et al., "Identification of three physically and functionally distinct binding sites for C3b in human complement Factor H by deletion mutagenesis," Proc Natl Acad Sci USA. 93(20):10996-11001 (1996).
Sheerin et al., "Leaked protein and interstitial damage in the kidney: is complement the missing link?" Clin Exp Immunol. 130(1):1-3 (2002).
Sigala et al., "Histological and lipid peroxidation changes after administration of 2-acetylaminofluorene in a rat liver injury model following selective periportal and pericentral damage," Toxicology. 196:155-63 (2004).
Skjodt et al., "MBL/Ficolin assocaited protein-1 (MAP-1) may function as a local lectin pathway specific complement inhibitor," Mol Immunol. 47:2229-30 (2010).
Smith et al., "Membrane-targeted complement inhibitors," Mol Immunol. 38:249-55 (2001).
Song et al., "Complement receptor 2-mediated targeting of complement inhibitors to sites of complement activation," J Clin Invest. 111(12):1875-1885 (2003).
Spriggs et al., "The extracellular domain of the Epstein-Barr virus BZLF2 protein binds the HLA-DR beta chain and inhibits antigen presentation," J Virol. 70:5557-63 (1996).
Strey et al., "The proinflammatory mediators C3a and C5a are essential for liver regeneration," J Exp Med. 198(6):913-23 (2003).
Stryer et al., Levels of Structure in Protein Architecture. *Biochemistry* (3rd edition). W H Freeman Company, 31-33 (1998).
Sugita et al., "Recombinant soluble CD59 inhibits reative haemolysis with complement," Immunol. 82(1):34-41 (1994).
Supplementary European Search Report for European Application No. 03796403.8, mailed Jul. 3, 2006 (4 pages).
Supplementary Partial European Search Report for European Application No. 03796403.8, mailed Apr. 3, 2006 (3 pages).
Szakonyi et al., "Structure of complement receptor 2 in complex with its C3d ligand," Science. 292:1725-1728 (2001).
Szakonyi et al., "Structure of the Epstein-Barr virus major envelope glycoprotein," Nature Struct Mol Biol. 13:996-1001 (2006).
Takahashi et al., "Mouse complement receptors type 1 (CR1;CD35) and type 2 (CR2;CD21): expression on normal B cell subpopulations and decreased levels during the development of autoimmunity in MRL/lpr mice," J Immunol. 159:1557-69 (1997).
Takeda et al., "Number of hits necessary for complement-mediated hemolysis," Microbiol Immunol. 30(5):461-8 (1986).
Tanner et al., "Epstein-Barr virus gp350/220 binding to the B lymphocyte C3d receptor mediates adsorption, capping, and endocytosis," Cell. 50:203-13 (1987).
Taub, "Liver regeneration: from myth to mechanism," Nat Rev Mol Cell Biol. 5:836-47 (2004).
Ten et al., "The signal transduction pathway of CD23 (FceRIIb) targets IkB kinase," J Immunol. 163(7):3851-7 (1999).
Teoh et al., "Dual role of tumor necrosis factor-alpha in hepatic ischemia-reperfusion injury: studies in tumor necrosis factor-alpha gene knockout mice," Hepatology. 39:412-21 (2004).
Tian et al., "Kupffer cell-dependent TNF-alpha signaling mediates injury in the arterialized small-for-size liver transplantation in the mouse," Proc Natl Acad Sci USA. 103(12):4598-603 (2006).
Tolnay et al., "Complement receptor 2 in the regulation of the immune response," Clin Immunol Immunopathol. 88:123-32 (1998).
Tsutsumi et al., "Site-specific chemical modification with polyethylene glycol of recombinant immunotoxin anti-Tac(Fv)-PE38 (LMB-2) improves antitumor activity and reduces animal toxicity and immunogenicity," Proc Natl Acad Sci USA. 97(15):8548-53 (2000).
Tuveson et al., "Molecular interactions of complement receptors on B lymphocytes: a CR1/CR2 complex distinct from the CR2/CD19 complex," J Exp Med. 173:1083-9 (1991).
Van Harmelen et al., "Mechanisms involved in the regulation of free fatty acid release from isolated human fat cells by acylation-stimulating protein and insulin," J Biol Chem. 274(26):18243-51 (1999).
Vranken et al., "The CCPN data model for NMR spectroscopy: development of a software pipeline," Proteins. 59:687-96 (2005).
Ward et al., "Decay-accelerating factor CD55 is identified as the receptor for echovirus 7 using Celics, a rapid immuno-focal cloning method," EMBO J. 13(21):5070-4 (1994).
Watanabe et al., "Co-protective effect of Crry and CD59 in rat kidney against complement attack," Proceedings of the Joint Academic Meeting of the Complement Symposium and Japanese Society for Host Defense Research, 37(11):19-20 (2000).
Weis et al., "Identification of a partial cDNA clone for the C3d/Epstein-Barr virus receptor of human B lymphocytes: homology with the receptor for fragments C3b and C4b of the third and fourth components of complement," Proc Natl Aced Sci USA. 83:5639-43 (1986).
Weis et al., "Structure of the human B lymphocyte receptor for C3d and the Epstein-Barr virus and relatedness to other members of the family of C3/C4 binding proteins," J Exp Med. 167:1047-66 (1988).
Wiles et al., "NMR studies of a viral protein that mimics the regulators of complement activation," J Mol Biol. 272(2):253-265 (1997).
Wiseman et al., "Rapid measurement of binding constants and heats of binding using a new titration calorimeter," Anal Biochem. 179:131-7 (1989).
Wittekind et al., "A high sensitivity 3D NMR experiment to correlate amide-proton and nitrogen resonances with the alpha-carbon and beta-carbon resonances in proteins," J Magn Reson. 101:201-5 (1993).
Wullaert et al., "Hepatic tumor necrosis factor signaling and nuclear factor-kappaB: effects on liver homeostasis and beyond," Endocr Rev. 28(4):365-86 (2007).
Xia et al., "Acylation-stimulating protein (ASP) deficiency induces obesity resistance and increased energy expenditure in ob/ob mice," J Biol Chem. 277:45874-9 (2002).
Yamaji et al., "Up-regulation of hepatic heme oxygenase-1 expression by locally induced interleukin-6 in rats administered carbon tetrachloride intraperitoneally," Toxicol Lett. 179:124-9 (2008).
Yang et al., "An engineered complement receptor 1 composed of two functional domains can protect against immune-mediated hemolysis," Protein Expr Purif. 66(1):28-34 (2009).
Young et al., "Isolating the Epstein-Barr virus gp350/220 binding site on complement receptor type 2 (CR2/CD21)," J Biol Chem. 282(50):36614-25 (2007).
Young et al., "Molecular basis of the interaction between complement receptor type 2 (CR2/CD21) and Epstein-Barr virus glycoprotein gp350," J Virol. 82:11217-27 (2008).
Yu et al., "Protection of human breast cancer cells from complement-mediated lysis by expression of heterologous CD59," Clin Exp Immunol. 115(1):13-8 (1999).
Zhang et al., "Immunophysical exploration of C3d-CR2(CCP1-2) interaction using molecular dynamics and electrostatics," J Mol Biol. 369:567-83 (2007).
Zhang et al., "Targeting of functional antibody-CD59 fusion proteins to a cell surface," J Clin Invest. 103(1):55-61 (1999).
Zhang et al., "Targeting of functional antibody-decay-accelerating factor fusion proteins to a cell surface," J Biol Chem. 276(29):27290-5 (2001).
Zhong et al., "NIM811, a mitochondrial permeability transition inhibitor, prevents mitochondrial depolarization in small-for-size rat liver grafts," Am J Transplant. 7:1103-11 (2007).
Zhu et al., "Inhibition of tumor growth and metastasis by targeting tumor-associated angiogenesis with antagonists to the receptors of vascular endothelial growth factor," Invest New Drugs. 17(3):195-212 (1999).
Zipfel, "Complement factor H: physiology and pathophysiology," Semin Thromb Hemost. 27(3):191-9 (2001).
Zuiderweg et al., "Heteronuclear three-dimensional NMR spectroscopy of the inflammatory protein C5a," Biochemistry. 28:2387-91 (1989).

(56) References Cited

OTHER PUBLICATIONS

Ali et al., "The use of DNA viruses as vectors for gene therapy," *Gene Therapy*, (1994), vol. 1, pp. 367-384.
Crystal, "The Gene As the drug," *Nature Medicine*, (1995), vol. 1, pp. 15-17.
Hetherington et al., "Phase I Dose Escalation Study to Evaluate the Safety and Pharmacokinetic Profile of Tefibazumab in Subjects with End-Stage Renal Disease Requiting Hemodialysis," *Antimicrobial Agents and Chemotherapy*, (2006), vol. 50, No. 10, pp. 3499-3500.
Hezareh et al., "Effector Function Activities of a Panel of Mutants of a Broadly Neutralizing Antibody against Human Immunodeficiency Virus Type 1," *Journal of Virology*, (2001), vol. 75, pp. 12161-12168.
Hillmen et al. "Effect of Eculizumab on Hemolysis and Transfusion Requirements in Patients with Paroxysmal Nocturnal Hemoglobinuria," *The New England Journal of Medicine* (2004) vol. 350 pp. 552.
Kaszubska et al., "Expression, Purification, and Characterization of Human Recombinant Thrombopoietin in Chinese Hamster Ovary Cells", (2000) *Protein Expression and Purification* 18: 213-220).
Mullett et al, "Surface Plasmon Resonance-Based Immunoassays", Methods 22, 77-91 (2000).
Poljak "Production and structure of diabodies" Structure Dec. 15, 1994, 2(12):1121-1123.
Pollock et al. "Transgenic milk as a method for the production of recombinant antibodies", Journal of Immunol Methods 231 (1999) 147-157.
Rich et al., "Advances in surface plasmon resonance biosensor analysis", (2000) Curr Opin Biotechnol 11: 54-61.
Schoonooghe et al., "Efficient production of human bivalent and trivalent anti-MUCI Fab-scFv antibodies in Pichia pastoris", (2009) *BMC Biotechnol.2_:70*), pp. 1-14.
van Gurp et al., "Phase 1 Dose-Escalation Study of CP-690 550 in Stable Renal allograft Receipients: Preliminary Findings of Safety, Tolerability, Effects on Lymphocyte Subsets and Pharmacokinetics", (2008) *Am J Transplantation* 8 (8) 1711-1718.
van Kuik-Romeijn et al., "Expression of a functional mouse-human chimeric anti-CD19 antibody in the milk of transgenic mice", (2000) *Transgenic Res* 9(2):155-159.
Zapata et al., "Engineering linear F(ab')$_2$ fragments for efficient production in *Escherichia coli* and enhanced antiproliferative activity", (1995) *Protein Eng.* 8(10):1057-1062.
Complement Receptor Type 2 isoform 1 precursor [*Homo sapiens*], Ref. Seq. Accession NM 007758.2, dated Jun. 19, 2011.
Complement Receptor Type 2 isoform 1 precursor [Mus musculus], Ref. Seq. Accession No. NM 001006658.2, dated May 28, 2011.
Record for UniProt Accession No. O55186, version 83, dated May 3, 2011.
Record for UniProt Accession No. P0609, version 98, dated May 3, 2011.
Record for UniProt Accession No. P08173, version 109, dated Apr. 5, 2011.
Record for UniProt Accession No. P08603, version 150, dated May 31, 2011.
Record for UniProt Accession No. P13987, version 1, dated May 3, 2011.
Record for UniProt Accession No. P15529, version 140, dated Jun. 28, 2011.
Record for UniProt Accession No. P17927, version 127, dated May 3, 2011.
Record for UniProt Accession No. P58019, version 69, dated May 31, 2011.
Record for UniProt Accession No. Q61475, version 81, dated May 3, 2011.
Record for UniProt Accession No. Q91132, version 63, dated Apr. 5, 2011.
Certificate of Deposit for ATCC Patent Deposit Designations PTA-11010, PTA-11011 and PTA-11012, Jun. 14, 2010.
Certificate of Deposit for ATCC Patent Deposit Designations PTA-11025, PTA-11026 and PTA-11027, Jun. 21, 2010.
Certificate of Deposit for ATCC Patent Deposit Designations PTA-10998, PTA-10999 and PTA-11000, Jun. 8, 2010.
Anderson, "Human Gene Therapy," *Science* (1992), vol. 256, pp. 808-813.
Appel et al., "Membranoproliferative Glomerulonephritis Type II (Dense Deposit Disease): An Update" *Journal of the American Society of Nephrology*, (2005), vol. 16, pp. 1392-1404.
Baudino et al., "Crucial Role of Aspartic Acid at Position 265 in the CH2 Domain for Murine IgG2a and IgG2b Fc-Associated Effector Functions," *The Journal of Immunology*, (2008) vol. 181, pp. 6664-6669.
Brennan et al., "Preparation of Bispecific Antibodies by Chemical Recombination of Monoclonal Immunoglobulin G1 Fragments" *Science*, (1985), vol. 229, pp. 81-83.
Bruggemann et al., "Designer Mice: The Production of Human Antibody Repertoires in Transgenic Animals," *The Year in Immunology*, (1993), vol. 7, pp. 33-39.
Burton et al., "Human Antibody Effector Function," *Advances in Immunology*, (1992) vol. 51, pp. 1-18.
Canfield et al., "The Binding Affinity of Human IgG for its High Affinity Fc Receptor Is Determined by Multiple Amino Acids in the Ch2 Domain and Is Modulated by the Hinge Region," *Journal of Experimental Medicine*, (1991), vol. 173, pp. 1483-1491.
Caplen et al., "Liposome-mediated CFTR gene transfer to the nasal epithelium of patients with cystic fibrosis," *Nature Medicine*, (1995), vol. 1, pp. 39-46.
Caron et al., "Engineered Human Dimeric Forms of IgG Are More Effective Antibodies," (1992) *Journal of Experimental Medicine*, vol. 176, pp. 1191-1195.
Chothia et al., "Conformations of Immunoglobulin hypervariable regions," *Nature*, (1989), vol. 342, pp. 877-883.
Deans et al., "Expression of an immunoglobulin heavy chain gene transfected into lymphocytes," *Proceedings of the National Academy of Sciences* (1984), vol. 81, pp. 1292-1296.
Dong et al., "Some New Aspects in Biosensors," *Reviews in Molecular Biotechnology*, (2002), vol. 82, pp. 303-323.
Duchosal et al., "Immunization of hu-PBL-SCID mice and the rescue of human monoclonal fab fragments through combinatorial libraries," *Nature*, (1992), vol. 355, pp. 258-262.
Dumoulin et al., "A camelid antibody fragment inhibits the formation of amyloid fibrils by human lysozyme," *Nature*, (2003), vol. 424, pp. 783-788.
Duncan et al., "The binding site for Clq on IgG," *Nature*, (1988), vol. 322, pp. 738-740.
Fivash et al., "BIAcore for macromolecular interaction," (1998) *Current Opinion Biotechnology* vol. 9, pp. 97-101.
Flentke et al., "Purification and Crystallization of Rhizopuspepsin: The Use of Nickel Chelation Chromatography to Select for Catalytically Active Species," *Protein Expression and Purification*, vol. 16 (1999), pp. 213-220.
Gao et al., "A Novel Cationic Liposome Reagent for Efficient Transfection of Mammalian Cells," *Biochemical and Biophysical Research Communications*, (1991), vol. 179, pp. 280-285.
Green et al., Regulation of B Cell Development by Variable Gene Complexity in Mice Reconstituted with Human Immunoglobulin Yeast Artificial Chromosomes, *Journal of Experimental Medicine*, (1998), vol. 188, pp. 483-495.
Gruber et al., "Efficient tumor cell lysis mediated by a bispecific single chain antibody expressed in *Escherichia coli.,*" *the Journal of Immunology*, (1994) vol. 152, pp. 5368-5374.
Hanauske et al., "PhaseIbDose Escalation Study of Erlotinibin Combination with Infusional 5-Fluorouracil, Leucovorin, and Oxaliplatin in Patients with Advanced Solid Tumors," *Clinical Cancer Research*, (2007), vol. 13, pp. 523-531.
Henikoff et al., "Amino Acid substitution matrices from protein blocks," *Proceedings of the National Academy of Sciences*, (1992), vol. 89, pp. 10915-10919.
Holliger et al., "Diabodies: Small bivalent and bispecific antibody fragments," *Proceedings of the National Academy of Sciences*, (1993), vol. 90, pp. 6444-6448.
Holt et al., "Domain antibodies: proteins for Therapy," *TRENDS in Biotechnology*, (2003), vol. 21, No. 11, pp. 484-490.

(56) References Cited

OTHER PUBLICATIONS

Honegger et al., "Yet Another Numbering Scheme for Immunoglobulin Variable Domains: An Automatic Modeling and Analysis Tool," *Journal of Molecular Biology*, (2001), vol. 309, pp. 657-670.
Hoogenboom et al., "By-passing Immunisation Human Antibodies from Synthetic Repertoires of Germline VH Gene Segments Rearranged in Vitro," *Journal of Molecular Biology*, (1991), vol. 227, pp. 381-388.
Hou et al., "Expression of Active Thrombopoietin and Identification of Its Key Residues Responsible for Receptor Binding," *Cytokine*, (1998) vol. 10, pp. 319-30.
Hudson et al., "High avidity scFv multimers; diabodies and triabodies," *Journal of Immunological Methods*, (1999), vol. 23, pp. 177-189.
Israel et al., "Increased clearance of IgG in mice that lack β2-microglobulin: possible protective role of FcRn." *Immunology*, (1996) vol. 89, pp. 573-578.
Jakobovits et al., "Germ-line transmission and expression of a human-derived yeast artificial chromosome," *Nature*, (1993), vol. 362, pp. 255-258.
Jakobovits et al., "Analysis of homozygous mutant chimeric mice: Deletion of the immunoglobulin heavy-chain joining region blocks B-cell development and antibody production," *Proceedings of the National Academy of Sciences*, (1993), vol. 90, pp. 2551-2555.
Janssen et al., "Structure of C3b reveals conformational changes that underlie complement activity," *Nature*, (2006), vol. 444, pp. 213-216.
Johne et al. "Epitope mapping and binding kinetics of monoclonal antibodies studied by real time biospecific interaction analysis using surface plasmon resonance,"*Journal of Immunological Methods*, (1993), vol. 160, pp. 191-198.
Jones et al., "Replacing the complementarity-determining regions in a human antibody with those from a mouse," *Nature*, (1986), vol. 321, pp. 522-525.
Karlsson et al., "Affinity Measurement Using Surface Plasmon Resonance," *Methods in Molecular Biology*, (2004), vol. 248, pp. 389-415.
Kay et al., "In Vivo Gene Therapy of Hemophilia B: Sustained Partial Correction in Factor IX-Deficient Dogs," *Science*, (1993), vol. 262, pp. 117-119.
Kinstler et al., "Mono-N-terminal poly(ethylene glycol)-protein conjugates," *Advanced Drug Deliveries Reviews*, (2002), vol. 54, pp. 477-485.
Kiselyov et al., A Highly Regioselective Reaction of N-Fluoropyridinium Salts with Stabilized Sulfur, Oxygen, Nitrogen Nucleophiles: A Convenient Route to 2-Substituted Pyridines, *Molecular Immunology*, (1993), vol. 30, p. 1361.
Klein et al., "Expression of biological effector functions by immunoglobulin G molecules lacking the hinge region," *Proceedings of the National Academy of Sciences*, (1981), vol. 79, pp. 524-528.
Lee et al., "Prolonged Circulating Lives of Single Chain Fv Proteins Conjugated with Polyethylene Glycol: A Comparison of Conjugation Chemistries and Compounds," *Bioconjugate Chemistry* (1999) vol. 10, pp. 973-978.
Lei et al.,"Structure-Function Analysis of Human Glucose-6-phosphatase, the Enzyme Deficient in Glycogen Storage Disease Type 1a," *The Journal of Bioogical. Chemistry*, (1995), vol. 270, Issue 20, pp. 11882-11886.
Lemoli et al., "Immunological effects of omalizumab in chronic urticaria: a case report" *Journal Investigational Allergology Clinical Immunology*, (2010), vol. 20, pp. 252-254.
Lusky et al., "Inhibition of SV40 replication in simian cells by specific pBR322 DNA sequences," *Nature*, (1981), vol. 293, pp. 79-81.
Marks et al., "By-passing Immunization Human Antibodies from V-gene Libraries Displayed on Phage," *Journal of Molecular Biology* (1991), vol. 222, pp. 581-597.
Mendez et al., "Functional transplant of megabase human immunoglobulin loci recapitulates human antibody response in mice," *Nature Genetics*, (1998) vol. 15, pp. 146-156.

Mihu et al., "HELLP Syndrome—a Multisystemic Disorder," *Journal of Gastrointestinal and Liver Diseases*, (2007), vol. 16, pp. 419-424.
Milstein et al., "Hybrid hybridomas and their use in immunohistochemistry," *Nature*, (1983) vol. 305, pp. 537-539.
Mueller et al. "Humanized Porcine Vcam-Specific Monoclonal Antibodies with Chimeric IgG2/G4 Constant Regions, Block Human, Leukocyte Binding to Porcine Endothelial Cells," *Molecular Immunology*, (1997) vol. 34, No. 6, pp. 441-452.
Newkirk et al., "Differential clearance of glycoforms of IgG in normal and autoimmune-prone mice", *Clin Exp Immunol*, (1996), vol. 106, No. 2, pp. 259-264.
Ostberg et al., "Human x (Mouse x Human) Hybridomas Stably Producing Human Antibodies," *Hybridoma*, (1983), vol. 2, No. 4, pp. 361-367.
Pleschberger et al., "Generation of a Functional Monomolecular Protein Lattice Consisting of an S-Layer Fusion Protein Comprising the Variable Domain of a Camel Heavy Chain Antibody", *Bioconjugate Chem*, (2003), vol. 14, pp. 440-448.
Raghava et al., "Periocular routes for retinal drug delivery", *Expert Opin. Drug Deliv.*, (2004), vol. 1, No. 1, pp. 99-114.
Riechmann et al., " Reshaping human antibodies for therapy", *Nature*, (1988) vol. 332, pp. 323-327.
Sarver et al., "Transformation and replication in mouse cells of a bovine papillomavirus-pML2 plasmid vector that can be rescued in bacteria", *Proc Natl Acad Sci USA*, (1982) vol. 79, pp. 7147-7151.
Shalaby et al., "Development of Humanized Bispecific Antibodies Reactive with Cytotoxic Lympocytes and Tumor Cells Overexpressing the HER2 Protooncogene", *J Exp Med* (1992) vol. 175, pp. 217-225.
Shields et al., "High Resolution Mapping of the Binding Site on Human IgG1 for FcγRI, FcγRII, FcγRIII, and FcRn and Design of IgG1 Variants with Improved Binding to the FcγR", *J Biol Chem*, (2001), vol. 276 No. 9, pp. 6591-6604.
Shields et al., "Lack of Fucose on Human IgG1 N-Linked Oligosaccharide Improves Binding to Human FcγRIII and Antibody-dependent Cellular Toxicity", *J Biol Chem* (2002) vol. 277, No. 30 pp. 26733-26740.
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity", *J Biol Chem* (2003) vol. 278 No. 5, pp. 3466-3473.
Shopes, "A genetically engineered human IgG mutant with enhanced cytolytic activity", *J Immunol*, (1992), vol. 148, pp. 2918-2922.
Southern et al., "Transformation of Mammalian Cells to Antibiotic Resistance with a Bacterial Gene Under Control of the SV40 Early Region Promoter", *Mol Appl Genet*, (1982), vol. 1, No. 4, pp. 327-341.
Staelens et al., "Humanization by variable domain resurfacing and grafting on a human IgG4, using a new approach for determination of non-human like surface accessible framework residues based on homology modelling of variable domains," *Molecular Immunology*, (2006), vol. 43, pp. 1243-1257.
Stijlemans et al. "Efficent Targeting of Conserved Cryptic Epitopes of Infectious Agents by Single Domain Antibodies", *J Bioi Chem*, (2004), vol. 279, pp. 1256-1261.
Suresh et al. "Bispecific Monoclonal Antibodies from Hybrid Hybrid Hybridomas", *Methods in Enzymology* (1986) vol. 121, p. 210-228.
Thomas et al., "Inhibition of Complement Activity by Humanized Anti-C5 Antibody and Single-Chain Fv.," *Molecular Immunology* (1996) vol. 33, No. 17, pp. 1389-1401.
Tutt et al., "Trispecific F(ab')3 derivatives that use cooperative signaling via the TCR/CD3 complex and CD2 to activate and redirect resting cytotoxic T cells", *J Immunol*, (1991) vol. 147, pp. 60-69.
Umana et al., "Engineered glycoforms of an antineuroblastoma IgG1 with optimized antibodydependent cellular cytotoxic activity", *Nat Biotechnol*, (1999), vol. 17, No. 2, pp. 176-180.

(56) References Cited

OTHER PUBLICATIONS van den Elsen et al., "A Crystal Crystal Structure of the Complex Between Human Complement Receptor 2 and Its Ligand C3d", *Science*, (2011), vol. 332, pp. 608- 611.

Vaughan et al., "Human Antibodies with Sub-nanomolar Affinities Isolated from a Large Non-immunized Phage Display Library," *Nature Biotechnology*, (1996), vol. 14, pp. 309-314.

Verhoeyen et al., "Reshaping Human Antibodies: Grafting an Antilysozyme Activity", *Science*, (1988) vol. 239, pp. 1534-1536.

Wigler et al., "A Murine Leukemia Virus Mutant with a Temperature-Sensitive Defect in Membrance Glycoprotein Synthesis", *Cell*, (1979), vol. 16, pp. 77-88.

Wolff et al., "Direct Gene Transfer into Mouse Muscle in Vivo", *Science*, (1990) vol. 247, pp. 1465-1468.

Wright et al., "Effect of Altered $C_H2$-associated Carbohydrate Structure on the Functional Properties and In Vivo Fate of Chimeric Mouse-Human Immunoglobulin G1", *J Exp Med*, (1994) vol. 180, pp. 1087-1096.

Wright et al., "Effect of glycosylation on antibody function: implications for genetic engineering", *TIBTECH*, (1997), vol. 15, pp. 26-32.

Wu et al., "Simultaneous targeting of multiple disease mediators by a dual-variable-domain immunoglobulin", *Nat Biotechnol*, (2007), vol. 25, No. 11, pp. 1290-1297.

Xu et al., "In Vitro Characterization of Five Humanized OKT3 Effector Function Variant Antibodies", *Cell Immunol*, (2000), vol. 200, pp. 16-26.

\* cited by examiner

Figure 1
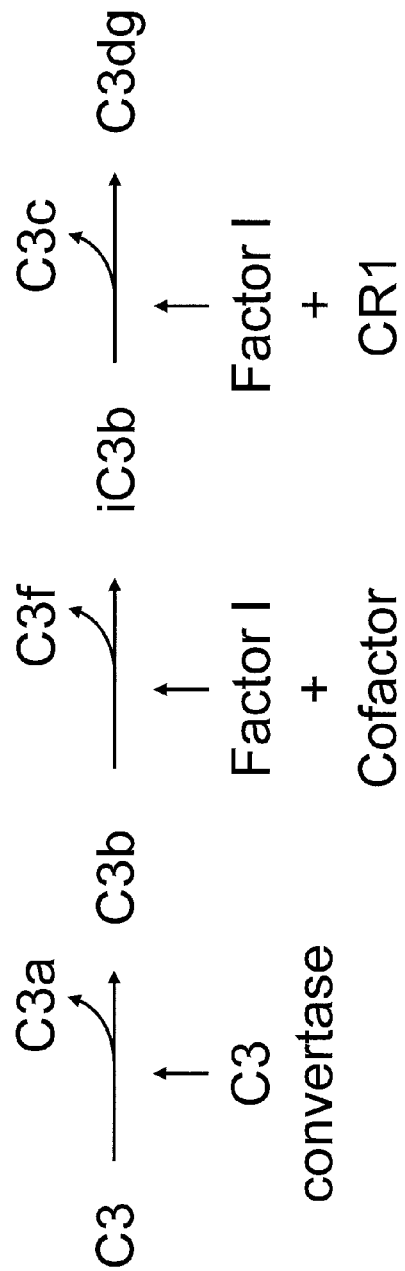
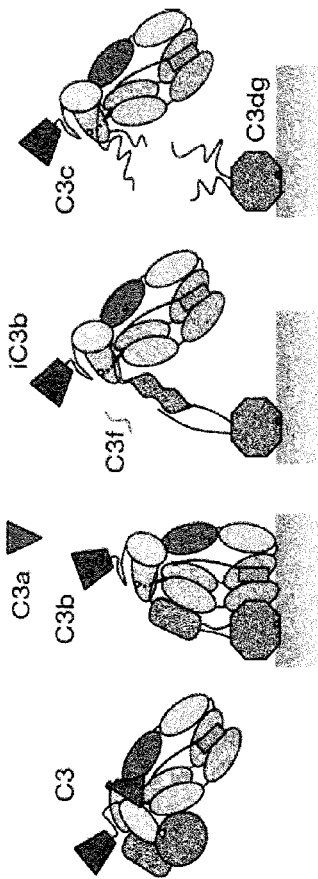

Figure 3. A Subset of mAbs (Group 1) Preferentially Bind C3d by Western Blot Analysis Binding to Native C3 Fragments - Opsonized Zymosan Particles Only By Group 1 Antibodies Biacore Analyses and Kd of Group 1 Monoclonal Antibodies

Figure 8

Summary of Key Characteristics of Test Monoclonal Antibodies

| | Designation | Isotype | hC3d binding by ELISA | Inhibition of hC3d-hCR2 binding | Zymosan activated serum binding | Mouse C3d binding | Cyno C3d binding |
|---|---|---|---|---|---|---|---|
| 1 | 3d3 | IgG1 | + | | | + | |
| 2 | 3d10 | IgG1 | + | | | + | |
| 3 | 3d11 | IgG1 | + | + | | + | + |
| 4 | 3d16 | IgG1 | + | +/- | | + | +/- |
| 5 | 3d9a | IgG2a/c | + | + | + | + | + |
| 6 | 3d15 | IgG2a/c | + | | | + | |
| 7 | 3d29 | IgG2a/c | + | + | + | + | + |
| 8 | 3d31 | IgG2a/c | + | + | | + | + |
| 9 | 3d8b | IgG2b | + | + | + | + | + |

Figure 9
Only Group 1 Monoclonal Antibodies Target Tissue-Bound C3 Fragments Following In Vivo Injection
A. Glomerular Anti-C3 Fragment Staining
Glomerular C3: iC3b, C3d
B. Glomerular Mouse IgG Staining
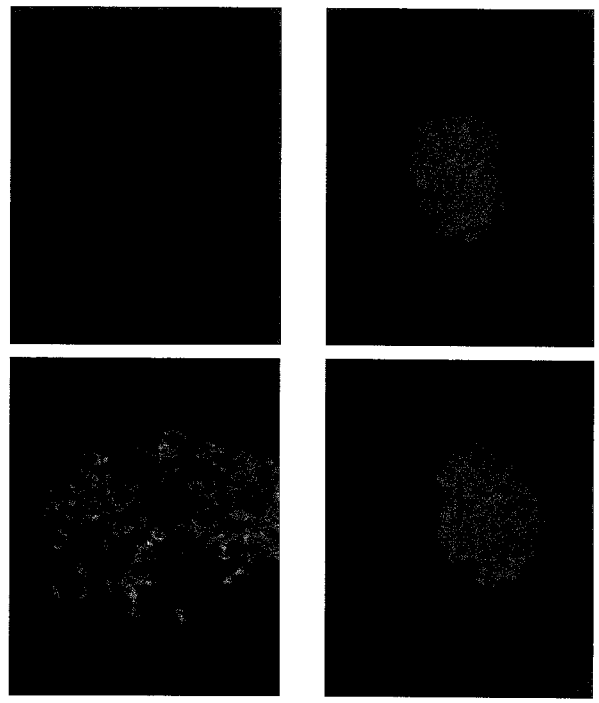

Protocol for Analysis of Effects of Anti-C3d Monoclonal Antibodies on Model Antigen Immune Response Figure 12 Inhibitory Effect of Group 1 Anti-C3d Monoclonal Antibodies on Model Sheep Red Blood Cell Antigen-Specific Immune Response
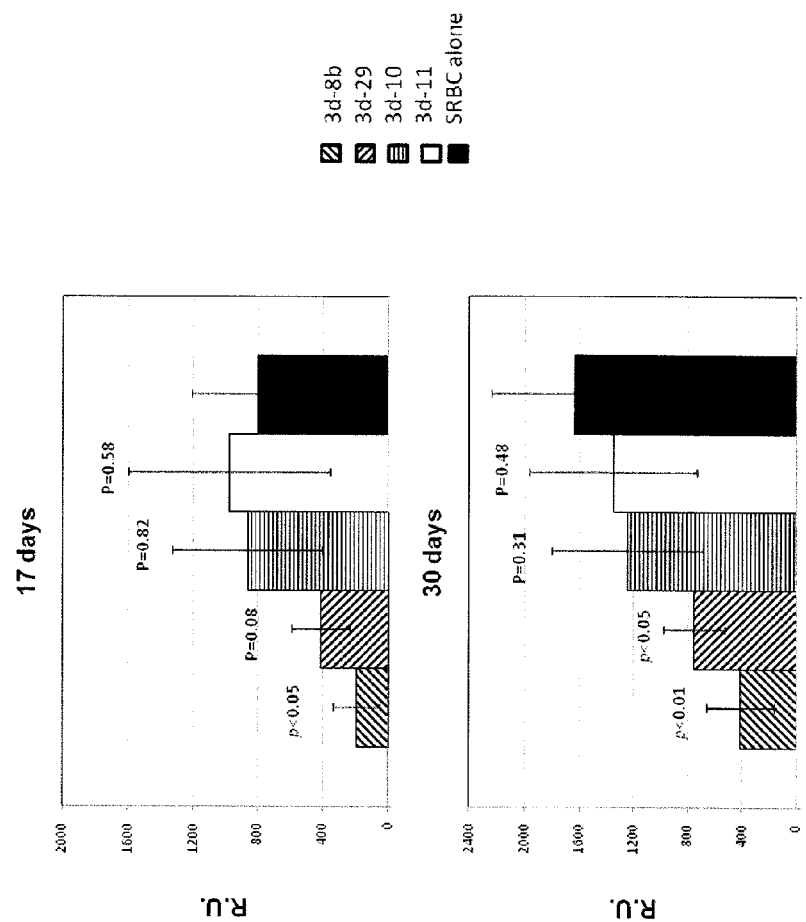

SEQUENCE LISTING

<160> NUMBER OF SEQ ID NOS: 35

<210> SEQ ID NO 1
<211> LENGTH: 392
<212> TYPE: PRT
<213> ORGANISM: Homo sapiens

<400> SEQUENCE: 1

Met Glu Pro Pro Gly Arg Arg Glu Cys Pro Phe Pro Ser Trp Arg Phe
1               5                   10                  15

Pro Gly Leu Leu Leu Ala Ala Met Val Leu Leu Leu Tyr Ser Phe Ser
            20                  25                  30

Asp Ala Cys Glu Glu Pro Pro Thr Phe Glu Ala Met Glu Leu Ile Gly
        35                  40                  45

Lys Pro Lys Pro Tyr Tyr Glu Ile Gly Glu Arg Val Asp Tyr Lys Cys
    50                  55                  60

Lys Lys Gly Tyr Phe Tyr Ile Pro Pro Leu Ala Thr His Thr Ile Cys
65                  70                  75                  80

Asp Arg Asn His Thr Trp Leu Pro Val Ser Asp Asp Ala Cys Tyr Arg
                85                  90                  95

Glu Thr Cys Pro Tyr Ile Arg Asp Pro Leu Asn Gly Gln Ala Val Pro
            100                 105                 110

Ala Asn Gly Thr Tyr Glu Phe Gly Tyr Gln Met His Phe Ile Cys Asn
        115                 120                 125

Glu Gly Tyr Tyr Leu Ile Gly Glu Glu Ile Leu Tyr Cys Glu Leu Lys
    130                 135                 140

Gly Ser Val Ala Ile Trp Ser Gly Lys Pro Pro Ile Cys Glu Lys Val
145                 150                 155                 160

Leu Cys Thr Pro Pro Lys Ile Lys Asn Gly Lys His Thr Phe Ser
            165                 170                 175

Glu Val Glu Val Phe Glu Tyr Leu Asp Ala Val Thr Tyr Ser Cys Asp
            180                 185                 190

Pro Ala Pro Gly Pro Asp Pro Phe Ser Leu Ile Gly Glu Ser Thr Ile
            195                 200                 205

Tyr Cys Gly Asp Asn Ser Val Trp Ser Arg Ala Ala Pro Glu Cys Lys
    210                 215                 220

Val Val Lys Cys Arg Phe Pro Val Val Glu Asn Gly Lys Gln Ile Ser
225                 230                 235                 240

Gly Phe Gly Lys Lys Phe Tyr Tyr Lys Ala Thr Val Met Phe Glu Cys
                245                 250                 255

Asp Lys Gly Phe Tyr Leu Asp Gly Ser Asp Thr Ile Val Cys Asp Ser
            260                 265                 270

Asn Ser Thr Trp Asp Pro Pro Val Pro Lys Cys Leu Lys Val Leu Pro
        275                 280                 285

Pro Ser Ser Thr Lys Pro Pro Ala Leu Ser His Ser Val Ser Thr Ser
    290                 295                 300

Ser Thr Thr Lys Ser Pro Ala Ser Ser Ala Ser Gly Pro Arg Pro Thr

```
                305                 310                 315                 320

Tyr Lys Pro Pro Val Ser Asn Tyr Pro Gly Tyr Pro Lys Pro Glu Glu
                    325                 330                 335

Gly Ile Leu Asp Ser Leu Asp Val Trp Val Ile Ala Val Ile Val Ile
                340                 345                 350

Ala Ile Val Val Gly Val Ala Val Ile Cys Val Val Pro Tyr Arg Tyr
                355                 360                 365

Leu Gln Arg Arg Lys Lys Gly Thr Tyr Leu Thr Asp Glu Thr His
        370                 375                 380

Arg Glu Val Lys Phe Thr Ser Leu
385                 390

<210> SEQ ID NO 2
<211> LENGTH: 381
<212> TYPE: PRT
<213> ORGANISM: Homo sapiens

<400> SEQUENCE: 2

Met Thr Val Ala Arg Pro Ser Val Pro Ala Leu Pro Leu Leu Gly
1               5                   10                  15

Glu Leu Pro Arg Leu Leu Leu Val Leu Leu Cys Leu Pro Ala Val
                20                  25                  30

Trp Gly Asp Cys Gly Leu Pro Pro Asp Val Pro Asn Ala Gln Pro Ala
                35                  40                  45

Leu Glu Gly Arg Thr Ser Phe Pro Glu Asp Thr Val Ile Thr Tyr Lys
        50                  55                  60

Cys Glu Glu Ser Phe Val Lys Ile Pro Gly Glu Lys Asp Ser Val Ile
65                  70                  75                  80

Cys Leu Lys Gly Ser Gln Trp Ser Asp Ile Glu Glu Phe Cys Asn Arg
                85                  90                  95

Ser Cys Glu Val Pro Thr Arg Leu Asn Ser Ala Ser Leu Lys Gln Pro
            100                 105                 110

Tyr Ile Thr Gln Asn Tyr Phe Pro Val Gly Thr Val Val Glu Tyr Glu
        115                 120                 125

Cys Arg Pro Gly Tyr Arg Arg Glu Pro Ser Leu Ser Pro Lys Leu Thr
    130                 135                 140

Cys Leu Gln Asn Leu Lys Trp Ser Thr Ala Val Glu Phe Cys Lys Lys
145                 150                 155                 160

Lys Ser Cys Pro Asn Pro Gly Glu Ile Arg Asn Gly Gln Ile Asp Val
                165                 170                 175

Pro Gly Gly Ile Leu Phe Gly Ala Thr Ile Ser Phe Ser Cys Asn Thr
            180                 185                 190

Gly Tyr Lys Leu Phe Gly Ser Thr Ser Ser Phe Cys Leu Ile Ser Gly
        195                 200                 205

Ser Ser Val Gln Trp Ser Asp Pro Leu Pro Glu Cys Arg Glu Ile Tyr
    210                 215                 220

Cys Pro Ala Pro Pro Gln Ile Asp Asn Gly Ile Ile Gln Gly Glu Arg
225                 230                 235                 240

Asp His Tyr Gly Tyr Arg Gln Ser Val Thr Tyr Ala Cys Asn Lys Gly
                245                 250                 255

Phe Thr Met Ile Gly Glu His Ser Ile Tyr Cys Thr Val Asn Asn Asp
            260                 265                 270

Glu Gly Glu Trp Ser Gly Pro Pro Pro Glu Cys Arg Gly Lys Ser Leu
        275                 280                 285
```

```
Thr Ser Lys Val Pro Pro Thr Val Gln Lys Pro Thr Val Asn Val
    290             295                 300

Pro Thr Thr Glu Val Ser Pro Thr Ser Gln Lys Thr Thr Lys Thr
305                 310                 315                 320

Thr Thr Pro Asn Ala Gln Ala Thr Arg Ser Thr Pro Val Ser Arg Thr
            325                 330                 335

Thr Lys His Phe His Glu Thr Thr Pro Asn Lys Gly Ser Gly Thr Thr
            340                 345                 350

Ser Gly Thr Thr Arg Leu Leu Ser Gly His Thr Cys Phe Thr Leu Thr
            355                 360                 365

Gly Leu Leu Gly Thr Leu Val Thr Met Gly Leu Leu Thr
370                 375                 380

<210> SEQ ID NO 3
<211> LENGTH: 390
<212> TYPE: PRT
<213> ORGANISM: Mus musculus

<400> SEQUENCE: 3

Met Ile Arg Gly Arg Ala Pro Arg Thr Arg Pro Ser Pro Pro Pro Pro
1               5                   10                  15

Leu Leu Pro Leu Leu Ser Leu Ser Leu Leu Leu Ser Pro Thr Val
                20                  25                  30

Arg Gly Asp Cys Gly Pro Pro Asp Ile Pro Asn Ala Arg Pro Ile
                35                  40                  45

Leu Gly Arg His Ser Lys Phe Ala Glu Gln Ser Lys Val Ala Tyr Ser
        50                  55                  60

Cys Asn Asn Gly Phe Lys Gln Val Pro Asp Lys Ser Asn Ile Val Val
65                  70                  75                  80

Cys Leu Glu Asn Gly Gln Trp Ser Ser His Glu Thr Phe Cys Glu Lys
                85                  90                  95

Ser Cys Val Ala Pro Glu Arg Leu Ser Phe Ala Ser Leu Lys Lys Glu
                100                 105                 110

Tyr Leu Asn Met Asn Phe Phe Pro Val Gly Thr Ile Val Glu Tyr Glu
                115                 120                 125

Cys Arg Pro Gly Phe Arg Lys Gln Pro Pro Leu Pro Gly Lys Ala Thr
130                 135                 140

Cys Leu Glu Asp Leu Val Trp Ser Pro Val Ala Gln Phe Cys Lys Lys
145                 150                 155                 160

Lys Ser Cys Pro Asn Pro Lys Asp Leu Asp Asn Gly His Ile Asn Ile
                165                 170                 175

Pro Thr Gly Ile Leu Phe Gly Ser Glu Ile Asn Phe Ser Cys Asn Pro
                180                 185                 190

Gly Tyr Arg Leu Val Gly Val Ser Ser Thr Phe Cys Ser Val Thr Gly
        195                 200                 205

Asn Thr Val Asp Trp Asp Asp Glu Phe Pro Val Cys Thr Glu Ile His
        210                 215                 220

Cys Pro Glu Pro Pro Lys Ile Asn Asn Gly Ile Met Arg Gly Glu Ser
225                 230                 235                 240

Asp Ser Tyr Thr Tyr Ser Gln Val Val Thr Tyr Ser Cys Asp Lys Gly
                245                 250                 255

Phe Ile Leu Val Gly Asn Ala Ser Ile Tyr Cys Thr Val Ser Lys Ser
                260                 265                 270

Asp Val Gly Gln Trp Ser Ser Pro Pro Pro Arg Cys Ile Glu Lys Ser
                275                 280                 285
```

```
Lys Val Pro Thr Lys Pro Thr Ile Asn Val Pro Ser Thr Gly Thr
        290                 295                 300

Pro Ser Thr Pro Gln Lys Pro Thr Glu Ser Val Pro Asn Pro Gly
305                 310                 315                 320

Asp Gln Pro Thr Pro Gln Lys Pro Ser Thr Val Lys Val Ser Ala Thr
                    325                 330                 335

Gln His Val Pro Val Thr Lys Thr Thr Val Arg His Pro Ile Arg Thr
                340                 345                 350

Ser Thr Asp Lys Gly Glu Pro Asn Thr Gly Gly Asp Arg Tyr Ile Tyr
        355                 360                 365

Gly His Thr Cys Leu Ile Thr Leu Thr Val Leu His Val Met Leu Ser
        370                 375                 380

Leu Ile Gly Tyr Leu Thr
385                 390

<210> SEQ ID NO 4
<211> LENGTH: 128
<212> TYPE: PRT
<213> ORGANISM: Homo sapiens

<400> SEQUENCE: 4

Met Gly Ile Gln Gly Gly Ser Val Leu Phe Gly Leu Leu Leu Val Leu
1               5                   10                  15

Ala Val Phe Cys His Ser Gly His Ser Leu Gln Cys Tyr Asn Cys Pro
                20                  25                  30

Asn Pro Thr Ala Asp Cys Lys Thr Ala Val Asn Cys Ser Ser Asp Phe
            35                  40                  45

Asp Ala Cys Leu Ile Thr Lys Ala Gly Leu Gln Val Tyr Asn Lys Cys
        50                  55                  60

Trp Lys Phe Glu His Cys Asn Phe Asn Asp Val Thr Thr Arg Leu Arg
65                  70                  75                  80

Glu Asn Glu Leu Thr Tyr Tyr Cys Cys Lys Lys Asp Leu Cys Asn Phe
                85                  90                  95

Asn Glu Gln Leu Glu Asn Gly Gly Thr Ser Leu Ser Glu Lys Thr Val
            100                 105                 110

Leu Leu Leu Val Thr Pro Phe Leu Ala Ala Ala Trp Ser Leu His Pro
        115                 120                 125

<210> SEQ ID NO 5
<211> LENGTH: 123
<212> TYPE: PRT
<213> ORGANISM: Mus musculus

<400> SEQUENCE: 5

Met Arg Ala Gln Arg Gly Leu Ile Leu Leu Leu Leu Leu Ala Val
1               5                   10                  15

Phe Cys Ser Thr Ala Val Ser Leu Thr Cys Tyr His Cys Phe Gln Pro
                20                  25                  30

Val Val Ser Ser Cys Asn Met Asn Ser Thr Cys Ser Pro Asp Gln Asp
            35                  40                  45

Ser Cys Leu Tyr Ala Val Ala Gly Met Gln Val Tyr Gln Arg Cys Trp
        50                  55                  60

Lys Gln Ser Asp Cys His Gly Glu Ile Ile Met Asp Gln Leu Glu Glu
65                  70                  75                  80

Thr Lys Leu Lys Phe Arg Cys Cys Gln Phe Asn Leu Cys Asn Lys Ser
                85                  90                  95
```

Asp Gly Ser Leu Gly Lys Thr Pro Leu Leu Gly Thr Ser Val Leu Val
            100                 105                 110

Ala Ile Leu Asn Leu Cys Phe Leu Ser His Leu
            115                 120

<210> SEQ ID NO 6
<211> LENGTH: 129
<212> TYPE: PRT
<213> ORGANISM: Mus musculus

<400> SEQUENCE: 6

Met Arg Ala Gln Arg Gly Leu Ile Leu Leu Leu Leu Leu Ala Val
1               5                   10                  15

Phe Cys Ser Thr Ala Val Ser Leu Lys Cys Tyr Asn Cys Phe Gln Phe
            20                  25                  30

Val Ser Ser Cys Lys Ile Asn Thr Thr Cys Ser Pro Asn Leu Asp Ser
            35                  40                  45

Cys Leu Tyr Ala Val Ala Gly Arg Gln Val Tyr Gln Gln Cys Trp Lys
        50                  55                  60

Leu Ser Asp Cys Asn Ser Asn Tyr Ile Met Ser Arg Leu Asp Val Ala
65                  70                  75                  80

Gly Ile Gln Ser Lys Cys Cys Gln Trp Gly Leu Cys Asn Lys Asn Leu
                85                  90                  95

Asp Gly Leu Glu Glu Pro Asn Asn Ala Glu Thr Ser Ser Leu Arg Lys
            100                 105                 110

Thr Ala Leu Leu Gly Thr Ser Val Leu Val Ala Ile Leu Lys Phe Cys
            115                 120                 125

Phe

<210> SEQ ID NO 7
<211> LENGTH: 483
<212> TYPE: PRT
<213> ORGANISM: Mus musculus

<400> SEQUENCE: 7

Met Glu Val Ser Ser Arg Ser Ser Glu Pro Leu Asp Pro Val Trp Leu
1               5                   10                  15

Leu Val Ala Phe Gly Arg Gly Gly Val Lys Leu Glu Val Leu Leu Leu
            20                  25                  30

Phe Leu Leu Pro Phe Thr Leu Gly Glu Leu Arg Gly Gly Leu Gly Lys
            35                  40                  45

His Gly His Thr Val His Arg Glu Pro Ala Val Asn Arg Leu Cys Ala
        50                  55                  60

Asp Ser Lys Arg Trp Ser Gly Leu Pro Val Ser Ala Gln Arg Pro Phe
65                  70                  75                  80

Pro Met Gly His Cys Pro Ala Pro Ser Gln Leu Pro Ser Ala Lys Pro
                85                  90                  95

Ile Asn Leu Thr Asp Glu Ser Met Phe Pro Ile Gly Thr Tyr Leu Leu
            100                 105                 110

Tyr Glu Cys Leu Pro Gly Tyr Ile Lys Arg Gln Phe Ser Ile Thr Cys
            115                 120                 125

Lys Gln Asp Ser Thr Trp Thr Ser Ala Glu Asp Lys Cys Ile Arg Lys
            130                 135                 140

Gln Cys Lys Thr Pro Ser Asp Pro Glu Asn Gly Leu Val His Val His
145                 150                 155                 160

```
Thr Gly Ile Gln Phe Gly Ser Arg Ile Asn Tyr Thr Cys Asn Gln Gly
            165                 170                 175

Tyr Arg Leu Ile Gly Ser Ser Ala Val Cys Val Ile Thr Asp Gln
        180                 185                 190

Ser Val Asp Trp Asp Thr Glu Ala Pro Ile Cys Glu Trp Ile Pro Cys
        195                 200                 205

Glu Ile Pro Pro Gly Ile Pro Asn Gly Asp Phe Phe Ser Ser Thr Arg
210                 215                 220

Glu Asp Phe His Tyr Gly Met Val Val Thr Tyr Arg Cys Asn Thr Asp
225                 230                 235                 240

Ala Arg Gly Lys Ala Leu Phe Asn Leu Val Gly Glu Pro Ser Leu Tyr
                245                 250                 255

Cys Thr Ser Asn Asp Gly Glu Ile Gly Val Trp Ser Gly Pro Pro Pro
                260                 265                 270

Gln Cys Ile Glu Leu Asn Lys Cys Thr Pro Pro Tyr Val Glu Asn
            275                 280                 285

Ala Val Met Leu Ser Glu Asn Arg Ser Leu Phe Ser Leu Arg Asp Ile
        290                 295                 300

Val Glu Phe Arg Cys His Pro Gly Phe Ile Met Lys Gly Ala Ser Ser
305                 310                 315                 320

Val His Cys Gln Ser Leu Asn Lys Trp Glu Pro Glu Leu Pro Ser Cys
                325                 330                 335

Phe Lys Gly Val Ile Cys Arg Leu Pro Gln Glu Met Ser Gly Phe Gln
            340                 345                 350

Lys Gly Leu Gly Met Lys Lys Glu Tyr Tyr Tyr Gly Glu Asn Val Thr
        355                 360                 365

Leu Glu Cys Glu Asp Gly Tyr Thr Leu Glu Gly Ser Ser Gln Ser Gln
370                 375                 380

Cys Gln Ser Asp Gly Ser Trp Asn Pro Leu Leu Ala Lys Cys Val Ser
385                 390                 395                 400

Arg Ser Ile Ser Gly Leu Ile Val Gly Ile Phe Ile Gly Ile Ile Val
                405                 410                 415

Phe Ile Leu Val Ile Ile Val Phe Ile Trp Met Ile Leu Lys Tyr Lys
            420                 425                 430

Lys Arg Asn Thr Thr Asp Glu Lys Tyr Lys Glu Val Gly Ile His Leu
        435                 440                 445

Asn Tyr Lys Glu Asp Ser Cys Val Arg Leu Gln Ser Leu Leu Thr Ser
        450                 455                 460

Gln Glu Asn Ser Ser Thr Thr Ser Pro Ala Arg Asn Ser Leu Thr Gln
465                 470                 475                 480

Glu Val Ser

<210> SEQ ID NO 8
<211> LENGTH: 2039
<212> TYPE: PRT
<213> ORGANISM: Homo sapiens

<400> SEQUENCE: 8

Met Gly Ala Ser Ser Pro Arg Ser Pro Glu Pro Val Gly Pro Pro Ala
1               5                   10                  15

Pro Gly Leu Pro Phe Cys Cys Gly Gly Ser Leu Leu Ala Val Val Val
            20                  25                  30

Leu Leu Ala Leu Pro Val Ala Trp Gly Gln Cys Asn Ala Pro Glu Trp
        35                  40                  45
```

-continued

```
Leu Pro Phe Ala Arg Pro Thr Asn Leu Thr Asp Glu Phe Glu Phe Pro
 50                  55                  60

Ile Gly Thr Tyr Leu Asn Tyr Glu Cys Arg Pro Gly Tyr Ser Gly Arg
 65                      70                  75                  80

Pro Phe Ser Ile Ile Cys Leu Lys Asn Ser Val Trp Thr Gly Ala Lys
                     85                  90                  95

Asp Arg Cys Arg Arg Lys Ser Cys Arg Asn Pro Pro Asp Pro Val Asn
                100                 105                 110

Gly Met Val His Val Ile Lys Gly Ile Gln Phe Gly Ser Gln Ile Lys
                115                 120                 125

Tyr Ser Cys Thr Lys Gly Tyr Arg Leu Ile Gly Ser Ser Ser Ala Thr
                130                 135                 140

Cys Ile Ile Ser Gly Asp Thr Val Ile Trp Asp Asn Glu Thr Pro Ile
145                 150                 155                 160

Cys Asp Arg Ile Pro Cys Gly Leu Pro Pro Thr Ile Thr Asn Gly Asp
                165                 170                 175

Phe Ile Ser Thr Asn Arg Glu Asn Phe His Tyr Gly Ser Val Val Thr
                180                 185                 190

Tyr Arg Cys Asn Pro Gly Ser Gly Arg Lys Val Phe Glu Leu Val
                195                 200                 205

Gly Glu Pro Ser Ile Tyr Cys Thr Ser Asn Asp Asp Gln Val Gly Ile
210                 215                 220

Trp Ser Gly Pro Ala Pro Gln Cys Ile Ile Pro Asn Lys Cys Thr Pro
225                 230                 235                 240

Pro Asn Val Glu Asn Gly Ile Leu Val Ser Asp Asn Arg Ser Leu Phe
                245                 250                 255

Ser Leu Asn Glu Val Val Glu Phe Arg Cys Gln Pro Gly Phe Val Met
                260                 265                 270

Lys Gly Pro Arg Arg Val Lys Cys Gln Ala Leu Asn Lys Trp Glu Pro
                275                 280                 285

Glu Leu Pro Ser Cys Ser Arg Val Cys Gln Pro Pro Asp Val Leu
                290                 295                 300

His Ala Glu Arg Thr Gln Arg Asp Lys Asp Asn Phe Ser Pro Gly Gln
305                 310                 315                 320

Glu Val Phe Tyr Ser Cys Glu Pro Gly Tyr Asp Leu Arg Gly Ala Ala
                325                 330                 335

Ser Met Arg Cys Thr Pro Gln Gly Asp Trp Ser Pro Ala Ala Pro Thr
                340                 345                 350

Cys Glu Val Lys Ser Cys Asp Asp Phe Met Gly Gln Leu Leu Asn Gly
                355                 360                 365

Arg Val Leu Phe Pro Val Asn Leu Gln Leu Gly Ala Lys Val Asp Phe
370                 375                 380

Val Cys Asp Glu Gly Phe Gln Leu Lys Gly Ser Ser Ala Ser Tyr Cys
385                 390                 395                 400

Val Leu Ala Gly Met Glu Ser Leu Trp Asn Ser Ser Val Pro Val Cys
                405                 410                 415

Glu Gln Ile Phe Cys Pro Ser Pro Val Ile Pro Asn Gly Arg His
                420                 425                 430

Thr Gly Lys Pro Leu Glu Val Phe Pro Phe Gly Lys Ala Val Asn Tyr
                435                 440                 445

Thr Cys Asp Pro His Pro Asp Arg Gly Thr Ser Phe Asp Leu Ile Gly
                450                 455                 460

Glu Ser Thr Ile Arg Cys Thr Ser Asp Pro Gln Gly Asn Gly Val Trp
```

```
              465                 470                 475                 480
         Ser Ser Pro Ala Pro Arg Cys Gly Ile Leu Gly His Cys Gln Ala Pro
                         485                 490                 495

Asp His Phe Leu Phe Ala Lys Leu Lys Thr Gln Thr Asn Ala Ser Asp
                         500                 505                 510

Phe Pro Ile Gly Thr Ser Leu Lys Tyr Glu Cys Arg Pro Glu Tyr Tyr
                         515                 520                 525

Gly Arg Pro Phe Ser Ile Thr Cys Leu Asp Asn Leu Val Trp Ser Ser
                         530                 535                 540

Pro Lys Asp Val Cys Lys Arg Lys Ser Cys Lys Thr Pro Pro Asp Pro
         545                 550                 555                 560

Val Asn Gly Met Val His Val Ile Thr Asp Ile Gln Val Gly Ser Arg
                         565                 570                 575

Ile Asn Tyr Ser Cys Thr Thr Gly His Arg Leu Ile Gly His Ser Ser
                         580                 585                 590

Ala Glu Cys Ile Leu Ser Gly Asn Ala Ala His Trp Ser Thr Lys Pro
                         595                 600                 605

Pro Ile Cys Gln Arg Ile Pro Cys Gly Leu Pro Pro Thr Ile Ala Asn
                         610                 615                 620

Gly Asp Phe Ile Ser Thr Asn Arg Glu Asn Phe His Tyr Gly Ser Val
         625                 630                 635                 640

Val Thr Tyr Arg Cys Asn Pro Gly Ser Gly Gly Arg Lys Val Phe Glu
                         645                 650                 655

Leu Val Gly Glu Pro Ser Ile Tyr Cys Thr Ser Asn Asp Asp Gln Val
                         660                 665                 670

Gly Ile Trp Ser Gly Pro Ala Pro Gln Cys Ile Ile Pro Asn Lys Cys
                         675                 680                 685

Thr Pro Pro Asn Val Glu Asn Gly Ile Leu Val Ser Asp Asn Arg Ser
                         690                 695                 700

Leu Phe Ser Leu Asn Glu Val Val Glu Phe Arg Cys Gln Pro Gly Phe
         705                 710                 715                 720

Val Met Lys Gly Pro Arg Arg Val Lys Cys Gln Ala Leu Asn Lys Trp
                         725                 730                 735

Glu Pro Glu Leu Pro Ser Cys Ser Arg Val Cys Gln Pro Pro Pro Asp
                         740                 745                 750

Val Leu His Ala Glu Arg Thr Gln Arg Asp Lys Asp Asn Phe Ser Pro
                         755                 760                 765

Gly Gln Glu Val Phe Tyr Ser Cys Glu Pro Gly Tyr Asp Leu Arg Gly
                         770                 775                 780

Ala Ala Ser Met Arg Cys Thr Pro Gln Gly Asp Trp Ser Pro Ala Ala
         785                 790                 795                 800

Pro Thr Cys Glu Val Lys Ser Cys Asp Asp Phe Met Gly Gln Leu Leu
                         805                 810                 815

Asn Gly Arg Val Leu Phe Pro Val Asn Leu Gln Leu Gly Ala Lys Val
                         820                 825                 830

Asp Phe Val Cys Asp Glu Gly Phe Gln Leu Lys Gly Ser Ser Ala Ser
                         835                 840                 845

Tyr Cys Val Leu Ala Gly Met Glu Ser Leu Trp Asn Ser Ser Val Pro
                         850                 855                 860

Val Cys Glu Gln Ile Phe Cys Pro Ser Pro Val Ile Pro Asn Gly Arg
         865                 870                 875                 880

Arg His Thr Gly Lys Pro Leu Glu Val Phe Pro Phe Gly Lys Ala Val
                         885                 890                 895
```

-continued

```
Asn Tyr Thr Cys Asp Pro His Pro Asp Arg Gly Thr Ser Phe Asp Leu
                900                 905                 910
Ile Gly Glu Ser Thr Ile Arg Cys Thr Ser Asp Pro Gln Gly Asn Gly
        915                 920                 925
Val Trp Ser Ser Pro Ala Pro Arg Cys Gly Ile Leu Gly His Cys Gln
    930                 935                 940
Ala Pro Asp His Phe Leu Phe Ala Lys Leu Lys Thr Gln Thr Asn Ala
945                 950                 955                 960
Ser Asp Phe Pro Ile Gly Thr Ser Leu Lys Tyr Glu Cys Arg Pro Glu
                965                 970                 975
Tyr Tyr Gly Arg Pro Phe Ser Ile Thr Cys Leu Asp Asn Leu Val Trp
        980                 985                 990
Ser Ser Pro Lys Asp Val Cys Lys Arg Lys Ser Cys Lys Thr Pro Pro
    995                 1000                1005
Asp Pro Val Asn Gly Met Val His Val Ile Thr Asp Ile Gln Val
    1010                1015                1020
Gly Ser Arg Ile Asn Tyr Ser Cys Thr Thr Gly His Arg Leu Ile
    1025                1030                1035
Gly His Ser Ser Ala Glu Cys Ile Leu Ser Gly Asn Thr Ala His
    1040                1045                1050
Trp Ser Thr Lys Pro Pro Ile Cys Gln Arg Ile Pro Cys Gly Leu
    1055                1060                1065
Pro Pro Thr Ile Ala Asn Gly Asp Phe Ile Ser Thr Asn Arg Glu
    1070                1075                1080
Asn Phe His Tyr Gly Ser Val Val Thr Tyr Arg Cys Asn Leu Gly
    1085                1090                1095
Ser Arg Gly Arg Lys Val Phe Glu Leu Val Gly Glu Pro Ser Ile
    1100                1105                1110
Tyr Cys Thr Ser Asn Asp Asp Gln Val Gly Ile Trp Ser Gly Pro
    1115                1120                1125
Ala Pro Gln Cys Ile Ile Pro Asn Lys Cys Thr Pro Pro Asn Val
    1130                1135                1140
Glu Asn Gly Ile Leu Val Ser Asp Asn Arg Ser Leu Phe Ser Leu
    1145                1150                1155
Asn Glu Val Val Glu Phe Arg Cys Gln Pro Gly Phe Val Met Lys
    1160                1165                1170
Gly Pro Arg Arg Val Lys Cys Gln Ala Leu Asn Lys Trp Glu Pro
    1175                1180                1185
Glu Leu Pro Ser Cys Ser Arg Val Cys Gln Pro Pro Pro Glu Ile
    1190                1195                1200
Leu His Gly Glu His Thr Pro Ser His Gln Asp Asn Phe Ser Pro
    1205                1210                1215
Gly Gln Glu Val Phe Tyr Ser Cys Glu Pro Gly Tyr Asp Leu Arg
    1220                1225                1230
Gly Ala Ala Ser Leu His Cys Thr Pro Gln Gly Asp Trp Ser Pro
    1235                1240                1245
Glu Ala Pro Arg Cys Ala Val Lys Ser Cys Asp Asp Phe Leu Gly
    1250                1255                1260
Gln Leu Pro His Gly Arg Val Leu Phe Pro Leu Asn Leu Gln Leu
    1265                1270                1275
Gly Ala Lys Val Ser Phe Val Cys Asp Glu Gly Phe Arg Leu Lys
    1280                1285                1290
```

```
Gly Ser Ser Val Ser His Cys Val Leu Val Gly Met Arg Ser Leu
1295             1300                 1305

Trp Asn Asn Ser Val Pro Val Cys Glu His Ile Phe Cys Pro Asn
1310             1315                 1320

Pro Pro Ala Ile Leu Asn Gly Arg His Thr Gly Thr Pro Ser Gly
1325             1330                 1335

Asp Ile Pro Tyr Gly Lys Glu Ile Ser Tyr Thr Cys Asp Pro His
1340             1345                 1350

Pro Asp Arg Gly Met Thr Phe Asn Leu Ile Gly Glu Ser Thr Ile
1355             1360                 1365

Arg Cys Thr Ser Asp Pro His Gly Asn Gly Val Trp Ser Ser Pro
1370             1375                 1380

Ala Pro Arg Cys Glu Leu Ser Val Arg Ala Gly His Cys Lys Thr
1385             1390                 1395

Pro Glu Gln Phe Pro Phe Ala Ser Pro Thr Ile Pro Ile Asn Asp
1400             1405                 1410

Phe Glu Phe Pro Val Gly Thr Ser Leu Asn Tyr Glu Cys Arg Pro
1415             1420                 1425

Gly Tyr Phe Gly Lys Met Phe Ser Ile Ser Cys Leu Glu Asn Leu
1430             1435                 1440

Val Trp Ser Ser Val Glu Asp Asn Cys Arg Arg Lys Ser Cys Gly
1445             1450                 1455

Pro Pro Pro Glu Pro Phe Asn Gly Met Val His Ile Asn Thr Asp
1460             1465                 1470

Thr Gln Phe Gly Ser Thr Val Asn Tyr Ser Cys Asn Glu Gly Phe
1475             1480                 1485

Arg Leu Ile Gly Ser Pro Ser Thr Thr Cys Leu Val Ser Gly Asn
1490             1495                 1500

Asn Val Thr Trp Asp Lys Lys Ala Pro Ile Cys Glu Ile Ile Ser
1505             1510                 1515

Cys Glu Pro Pro Pro Thr Ile Ser Asn Gly Asp Phe Tyr Ser Asn
1520             1525                 1530

Asn Arg Thr Ser Phe His Asn Gly Thr Val Val Thr Tyr Gln Cys
1535             1540                 1545

His Thr Gly Pro Asp Gly Glu Gln Leu Phe Glu Leu Val Gly Glu
1550             1555                 1560

Arg Ser Ile Tyr Cys Thr Ser Lys Asp Asp Gln Val Gly Val Trp
1565             1570                 1575

Ser Ser Pro Pro Pro Arg Cys Ile Ser Thr Asn Lys Cys Thr Ala
1580             1585                 1590

Pro Glu Val Glu Asn Ala Ile Arg Val Pro Gly Asn Arg Ser Phe
1595             1600                 1605

Phe Ser Leu Thr Glu Ile Ile Arg Phe Arg Cys Gln Pro Gly Phe
1610             1615                 1620

Val Met Val Gly Ser His Thr Val Gln Cys Gln Thr Asn Gly Arg
1625             1630                 1635

Trp Gly Pro Lys Leu Pro His Cys Ser Arg Val Cys Gln Pro Pro
1640             1645                 1650

Pro Glu Ile Leu His Gly Glu His Thr Leu Ser His Gln Asp Asn
1655             1660                 1665

Phe Ser Pro Gly Gln Glu Val Phe Tyr Ser Cys Glu Pro Ser Tyr
1670             1675                 1680

Asp Leu Arg Gly Ala Ala Ser Leu His Cys Thr Pro Gln Gly Asp
```

```
                   1685                1690                1695

Trp Ser  Pro Glu Ala Pro Arg Cys Thr Val Lys Ser  Cys Asp Asp
         1700                1705                1710

Phe Leu  Gly Gln Leu Pro His Gly Arg Val Leu Leu  Pro Leu Asn
    1715                1720                1725

Leu Gln  Leu Gly Ala Lys Val Ser Phe Val Cys Asp  Glu Gly Phe
    1730                1735                1740

Arg Leu  Lys Gly Arg Ser Ala Ser His Cys Val Leu  Ala Gly Met
    1745                1750                1755

Lys Ala  Leu Trp Asn Ser Ser Val Pro Val Cys Glu  Gln Ile Phe
    1760                1765                1770

Cys Pro  Asn Pro Pro Ala Ile Leu Asn Gly Arg His  Thr Gly Thr
    1775                1780                1785

Pro Phe  Gly Asp Ile Pro Tyr Gly Lys Glu Ile Ser  Tyr Ala Cys
    1790                1795                1800

Asp Thr  His Pro Asp Arg Gly Met Thr Phe Asn Leu  Ile Gly Glu
    1805                1810                1815

Ser Ser  Ile Arg Cys Thr Ser Asp Pro Gln Gly Asn  Gly Val Trp
    1820                1825                1830

Ser Ser  Pro Ala Pro Arg Cys Glu Leu Ser Val Pro  Ala Ala Cys
    1835                1840                1845

Pro His  Pro Pro Lys Ile Gln Asn Gly His Tyr Ile  Gly Gly His
    1850                1855                1860

Val Ser  Leu Tyr Leu Pro Gly Met Thr Ile Ser Tyr  Thr Cys Asp
    1865                1870                1875

Pro Gly  Tyr Leu Leu Val Gly Lys Gly Phe Ile Phe  Cys Thr Asp
    1880                1885                1890

Gln Gly  Ile Trp Ser Gln Leu Asp His Tyr Cys Lys  Glu Val Asn
    1895                1900                1905

Cys Ser  Phe Pro Leu Phe Met Asn Gly Ile Ser Lys  Glu Leu Glu
    1910                1915                1920

Met Lys  Lys Val Tyr His Tyr Gly Asp Tyr Val Thr  Leu Lys Cys
    1925                1930                1935

Glu Asp  Gly Tyr Thr Leu Glu Gly Ser Pro Trp Ser  Gln Cys Gln
    1940                1945                1950

Ala Asp  Asp Arg Trp Asp Pro Pro Leu Ala Lys Cys  Thr Ser Arg
    1955                1960                1965

Ala His  Asp Ala Leu Ile Val Gly Thr Leu Ser Gly  Thr Ile Phe
    1970                1975                1980

Phe Ile  Leu Leu Ile Ile Phe Leu Ser Trp Ile Ile  Leu Lys His
    1985                1990                1995

Arg Lys  Gly Asn Asn Ala His Glu Asn Pro Lys Glu  Val Ala Ile
    2000                2005                2010

His Leu  His Ser Gln Gly Gly Ser Ser Val His Pro  Arg Thr Leu
    2015                2020                2025

Gln Thr  Asn Glu Glu Asn Ser Arg Val Leu Pro
    2030                2035

<210> SEQ ID NO 9
<211> LENGTH: 1231
<212> TYPE: PRT
<213> ORGANISM: Homo sapiens

<400> SEQUENCE: 9
```

-continued

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
```

-continued

```
            420             425             430
Glu Asn Gly Trp Ser Pro Thr Pro Arg Cys Ile Arg Val Lys Thr Cys
            435             440             445
Ser Lys Ser Ser Ile Asp Ile Glu Asn Gly Phe Ile Ser Glu Ser Gln
            450             455             460
Tyr Thr Tyr Ala Leu Lys Glu Lys Ala Lys Tyr Gln Cys Lys Leu Gly
465             470             475             480
Tyr Val Thr Ala Asp Gly Glu Thr Ser Gly Ser Ile Thr Cys Gly Lys
            485             490             495
Asp Gly Trp Ser Ala Gln Pro Thr Cys Ile Lys Ser Cys Asp Ile Pro
            500             505             510
Val Phe Met Asn Ala Arg Thr Lys Asn Asp Phe Thr Trp Phe Lys Leu
            515             520             525
Asn Asp Thr Leu Asp Tyr Glu Cys His Asp Gly Tyr Glu Ser Asn Thr
            530             535             540
Gly Ser Thr Thr Gly Ser Ile Val Cys Gly Tyr Asn Gly Trp Ser Asp
545             550             555             560
Leu Pro Ile Cys Tyr Glu Arg Glu Cys Glu Leu Pro Lys Ile Asp Val
                565             570             575
His Leu Val Pro Asp Arg Lys Lys Asp Gln Tyr Lys Val Gly Glu Val
            580             585             590
Leu Lys Phe Ser Cys Lys Pro Gly Phe Thr Ile Val Gly Pro Asn Ser
            595             600             605
Val Gln Cys Tyr His Phe Gly Leu Ser Pro Asp Leu Pro Ile Cys Lys
            610             615             620
Glu Gln Val Gln Ser Cys Gly Pro Pro Pro Glu Leu Leu Asn Gly Asn
625             630             635             640
Val Lys Glu Lys Thr Lys Glu Glu Tyr Gly His Ser Glu Val Val Glu
                645             650             655
Tyr Tyr Cys Asn Pro Arg Phe Leu Met Lys Gly Pro Asn Lys Ile Gln
            660             665             670
Cys Val Asp Gly Glu Trp Thr Thr Leu Pro Val Cys Ile Val Glu Glu
            675             680             685
Ser Thr Cys Gly Asp Ile Pro Glu Leu Glu His Gly Trp Ala Gln Leu
            690             695             700
Ser Ser Pro Pro Tyr Tyr Tyr Gly Asp Ser Val Glu Phe Asn Cys Ser
705             710             715             720
Glu Ser Phe Thr Met Ile Gly His Arg Ser Ile Thr Cys Ile His Gly
                725             730             735
Val Trp Thr Gln Leu Pro Gln Cys Val Ala Ile Asp Lys Leu Lys Lys
            740             745             750
Cys Lys Ser Ser Asn Leu Ile Ile Leu Glu Glu His Leu Lys Asn Lys
            755             760             765
Lys Glu Phe Asp His Asn Ser Asn Ile Arg Tyr Arg Cys Arg Gly Lys
            770             775             780
Glu Gly Trp Ile His Thr Val Cys Ile Asn Gly Arg Trp Asp Pro Glu
785             790             795             800
Val Asn Cys Ser Met Ala Gln Ile Gln Leu Cys Pro Pro Pro Pro Gln
                805             810             815
Ile Pro Asn Ser His Asn Met Thr Thr Thr Leu Asn Tyr Arg Asp Gly
            820             825             830
Glu Lys Val Ser Val Leu Cys Gln Glu Asn Tyr Leu Ile Gln Glu Gly
            835             840             845
```

Glu Glu Ile Thr Cys Lys Asp Gly Arg Trp Gln Ser Ile Pro Leu Cys
850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
                900                 905                 910

Thr Thr Cys Tyr Met Gly Lys Trp Ser Ser Pro Pro Gln Cys Glu Gly
                915                 920                 925

Leu Pro Cys Lys Ser Pro Pro Glu Ile Ser His Gly Val Val Ala His
930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
                980                 985                 990

Pro Ser Phe Glu Asn Ala Ile Pro Met Gly Glu Lys Lys Asp Val Tyr
                995                 1000                1005

Lys Ala Gly Glu Gln Val Thr Tyr Thr Cys Ala Thr Tyr Tyr Lys
1010                1015                1020

Met Asp Gly Ala Ser Asn Val Thr Cys Ile Asn Ser Arg Trp Thr
1025                1030                1035

Gly Arg Pro Thr Cys Arg Asp Thr Ser Cys Val Asn Pro Pro Thr
1040                1045                1050

Val Gln Asn Ala Tyr Ile Val Ser Arg Gln Met Ser Lys Tyr Pro
1055                1060                1065

Ser Gly Glu Arg Val Arg Tyr Gln Cys Arg Ser Pro Tyr Glu Met
1070                1075                1080

Phe Gly Asp Glu Glu Val Met Cys Leu Asn Gly Asn Trp Thr Glu
1085                1090                1095

Pro Pro Gln Cys Lys Asp Ser Thr Gly Lys Cys Gly Pro Pro Pro
1100                1105                1110

Pro Ile Asp Asn Gly Asp Ile Thr Ser Phe Pro Leu Ser Val Tyr
1115                1120                1125

Ala Pro Ala Ser Ser Val Glu Tyr Gln Cys Gln Asn Leu Tyr Gln
1130                1135                1140

Leu Glu Gly Asn Lys Arg Ile Thr Cys Arg Asn Gly Gln Trp Ser
1145                1150                1155

Glu Pro Pro Lys Cys Leu His Pro Cys Val Ile Ser Arg Glu Ile
1160                1165                1170

Met Glu Asn Tyr Asn Ile Ala Leu Arg Trp Thr Ala Lys Gln Lys
1175                1180                1185

Leu Tyr Ser Arg Thr Gly Glu Ser Val Glu Phe Val Cys Lys Arg
1190                1195                1200

Gly Tyr Arg Leu Ser Ser Arg Ser His Thr Leu Arg Thr Thr Cys
1205                1210                1215

Trp Asp Gly Lys Leu Glu Tyr Pro Thr Cys Ala Lys Arg
1220                1225                1230

<210> SEQ ID NO 10
<211> LENGTH: 1234

```
<212> TYPE: PRT
<213> ORGANISM: Mus musculus

<400> SEQUENCE: 10
```

| | | | | | | | | | | | | | | |
|---|---|---|---|---|---|---|---|---|---|---|---|---|---|---|
| Met | Arg | Leu | Ser | Ala | Arg | Ile | Ile | Trp | Leu | Ile | Leu | Trp | Thr | Val | Cys |
| 1 | | | | 5 | | | | | 10 | | | | | 15 | |
| Ala | Ala | Glu | Asp | Cys | Lys | Gly | Pro | Pro | Arg | Glu | Asn | Ser | Glu | Ile | |
| | | | 20 | | | | | 25 | | | | | 30 | | |
| Leu | Ser | Gly | Ser | Trp | Ser | Glu | Gln | Leu | Tyr | Pro | Glu | Gly | Thr | Gln | Ala |
| | | | 35 | | | | | 40 | | | | | 45 | | |
| Thr | Tyr | Lys | Cys | Arg | Pro | Gly | Tyr | Arg | Thr | Leu | Gly | Thr | Ile | Val | Lys |
| | | 50 | | | | | 55 | | | | | 60 | | | |
| Val | Cys | Lys | Asn | Gly | Lys | Trp | Val | Ala | Ser | Asn | Pro | Ser | Arg | Ile | Cys |
| 65 | | | | | 70 | | | | | 75 | | | | | 80 |
| Arg | Lys | Lys | Pro | Cys | Gly | His | Pro | Gly | Asp | Thr | Pro | Phe | Gly | Ser | Phe |
| | | | | 85 | | | | | 90 | | | | | 95 | |
| Arg | Leu | Ala | Val | Gly | Ser | Gln | Phe | Glu | Phe | Gly | Ala | Lys | Val | Val | Tyr |
| | | | 100 | | | | | 105 | | | | | 110 | | |
| Thr | Cys | Asp | Asp | Gly | Tyr | Gln | Leu | Leu | Gly | Glu | Ile | Asp | Tyr | Arg | Glu |
| | | | 115 | | | | | 120 | | | | | 125 | | |
| Cys | Gly | Ala | Asp | Gly | Trp | Ile | Asn | Asp | Ile | Pro | Leu | Cys | Glu | Val | Val |
| | | | 130 | | | | | 135 | | | | | 140 | | |
| Lys | Cys | Leu | Pro | Val | Thr | Glu | Leu | Glu | Asn | Gly | Arg | Ile | Val | Ser | Gly |
| 145 | | | | | 150 | | | | | 155 | | | | | 160 |
| Ala | Ala | Glu | Thr | Asp | Gln | Glu | Tyr | Tyr | Phe | Gly | Gln | Val | Val | Arg | Phe |
| | | | | 165 | | | | | 170 | | | | | 175 | |
| Glu | Cys | Asn | Ser | Gly | Phe | Lys | Ile | Glu | Gly | His | Lys | Glu | Ile | His | Cys |
| | | | | 180 | | | | | 185 | | | | | 190 | |
| Ser | Glu | Asn | Gly | Leu | Trp | Ser | Asn | Glu | Lys | Pro | Arg | Cys | Val | Glu | Ile |
| | | | 195 | | | | | 200 | | | | | 205 | | |
| Leu | Cys | Thr | Pro | Pro | Arg | Val | Glu | Asn | Gly | Asp | Gly | Ile | Asn | Val | Lys |
| | | 210 | | | | | 215 | | | | | 220 | | | |
| Pro | Val | Tyr | Lys | Glu | Asn | Glu | Arg | Tyr | His | Tyr | Lys | Cys | Lys | His | Gly |
| 225 | | | | | 230 | | | | | 235 | | | | | 240 |
| Tyr | Val | Pro | Lys | Glu | Arg | Gly | Asp | Ala | Val | Cys | Thr | Gly | Ser | Gly | Trp |
| | | | | 245 | | | | | 250 | | | | | 255 | |
| Ser | Ser | Gln | Pro | Phe | Cys | Glu | Glu | Lys | Arg | Cys | Ser | Pro | Pro | Tyr | Ile |
| | | | 260 | | | | | 265 | | | | | 270 | | |
| Leu | Asn | Gly | Ile | Tyr | Thr | Pro | His | Arg | Ile | Ile | His | Arg | Ser | Asp | Asp |
| | | | 275 | | | | | 280 | | | | | 285 | | |
| Glu | Ile | Arg | Tyr | Glu | Cys | Asn | Tyr | Gly | Phe | Tyr | Pro | Val | Thr | Gly | Ser |
| | | 290 | | | | | 295 | | | | | 300 | | | |
| Thr | Val | Ser | Lys | Cys | Thr | Pro | Thr | Gly | Trp | Ile | Pro | Val | Pro | Arg | Cys |
| 305 | | | | | 310 | | | | | 315 | | | | | 320 |
| Thr | Leu | Lys | Pro | Cys | Glu | Phe | Pro | Gln | Phe | Lys | Tyr | Gly | Arg | Leu | Tyr |
| | | | | 325 | | | | | 330 | | | | | 335 | |
| Tyr | Glu | Glu | Ser | Leu | Arg | Pro | Asn | Phe | Pro | Val | Ser | Ile | Gly | Asn | Lys |
| | | | | 340 | | | | | 345 | | | | | 350 | |
| Tyr | Ser | Tyr | Lys | Cys | Asp | Asn | Gly | Phe | Ser | Pro | Pro | Ser | Gly | Tyr | Ser |
| | | | 355 | | | | | 360 | | | | | 365 | | |
| Trp | Asp | Tyr | Leu | Arg | Cys | Thr | Ala | Gln | Gly | Trp | Glu | Pro | Glu | Val | Pro |
| | | 370 | | | | | 375 | | | | | 380 | | | |
| Cys | Val | Arg | Lys | Cys | Val | Phe | His | Tyr | Val | Glu | Asn | Gly | Asp | Ser | Ala |
| 385 | | | | | 390 | | | | | 395 | | | | | 400 |

-continued

```
Tyr Trp Glu Lys Val Tyr Val Gln Gly Gln Ser Leu Lys Val Gln Cys
            405                 410                 415
Tyr Asn Gly Tyr Ser Leu Gln Asn Gly Gln Asp Thr Met Thr Cys Thr
                420                 425                 430
Glu Asn Gly Trp Ser Pro Pro Lys Cys Ile Arg Ile Lys Thr Cys
            435                 440                 445
Ser Ala Ser Asp Ile His Ile Asp Asn Gly Phe Leu Ser Glu Ser Ser
    450                 455                 460
Ser Ile Tyr Ala Leu Asn Arg Glu Thr Ser Tyr Arg Cys Lys Gln Gly
465                 470                 475                 480
Tyr Val Thr Asn Thr Gly Glu Ile Ser Gly Ser Ile Thr Cys Leu Gln
                485                 490                 495
Asn Gly Trp Ser Pro Gln Pro Ser Cys Ile Lys Ser Cys Asp Met Pro
            500                 505                 510
Val Phe Glu Asn Ser Ile Thr Lys Asn Thr Arg Thr Trp Phe Lys Leu
            515                 520                 525
Asn Asp Lys Leu Asp Tyr Glu Cys Leu Val Gly Phe Glu Asn Glu Tyr
    530                 535                 540
Lys His Thr Lys Gly Ser Ile Thr Cys Thr Tyr Tyr Gly Trp Ser Asp
545                 550                 555                 560
Thr Pro Ser Cys Tyr Glu Arg Glu Cys Ser Val Pro Thr Leu Asp Arg
                565                 570                 575
Lys Leu Val Val Ser Pro Arg Lys Glu Lys Tyr Arg Val Gly Asp Leu
                580                 585                 590
Leu Glu Phe Ser Cys His Ser Gly His Arg Val Gly Pro Asp Ser Val
            595                 600                 605
Gln Cys Tyr His Phe Gly Trp Ser Pro Gly Phe Pro Thr Cys Lys Gly
    610                 615                 620
Gln Val Ala Ser Cys Ala Pro Pro Leu Glu Ile Leu Asn Gly Glu Ile
625                 630                 635                 640
Asn Gly Ala Lys Lys Val Glu Tyr Ser His Gly Glu Val Val Lys Tyr
                645                 650                 655
Asp Cys Lys Pro Arg Phe Leu Leu Lys Gly Pro Asn Lys Ile Gln Cys
            660                 665                 670
Val Asp Gly Asn Trp Thr Thr Leu Pro Val Cys Ile Glu Glu Arg
            675                 680                 685
Thr Cys Gly Asp Ile Pro Glu Leu Glu His Gly Ser Ala Lys Cys Ser
    690                 695                 700
Val Pro Pro Tyr His His Gly Asp Ser Val Glu Phe Ile Cys Glu Glu
705                 710                 715                 720
Asn Phe Thr Met Ile Gly His Gly Ser Val Ser Cys Ile Ser Gly Lys
                725                 730                 735
Trp Thr Gln Leu Pro Lys Cys Val Ala Thr Asp Gln Leu Glu Lys Cys
            740                 745                 750
Arg Val Leu Lys Ser Thr Gly Ile Glu Ala Ile Lys Pro Lys Leu Thr
    755                 760                 765
Glu Phe Thr His Asn Ser Thr Met Asp Tyr Lys Cys Arg Asp Lys Gln
    770                 775                 780
Glu Tyr Glu Arg Ser Ile Cys Ile Asn Gly Lys Trp Asp Pro Glu Pro
785                 790                 795                 800
Asn Cys Thr Ser Lys Thr Ser Cys Pro Pro Pro Gln Ile Pro Asn
            805                 810                 815
```

```
Thr Gln Val Ile Glu Thr Thr Val Lys Tyr Leu Asp Gly Glu Lys Leu
            820                 825                 830

Ser Val Leu Cys Gln Asp Asn Tyr Leu Thr Gln Asp Ser Glu Met
    835                 840                 845

Val Cys Lys Asp Gly Arg Trp Gln Ser Leu Pro Arg Cys Ile Glu Lys
    850                 855                 860

Ile Pro Cys Ser Gln Pro Pro Thr Ile Glu His Gly Ser Ile Asn Leu
865                 870                 875                 880

Pro Arg Ser Ser Glu Arg Arg Asp Ser Ile Glu Ser Ser Ser His
                885                 890                 895

Glu His Gly Thr Thr Phe Ser Tyr Val Cys Asp Asp Gly Phe Arg Ile
                900                 905                 910

Pro Glu Glu Asn Arg Ile Thr Cys Tyr Met Gly Lys Trp Ser Thr Pro
                915                 920                 925

Pro Arg Cys Val Gly Leu Pro Cys Gly Pro Pro Ser Ile Pro Leu
    930                 935                 940

Gly Thr Val Ser Leu Glu Leu Glu Ser Tyr Gln His Gly Glu Glu Val
945                 950                 955                 960

Thr Tyr His Cys Ser Thr Gly Phe Gly Ile Asp Gly Pro Ala Phe Ile
                965                 970                 975

Ile Cys Glu Gly Gly Lys Trp Ser Asp Pro Pro Lys Cys Ile Lys Thr
                980                 985                 990

Asp Cys Asp Val Leu Pro Thr Val Lys Asn Ala Ile Ile Arg Gly Lys
                995                 1000                1005

Ser Lys Lys Ser Tyr Arg Thr Gly Glu Gln Val Thr Phe Arg Cys
    1010                1015                1020

Gln Ser Pro Tyr Gln Met Asn Gly Ser Asp Thr Val Thr Cys Val
    1025                1030                1035

Asn Ser Arg Trp Ile Gly Gln Pro Val Cys Lys Asp Asn Ser Cys
    1040                1045                1050

Val Asp Pro Pro His Val Pro Asn Ala Thr Ile Val Thr Arg Thr
    1055                1060                1065

Lys Asn Lys Tyr Leu His Gly Asp Arg Val Arg Tyr Glu Cys Asn
    1070                1075                1080

Lys Pro Leu Glu Leu Phe Gly Gln Val Glu Val Met Cys Glu Asn
    1085                1090                1095

Gly Ile Trp Thr Glu Lys Pro Lys Cys Arg Asp Ser Thr Gly Lys
    1100                1105                1110

Cys Gly Pro Pro Pro Pro Ile Asp Asn Gly Asp Ile Thr Ser Leu
    1115                1120                1125

Ser Leu Pro Val Tyr Glu Pro Leu Ser Ser Val Glu Tyr Gln Cys
    1130                1135                1140

Gln Lys Tyr Tyr Leu Leu Lys Gly Lys Lys Thr Ile Thr Cys Thr
    1145                1150                1155

Asn Gly Lys Trp Ser Glu Pro Pro Thr Cys Leu His Ala Cys Val
    1160                1165                1170

Ile Pro Glu Asn Ile Met Glu Ser His Asn Ile Ile Leu Lys Trp
    1175                1180                1185

Arg His Thr Glu Lys Ile Tyr Ser His Ser Gly Glu Asp Ile Glu
    1190                1195                1200

Phe Gly Cys Lys Tyr Gly Tyr Tyr Lys Ala Arg Asp Ser Pro Pro
    1205                1210                1215

Phe Arg Thr Lys Cys Ile Asn Gly Thr Ile Asn Tyr Pro Thr Cys
```

Val

```
<210> SEQ ID NO 11
<211> LENGTH: 1642
<212> TYPE: PRT
<213> ORGANISM: Naja kaouthia

<400> SEQUENCE: 11
```

| | | | | | | | | | | | | | | |
|---|---|---|---|---|---|---|---|---|---|---|---|---|---|---|
| Met | Glu | Arg | Met | Ala | Leu | Tyr | Leu | Val | Ala | Ala | Leu | Leu | Ile | Gly | Phe |
| 1 | | | | 5 | | | | | 10 | | | | | 15 | |

Pro Gly Ser Ser His Gly Ala Leu Tyr Thr Leu Ile Thr Pro Ala Val
           20                  25                  30

Leu Arg Thr Asp Thr Glu Glu Gln Ile Leu Val Glu Ala His Gly Asp
           35                  40                  45

Ser Thr Pro Lys Gln Leu Asp Ile Phe Val His Asp Phe Pro Arg Lys
 50                  55                  60

Gln Lys Thr Leu Phe Gln Thr Arg Val Asp Met Asn Pro Ala Gly Gly
65                  70                  75                  80

Met Leu Val Thr Pro Thr Ile Glu Ile Pro Ala Lys Glu Val Ser Thr
           85                  90                  95

Asp Ser Arg Gln Asn Gln Tyr Val Val Gln Val Thr Gly Pro Gln
          100                 105                 110

Val Arg Leu Glu Lys Val Val Leu Ser Tyr Gln Ser Ser Phe Leu
          115                 120                 125

Phe Ile Gln Thr Asp Lys Gly Ile Tyr Thr Pro Gly Ser Pro Val Leu
130                 135                 140

Tyr Arg Val Phe Ser Met Asp His Asn Thr Ser Lys Met Asn Lys Thr
145                 150                 155                 160

Val Ile Val Glu Phe Gln Thr Pro Glu Gly Ile Leu Val Ser Ser Asn
          165                 170                 175

Ser Val Asp Leu Asn Phe Phe Trp Pro Tyr Asn Leu Pro Asp Leu Val
          180                 185                 190

Ser Leu Gly Thr Trp Arg Ile Val Ala Lys Tyr Glu His Ser Pro Glu
          195                 200                 205

Asn Tyr Thr Ala Tyr Phe Asp Val Arg Lys Tyr Val Leu Pro Ser Phe
210                 215                 220

Glu Val Arg Leu Gln Pro Ser Glu Lys Phe Phe Tyr Ile Asp Gly Asn
225                 230                 235                 240

Glu Asn Phe His Val Ser Ile Thr Ala Arg Tyr Leu Tyr Gly Glu Glu
          245                 250                 255

Val Glu Gly Val Ala Phe Val Leu Phe Gly Val Lys Ile Asp Asp Ala
          260                 265                 270

Lys Lys Ser Ile Pro Asp Ser Leu Thr Arg Ile Pro Ile Ile Asp Gly
          275                 280                 285

Asp Gly Lys Ala Thr Leu Lys Arg Asp Thr Phe Arg Ser Arg Phe Pro
290                 295                 300

Asn Leu Asn Glu Leu Val Gly His Thr Leu Tyr Ala Ser Val Thr Val
305                 310                 315                 320

Met Thr Glu Ser Gly Ser Asp Met Val Val Thr Glu Gln Ser Gly Ile
          325                 330                 335

His Ile Val Ala Ser Pro Tyr Gln Ile His Phe Thr Lys Thr Pro Lys
          340                 345                 350

Tyr Phe Lys Pro Gly Met Pro Tyr Glu Leu Thr Val Tyr Val Thr Asn

```
                355                 360                 365
Pro Asp Gly Ser Pro Ala Ala His Val Pro Val Val Ser Glu Ala Phe
        370                 375                 380

His Ser Met Gly Thr Thr Leu Ser Asp Gly Thr Ala Lys Leu Ile Leu
385                 390                 395                 400

Asn Ile Pro Leu Asn Ala Gln Ser Leu Pro Ile Thr Val Arg Thr Asn
                405                 410                 415

His Gly Asp Leu Pro Arg Glu Arg Gln Ala Thr Lys Ser Met Thr Ala
            420                 425                 430

Ile Ala Tyr Gln Thr Gln Gly Gly Ser Gly Asn Tyr Leu His Val Ala
        435                 440                 445

Ile Thr Ser Thr Glu Ile Lys Pro Gly Asp Asn Leu Pro Val Asn Phe
    450                 455                 460

Asn Val Lys Gly Asn Ala Asn Ser Leu Lys Gln Ile Lys Tyr Phe Thr
465                 470                 475                 480

Tyr Leu Ile Leu Asn Lys Gly Lys Ile Phe Lys Val Gly Arg Gln Pro
                485                 490                 495

Arg Arg Asp Gly Gln Asn Leu Val Thr Met Asn Leu His Ile Thr Pro
            500                 505                 510

Asp Leu Ile Pro Ser Phe Arg Phe Val Ala Tyr Tyr Gln Val Gly Asn
        515                 520                 525

Asn Glu Ile Val Ala Asp Ser Val Trp Val Asp Val Lys Asp Thr Cys
    530                 535                 540

Met Gly Thr Leu Val Val Lys Gly Asp Asn Leu Ile Gln Met Pro Gly
545                 550                 555                 560

Ala Ala Met Lys Ile Lys Leu Glu Gly Asp Pro Gly Ala Arg Val Gly
                565                 570                 575

Leu Val Ala Val Asp Lys Ala Val Tyr Val Leu Asn Asp Lys Tyr Lys
            580                 585                 590

Ile Ser Gln Ala Lys Ile Trp Asp Thr Ile Glu Lys Ser Asp Phe Gly
        595                 600                 605

Cys Thr Ala Gly Ser Gly Gln Asn Asn Leu Gly Val Phe Glu Asp Ala
    610                 615                 620

Gly Leu Ala Leu Thr Thr Ser Thr Asn Leu Asn Thr Lys Gln Arg Ser
625                 630                 635                 640

Ala Ala Lys Cys Pro Gln Pro Ala Asn Arg Arg Arg Ser Ser Val
                645                 650                 655

Leu Leu Leu Asp Ser Asn Ala Ser Lys Ala Ala Glu Phe Gln Asp Gln
            660                 665                 670

Asp Leu Arg Lys Cys Cys Glu Asp Val Met His Glu Asn Pro Met Gly
        675                 680                 685

Tyr Thr Cys Glu Lys Arg Ala Lys Tyr Ile Gln Glu Gly Asp Ala Cys
    690                 695                 700

Lys Ala Ala Phe Leu Glu Cys Cys Arg Tyr Ile Lys Gly Val Arg Asp
705                 710                 715                 720

Glu Asn Gln Arg Glu Ser Glu Leu Phe Leu Ala Arg Asp Asp Asn Glu
                725                 730                 735

Asp Gly Phe Ile Ala Asp Ser Asp Ile Ile Ser Arg Ser Asp Phe Pro
            740                 745                 750

Lys Ser Trp Leu Trp Leu Thr Lys Asp Leu Thr Glu Glu Pro Asn Ser
        755                 760                 765

Gln Gly Ile Ser Ser Lys Thr Met Ser Phe Tyr Leu Arg Asp Ser Ile
    770                 775                 780
```

```
Thr Thr Trp Val Val Leu Ala Val Ser Phe Thr Pro Thr Lys Gly Ile
785                 790                 795                 800

Cys Val Ala Glu Pro Tyr Glu Ile Arg Val Met Lys Val Phe Phe Ile
            805                 810                 815

Asp Leu Gln Met Pro Tyr Ser Val Val Lys Asn Glu Gln Val Glu Ile
            820                 825                 830

Arg Ala Ile Leu His Asn Tyr Val Asn Glu Asp Ile Tyr Val Arg Val
            835                 840                 845

Glu Leu Leu Tyr Asn Pro Ala Phe Cys Ser Ala Ser Thr Lys Gly Gln
850                 855                 860

Arg Tyr Arg Gln Gln Phe Pro Ile Lys Ala Leu Ser Ser Arg Ala Val
865                 870                 875                 880

Pro Phe Val Ile Val Pro Leu Glu Gln Gly Leu His Asp Val Glu Ile
                885                 890                 895

Lys Ala Ser Val Gln Glu Ala Leu Trp Ser Asp Gly Val Arg Lys Lys
                900                 905                 910

Leu Lys Val Val Pro Glu Gly Val Gln Lys Ser Ile Val Thr Ile Val
            915                 920                 925

Lys Leu Asp Pro Arg Ala Lys Gly Val Gly Gly Thr Gln Leu Glu Val
930                 935                 940

Ile Lys Ala Arg Lys Leu Asp Asp Arg Val Pro Asp Thr Glu Ile Glu
945                 950                 955                 960

Thr Lys Ile Ile Ile Gln Gly Asp Pro Val Ala Gln Ile Ile Glu Asn
                965                 970                 975

Ser Ile Asp Gly Ser Lys Leu Asn His Leu Ile Ile Thr Pro Ser Gly
            980                 985                 990

Cys Gly Glu Gln Asn Met Ile Arg Met Ala Ala Pro Val Ile Ala Thr
            995                 1000                1005

Tyr Tyr Leu Asp Thr Thr Glu Gln Trp Glu Thr Leu Gly Ile Asn
    1010            1015            1020

Arg Arg Thr Glu Ala Val Asn Gln Ile Val Thr Gly Tyr Ala Gln
    1025            1030            1035

Gln Met Val Tyr Lys Lys Ala Asp His Ser Tyr Ala Ala Phe Thr
    1040            1045            1050

Asn Arg Ala Ser Ser Ser Trp Leu Thr Ala Tyr Val Val Lys Val
    1055            1060            1065

Phe Ala Met Ala Ala Lys Met Val Ala Gly Ile Ser His Glu Ile
    1070            1075            1080

Ile Cys Gly Gly Val Arg Trp Leu Ile Leu Asn Arg Gln Gln Pro
    1085            1090            1095

Asp Gly Ala Phe Lys Glu Asn Ala Pro Val Leu Ser Gly Thr Met
    1100            1105            1110

Gln Gly Gly Ile Gln Gly Ala Glu Glu Glu Val Tyr Leu Thr Ala
    1115            1120            1125

Phe Ile Leu Val Ala Leu Leu Glu Ser Lys Thr Ile Cys Asn Asp
    1130            1135            1140

Tyr Val Asn Ser Leu Asp Ser Ser Ile Lys Lys Ala Thr Asn Tyr
    1145            1150            1155

Leu Leu Lys Lys Tyr Glu Lys Leu Gln Arg Pro Tyr Thr Thr Ala
    1160            1165            1170

Leu Thr Ala Tyr Ala Leu Ala Ala Ala Asp Gln Leu Asn Asp Asp
    1175            1180            1185
```

```
Arg Val Leu Met Ala Ala Ser Thr Gly Arg Asp His Trp Glu Glu
    1190                1195                1200

Tyr Asn Ala His Thr His Asn Ile Glu Gly Thr Ser Tyr Ala Leu
    1205                1210                1215

Leu Ala Leu Leu Lys Met Lys Lys Phe Asp Gln Thr Gly Pro Ile
    1220                1225                1230

Val Arg Trp Leu Thr Asp Gln Asn Phe Tyr Gly Glu Thr Tyr Gly
    1235                1240                1245

Gln Thr Gln Ala Thr Val Met Ala Phe Gln Ala Leu Ala Glu Tyr
    1250                1255                1260

Glu Ile Gln Met Pro Thr His Lys Asp Leu Asn Leu Asp Ile Thr
    1265                1270                1275

Ile Glu Leu Pro Asp Arg Glu Val Pro Ile Arg Tyr Arg Ile Asn
    1280                1285                1290

Tyr Glu Asn Ala Leu Leu Ala Arg Thr Val Glu Thr Lys Leu Asn
    1295                1300                1305

Gln Asp Ile Thr Val Thr Ala Ser Gly Asp Gly Lys Ala Thr Met
    1310                1315                1320

Thr Ile Leu Thr Phe Tyr Asn Ala Gln Leu Gln Glu Lys Ala Asn
    1325                1330                1335

Val Cys Asn Lys Phe His Leu Asn Val Ser Val Glu Asn Ile His
    1340                1345                1350

Leu Asn Ala Met Gly Ala Lys Gly Ala Leu Met Leu Lys Ile Cys
    1355                1360                1365

Thr Arg Tyr Leu Gly Glu Val Asp Ser Thr Met Thr Ile Ile Asp
    1370                1375                1380

Ile Ser Met Leu Thr Gly Phe Leu Pro Asp Ala Glu Asp Leu Thr
    1385                1390                1395

Arg Leu Ser Lys Gly Val Asp Arg Tyr Ile Ser Arg Tyr Glu Val
    1400                1405                1410

Asp Asn Asn Met Ala Gln Lys Val Ala Val Ile Ile Tyr Leu Asn
    1415                1420                1425

Lys Val Ser His Ser Glu Asp Glu Cys Leu His Phe Lys Ile Leu
    1430                1435                1440

Lys His Phe Glu Val Gly Phe Ile Gln Pro Gly Ser Val Lys Val
    1445                1450                1455

Tyr Ser Tyr Tyr Asn Leu Asp Glu Lys Cys Thr Lys Phe Tyr His
    1460                1465                1470

Pro Asp Lys Gly Thr Gly Leu Leu Asn Lys Ile Cys Ile Gly Asn
    1475                1480                1485

Val Cys Arg Cys Ala Gly Glu Thr Cys Ser Ser Leu Asn His Gln
    1490                1495                1500

Glu Arg Ile Asp Val Pro Leu Gln Ile Glu Lys Ala Cys Glu Thr
    1505                1510                1515

Asn Val Asp Tyr Val Tyr Lys Thr Lys Leu Leu Arg Ile Glu Glu
    1520                1525                1530

Gln Asp Gly Asn Asp Ile Tyr Val Met Asp Val Leu Glu Val Ile
    1535                1540                1545

Lys Gln Gly Thr Asp Glu Asn Pro Arg Ala Lys Thr His Gln Tyr
    1550                1555                1560

Ile Ser Gln Arg Lys Cys Gln Glu Ala Leu Asn Leu Lys Val Asn
    1565                1570                1575

Asp Asp Tyr Leu Ile Trp Gly Ser Arg Ser Asp Leu Leu Pro Thr
```

```
            1580                1585                1590
Lys Asp Lys Ile Ser Tyr Ile Ile Thr Lys Asn Thr Trp Ile Glu
        1595                1600                1605
Arg Trp Pro His Glu Asp Glu Cys Gln Glu Glu Phe Gln Lys
    1610                1615                1620
Leu Cys Asp Asp Phe Ala Gln Phe Ser Tyr Thr Leu Thr Glu Phe
    1625                1630                1635
Gly Cys Pro Thr
    1640

<210> SEQ ID NO 12
<211> LENGTH: 2
<212> TYPE: PRT
<213> ORGANISM: Artificial Sequence
<220> FEATURE:
<223> OTHER INFORMATION: Synthetic Construct

<400> SEQUENCE: 12

Gly Ser
1

<210> SEQ ID NO 13
<211> LENGTH: 4
<212> TYPE: PRT
<213> ORGANISM: Artificial Sequence
<220> FEATURE:
<223> OTHER INFORMATION: Synthetic Construct

<400> SEQUENCE: 13

Gly Ser Gly Ser
1

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct

<400> SEQUENCE: 14

Gly Ser Gly Ser Gly Ser
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Gly Ser Gly Ser Gly Ser Gly Ser
1               5

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Gly Ser Gly Ser Gly Ser Gly Ser Gly Ser
1               5                   10
```

```
<210> SEQ ID NO 17
<211> LENGTH: 12
<212> TYPE: PRT
<213> ORGANISM: Artificial Sequence
<220> FEATURE:
<223> OTHER INFORMATION: Synthetic Construct

<400> SEQUENCE: 17

Gly Ser Gly Ser Gly Ser Gly Ser Gly Ser Gly Ser
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct

<400> SEQUENCE: 18

Gly Ser Gly Ser Gly Ser Gly Ser Gly Ser Gly Ser Gly Ser
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Synthetic Construct

<400> SEQUENCE: 19

Gly Ser Gly Ser Gly Ser Gly Ser Gly Ser Gly Ser Gly Ser Gly Ser
1               5                   10                  15

<210> SEQ ID NO 20
<211> LENGTH: 4
<212> TYPE: PRT
<213> ORGANISM: Artificial Sequence
<220> FEATURE:
<223> OTHER INFORMATION: Synthetic Construct

<400> SEQUENCE: 20

Gly Gly Gly Ser
1

<210> SEQ ID NO 21
<211> LENGTH: 8
<212> TYPE: PRT
<213> ORGANISM: Artificial Sequence
<220> FEATURE:
<223> OTHER INFORMATION: Synthetic Construct

<400> SEQUENCE: 21

Gly Gly Gly Ser Gly Gly Gly Ser
1               5

<210> SEQ ID NO 22
<211> LENGTH: 12
<212> TYPE: PRT
<213> ORGANISM: Artificial Sequence
<220> FEATURE:
<223> OTHER INFORMATION: Synthetic Construct

<400> SEQUENCE: 22

Gly Gly Gly Ser Gly Gly Gly Ser Gly Gly Gly Ser
1               5                   10
```

```
<210> SEQ ID NO 23
<211> LENGTH: 16
<212> TYPE: PRT
<213> ORGANISM: Artificial Sequence
<220> FEATURE:
<223> OTHER INFORMATION: Synthetic Construct

<400> SEQUENCE: 23

Gly Gly Gly Ser Gly Gly Gly Ser Gly Gly Gly Ser Gly Gly Gly Ser
1               5                   10                  15

<210> SEQ ID NO 24
<211> LENGTH: 5
<212> TYPE: PRT
<213> ORGANISM: Artificial Sequence
<220> FEATURE:
<223> OTHER INFORMATION: Synthetic Construct

<400> SEQUENCE: 24

Gly Gly Gly Gly Ser
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic Construct

<400> SEQUENCE: 25

Gly Gly Gly Gly Ser Gly Gly Gly Gly Ser
1               5                   10

<210> SEQ ID NO 26
<211> LENGTH: 15
<212> TYPE: PRT
<213> ORGANISM: Artificial Sequence
<220> FEATURE:
<223> OTHER INFORMATION: Synthetic Construct

<400> SEQUENCE: 26

Gly Gly Gly Gly Ser Gly Gly Gly Gly Ser Gly Gly Gly Gly Ser
1               5                   10                  15

<210> SEQ ID NO 27
<211> LENGTH: 20
<212> TYPE: PRT
<213> ORGANISM: Artificial Sequence
<220> FEATURE:
<223> OTHER INFORMATION: Synthetic Construct

<400> SEQUENCE: 27

Gly Gly Gly Gly Ser Gly Gly Gly Gly Ser Gly Gly Gly Gly Ser Gly
1               5                   10                  15
Gly Gly Gly Ser
            20

<210> SEQ ID NO 28
<211> LENGTH: 25
<212> TYPE: PRT
<213> ORGANISM: Artificial Sequence
<220> FEATURE:
<223> OTHER INFORMATION: Synthetic Construct

<400> SEQUENCE: 28

Gly Gly Gly Gly Ser Gly Gly Gly Gly Ser Gly Gly Gly Gly Ser Gly
1               5                   10                  15
```

Gly Gly Gly Ser Gly Gly Gly Ser
         20              25

<210> SEQ ID NO 29
<211> LENGTH: 30
<212> TYPE: PRT
<213> ORGANISM: Artificial Sequence
<220> FEATURE:
<223> OTHER INFORMATION: Synthetic Construct

<400> SEQUENCE: 29

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
         20              25                  30

<210> SEQ ID NO 30
<211> LENGTH: 35
<212> TYPE: PRT
<213> ORGANISM: Artificial Sequence
<220> FEATURE:
<223> OTHER INFORMATION: Synthetic Construct

<400> SEQUENCE: 30

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
         20              25                  30

Gly Gly Ser
         35

<210> SEQ ID NO 31
<211> LENGTH: 40
<212> TYPE: PRT
<213> ORGANISM: Artificial Sequence
<220> FEATURE:
<223> OTHER INFORMATION: Synthetic Construct

<400> SEQUENCE: 31

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
         20              25                  30

Gly Gly Ser Gly Gly Gly Gly Ser
         35              40

<210> SEQ ID NO 32
<211> LENGTH: 4
<212> TYPE: PRT
<213> ORGANISM: Artificial Sequence
<220> FEATURE:
<223> OTHER INFORMATION: Synthetic Construct

<400> SEQUENCE: 32

Gly Ser Ser Gly
1

<210> SEQ ID NO 33
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 33

Gly Ser Ser Gly Gly Ser Ser Gly
1               5

<210> SEQ ID NO 34
<211> LENGTH: 12
<212> TYPE: PRT
<213> ORGANISM: Artificial Sequence
<220> FEATURE:
<223> OTHER INFORMATION: Synthetic Construct

<400> SEQUENCE: 34

Gly Ser Ser Gly Gly Ser Ser Gly Gly Ser Ser Gly
1               5                   10

<210> SEQ ID NO 35
<211> LENGTH: 16
<212> TYPE: PRT
<213> ORGANISM: Artificial Sequence
<220> FEATURE:
<223> OTHER INFORMATION: Synthetic Construct

<400> SEQUENCE: 35

Gly Ser Ser Gly Gly Ser Ser Gly Gly Ser Ser Gly Gly Ser Ser Gly
1               5                   10                  15
```

ANTIBODIES TO THE C3D FRAGMENT OF COMPLEMENT COMPONENT 3

RELATED APPLICATION

This application is the U.S. National Stage filing under 35 U.S.C. §371 of International Application No. PCT/US2011/041517, filed Jun. 22, 2011, which claims the benefit of U.S. provisional patent application Ser. No. 61/357,499, filed on Jun. 22, 2010, the disclosure of which is incorporated herein by reference in its entirety.

FIELD OF THE INVENTION

The present invention relates to methods and materials for modulating the complement alternative pathway (CAP), the complement classical pathway (CCP), the complement lectin/mannose pathway (CMP), or combinations thereof, as well as methods and materials for targeting diagnostic, prophylactic and therapeutic agents to localized areas of tissue within the body where they may more directly exert their effects upon the intended target cells or tissue, with reduced, associated systemic effects compared with administration of the same or similar agents in an untargeted, systemic manner. The methods and materials of the present invention may therefore allow for increased efficacy, lower threshold effective dosages and/or lower effective maintenance doses, and/or reduced associated undesired or adverse effects in terms of frequency or severity of occurrence, or both. The present invention also relates to methods and materials for modulating a host humoral immune response, especially reducing, inhibiting, or preventing a host humoral immune response, e.g., to self antigens as occurs in patients with autoimmune disease.

BACKGROUND OF THE INVENTION

The complement system plays an important role in the pathology of many autoimmune, inflammatory and ischemic diseases. Inappropriate complement activation and its deposition on host cells can lead to complement-mediated lysis and/or injury of cells and target tissues, as well as tissue destruction due to the generation of powerful mediators of inflammation. Key to the activity of the complement system is the covalent attachment of processed protein fragments derived from a serum protein, complement C3, to tissue sites of complement activation. This unusual property is due to the presence of a thioester bond in C3 that, when cleaved during C3 activation, converts C3 to a form designated C3b which can then utilize ester or amide bonds to link to cell and tissue-attached molecules. Once C3b is covalently attached, it is rapidly processed to the iC3b, C3dg and C3d forms, each of which remain covalently attached to the target tissue site. This process results in the "marking" of the tissue as one in which an inflammatory injury or other complement-related process is underway.

Complement can be activated by any of three pathways: the classical, lectin and alternative pathways. The classical pathway is activated through the binding of the complement system protein C1q to antigen-antibody complexes, pentraxins or apoptotic cells. The pentraxins include C-reactive protein and serum amyloid P component. The lectin pathway is initiated by binding of microbial carbohydrates to mannose-binding lectin or by the binding of ficolins to carbohydrates or acetylated molecules.

The alternative pathway is activated on surfaces of pathogens that have neutral or positive charge characteristics and do not express or contain complement inhibitors. This results from the process termed 'tickover' of C3 that occurs spontaneously, involving the interaction of conformationally altered C3 with factor B, and results in the fixation of active C3b on pathogens or other surfaces. The alternative pathway can also be initiated when certain antibodies block endogenous regulatory mechanisms, by IgA-containing immune complexes, or when expression of complement regulatory proteins is decreased. In addition, the alternative pathway is activated by a mechanism called the 'amplification loop' when C3b that is deposited onto targets via the classical or lectin pathway, or indeed through the tickover process itself, binds factor B. See Muller-Eberhard (1988) Ann. Rev. Biochem. 57:321. For example, Holers and colleagues have shown that the alternative pathway is amplified at sites of local injury when inflammatory cells are recruited following initial complement activation. Girardi et al., *J. Clin. Invest.* 2003, 112:1644. Dramatic complement amplification through the alternative pathway then occurs through a mechanism that involves either the additional generation of injured cells that fix complement, local synthesis of alternative pathway components, or more likely because infiltrating inflammatory cells that carry preformed C3 and properdin greatly increase activation specifically at that site.

Alternative pathway amplification is initiated when circulating factor B binds to activated C3b. This complex is then cleaved by circulating factor D to yield an enzymatically active C3 convertase complex, C3bBb. C3bBb cleaves additional C3 generating C3b, which drives inflammation and also further amplifies the activation process, generating a positive feedback loop. Factor H is a key regulator (inhibitor) of the alternative complement pathway activation and initiation mechanisms that competes with factor B for binding to conformationally altered C3 in the tickover mechanism and to C3b in the amplification loop. Binding of C3b to Factor H also leads to degradation of C3b by factor I to the inactive form iC3b (also designated C3bi), thus exerting a further check on complement activation. Factor H regulates complement in the fluid phase, circulating at a plasma concentration of approximately 500 µg/ml, but its binding to cells is a regulated phenomenon enhanced by the presence of a negatively charged surface as well as fixed C3b, iC3b, C3dg or C3d. Jozsi et al., *Histopathol.* (2004) 19:251-258.

Complement activation, C3 fragment fixation and complement-mediated inflammation are involved in the etiology and progression of numerous diseases. The down-regulation of complement activation has been shown to be effective in treating several diseases in animal models and in ex vivo studies, including, for example, systemic lupus erythematosus and glomerulonephritis (Y. Wang et al., *Proc. Nat'l Acad. Sci. USA* (1996) 93:8563-8568), rheumatoid arthritis (Y. Wang et al., *Proc. Nat'l Acad. Sci. USA* (1995) 92:8955-8959), cardiopulmonary bypass and hemodialysis (C. S. Rinder, *J. Clin. Invest.* (1995) 96:1564-1572), hyperacute rejection in organ transplantation (T. J. Kroshus et al., *Transplantation* (1995) 60:1194-1202), myocardial infarction (J. W. Homeister et al., *J. Immunol.* (1993) 150:1055-1064; H. F. Weisman et al., *Science* (1990) 249:146-151), ischemia/reperfusion injury (E. A. Amsterdam et al., *Am. J. Physiol.* (1995) 268:H448-H457), antibody-mediated allograft rejection, for example, in the kidneys (J. B. Colvin, *J. Am. Soc. Nephrol.* (2007) 18(4):1046-56), and adult respiratory distress syndrome (R. Rabinovici et al., *J. Immunol.* (1992) 149:1744-1750). Moreover, other inflammatory conditions and autoimmune/immune complex diseases are also closely associated with complement activation (B. P.

Morgan. *Eur. J. Clin. Invest*. (1994) 24:219-228), including, but not limited to, thermal injury, severe asthma, anaphylactic shock, bowel inflammation, urticaria, angioedema, vasculitis, multiple sclerosis, myasthenia gravis, myocarditis, membranoproliferative glomerulonephritis, atypical hemolytic uremic syndrome, Sjögren's syndrome, renal and pulmonary ischemia/reperfusion, and other organ-specific inflammatory disorders. It is currently uncertain whether complement activation is essential to the pathogenesis and injury of all diseases in which local tissue C3 activation and inflammatory injury occurs; nevertheless, C3 fragment fixation is almost universally found as an associated event.

The use of complement receptor 2 (CR2), or functional fragments thereof, to target complement modulators to tissues which exhibit or express C3, or fragments of C3 to which the CR2 is able to bind, including C3b, iC3b, C3d and C3dg, is described in US 2008/0267980 and US 2008/0221011, the disclosures of which are hereby incorporated herein by reference. Such CR2 molecules, and functional fragments thereof, can be used for targeting because the first two N-terminal short consensus repeat domains (SCRs) comprise an active binding site for the exposed C3d domain that is contained within iC3b and C3dg.

The disclosures of all publications, patents, patent applications and published patent applications referred to herein are hereby incorporated herein by reference in their entirety.

SUMMARY OF THE INVENTION

Because C3 fragments are expressed and exhibited on tissue and cells which have been subject to physical, chemical or other insult or injury, the present inventors hypothesized that modulation of complement may be effected using antibodies to C3 fragments, such as C3d. Moreover, by targeting a therapeutic or prophylactic agent to the sites of such insult or injury, more effective treatment or prevention of complement-related disorders may result. Such targeting can be accomplished, for example, by joining such therapeutic or prophylactic agents to a targeting moiety that is able to bind to C3 fragments, such as an antibody against C3d or C3dg. Using such means, elevated local concentrations of targeted therapeutic or prophylactic agents can be achieved at the site of such injury when the agent is administered systemically. Thus, therapeutic levels of agent may be achieved at the site of complement activation through systemic administration, using lower concentrations of and/or less frequent dosage regimens than would be necessary for an untargeted therapeutic. Because the agent is targeted to the tissue and cells where the agent may exert the greatest effect, the desired therapeutic or prophylactic concentrations and results may be achieved with reduced systemic side effects. Accordingly, the present disclosure provides materials and methods for targeting therapeutic and/or prophylactic agents to tissue and cells at the site of an injury or insult using targeting moieties that are capable of binding to C3 fragments, namely antibodies to C3d.

The inventors herefor have found that binding to the C3d fragment of complement provides for optimal modulation of the complement alternative pathway at sites of local complement activation in vivo. Thus, the inventors have identified novel methods and materials for the utilization of the unique "flag" or "target" provided by covalent decoration of inflamed tissues with the complement C3 fragments C3dg and/or C3d in order to provide novel methods and materials by which therapeutic or diagnostic agents can be directed preferentially to areas of such inflamed tissues.

Accordingly, in one aspect, the present disclosure provides an isolated antibody or antigen-binding fragment thereof specifically binding to complement protein C3d or C3dg. In some embodiments, the isolated antibody or antigen-binding fragment thereof disclosed herein specifically binds to mammalian C3d or C3dg, e.g., human C3d or C3dg.

In another aspect, the present disclosure provides an isolated anti-C3d/C3dg antibody or antigen-binding fragment thereof, wherein said antibody or antigen-binding fragment thereof has a binding affinity to C3d of 1.1 nM or better (in $K_D$ value). (The term "C3d/C3dg" as used throughout this disclosure means either C3d and/or C3dg.) In some embodiments, the isolated anti-C3d/C3dg antibody or antigen-binding fragment thereof described in the present disclosure has a binding affinity to C3d of 0.5 nM or better (in $K_D$ value). In some embodiments, the isolated antibody or antigen-binding fragment thereof disclosed herein binds to human C3d or C3dg with a $K_D$ of 1.1 nM or better (i.e., with a lower $K_D$ value). In some embodiments, such $K_D$ to human C3d/C3dg is of 0.5 nM or better.

In another aspect, the present disclosure provides an isolated anti-C3d/C3dg antibody or antigen-binding fragment thereof, wherein said antibody or antigen-binding fragment thereof preferably binds to C3d, C3dg or iC3b compared to binding to complement proteins C3, C3a, C3b, C3c or C3f. Generally, the preference described herein refers to a preference to C3d/C3dg of a species over the C3, C3a, C3b, C3c or C3f protein of the same species, which includes, e.g., human, non-human mammals (e.g., cynomolgus monkey), mouse, or rat. Further, the preference described herein refers to either in vitro or in vivo or both in vitro and in vivo preferences, which can be determined by many well-known measurements, e.g., standard affinity determination techniques or competitive binding techniques, many of which are recited and/or described herein. In some embodiments, the isolated anti-C3d/C3dg antibody or antigen-binding fragment thereof described in the present disclosure does not bind to complement proteins C3, C3a, C3b, C3c or C3f of human or other mammalian species in vitro or in vivo. In some embodiments, the disclosure features an isolated anti-C3d/C3dg antibody or antigen-binding fragment thereof that binds to C3d or C3dg of human or other mammalian species with an affinity that is at least 2 (e.g., at least 2, 3, 4, 5, 6, 7, 8, 9, 10, 15, 20, 25, 30, 35, 40, 45, 50, 60, 70, 80, 90, 100, 150, 200, 300, 400, or 500, or more) -fold greater than its corresponding affinity for uncleaved, native C3 protein or other C3 fragments C3a, C3b, C3c or C3f from the same species. For example, an anti-C3d/C3dg antibody or antigen-binding fragment thereof described herein can, in some embodiments, bind to human C3d/C3dg with a $K_D$ of 0.5 nM and to at least a subpopulation of uncleaved human C3 protein, or other human C3 fragments C3a, C3b, C3c or C3f, with a $K_D$ that is at least 2-fold higher (e.g., at least 1 nM). In just another embodiment, the disclosure features an isolated anti-C3d/C3dg antibody or antigen-binding fragment thereof that binds to C3d/C3dg polypeptide from human or other species with a $K_D$ that is less than 1.1 nM, or less than 0.5 nM, in the presence of a molar excess (e.g., a 2, 3, 4, 5, 6, 7, 8, 9, 10, 15, 20, 25, 30, 35, 40, 45, 50, 60, 70, 80, 90, 100, 150, 200, 300, 400, or 500-fold molar excess) of uncleaved, native C3 or other C3 fragments C3a, C3b, C3c or C3f from the same species over C3d/C3dg.

In some embodiments, the present disclosure provides an isolated anti-C3d/C3dg antibody or antigen-binding fragment thereof, wherein the antibody or antigen-binding fragment thereof binds to deposited C3 fragments. In some embodiments, the isolated anti-C3d/C3dg antibody or antigen-binding fragment thereof described herein preferentially binds to deposited C3 fragments compared to binding to free or circulating or undeposited C3 or C3 fragments. The deposited C3 fragments described herein include, but are not limited to, C3d, C3dg, and iC3b. The free or circulating or undeposited C3 includes, but is not limited to, C3 and (C3H$_2$O). The free or undeposited C3 fragments include, but are not limited to, C3a, C3b, C3c and C3f. In some embodiments, the disclosure features an isolated anti-C3d/C3dg antibody or antigen-binding fragment thereof that binds to deposited C3 fragments, e.g., C3d or C3dg, from human or other species with an affinity that is at least 2 (e.g., at least 2, 3, 4, 5, 6, 7, 8, 9, 10, 15, 20, 25, 30, 35, 40, 45, 50, 60, 70, 80, 90, 100, 150, 200, 300, 400, or 500, or more) -fold greater than its corresponding affinity for free or undeposited C3 protein (e.g., C3 or (C3H$_2$O)) or other C3 fragments C3a, C3b, C3c or C3f from the same species.

In some embodiments, the present disclosure provides an isolated anti-C3d/C3dg antibody or antigen-binding fragment thereof, wherein the antibody or antigen-binding fragment thereof binds to C3d or C3dg proteins of at least two species (such antibodies can be referred to herein as species cross-reactive antibodies). In some embodiments, at least one of such species is a mammal. In some embodiments, the mammal described herein includes, but is not limited to, human, cynomolgus monkey, mouse, and rat. In some embodiments, the isolated antibody or antigen-binding fragment thereof described herein binds to both human and cynomolgus C3d or C3dg. In another embodiment, the isolated antibody or antigen-binding fragment thereof described herein binds to both human and rodent C3d or C3dg. In some embodiments, the isolated antibody or antigen-binding fragment thereof described herein binds to both human and mouse C3d or C3dg.

In some embodiments, the present disclosure provides an isolated anti-C3d/C3dg antibody or antigen-binding fragment thereof, wherein the antibody or antigen-binding fragment thereof competes with complement receptor 2 (CR2) for binding to C3d/C3dg. In some embodiments, the isolated antibody or antigen-binding fragment thereof described herein decreases, at a 1:1 molar concentration ratio, the binding of CR2 for C3d/C3dg in vitro or in vivo by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In another embodiment, the isolated antibody or antigen-binding fragment thereof described herein decreases the binding of CR2 to C3d/C3dg in vitro or in vivo by any of about 20%, 25%, 30%, 35%, 40%, 45%, 50%, 55%, 60%, 65%, 70%, 75%, 80%, 85%, 90%, 95%, or 100%, inclusive, as well as any numerical value in between these percentages. In some embodiments, the competition with CR2 for binding to C3d/C3dg by the antibody or antigen-binding fragment thereof described herein leads to decreased or inhibited B cell activation. In some embodiments, such competition described herein leads to decreased, reduced or inhibited host humoral immune response. Thus, the present disclosure also provides an isolated anti-C3d/C3dg antibody or antigen-binding fragment thereof capable of decreasing, reducing or inhibiting host B cell activation. The present disclosure further provides an isolated anti-C3d/C3dg antibody or antigen-binding fragment thereof capable of decreasing, reducing or inhibiting host humoral immune response.

In another aspect, the present disclosure provides an isolated anti-C3d antibody or antigen-binding fragment thereof, wherein the antibody or antigen-binding fragment thereof does not enhance complement activation. In some embodiments, a host being treated with the antibody or antigen-binding fragment thereof described herein has a complement activity level of about 10%, 20%, 25%, 30%, 35%, 40%, 45%, 50%, 55%, 60%, 65%, 70%, 75%, 80%, 85%, 90%, 95%, or 100%, inclusive, as well as any numerical value in between these percentages, of the complement activity level in that host before being treated with the antibody or fragment.

In some embodiments, the present disclosure provides an isolated anti-C3d antibody or antigen-binding fragment thereof, wherein the antibody or antigen-binding fragment thereof does not compete with factor H binding to C3, C3(H$_2$O), C3b and C3dg.

In some embodiments, the present disclosure provides an isolated anti-C3d antibody or antigen-binding fragment thereof, wherein the antibody or antigen-binding fragment thereof does not activate C3 or stabilize complement alternative pathway (CAP) or complement classical pathway (CCP)C3/C5 convertases.

In some embodiments, the isolated anti-C3d antibody or antigen-binding fragment thereof described in the present disclosure includes, but is not limited to, a monoclonal antibody or antibody fragment, a diabody, a chimerized or chimeric antibody or antibody fragment, a humanized antibody or antibody fragment, a deimmunized human antibody or antibody fragment, a fully human antibody or antibody fragment, a bispecific antibody or antibody fragment, a monovalent antibody or antibody fragment, a single chain antibody, an Fv, an Fd, an Fab, an Fab', and an F(ab')$_2$. In some embodiments, the antibody described herein is a monoclonal antibody. In some embodiments, the antibody described herein is the mAb 3d8b, produced by hybridoma cell line 3d-8b/2 (ATCC Deposit PTA-10999). In some embodiments, the antibody described herein is mAb 3d9a, produced by hybridoma cell line 3d-9a/25 (ATCC Deposit PTA-10998). In some embodiments, the antibody described herein is mAb 3d29, produced by hybridoma cell line 3d-29/5/2 (ATCC Deposit PTA-11000). In some embodiments, the antibody or antigen-binding fragment thereof described in the present disclosure includes, but is not limited to, any engineered or recombinant antibody or antigen-binding fragment thereof originated from mAb 3d8b, 3d9a, 3d29, or other mAb described in this disclosure, which can be easily screened or produced by standard methods well known in the art, many of which are discussed in this disclosure. Generally, all these antibodies or fragments originating from mAbs in this disclosure may be designed, screened, produced and/or tested to modify, without being limiting, their binding affinity, avidity, or cross-species activity to the C3d/C3dg protein, selectivity over C3 or other C3 fragments, or their expression pattern and solubility, stability, half-life, cross-reactivity to other proteins/targets, or other inherent activities or characteristics of these antibodies or fragments, such as the effector activity.

In another aspect, the present disclosure provides a hybridoma cell selected from the group consisting of: 3d-8b/2 (ATCC Deposit PTA-10999), 3d-9a/25 (ATCC Deposit number: PTA-10998), 3d-29/5/2 (ATCC Deposit number: PTA-11000), 3d-11/14 (ATCC Deposit number: PTA-11011), 3d-31/A6/9 (ATCC Deposit number: PTA-11027), 3d-3/28/4 (ATCC Deposit number: PTA-11025), 3d-15A9 (ATCC Deposit number: PTA-11012), 3d-10/14/1 (ATCC Deposit number: PTA-11010), and 3d-16/3/3 (ATCC Deposit number: PTA-11026).

In another aspect, the present disclosure provides an isolated antibody produced by the above-listed hybridoma cells. In yet another aspect, the disclosure features a humanized, primatized, or chimerized antibody comprising the set of six (6) CDRs of any of the antibodies produced by the above-listed hybridomas.

In another aspect, the present disclosure provides an isolated nucleic acid molecule encoding the antibody or antigen-binding fragment thereof described in this disclosure.

In another aspect, the present disclosure provides a vector containing the nucleic acid sequence of an isolated nucleic acid encoding the antibody or antigen-binding fragment thereof described in this disclosure. Such a vector includes, but is not limited to, a plasmid vector, a cosmid vector, a viral vector, a shuttle vector, or any vector well known in the art for expression in prokaryotic or eukaryotic cells.

In another aspect, the present disclosure provides a cell containing a vector containing the nucleic acid sequence of an isolated nucleic acid encoding the antibody or antigen-binding fragment thereof described in this disclosure. Such a cell includes, for example, a prokaryotic cell or a eukaryotic cell.

In another aspect, the present disclosure provides a pharmaceutical composition comprising any of the isolated antibodies or antigen-binding fragments thereof described in this disclosure. In some embodiments, the present disclosure provides a pharmaceutical composition comprising a nucleic acid encoding the antibody or antigen-binding fragment thereof described in this disclosure. In some embodiments, the present disclosure provides a pharmaceutical composition comprising a vector containing the nucleic acid sequence of an isolated nucleic acid encoding the antibody or antigen-binding fragment thereof described in this disclosure. In some embodiments, the present disclosure provides a pharmaceutical composition comprising a cell containing such vector described herein.

In another aspect, the present disclosure provides a pharmaceutical composition comprising any of the isolated antibodies or antigen-binding fragments thereof described in this disclosure and a therapeutically acceptable excipient. Suitable excipients are well known in the art and recited herein.

Such antibodies described herein may be useful as modulators of complement activity and, in particular, of complement alternative pathway (CAP), such that complement activation can be modulated, stabilized or reduced as part of a prophylactic or therapeutic regimen. In addition, such antibodies may find use as targeting moieties for the targeting of prophylactic or therapeutic agents, such as complement inhibitors, to areas of local complement activation, in order to modulate, stabilize or reduce complement activation. For example, such antibodies or targeted modulators of complement activity may be useful in controlling or lessening an inflammatory response, including localized inflammatory response or systemic inflammatory responses.

Modulation of the complement system represents a therapeutic modality for numerous pathologic conditions associated with complement activation. It has previously been postulated by the inventors herein that targeting complement inhibitors to the sites of complement activation and disease can facilitate the effectiveness of said complement inhibitors. The present inventors postulated that this is in part because targeting to the sites of complement activation allows the complement inhibitors to act in a more focused area, achieving therapeutic results at the site or sites of complement activation, allowing lower systemic doses to be effective while avoiding or reducing adverse or undesired systemic effects.

The present inventors have found that targeting of prophylactic or therapeutic agents to particular epitopes present on the C3d fragment of complement is surprisingly effective in terms of localizing the prophylactic or therapeutic agents such that they can exert optimal effects on tissue or cells which are the site of complement activation. Thus, the present inventors have isolated antibodies which bind to the C3d fragment of complement and used them for the targeting of prophylactic and therapeutic agents.

Accordingly, in another aspect, the present disclosure provides a construct comprising: (a) a C3d binding portion; and (b) a complement modulator portion, wherein (a) and (b) are joined. In some embodiments, (a) is amino-terminal to (b). In some embodiments, (b) is amino-terminal to (a).

In some embodiments, the C3d binding portion comprises any of the anti-C3d/C3dg antibodies or antigen-binding fragments thereof described herein. In some embodiments, the complement modulatory portion is a compound, composition, or protein.

In yet another aspect, the disclosure provides a construct for modulating complement activation, comprising: (a) a C3d binding portion comprising said anti-C3d antibody or antigen-binding fragment thereof described herein; and (b) a complement modulatory portion which is a compound, composition, or protein.

In some embodiments, the construct disclosed herein modulates complement activity in the complement alternative pathway (CAP). In some embodiments, the construct disclosed herein is a fusion protein.

In some embodiments, said C3d binding portion and said complement modulator portion of the construct disclosed herein are joined directly without a linker. In some embodiments, such two portions are joined directly through a chemical bond. In other embodiments, such two portions are joined by a linker. Such linker may include, but is not limited to, a peptide. An exemplary peptide linker is, but is not limited to, (GlySer)$_n$, wherein n=1 (SEQ ID NO:12), 2 (SEQ ID NO:13), 3 (SEQ ID NO:14), 4 (SEQ ID NO:15), 5 (SEQ ID NO:16), 6 (SEQ ID NO:17), 7 (SEQ ID NO:18), or 8 (SEQ ID NO:19); (GlyGlyGlySer)$_n$, wherein n=1 (SEQ ID NO:20), 2 (SEQ ID NO:21), 3 (SEQ ID NO:22), or 4 (SEQ ID NO:23); (GlyGlyGlyGlySer)$_n$, wherein n=1 (SEQ ID NO:24), 2 (SEQ ID NO:25), 3 (SEQ ID NO:26), 4 (SEQ ID NO:27), 5 (SEQ ID NO:28), 6 (SEQ ID NO:29), 7 (SEQ ID NO:30), or 8 (SEQ ID NO:31); or (GlySerSerGly)$_n$, wherein n=1 (SEQ ID NO:32), 2 (SEQ ID NO:33), 3 (SEQ ID NO:34), or 4 (SEQ ID NO:35).

In some embodiments, said complement modulator portion comprises a complement inhibitor or biologically active fragment thereof. In some embodiments, such complement inhibitor is selected from the group consisting of: human membrane complement protein (MCP), human decay accelerating factor (DAF), mouse DAF, mouse complement receptor 1-related gene/protein y (Crry), human CD59, mouse CD59 isoform A, mouse CD59 isoform B, human complement receptor 1 (CR1), human factor H, and mouse factor H, and biologically active fragments thereof. Such biologically active fragment described herein may include, but is not limited to, SCRs 1-4 (amino acids 35-285 of SEQ ID NO:1) of human MCP, SCRs 1-4 plus the serine/threonine-rich domain (amino acids 35-326 of SEQ ID NO:1) of human MCP, the extracellular domain (amino acids 35-343 of SEQ ID NO:1) of human MCP, SCRs 1-4 (amino acids 25-285 of SEQ ID NO:2) of human DAF, SCRs 1-4 plus the O-glycosylated serine/threonine-rich domain (amino acids 25-353 of SEQ ID NO:2) of human DAF, SCRs 1-4 (amino acids 35-286 of SEQ ID NO:3) of mouse DAF, SCRs 1-4 plus the O-glycosylated serine/threonine-rich domain (amino acids 35-362 of SEQ ID NO:3) of mouse DAF, SCRs 1-5 (amino acids 41-400 of SEQ ID NO:7) of Crry, the extracellular domain (amino acids 41-405 of SEQ ID NO:7) of Crry, the extracellular domain of human CD59 lacking its GPI anchor (amino acids 26-101 of SEQ ID NO:4), the extracellular domain of mouse CD59 isoform A lacking its GPI anchor (amino acids 24-95 of SEQ ID NO:5), the extracellular domain of mouse CD59 isoform B lacking its GPI anchor (amino acids 24-103 of SEQ ID NO:6), SCRs 1-3 (amino acids of 42-234 of SEQ ID NO:8) of human CR1, SCRs 1-4 (amino acids 42-295 of SEQ ID NO:8) of human CR1, SCRs 1-10 (amino acids 42-684 of SEQ ID NO:8) of human CR1, SCRs 8-10 (amino acids of 491-684 of SEQ ID NO:8) of human CR1, SCRs 8-11 (amino acids 491-745 of SEQ ID NO:8) of human CR1, SCRs 15-17 (amino acids of 941-1134 of SEQ ID NO:8) of human CR1, SCRs 15-18 (amino acids 941-1195 of SEQ ID NO:8) of human CR1, SCRs 22-28 (amino acids 1394-1842 of SEQ ID NO:8) of human CR1, SCRs 1-4 (amino acids 21-262 of SEQ ID NO:9) of human factor H, SCRs 1-5 (amino acids 21-320 of SEQ ID NO:9) of human factor H, SCRs 1-8 (amino acids 21-507 of SEQ ID NO:9) of human factor H, SCRs 1-18 (amino acids 21-1104 of SEQ ID NO:9) of human factor H, SCRs 1-4 (amino acids 19-264 of SEQ ID NO:10) of mouse factor H, SCRs 1-5 (amino acids 19-322 of SEQ ID NO:10) of mouse factor H, SCRs 1-8 (amino acids 19-507 of SEQ ID NO:10) of mouse factor H, and SCRs 1-18 (amino acids 19-1109 of SEQ ID NO:10) of mouse factor H.

In some embodiments, said complement modulator portion comprises a complement activator or biologically active fragment thereof. In some embodiments, such complement activator is selected from the group consisting of: human IgG1, human IgG1 Fc domain, human IgM, human IgM Fc domain, mouse IgG3, mouse IgG3 Fc domain, mouse IgM, mouse IgM Fc domain, and cobra venom factor (CVF).

In another aspect, the present disclosure provides an isolated nucleic acid molecule encoding the fusion construct described herein.

In another aspect, the present disclosure provides a vector containing the nucleic acid sequence of the fusion construct described in this disclosure. Such vector includes, but is not limited to, a plasmid vector, a cosmid vector, a viral vector, a shuttle vector, or any vector well known in the art for expression in prokaryotic or eukaryotic cells.

In another aspect, the present disclosure provides a cell containing a vector containing the nucleic acid sequence of an isolated nucleic acid encoding the fusion construct described in this disclosure. Such cell includes, for example, a prokaryotic cell or a eukaryotic cell.

In another aspect, the present disclosure provides a pharmaceutical composition comprising the fusion construct described in this disclosure. In some embodiments, the present disclosure provides a pharmaceutical composition comprising a nucleic acid encoding the fusion construct described in this disclosure. In some embodiments, the present disclosure provides a pharmaceutical composition comprising a vector containing the nucleic acid sequence of the fusion construct described in this disclosure. In some embodiments, the present disclosure provides a pharmaceutical composition comprising a cell containing such vector described herein.

In another aspect, the present disclosure provides a pharmaceutical composition comprising the fusion construct described in this disclosure and further comprising a therapeutically acceptable excipient. Such excipient includes any excipient well known in the art.

In another aspect, the disclosure features: (a) a nucleic acid encoding any one of the antibodies, antigen-binding fragments, or constructs described herein; (b) a vector (e.g., an expression vector) comprising the nucleic acid; and (c) a cell (e.g., a bacterial, plant, fungal, insect, or mammalian cell) comprising the vector or expression vector.

In yet another aspect, the disclosure features a method for producing an antibody, an antigen-binding fragment of the antibody, or a construct described herein. The method includes culturing the aforementioned cell under conditions suitable to allow for expression of the antibody, fragment, or construct by the cell. The method can optionally include purifying the antibody, fragment, or construct from the cell or from the media in which the cell is cultured.

As described above, the disclosure also provides the results of experiments in which the inventors observed that an antagonist anti-C3d antibody (one that prevents the association between C3d and CR2) was capable of reducing antibody production in a mammal. While not bound by any particular theory or mechanism of action, the inventors believe that inhibition of the interaction between C3d or C3dg and CR2 on host B cells reduces B cell activation and/or activity. Accordingly, the disclosure provides antibodies (e.g., anti-C3d, anti-CR2, or anti-C3dg antibodies), antigen-binding fragments of the antibodies, and constructs that are useful for inhibiting B cell activation and/or activity, all of which can be used for, among other things, reducing a humoral immune response (e.g., in a mammal afflicted with an autoimmune disease).

For example, the aforementioned constructs contain a first portion that is capable of inhibiting B cell activation or activity and a second portion that is capable of inhibiting complement activity. The first portion can be, e.g., an antibody or an antigen-binding fragment thereof that binds to a natural ligand of CR2 such as C3d, C3dg, and iC3b. The antibody or antigen-binding fragment thereof can be any of the antibodies described herein. In some embodiments, the first portion comprises an antagonist anti-CR2 antibody (or antigen-binding fragment thereof) that inhibits the interaction between CR2 and C3d or C3dg. In some embodiments, the second portion can be, e.g., any of the complement inhibitor polypeptides (including variants and functional fragments) described herein.

In another aspect, the present disclosure provides a method of decreasing a humoral immune response in a subject comprising administering to said subject the isolated antibody or antigen-binding fragment thereof disclosed herein. In some embodiments, the isolated antibody or antigen-binding fragment thereof disclosed herein reduces B cell stimulation in said subject. In some embodiments, the isolated antibody or antigen-binding fragment thereof reduces B cell stimulation by its competition with CR2 for binding to C3d in said subject. In some embodiments, the subject is a mammal. In some embodiments, the mammal is a human.

In another aspect, the present disclosure provides a method of modulating complement activation in a subject, the method comprising administering to said subject an effective amount of a fusion construct disclosed herein.

In another aspect, the present disclosure provides a method of decreasing or inhibiting complement activation in a subject, which method comprises administering to said subject an effective amount of a fusion construct described herein.

In another aspect, the present disclosure provides a method of increasing complement activation in a subject. The method comprises administering to said subject an effective amount of a fusion construct disclosed herein.

In another aspect, the present disclosure provides a method of decreasing complement activation and humoral immune response simultaneously in a subject. The method includes administering to said subject the fusion construct described herein.

In another aspect, provided herein is a method of treating a subject having or suspected of having a disease or preventing a subject from developing a disease wherein said disease is selected from the group consisting of: tissue damage resulting from ischemia-reperfusion injury, an inflammatory disorder, transplant rejection, a pregnancy-related disease, an adverse drug reaction, and an autoimmune or immune complex disorder, said method comprising administering to said subject a therapeutically effective amount of the isolated antibody or antigen-binding fragment thereof described herein. In some embodiments, said tissue damage resulting from ischemia-reperfusion injury is associated with a disorder selected from the group consisting of: myocardial infarction, aneurysm, stroke, hemorrhagic shock, crush injury, multiple organ failure, hypovolemic shock, intestinal ischemia, spinal cord injury and traumatic brain injury. In some embodiments, said inflammatory disorder is selected from the group consisting of: burns, endotoxemia, septic shock, adult respiratory distress syndrome, cardiopulmonary bypass, hemodialysis, anaphylactic shock, asthma, angioedema, Crohn's disease, sickle cell anemia, poststreptococcal glomerulonephritis, membranous nephritis, and pancreatitis. In some embodiments, said transplant rejection is hyperacute xenograft rejection. In some embodiments, said pregnancy-related disease is selected from the group consisting of: recurrent fetal loss and pre-eclampsia. In some embodiments, said adverse drug reaction is selected from the group consisting of: drug allergy and IL-2 induced vascular leakage syndrome. In a further embodiment, said autoimmune or immune complex disorder is selected from the group consisting of: myasthenia gravis, Alzheimer's disease, multiple sclerosis, rheumatoid arthritis, systemic lupus erythematosus, lupus nephritis, insulin-dependent diabetes mellitus, acute disseminated encephalomyelitis, Addison's disease, antiphospholipid antibody syndrome, autoimmune hepatitis, Crohn's disease, Goodpasture's syndromes, Graves' disease, Guillain-Barré syndrome, Hashimoto's disease, idiopathic thrombocytopenic purpura, pemphigus, Sjögren's syndrome, Takayasu's arteritis, autoimmune glomerulonephritis, membranoproliferative glomerulonephritis type II, paroxysmal nocturnal hemoglobinuria, age-related macular degeneration, diabetic maculopathy, uveitis, retinal degeneration disorders, diabetic nephropathy, focal segmental glomerulosclerosis, ANCA associated vasculitis, hemolytic uremic syndrome, and atypical hemolytic uremic syndrome. In some embodiments, said autoimmune glomerulonephritis is selected from the group consisting of: immunoglobulin A nephropathy and membranoproliferative glomerulonephritis type I.

In one aspect, provided herein is a method of treating a subject having or suspected of having a disease or preventing a subject from developing a disease wherein said disease is selected from the group consisting of: cancer, a viral infection, a bacterial infection, a parasitic infection, and a fungal infection, said method comprising administering to said subject any of the constructs described herein (e.g., a construct described herein that activates complement) in an amount effective to increase complement activation in said subject.

In some embodiments of any of the methods described herein, the subject is a mammal. In some embodiments of any of the methods described herein, the subject is a human.

In another aspect, the present disclosure provides methods of targeting complement regulatory proteins to areas within an individual, such as tissue and/or cells, to which complement C3 activation fragments are covalently attached. The methods comprise: (a) administering to the individual a composition comprising an effective amount of a targeted complement regulatory protein as a therapeutic agent. In some embodiments, the individual is a mammal. In some embodiments, the mammal is a human, a non-human primate (e.g., cynomolgus monkey), a mouse, or a rat. In some embodiments, the composition is administered by injection. In some embodiments, the injection is parenteral, intraocular, intravenous, subcutaneous, or intramuscular.

The targeting moiety can be, e.g., a monoclonal antibody, which specifically binds to a binding partner selected from the group consisting of C3d and C3dg; or fragments thereof which retain the ability to bind to their respective binding partner. In some embodiments, the monoclonal antibody will bind to a binding partner selected from the group consisting of C3d and/or C3dg, but will not bind to C3, C3a, C3b, C3c or C3f (e.g., as determined by immunoprecipitation from activated serum).

In some embodiments, the targeting moiety comprises a fusion protein comprising a C3d binding Fv-domain fused to an Fc-domain of human immunoglobulin isotype $G_1$ ($IgG_1$) or $G_2$ ($IgG_2$). In some embodiments, the fusion protein comprises the Fv-domain of an antibody selected from 3d9a, 3d29 and 3d8b, fused to the Fc-domain of human immunoglobulin isotype $G_1$ ($IgG_1$) or other IgGs or $IgG_{2/4}$ grafts.

In any of the embodiments described herein, the complement-mediated inflammation may be associated with tissue damage resulting from ischemia-reperfusion injury, inflammatory disorders, transplant rejection, pregnancy-related diseases, adverse drug reactions, and autoimmune or immune complex disorders. In any of the embodiments described herein, the tissue damage resulting from ischemia-reperfusion injury may be associated with a disorder selected from the group consisting of myocardial infarction, aneurysm, stroke, hemorrhagic shock, crush injury, multiple organ failure, hypovolemic shock, intestinal ischemia, spinal cord injury and traumatic brain injury. In any of the embodiments described herein, the inflammatory disorder may be selected from the group consisting of burns, endotoxemia, septic shock, adult respiratory distress syndrome, cardiopulmonary bypass, hemodialysis, anaphylactic shock, asthma, angioedema, Crohn's disease, sickle cell anemia, poststreptococcal glomerulonephritis, membranous nephritis, and pancreatitis. In any of the embodiments described herein, the transplant rejection may be hyperacute xenograft rejection. In any of the embodiments described herein, the pregnancy-related disease may be selected from the group consisting of recurrent fetal loss and pre-eclampsia. In any of the embodiments described herein, the adverse drug reaction may be selected from the group consisting of drug allergy and IL-2 induced vascular leakage syndrome. In any of the embodiments described herein, the autoimmune or immune complex disorder may be selected from the group consisting of myasthenia gravis, Alzheimer's disease, multiple sclerosis, rheumatoid arthritis, systemic lupus erythematosus, lupus nephritis, insulin-dependent diabetes mellitus, acute disseminated encephalomyelitis, Addison's disease, antiphospholipid antibody syndrome, autoimmune hepatitis, Crohn's disease, Goodpasture's syndrome, Graves' disease, Guillain-Barré syndrome, Hashimoto's disease, idiopathic thrombocytopenic purpura, pemphigus, Sjögren's syndrome, Takayasu's arteritis, autoimmune glomerulonephritis, membranoproliferative glomerulonephritis type II, paroxysmal nocturnal hemoglobinuria, age-related macular degeneration, diabetic maculopathy, uveitis, retinal degeneration disorders, diabetic nephropathy, focal segmental glomerulosclerosis, ANCA associated vasculitis, hemolytic uremic syndrome, and atypical hemolytic uremic syndrome. In any of the embodiments described herein, the autoimmune glomerulonephritis may be selected from the group consisting of immunoglobulin A nephropathy and membranoproliferative glomerulonephritis type I.

In another aspect, provided herein is the use of any of the compositions as described herein in connection with the methods as described herein, unless otherwise noted or as is clear from the specific context. Any of the compositions as described herein may also be used in the preparation of a medicament for use in the methods as described herein.

In another aspect, provided herein are articles of manufacture or kits containing pharmaceutical compositions comprising an effective amount of any of the targeted prophylactic or therapeutic agent moieties and instructions for their use in the methods described herein. Thus, in some embodiments, the article of manufacture comprises instructions for the use of pharmaceutical compositions comprising an effective amount of a fusion protein comprising a monoclonal antibody which binds to a binding partner selected from C3d and C3dg, joined to a prophylactic or therapeutic moiety. The pharmaceutical compositions may further comprise one or more pharmaceutically acceptable excipients formulated for administration to an individual as described herein. The kit may further comprise means for administration, such as a syringe, inhaler or other device useful for systemic administration.

In yet another aspect, the disclosure features an article of manufacture comprising: a container comprising a label; and a composition comprising any of the antibodies or antigen-binding fragments or constructs described herein, wherein the label indicates that the composition is to be administered to a human having, suspected of having, or at risk for developing, a complement-associated disorder. The article of manufacture can comprise one or more additional active agents.

In another aspect, the disclosure features a therapeutic kit comprising: (i) any of the antibodies or antigen-binding fragments thereof described herein and (ii) means for delivering the antibody or antigen-binding fragment to a human; or (ii) any of the constructs described herein and (iv) means for delivering the construct to a human. The means can be suitable for subcutaneous delivery of the construct, or the antibody or antigen-binding fragment thereof, to the human. The means can be suitable for intraocular delivery of the construct, or the antibody or antigen-binding fragment thereof, to the human. The means can be suitable for intraarticular delivery of the construct, or the antibody or antigen-binding fragment thereof, to the human.

In some embodiments, the means can be a syringe, e.g., a double-barreled syringe. In some embodiments, the means can be a trans-scleral patch or a contact lens comprising the construct or the antibody or antigen-binding fragment thereof.

In some embodiments, the means is suitable for intrapulmonary delivery of the construct, or the antibody or antigen-binding fragment thereof, to the human. For example, the means can be an inhaler or a nebulizer.

In some embodiments, the kits include at least one additional active agent for use in treating a complement-associated disorder in a human.

In yet another aspect, the disclosure features a pre-filled syringe comprising: (a) any of the antibodies or antigen-binding fragments thereof described herein or any of the constructs described herein. The construct, or the antibody or antigen-binding fragment thereof, can be formulated for intraocular, intravitreal, or intraarticular administration.

In some embodiments, the construct, or the antibody or antigen-binding fragment thereof, is formulated for intramuscular or subcutaneous administration.

In some embodiments, the syringe comprises at least one pharmaceutical unit dosage form of the construct, or the antibody or antigen-binding fragment thereof. In some embodiments, the syringe comprises between 0.05 mg to 10 mg of the construct, or the antibody or antigen-binding fragment thereof. In some embodiments, the syringe comprises between about 1 mg and 100 mg of the construct, or the antibody or antigen-binding fragment thereof. In some embodiments, each pharmaceutical unit dosage form has a volume of between 0.02 mL to 1 mL, inclusive. In some embodiments, the pharmaceutical unit dosage form has a volume of no more than 0.05 mL.

The active prophylactic or therapeutic moiety is preferably a complement regulatory moiety, and is preferably capable of exerting a localized effect on surrounding cells and tissue when the targeting moiety binds its binding partner in vivo. Because the prophylactic or therapeutic moiety is targeted to localized tissue where complement is activated, one or more of the undesired systemic effects of such prophylactic or therapeutic moiety may be reduced or eliminated.

The interactions between complement receptor type 2 (CR2) and the complement components C3d, C3dg and iC3b are essential for the initiation of a normal immune response. A crystal structure of the two N-terminal short consensus repeat (SCR1-2) domains of CR2 in complex with C3d has previously been elucidated. However, a number of biochemical and biophysical studies targeting both CR2 and C3d appear to be in conflict with available structural data. For example, additional published mutagenesis and heteronuclear NMR spectroscopy studies directed towards the C3d-binding site on CR2 have indicated that the CR2-C3d co-crystal structure complex may reflect an incomplete reflection of complex formation under solution conditions. With regards to the CR2-binding site on C3d, mutagenesis studies by Isenman and coworkers have implicated an electronegative concave pocket on C3d in the binding process. This surface is discrete from the CR2-C3d interface identified in the crystal structure of the complex. A new publication by Isenman and colleagues has reported a co-crystal structure of CR2 with C3d consistent with binding of CR2 within the concave surface of C3d. See van den Elsen et al. A Crystal Structure of the Complex Between Human Complement Receptor 2 and Its Ligand C3d. *Science* 332, 608 (2011).

As used herein, the term "antibody fragment," "antigen-binding fragment," or similar terms refer to fragment of an antibody that retains the ability to bind to an antigen (e.g., a complement component C3dg, C3d, or CR2), e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, diabodies (Poljak (1994) Structure 2(12):1121-1123; Hudson et al. (1999) J. Immunol. Methods 23(1-2):177-189, the disclosures of each of which are incorporated herein by reference in their entirety), minibodies, triabodies (Schoonooghe et al. (2009) *BMC Biotechnol* 9:70), and domain antibodies (also known as "heavy chain immunoglobulins" or camelids; Holt et al. (2003) *Trends Biotechnol* 21(11): 484-490), (the disclosures of each of which are incorporated herein by reference in their entirety) that bind to a complement component C3d or C3dg protein can be incorporated into the compositions, and used in the methods, described herein.

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

In some embodiments of any of the constructs described herein, the complement modulator portion is a complement modulator polypeptide (e.g., a complement inhibitor polypeptide) such as, e.g., MCP, DAF, Crry, CR1, CD59, or factor H. The polypeptides can be human polypeptides or polypeptides of a non-human species. For example, the complement modulator polypeptides can be from a non-human primate (e.g., orangutan, chimpanzee, macaque, gorilla, lemur, or gibbon), horse, cow, pig, sheep, goat, dog, cat, or rodent (e.g., mouse, rabbit, hamster, gerbil, Guinea pig, or rat).

Variant complement modulator polypeptides, in some embodiments, contain no more than 60 (e.g., no more than 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, nine, eight, seven, six, five, four, three, two, or one) amino acid substitutions as compared to the corresponding wild-type sequence. The amino acid substitutions can be conservative, non-conservative, or a mixture of both. Variant polypeptides may, in some embodiments, contain one or more deletions or additions, or a combination of one or more deletions, additions, and substitutions. In some embodiments, the variant polypeptides contain no more than six (e.g., no more than five, four, three, two, or one) amino acid deletions, additions, or substitutions per 100 amino acids of the polypeptide. In embodiments where the complement modulator polypeptide comprises SCRs, variant polypeptides contain no amino acid substitutions, deletions, or additions in the complement modulator polypeptide SCRs.

In some embodiments, a variant complement modulator polypeptide comprises an amino acid sequence that is at least 70 (e.g., at least 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to the corresponding wild-type amino acid sequence. For example, a variant functional fragment of human MCP containing all four SCRs of hMCP can, in some embodiments, comprise an amino acid sequence that is at least 70 (e.g., at least 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to amino acids 35 to 285 of SEQ ID NO:1.

Functional fragments of a complement modulator polypeptide or variant polypeptide described herein are shorter than the full-length polypeptides. Variant polypeptides, and functional fragments of wild-type proteins or variants, retain at least 50 (e.g., at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 or greater) % of a complement modulatory activity of the corresponding wild-type polypeptide. For example, a variant soluble CD59 polypeptide (e.g., one that has 90% or greater identity with amino acids 26 to 102 of SEQ ID NO:4, soluble human CD59) retains at least 50% of the complement modulatory activity (e.g., the ability to inhibit formation of the terminal complement complex) of the corresponding wild-type soluble human CD59 protein having amino acids 26 to 102 of SEQ ID NO:4.

In some embodiments, a variant complement modulator polypeptide, or functional fragment of the complement modulator polypeptide, has greater than 100% of the ability of the corresponding wild-type protein to modulate complement activity. Methods for detecting and/or quantifying complement activity are known in the art and described herein.

As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

Unless otherwise defined, all technical and scientific terms used herein have the same meaning as commonly understood by one of ordinary skill in the art to which this disclosure pertains. In case of conflict, the present document, including definitions, will control. Exemplary methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating or preventing a complement-associated disorder, will be apparent from the following description, the examples, and from the claims.

BRIEF DESCRIPTION OF DEPOSITED MATERIAL

Hybridoma line 3d-9a/25 was deposited on May 26, 2010 and has been designated as ATCC Patent Deposit PTA-10998.

Hybridoma line 3d-8b/2 was deposited on May 26, 2010 and has been designated as ATCC Patent Deposit PTA-10999.

Hybridoma line 3d-29/5/2 was deposited on May 26, 2010 and has been designated as ATCC Patent Deposit PTA-11000.

Hybridoma line 3d-10/14/1 was deposited on Jun. 2, 2010 and has been designated as ATCC Patent Deposit PTA-11010.

Hybridoma line 3d-11/14 was deposited on Jun. 2, 2010 and has been designated as ATCC Patent Deposit PTA-11011.

Hybridoma line 3d-15A9 was deposited on Jun. 2, 2010 and has been designated as ATCC Patent Deposit PTA-11012.

Hybridoma line 3d-3/28/4 was deposited on Jun. 9, 2010 and has been designated as ATCC Patent Deposit PTA-11025.

Hybridoma line 3d-16/3/3 was deposited on Jun. 9, 2010 and has been designated as ATCC Patent Deposit PTA-11026.

Hybridoma line 3d-31/A6/9 was deposited on Jun. 9, 2010 and has been designated as ATCC Patent Deposit PTA-11027.

BRIEF DESCRIPTION OF THE FIGURES

FIG. 1 illustrates the cleavage of C3 which takes place under physiological conditions of complement activation at a local site. In the presence of a C3 convertase enzyme, C3 is cleaved into C3a and C3b, the latter of which becomes covalently attached to cells or tissues undergoing complement activation at that site. In the presence of Factor I and Cofactor, C3b is further rapidly cleaved into C3f and iC3b. In the presence of Factor I and CR1, iC3b is further cleaved into C3c, which is released, and C3dg, which remains attached to cells/tissues undergoing complement activation. C3dg is then converted to C3d by local action of proteases, which does not, however, change its receptor binding or cell/tissue attachment properties. In sum, relatively short-term markers of complement activity at the site include the presence of soluble C3a and tissue-bound C3b. Intermediate-term markers include iC3b, C3c and C3f. However, the most durable markers of complement activation are C3dg and C3d, which remain covalently attached to the cell/tissue for days to weeks. See Janssen et al., Nature 444:213 (2006) for a description of cleavage reactions.

FIG. 8 is a summary of characteristics of the monoclonal antibodies. Note monoclonal antibodies of Group 1 (3d8b, 3d9a and 3d29) share functional effects.

FIGS. 9A and 9B illustrate the binding of monoclonal antibodies 3d8b, 3d9a and 3d29, but not other anti-C3d antibodies illustrated by 3d31, to tissue bound iC3b and C3dg C3 fragments following injection in factor H deficient (fH−/−) mice of 0.5 mg of antibody (FIG. 9B). Note no glomerular IgG is present in the absence of anti-C3d monoclonal antibody injection in these mice. FIG. 9A is a positive control showing the presence of glomerular C3 fragments, which are primarily in the forms of iC3b and C3d, by staining with an anti-C3 fragment antibody.

FIG. 12 illustrates the effects of anti-C3d monoclonal antibodies on the humoral immune response, as assessed by antigen-specific IgG1 production at days 17 (top) and 30 (bottom). P values for individual monoclonal antibody effects on the antigen-specific immune response represent difference in IgG1 levels as compared to SRBC alone, and demonstrate inhibition by Group 1 monoclonal antibodies 3d8b and 3d29 as compared to other test antibodies.

DETAILED DESCRIPTION OF THE INVENTION

Figure 2:
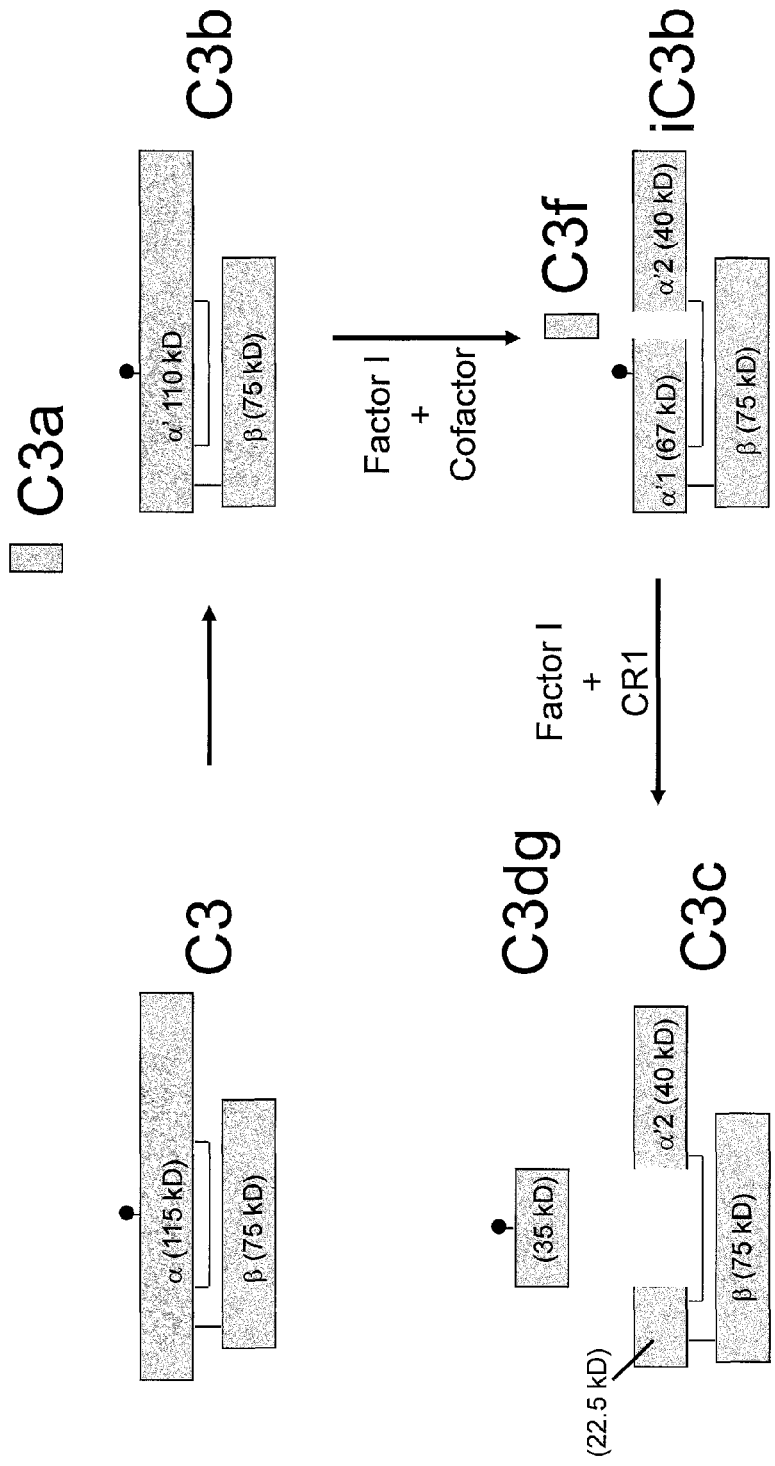
FIG. 2 illustrates the molecular weights and organization of the cleavage fragments of C3. It is anticipated, but not necessary, that monoclonal antibodies generated to C3dg might bind by Western blot or ELISA to the α peptide of C3 (115 kD); the α' peptide of C3b (110 kD); the α'1 peptide of iC3b (67 kD) or the ~35 kD fragment C3dg (or the slightly smaller C3d fragment). The preferred monoclonal antibodies of the present invention will bind only to the latter two, C3dg and C3d, or with preference to the latter two.
Figure 3:
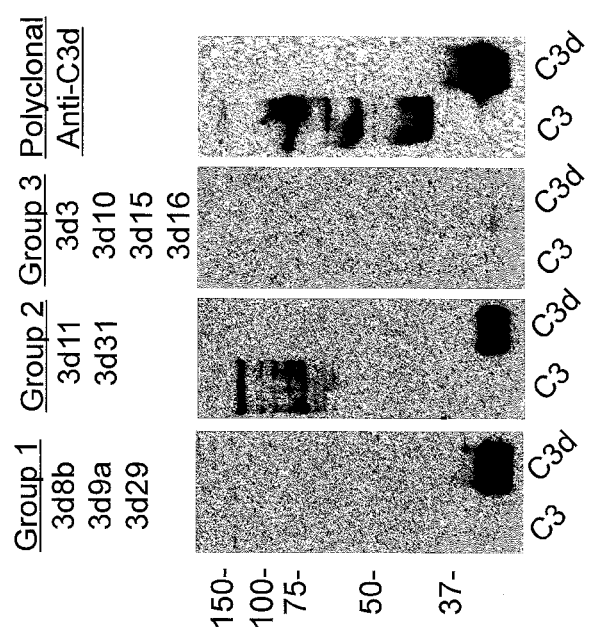
FIG. 3 illustrates the preferential binding to human C3d of monoclonal antibodies 3d8b, 3d9a and 3d29 in a Western blot analysis (Group 1). By comparison monoclonal antibodies 3d11 and 3d31 (Group 2) bind to both C3d and other C3 fragments in a Western blot analysis. Other anti-C3d antibodies (Group 3) do not clearly recognize fragments by Western blot analysis. As a positive control, a polyclonal anti-C3 antibody recognizes all bands.

The present disclosure provides, among other things, molecules that bind to complement component proteins, e.g., antibodies such as anti-C3dg antibodies or anti-C3d antibodies. The molecules are useful for, e.g., inhibiting the activity and/or activation of a B cell.

The molecules are also useful for targeting a complement modulator to local sites of complement activation. Accordingly, the present disclosure also provides fusion molecules/constructs comprising a targeting moiety (e.g., an anti-C3d or anti-C3dg antibody or antigen-binding fragment thereof described herein) and an active prophylactic, therapeutic, or diagnostic moiety. In some embodiments, the targeting moiety comprises a molecule that binds to complement-related proteins (e.g., an antibody or antigen-binding fragment thereof that binds to C3d and/or C3dg). The therapeutic moiety can be, e.g., a complement modulator polypeptide such as, but not limited to, DAF, CD59, Crry, factor H, MCP, or CR1.

Furthermore, the present disclosure provides methods for using one or more of the complement component protein-binding molecules and/or the fusion molecules to treat or prevent a disorder in a subject. For example, as elaborated on herein, an anti-C3d antibody or antigen-binding fragment thereof described herein is useful for inhibiting a humoral immune response in a subject (e.g., a human afflicted with an autoimmune disease). Also featured are novel methods of generating monoclonal antibodies by immunizing complement C3 deficient mice with human C3d and performing the fusion and initial screening with minimal exposure to C3 contained within serum-based growth conditions and feeder cell populations that are used to support hybridoma growth. Following extensive in vitro and in vivo analyses, a subset of the mAbs was found to possess unique characteristics that in aggregate provide proof that these mAbs can be used to identify in vivo sites of complement activation and by this capability direct linked functional modules to these sites.

While in no way intended to be limiting, exemplary compositions (e.g., pharmaceutical compositions and formulations) and methods for using the compositions are elaborated on below.

Compositions

The compositions described herein contain molecules that bind to complement component proteins. For example, these molecules include a small molecule, a nucleic acid or nucleic acid analog, a peptide, a peptidomimetic, or a macromolecule that is not a nucleic acid or a peptide. In some embodiments, these molecules are proteins or protein fragments. In some embodiments, these molecules are antibodies or antibody fragments which retain their antigen-binding activity. In some embodiments, these molecules are anti-C3dg antibodies, anti-C3d antibodies, or antigen-binding fragments of any of the foregoing.

As used herein, the term "antibody" or "immunoglobulin" refers to proteins (including glycoproteins) of the immunoglobulin (Ig) superfamily of proteins. An antibody or immunoglobulin (Ig) molecule is tetrameric, comprising two identical light chain polypeptides and two identical heavy chain polypeptides. The two heavy chains are linked together by disulfide bonds, and each heavy chain is linked to a light chain by a disulfide bond. Each full-length Ig molecule contains at least two binding sites for a specific target or antigen.

The immune system produces several different classes of Ig molecules (isotypes), including IgA, IgD, IgE, IgG, and IgM, each distinguished by the particular class of heavy chain polypeptide present: alpha (α) found in IgA, delta (δ) found in IgD, epsilon (ε) found in IgE, gamma (γ) found in IgG, and mu (μ) found in IgM. There are at least five different γ heavy chain polypeptides (isotypes) found in IgG. In contrast, there are only two light chain polypeptide isotypes, referred to as kappa (κ) and lambda (λ) chains. The distinctive characteristics of antibody isotypes are defined by sequences of the constant domains of the heavy chain.

An IgG molecule comprises two light chains (either κ or λ form) and two heavy chains (γ form) bound together by disulfide bonds. The κ and λ forms of IgG light chain each contain a domain of relatively variable amino acid sequences, called the variable region (variously referred to as a "$V_L$-," "$V_\kappa$-," or "$V_\lambda$-region") and a domain of relatively conserved amino acid sequences, called the constant region ($C_L$-region). Similarly, each IgG heavy chain contains a variable region ($V_H$-region) and one or more conserved regions: a complete IgG heavy chain contains three constant domains ("$C_H1$-," "$C_H2$-," and "$C_H3$-regions") and a hinge region. Within each $V_L$- or $V_H$-region, hypervariable regions, also known as complementarity-determining regions ("CDR"), are interspersed between relatively conserved framework regions ("FR"). Generally, the variable region of a light or heavy chain polypeptide contains four FRs and three CDRs arranged in the following order along the polypeptide: $NH_2$-FR1-CDR1-FR2-CDR2-FR3-CDR3-FR4-COOH. Together the CDRs and FRs determine the three-dimensional structure of the IgG binding site and thus, the specific target protein or antigen to which that IgG molecule binds. Each IgG molecule is dimeric, able to bind two antigen molecules. Cleavage of a dimeric IgG with the protease papain produces two identical antigen-binding fragments ("Fab"') and an "Fc" fragment or Fc domain, so named because it is readily crystallized.

As used throughout the present disclosure, the term "antibody" further refers to a whole or intact antibody (e.g., IgM, IgG, IgA, IgD, or IgE) molecule that is generated by any one of a variety of methods that are known in the art and described herein. The term "antibody" includes a polyclonal antibody, a monoclonal antibody, a chimerized or chimeric antibody, a humanized antibody, a deimmunized human antibody, and a fully human antibody. The antibody can be made in or derived from any of a variety of species, e.g., mammals such as humans, non-human primates (e.g., monkeys, baboons, or chimpanzees), horses, cattle, pigs, sheep, goats, dogs, cats, rabbits, guinea pigs, gerbils, hamsters, rats, and mice. The antibody can be a purified or a recombinant antibody.

Antibodies to C3 and C3 Fragments.

The compositions described herein can contain antibodies which bind to C3 or C3 fragments such as iC3b, C3d and C3dg, or an antigen-binding fragment thereof, such as the antibodies produced by the hybridoma cell lines deposited with the ATCC described herein. In some embodiments, an antibody described herein binds to C3d with greater specificity and broader species cross-reactivity than commercially available anti-human C3d antibodies. In some embodiments, the commercially available anti-C3d antibodies are designated by the Quidel catalog numbers A207 and A250, and are commercially available from the Quidel Corporation (Quidel Corp., San Diego and Santa Clara, Calif.). Antibodies that bind to C3 and to cleavage fragments C3b, iC3b and C3d, are known. For example, see U.S. Pat. No. 6,572,856, Taylor; Tosic et al., J. Immunological Methods, 120:241-249 (1989); Sokoloff et al., Cancer Immunology and Immunotherapy, 49:551-562 (2000); Mastellos et al., Molecular Immunology, 40:1213-1221 (2004); Dilillo et al., Molecular Immunology, 43:1010-1019 (2006); Campagne, US 2009/0081211; Etemad-Gilbertson et al., U.S. patent application publication no. 2009/0175875; Aguado et al., J. Clin. Invest., 76:1418-1426 (1985). The disclosures of these documents are incorporated herein by reference in their entirety. Such antibodies, and functional fragments thereof, may be useful in the present invention as the targeting moiety for directing therapeutic fragments to tissue experiencing activated complement activity, and thus expressing C3 or its fragments.

However, the previously known antibodies to C3, C3b and C3d do not include all of the characteristics of the antibodies identified herein.

In some embodiments, the disclosure features an antibody, or antigen-binding fragment thereof, that binds to an epitope in the human C3d protein. In some embodiments, the disclosure features an antibody, or antigen-binding fragment thereof, that binds to an epitope in the human C3dg protein. For example, the anti-C3d or anti-C3dg antibody can bind to an epitope within, or overlapping with, an antigenic peptide fragment of a human complement component C3d protein, or to an epitope in the human complement component C3dg protein. In some embodiments, these anti-C3d or anti-C3dg antibodies are monoclonal antibodies or antibody fragments maintaining the antigen-binding activity. In some embodiments, these monoclonal antibodies include those produced by hybridoma cells 3d-8b/2 (ATCC Deposit number: PTA-10999), 3d-9a/25 (ATCC Deposit number: PTA-10998), 3d-29/5/2 (ATCC Deposit number: PTA-11000), 3d-11/14 (ATCC Deposit number: PTA-11011), 3d-31/A6/9 (ATCC Deposit number: PTA-11027), 3d3/28/4 (ATCC Deposit number: PTA-11025), 3d-15A9 (ATCC Deposit number: PTA-11012), 3d-10/14/1 (ATCC Deposit number: PTA-11010), and 3d-16/3/3 (ATCC Deposit number: PTA-11026). In some embodiments, the present disclosure provides antibodies, or antigen-binding fragments thereof, that bind to an epitope within, or overlapping with, an epitope recognized by any one of antibodies 3d8b, 3d9a, 3d29, 3d11, 3d31, 3d3, 3d15, 3d10, and 3d16. In some embodiments, these antibodies, or antigen-binding fragments thereof, which bind to an epitope within, or overlapping with, an epitope recognized by any one of antibodies 3d8b, 3d9a, 3d29, 3d11, 3d31, 3d3, 3d15, 3d10, and 3d16, do not compete with any one of antibodies 3d8b, 3d9a, 3d29, 3d11, 3d31, 3d3, 3d15, 3d10, and 3d16 for binding to C3d or C3dg. In some embodiments, these antibodies, or antigen-binding fragments thereof, which bind to an epitope within, or overlapping with, an epitope recognized by any one of antibodies 3d8b, 3d9a, 3d29, 3d11, 3d31, 3d3, 3d15, 3d10, and 3d16, compete with at least one of antibodies including 3d8b, 3d9a, 3d29, 3d11, 3d31, 3d3, 3d15, 3d10, and 3d16 for binding to C3d or C3dg. In some embodiments, these antibodies, or antigen-binding fragments thereof, which bind to an epitope within, or overlapping with, an epitope recognized by any one of antibodies 3d8b, 3d9a, 3d29, 3d11, 3d31, 3d3, 3d15, 3d10, and 3d16, inhibit at least one of antibodies 3d8b, 3d9a, 3d29, 3d11, 3d31, 3d3, 3d15, 3d10, and 3d16 for binding to C3d or C3dg.

As used herein, the term "epitope" refers to the site on a protein (e.g., a human complement component C3d or C3dg protein) that is bound by an antibody. "Overlapping epitopes" include at least one (e.g., two, three, four, five, or six) common amino acid residue(s).

As used herein, the terms "specific binding" or "specifically binds" refer to two molecules forming a complex (e.g., a complex between an antibody and a complement component C3d or C3dg protein) that is relatively stable under physiologic conditions. Typically, binding is considered specific when the association constant ($K_a$) is higher than $10^6$ $M^{-1}$. Thus, an antibody can specifically bind to a C3d or C3dg protein with a $K_a$ of at least (or greater than $10^6$ (e.g., at least or greater than $10^7$, $10^8$, $10^9$, $10^{10}$, $10^{11}$, $10^{12}$, $10^{13}$, $10^{14}$, or $10^{15}$ or higher) $M^{-1}$.

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, surface plasmon resonance method (e.g., BIAcore system; Pharmacia Biosensor AB, Uppsala, Sweden and Piscataway, N.J.), or enzyme-linked immunosorbent assays (ELISA). See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," 2nd Edition, Oxford University Press, NY, Oxford; Johne et al. (1993) J. Immunol. Meth. 160:191-198; Jonsson et al. (1993) Ann Biol. Clin. 51:19-26; and Jonsson et al. (1991) Biotechniques 11:620-627. See also, U.S. Pat. No. 6,355,245.

In some embodiments, the anti-C3d or anti-C3dg antibody, or antigen-binding fragment thereof, provided in the present disclosure can crossblock binding of another antibody or binding partner that binds to an epitope within, or overlapping with, a human complement component C3d or C3dg protein. In some embodiments, the anti-C3d or anti-C3dg antibody, or antigen-binding fragment thereof, can crossblock binding of an antibody that binds to an epitope within, or overlapping with, a peptide fragment of a human complement component C3d or C3dg protein.

As used herein, the term "crossblocking antibody" refers to an antibody, or antibody fragment thereof maintaining its antigen-binding activity, that lowers the amount of binding of anti-C3d or anti-C3dg antibody, or antibody fragment thereof maintaining its antigen-binding activity, to an epitope on a complement component C3d or C3dg protein relative to the amount of binding of the anti-C3d or anti-C3dg antibody, or antibody fragment thereof maintaining its antigen-binding activity, to the epitope in the absence of the crossblocking antibody, or antibody fragment thereof maintaining its antigen-binding activity. Suitable methods for determining whether a first antibody, or antibody fragment thereof, crossblocks binding of a second antibody, or antibody fragment thereof, to an epitope are known in the art. For example, crossblocking antibodies can be identified by comparing the binding of the 3d-9a/25anti-C3d monoclonal antibody (produced by the hybridoma cell line ATCC designation PTA-11025) to C3d in the presence and absence of a test antibody. In such a case, decreased binding of the 3d-9a/25 antibody in the presence of the test antibody as compared to binding of the 3d-9a/25 antibody in the absence of the test antibody indicates that the test antibody is a crossblocking antibody.

Methods for identifying the epitope to which a particular antibody (e.g., an anti-C3d or anti-C3dg antibody) binds are also known in the art. For example, the binding epitope of an anti-C3d or anti-C3dg antibody can be identified by measuring the binding of the antibody to several (e.g., three, four, five, six, seven, eight, nine, 10, 15, 20, or 30 or more) overlapping peptide fragments of a complement component C3d or C3dg protein. Each of the different overlapping peptides is then bound to a unique address on a solid support, e.g., separate wells of a multi-well assay plate. Next, the anti-C3d or anti-C3dg antibody is interrogated by contacting it to each of the peptides in the assay plate for an amount of time and under conditions that allow for the antibody to bind to its epitope. Unbound anti-C3d or anti-C3dg antibody is removed by washing each of the wells. Next, a detectably-labeled secondary antibody that binds to the anti-C3d or anti-C3dg antibody, if present in a well of the plate, is contacted to each of the wells, and unbound secondary antibody is removed by washing steps. The presence or amount of the detectable signal produced by the detectably-labeled secondary antibody in a well is an indication that the anti-C3d or anti-C3dg antibody binds to the particular peptide fragment associated with the well. For a similar method for identifying the epitope to which an anti-05 antibody binds, see, e.g., Harlow and Lane (supra), Benny K. C. Lo (supra), and U.S. Patent Application Publication No. 20060153836, the disclosure of which is incorporated by reference in its entirety. A particular epitope to which an antibody binds can also be identified using BIAcore chromatographic techniques (see, e.g., Pharmacia BIAtechnology Handbook, "Epitope Mapping," Section 6.3.2, (May 1994); and Johne et al. (1993) J. Immunol. Methods 160: 191-8).

In some embodiments, the present disclosure provides an anti-C3d or anti-C3dg antibody, or antigen-binding fragment thereof, which specifically binds to human C3d with a $K_D$ value of $1.1 \times 10^{-9}$ M or better. In some embodiments, such a $K_D$ value is in the range from $1.1 \times 10^{-9}$ M to $3.6 \times 10^{-10}$ M. In some embodiments, the antibody or antigen-binding fragment thereof binds to human C3d with an affinity about $K_D=1.06 \times 10^{-9}$ M. In some embodiments, the antibody is mAb 3d29. In some embodiments, the antibody or antigen-binding fragment thereof binds to human C3d with an affinity about $K_D=4.65 \times 10^{-10}$ M. In some embodiments, the antibody is mAb 3d8b. In some embodiments, the antibody or antigen-binding fragment thereof binds to human C3d with an affinity about $K_D=3.67 \times 10^{-10}$ M. In some embodiments, the antibody is mAb 3d9a.

Measurements to determine antibody affinity are standard and well known techniques. As an exemplary method to measure affinity, BIAcore analysis was used to quantify humanized antibodies' respective affinities for human C5a. See, e.g., Karlsson and Larsson (2004) Methods Mol Biol 248:389-415. Briefly, each of the humanized antibodies was screened with 3-4 concentrations of human C5a (antigen) using a capture technique. The antibodies were captured by an anti-Fc (human) directly immobilized on a CM5 sensor chip with various concentrations in the range from 0.6 nM to 5.9 nM of human C5a passed over the sensor chip surface. The surface was regenerated with 20 mM HCl, 0.02% P20 after each cycle to remove bound antibody and antigen. The data were evaluated using Biacore BIAevaluation software using a 1:1 Langmuir Model Fit (Rmax:Global Fit; RI:Local Fit). Kinetics information such as ($k_a$: Association Rate constant), ($k_d$:Dissociation Rate constant) and $K_D$ (Equilibrium Dissociation constant) was obtained from the fit. These and similar techniques are applicable to other antibodies such as those that bind to C3d or C3dg.

In some embodiments, the disclosure provides an antibody, or antigen-binding fragment thereof, which preferably binds to C3d or C3dg compared to binding to complement component proteins C3, C3a, C3b, C3c, or C3f. In some embodiments, the antibody is 3d8b, 3d9a, or 3d29. In some embodiments, an anti-C3d or anti-C3dg antibody described herein binds to C3d or C3dg but not to any one of complement component proteins C3, C3a, C3b, C3c, or C3f. In some embodiments, the present disclosure provides an antibody, or antigen-binding fragment thereof, which binds to C3d or C3dg at a comparable affinity as its binding to complement component proteins C3, C3a, C3b, C3c, or C3f. In some embodiments, the antibody is 3d11, or 3d31. In some embodiments, the present disclosure provides an antibody, or antigen-binding fragment thereof, which binds weakly to C3d or C3dg but not to any one of complement component proteins C3, C3a, C3b, C3c, or C3f. In some embodiments, the antibody is 3d3, or 3d15.

Thus, in some embodiments, an antibody or antigen-binding fragment thereof binds to free C3d or C3dg (e.g., hC3d or hC3dg) with an affinity that is at least 10 (e.g., at least 10, 20, 30, 40, 50, 60, 70, 80, 90, 100, 110, 120, 130, 140, 150, 160, 170, 180, 190, 200, 225, 250, 275, 300, 400, 500, 600, 700, 800, 900, 1000, 2000, 3000, 4000, 5000, 6000, 7000, 8000, 9000, or 10000)-fold greater than its corresponding affinity for uncleaved, native C3 protein.

In some embodiments, the disclosure provides an antibody, or antigen-binding fragment thereof, which preferably binds to deposited or opsonized C3 fragments, e.g., C3d or C3dg, compared to binding to free or circulating or undeposited C3 fragments. In some embodiments, such an antibody or antigen-binding fragment thereof only binds to deposited C3 fragments but not free C3 or C3 fragments. In other embodiments, the present disclosure comprises antibodies which bind to complement fragment C3d and are able to discriminate between tissue bound C3 fragments from circulating C3 (e.g., C3, C3b, or (C3H$_2$O). In some embodiments, such antibodies include mAbs 3d9a, 3d29 and 3d8b. In some embodiments, antibodies of the invention bind to C3d with greater specificity than commercially available anti-C3d antibodies. In some embodiments, the commercially available anti-C3d antibodies are designated by the Quidel catalog numbers A207 and A250, and are commercially available from the Quidel Corporation (Quidel Corp., San Diego and Santa Clara, Calif.).

Each of the 3d9a, 3d29 and 3d8b antibodies was found to bind to kidney tissue sections exhibiting inflammation when injected into mice intravenously, and bind to C3-opsonized zymosan, which is known to express iC3b but not C3b. Thus, these antibodies are able to distinguish between tissue bound fragment C3d, and circulating native C3 and the fragment C3b.

In some embodiments, the disclosure comprises an antibody, or antigen-binding fragment thereof, that binds to C3d or C3dg from multiple species (species cross-reactive). In some embodiments, such an antibody or antigen-binding fragment thereof binds to C3d or C3dg from at least one species selected from human, non-human mammals (e.g., cynomolgus monkey or cynomolgus macaque, rhesus macaque, ape, baboon, chimpanzee, orangutan, or gorilla), rodents (e.g., mouse, rat, hamster, Guinea pig, gerbil, or rabbit), cattle, sheep, goat, donkey, pig, dog, cat, horse, and camel. In some embodiments, such an antibody or antigen-binding fragment thereof binds to cynomolgus macaque C3d or C3dg. In some embodiments, an antibody or antigen-binding fragment thereof described herein binds to C3d or C3dg from at least two species selected from the above list. In some embodiments, such an antibody or antigen-binding fragment thereof binds to both human and cynomolgus macaque C3d or C3dg. In some embodiments, such an antibody is 3d8b, 3d9a, 3d29, 3d11, 3d31, 3d3, 3d15, 3d10, or 3d16.

In some embodiments, the disclosure provides an anti-C3d or anti-C3dg antibody, or antigen-binding fragment thereof, which competes with CR2 for binding to C3d or C3dg. In some embodiments, such an antibody or antigen-binding fragment thereof reduces the ability of a CR2 protein to bind to human complement component C3d or C3dg by greater than 50 (e.g., greater than 55, 60, 65, 70, 75, 80, 85, 90, or 95 or more) %. In some embodiments, such an antibody is mAb 3d11, 3d9a, 3d16, 3d29, 3d31 or 3d8b. In some embodiments, such an antibody or antigen-binding fragment thereof decreases CR2-C3d binding to at least 60%. In some embodiments, such an antibody or antigen-binding fragment thereof decreases CR2-C3d binding to at least 40%. In some embodiments, such an antibody or antigen-binding fragment thereof significantly inhibits or blocks CR2 binding to C3d. In some embodiments, such an antibody is 3d9a, 3d29 or 3d8b.

Immunoassays which can be used to analyze immunospecific binding and cross-reactivity of the antibodies include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

Antibodies can also be assayed using any surface plasmon resonance (SPR)-based assays known in the art for characterizing the kinetic parameters of the interaction of the antibody with C3d or C3dg. Any SPR instrument commercially available including, but not limited to, BIAcore Instruments (Biacore AB; Uppsala, Sweden); lAsys instruments (Affinity Sensors; Franklin, Mass.); IBIS system (Windsor Scientific Limited; Berks, UK), SPR-CELLIA systems (Nippon Laser and Electronics Lab; Hokkaido, Japan), and SPR Detector Spreeta (Texas Instruments; Dallas, Tex.) can be used in the methods described herein. See, e.g., Mullett et al. (2000) Methods 22: 77-91; Dong et al. (2002) Reviews in Mol Biotech 82: 303-323; Fivash et al. (1998) Curr Opin Biotechnol 9: 97-101; and Rich et al. (2000) Curr Opin Biotechnol 11: 54-61.

In some embodiments, the present disclosure provides an anti-C3d antibody or anti-C3dg antibody, or antigen-binding fragment thereof, which does not enhance complement activation. In some embodiments, such an antibody is mAb3d11, 3d9a, 3d16, 3d29, 3d31 or 3d8b.

While the disclosure is in no way limited by one particular theory or mechanism of action, the inventors assert that an anti-C3d or anti-C3dg antibody, or antigen-binding fragment thereof, disclosed herein is able to compete with CR2 on the membrane of host B cells for binding to C3d or C3dg or antigen-C3d/C3dg immune complexes, thereby reducing or inhibiting the downstream signaling through CR2, which is crucial for B cell activation and antibody production. As used herein, B cell activation or activity refers to any aspect of: (a) antigen-specific production or secretion of an antibody by a B cell or plasma cell; (b) proliferation of a B cell or plasma cell; (c) antigen processing by B cells; (d) antigen presentation by B cells to T cells; (e) upregulation of B cell cell surface markers; and/or (f) differentiation (e.g., antigen-driven) of a B cell into an antibody-producing plasma cell. Thus, in some embodiments, the disclosure features an anti-C3d or anti-C3dg antibody, or antigen-binding fragment thereof, which can decrease or inhibit host humoral immune response. In some embodiments, such an antibody or anti-gen-binding fragment thereof decreases or inhibits host antibody production. In some embodiments, such an antibody or antigen-binding fragment thereof reduces host immune response by greater than 20 (e.g., greater than 25, 30, 35, 40, 45, 50, 55, 60, 65, 70, 75, 80, 85, 90, or 95 or more) %. In some embodiments, such an antibody or antigen-binding fragment thereof reduces host immune response by at least 50%. In some embodiments, such an antibody is mAb 3d11, 3d9a, 3d16, 3d29, 3d31 or 3d8b. In some embodiments, such an antibody is 3d9a, 3d29, or 3d8b. Methods for determining whether an antibody or antigen-binding fragment thereof has reduced an immune response (e.g., an autoimmune response) in a mammal are well known in the art (e.g., mixed lymphocyte reaction (MLR)) and described in e.g., U.S. Pat. No. 7,576,182, and Lemoli et al. Immunological effects of omalizumab in chronic urticaria: a case report. *J Investig Allergol Clin Immunol.* 2010; 20(3): 252-4.

In some embodiments, the present disclosure also provides antibodies, or antigen-binding fragments thereof, which are variants of mouse monoclonal antibodies 3d8b, 3d9a, 3d29, 3d11, 3d31, 3d3, 3d15, 3d10, and 3d16 and maintain the C3d binding ability of these mouse antibodies. For example, the present disclosure provides an anti-C3d or anti-C3dg antibody, or antigen-binding fragments thereof, which is a polyclonal antibody, a monoclonal antibody or antibody fragment, a diabody, a chimerized or chimeric antibody or antibody fragment, a humanized antibody or antibody fragment, a deimmunized human antibody or antibody fragment, a fully human antibody or antibody fragment, a bispecific antibody or antibody fragment, a monovalent antibody or antibody fragment, a single chain antibody, an Fv, an Fab, an Fab', and an F(ab')$_2$. For example, the present disclosure provides chimerized, humanized, or single-chain versions of 3db8, 3d9a, 3d29, etc.

Methods for preparing a hybridoma cell line include immunizing Balb/c mice by injecting subcutaneously and/or intraperitoneally an immunogenic composition containing human C3d or C3dg protein (or an immunogenic fragment thereof) several times, e.g., four to six times, over several months, e.g., between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described supra, supplemented with a selection medium, for example HAT medium, at regular intervals in order to prevent normal myeloma cells from overgrowing the desired hybridoma cells.

The antibodies and fragments thereof can be, in some embodiments, "chimeric." Chimeric antibodies and antigen-binding fragments thereof comprise portions from two or more different species (e.g., mouse and human). Chimeric antibodies can be produced with mouse variable regions of desired specificity spliced onto human constant domain gene segments (see, for example, U.S. Pat. No. 4,816,567). In this manner, non-human antibodies can be modified to make them more suitable for human clinical application (e.g., methods for treating or preventing a complement associated disorder in a human subject).

The monoclonal antibodies of the present disclosure include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Methods of preparing humanized antibodies are generally well known in the art. For example, humanization can be essentially performed following the method of Winter and co-workers (see, e.g., Jones et al. (1986) Nature 321: 522-525; Riechmann et al. (1988) Nature 332:323-327; and Verhoeyen et al. (1988) Science 239:1534-1536), by substituting rodent CDRs or CDR sequences for the corresponding sequences of a human antibody. Also see, e.g., Staelens et al.

(2006) Mol Immunol 43:1243-1257. In some embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production. (See, e.g., Jakobovits et al. (1993) Proc. Natl. Acad. Sci. USA 90:2551; Jakobovits et al. (1993) Nature 362:255-258; Bruggemann et al. (1993) Year in Immunol. 7:33; and Duchosal et al. (1992) Nature 355:258.) Transgenic mice strains can be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The transgenic mice can be immunized with the target protein (e.g., a complement component C3d or C3dg protein, fragments thereof, or cells expressing C3d or C3dg protein) to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be screened for display of antibodies binding to a target.

Thus, in some embodiments, the disclosure provides, e.g., humanized, deimmunized or primatized antibodies comprising one or more of the complementarity determining regions (CDRs) of the mouse monoclonal antibodies described herein, which retain the ability (e.g., at least 50, 60, 70, 80, 90, or 100%, or even greater than 100%) of the mouse monoclonal antibody counterpart to bind to its antigen (e.g., C3d or C3dg). For example, the disclosure features a humanized antibody comprising the set of six CDRs (e.g., heavy chain CDR1, heavy chain CDR2, heavy chain CDR3, light chain CDR1, light chain CDR2, and light chain CDR3) of any one of mouse monoclonal antibodies 3d8b, 3d9a, 3d29, 3d11, 3d31, 3d3, 3d15, 3d10, or 3d16 and human framework regions (with or without human constant or Fc regions).

The exact boundaries of CDRs and framework regions have been defined differently according to different methods and are well known to one of ordinary skill in the art of antibody engineering. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, Md.]. In such cases, the CDRs can be referred to as "Kabat CDRs" (e.g., "Kabat LCDR2" or "Kabat HCDR1") and the framework regions can be referred to as "Kabat framework regions," (e.g., "Kabat LFR1" or "Kabat HFR3"). In some embodiments, the positions of the CDRs or framework regions of a light or heavy chain variable region can be as defined by Chothia et al. (1989) Nature 342:877-883. Accordingly, these regions can be referred to as "Chothia CDRs" (e.g., "Chothia LCDR2" or "Chothia HCDR3") or "Chothia framework regions" (e.g., "Chothia LFR1" or "Chothia LFR3"), respectively. In some embodiments, the positions of the CDRs or framework regions of the light and heavy chain variable regions can be as defined by a Kabat-Chothia combined definition. In such embodiments, these regions can be referred to as "combined Kabat-Chothia CDRs" or "combined Kabat-Chothia framework regions," respectively. Thomas et al. [(1996) Mol Immunol 33(17/18):1389-1401] exemplifies the identification of CDRs and framework region boundaries according to Kabat and Chothia definitions.

In some embodiments, the positions of the CDRs and/or framework regions with a light or heavy chain variable domain can be as defined by Honnegger and Plückthun [(2001) J Mol Biol 309: 657-670].

In addition, human antibodies can be derived from phage-display libraries (Hoogenboom et al. (1991) J. Mol. Biol. 227:381; Marks et al. (1991) J. Mol. Biol., 222:581-597; and Vaughan et al. (1996) Nature Biotech 14:309 (1996)). Synthetic phage libraries can be created which use randomized combinations of synthetic human antibody V-regions. By selection on antigen fully human antibodies can be made in which the V-regions are very human-like in nature. See, e.g., U.S. Pat. Nos. 6,794,132, 6,680,209, 4,634,666, and Ostberg et al. (1983), Hybridoma 2:361-367, the contents of each of which are incorporated herein by reference in their entirety.

For the generation of human antibodies, also see Mendez et al. (1998) Nature Genetics 15:146-156 and Green and Jakobovits (1998) J. Exp. Med. 188:483-495, the disclosures of which are hereby incorporated by reference in their entirety. Human antibodies are further discussed and delineated in U.S. Pat. Nos. 5,939,598; 6,673,986; 6,114,598; 6,075,181; 6,162,963; 6,150,584; 6,713,610; and 6,657,103 as well as U.S. Patent Application Publication Nos. 2003-

0229905 A1, 2004-0010810 A1, US 2004-0093622 A1, 2006-0040363 A1, 2005-0054055 A1, 2005-0076395 A1, and 2005-0287630 A1. See also International Publication Nos. WO 94/02602, WO 96/34096, and WO 98/24893, and European Patent No. EP 0 463 151 B1. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more VH genes, one or more DH genes, one or more JH genes, a mu constant region, and a second constant region (preferably a gamma constant region) are formed into a construct for insertion into an animal. This approach is described in, e.g., U.S. Pat. Nos. 5,545,807; 5,545,806; 5,625,825; 5,625,126; 5,633,425; 5,661,016; 5,770,429; 5,789,650; and 5,814,318; 5,591,669; 5,612,205; 5,721,367; 5,789,215; 5,643,763; 5,569,825; 5,877,397; 6,300,129; 5,874,299; 6,255,458; and 7,041,871, the disclosures of which are hereby incorporated by reference. See also European Patent No. 0 546 073 B1, International Patent Publication Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of each of which are hereby incorporated by reference in their entirety. See further Taylor et al. (1992) Nucleic Acids Res. 20: 6287; Chen et al. (1993) Int. Immunol. 5: 647; Tuaillon et al. (1993) Proc. Natl. Acad. Sci. USA 90: 3720-4; Choi et al. (1993) Nature Genetics 4: 117; Lonberg et al. (1994) Nature 368: 856-859; Taylor et al. (1994) International Immunology 6: 579-591; Tuaillon et al. (1995) J. Immunol. 154: 6453-65; Fishwild et al. (1996) Nature Biotechnology 14: 845; and Tuaillon et al. (2000) Eur. J. Immunol. 10: 2998-3005, the disclosures of each of which are hereby incorporated by reference in their entirety.

In some embodiments, de-immunized antibodies or antigen-binding fragments thereof are provided. De-immunized antibodies or antigen-binding fragments thereof are antibodies that have been modified so as to render the antibody or antigen-binding fragment thereof non-immunogenic, or less immunogenic, to a given species (e.g., to a human). De-immunization can be achieved by modifying the antibody or antigen-binding fragment thereof utilizing any of a variety of techniques known to those skilled in the art (see, e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more of the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., PCT Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized anti-C3d or -C3dg antibodies described herein include de-immunized antigen-binding fragments, Fab, Fv, scFv, Fab' and $F(ab')_2$, monoclonal antibodies, murine antibodies, engineered antibodies (such as, for example, chimeric, single chain, CDR-grafted, humanized, fully human antibodies, and artificially selected antibodies), synthetic antibodies and semi-synthetic antibodies.

In some embodiments, the present disclosure also provides bispecific antibodies. Bispecific antibodies are monoclonal, preferably human or humanized, antibodies that have binding specificities for at least two different antigens. In the present case, one of the binding specificities is for C3d or C3dg, the other one is for any other antigen.

Methods for making bispecific antibodies are within the purview of those skilled in the art. Traditionally, the recombinant production of bispecific antibodies is based on the co-expression of two immunoglobulin heavy-chain/light-chain pairs, where the two heavy chain/light-chain pairs have different specificities (Milstein and Cuello (1983) Nature 305:537-539). Antibody variable domains with the desired binding specificities (antibody-antigen combining sites) can be fused to immunoglobulin constant domain sequences. The fusion of the heavy chain variable region is preferably with an immunoglobulin heavy-chain constant domain, including at least part of the hinge, CH2, and CH3 regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al. (1986) Methods in Enzymology 121:210; PCT Publication No. WO 96/27011; Brennan et al. (1985) Science 229:81; Shalaby et al., J Exp Med (1992) 175:217-225; Kostelny et al. (1992) J Immunol 148(5):1547-1553; Hollinger et al. (1993) Proc Natl Acad Sci USA 90:6444-6448; Gruber et al. (1994) J Immunol 152:5368; and Tutt et al. (1991) J Immunol 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) J Immunol 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) *Proc Natl Acad Sci USA* 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) *J Immunol* 152:5368. Alternatively, the antibodies can be "linear antibodies" as described in, e.g., Zapata et al. (1995) *Protein Eng.* 8(10):1057-1062. Briefly, these antibodies comprise a pair of tandem Fd segments ($V_H$—$C_H$1-$V_H$—$C_H$1) which form a pair of antigen binding regions. Linear antibodies can be bispecific or monospecific.

Antibodies with more than two valencies (e.g., trispecific antibodies) are contemplated and described in, e.g., Tutt et al. (1991) *J Immunol* 147:60.

The disclosure also embraces variant forms of multispecific antibodies such as the dual variable domain immunoglobulin (DVD-Ig) molecules described in Wu et al. (2007) *Nat Biotechnol* 25(11):1290-1297. The DVD-Ig molecules are designed such that two different light chain variable domains (VL) from two different parent antibodies are linked in tandem directly or via a short linker by recombinant DNA techniques, followed by the light chain constant domain. Similarly, the heavy chain comprises two different heavy chain variable domains (VH) linked in tandem, followed by the constant domain $C_H$1 and Fc region. Methods for making DVD-Ig molecules from two parent antibodies are further described in, e.g., PCT Publication Nos. WO 08/024,188 and WO 07/024,715.

The disclosure also provides camelid or dromedary antibodies (e.g., antibodies derived from *Camelus bactrianus, Calelus dromaderius,* or *lama paccos*). Such antibodies, unlike the typical two-chain (fragment) or four-chain (whole antibody) antibodies from most mammals, generally lack light chains. See U.S. Pat. No. 5,759,808; Stijlemans et al. (2004) *J Biol Chem* 279:1256-1261; Dumoulin et al. (2003) Nature 424:783-788; and Pleschberger et al. (2003) Bioconjugate Chem 14:440-448.

Engineered libraries of camelid antibodies and antibody fragments are commercially available, for example, from Ablynx (Ghent, Belgium). As with other antibodies of non-human origin, an amino acid sequence of a camelid antibody can be altered recombinantly to obtain a sequence that more closely resembles a human sequence, i.e., the nanobody can be "humanized" to thereby further reduce the potential immunogenicity of the antibody.

In some embodiments, the present disclosure also provides antibodies, or antigen-binding fragments thereof, which are mutants of mouse monoclonal antibodies 3d8b, 3d9a, 3d29, 3d11, 3d31, 3d3, 3d15, 3d10, and 3d16, or their variant antibodies, or antigen-binding fragments thereof, as described above and therein. Preferably, such a mutant antibody or antigen-binding fragments thereof maintain the C3d binding ability of the parent mouse mAbs. Such mutations and the methods to prepare these mutants are standard practices and well known in the art. In some embodiments, such a mutation introduces at least a single amino acid substitution, deletion, insertion, or other modification. In some embodiments, an antibody or antigen-binding fragment thereof described herein (e.g., mouse monoclonal antibodies 3d8b, 3d9a, 3d29, 3d11, 3d31, 3d3, 3d15, 3d10, or 3d16) comprises no more than 20 (e.g., no more than 19, 18, 17, 16, 15, 14, 13, 12, 11, 10, nine, eight, seven, six, five, four, three, two, or one) amino acid modifications (e.g., amino acid substitutions, deletions, or additions). In some embodiments, an antibody or antigen-binding fragment thereof described herein does not contain an amino acid modification in its CDRs. In some embodiments, an antibody or antigen-binding fragment thereof described herein does not contain an amino acid modification in the CDR3 of the heavy chain.

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. Substitution of one amino acid residue for another from a different class or group is referred to herein as a "non-conservative" substitution. In contrast, non-conservative amino acid substitutions tend to disrupt conformation and function of a protein.

TABLE 1

| Example of amino acid classification | |
|---|---|
| Small/Aliphatic residues: | Gly, Ala, Val, Leu, Ile |
| Cyclic Imino Acid: | Pro |
| Hydroxyl-containing Residues: | Ser, Thr |
| Acidic Residues: | Asp, Glu |
| Amide Residues: | Asn, Gln |
| Basic Residues: | Lys, Arg |
| Imidazole Residue: | His |
| Aromatic Residues: | Phe, Tyr, Trp |
| Sulfur-containing Residues: | Met, Cys |

In some embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., BIOCHEMISTRY at pp. 13-15, 2$^{nd}$ ed. Lubert Stryer ed. (Stanford University); Henikoff et al., *Proc. Nat'l Acad. Sci. USA* (1992) 89:10915-10919; Lei et al., *J. Biol. Chem.* (1995) 270(20):11882-11886).

In some embodiments, the non-conservative amino acid substitution comprises substituting any of glycine (G), alanine (A), isoleucine (I), valine (V), and leucine (L) for any of serine (S), threonine (T), aspartic acid (D), glutamic acid (E), glutamine (Q), asparagine (N), lysine (K), arginine (R), phenylalanine (F), tyrosine (Y), tryptophan (W), methionine (M), cysteine (C), histidine (H), and proline (P). In some embodiments, the non-conservative amino acid substitution comprises substituting any of serine (S) and threonine (T) for any of glycine (G), alanine (A), isoleucine (I), valine (V), leucine (L), aspartic acid (D), glutamic acid (E), glutamine (Q), asparagine (N), lysine (K), arginine (R), phenylalanine (F), tyrosine (Y), tryptophan (W), methionine (M), cysteine (C), histidine (H) and proline (P). In some embodiments, the non-conservative amino acid substitution comprises substituting any of aspartic acid (D) and glutamic acid (E) for any of glycine (G), alanine (A), isoleucine (I), valine (V), leucine (L), serine (S), threonine (T), glutamine (Q), asparagine (N), lysine (K), arginine (R), phenylalanine (F), tyrosine (Y), tryptophan (W), methionine (M), cysteine (C), histidine (H), and proline (P). In some embodiments, the non-conservative amino acid substitution comprises substituting any of glutamine (Q) and asparagine (N) for any of glycine (G), alanine (A), isoleucine (I), valine (V), leucine (L), serine (S), threonine (T), aspartic acid (D), glutamic acid (E), lysine (K), arginine (R), phenylalanine (F), tyrosine (Y), tryptophan (W), methionine (M), cysteine (C), histidine (H), and proline (P). In some embodiments, the non-conservative amino acid substitution comprises substituting any of lysine (K) and arginine (R) for any of glycine (G), alanine (A), isoleucine (I), valine (V), leucine (L), serine (S), threonine (T), aspartic acid (D), glutamic acid (E), glutamine (Q), asparagine (N), phenylalanine (F), tyrosine (Y), tryptophan (W), methionine (M), cysteine (C), histidine (H), and proline (P). In some embodiments, the non-conservative amino acid substitution comprises substituting any of phenylalanine (F), tyrosine (Y), and tryptophan (W) for any of glycine (G), alanine (A), isoleucine (I), valine (V), leucine (L), serine (S), threonine (T), aspartic acid (D), glutamic acid (E), glutamine (Q), asparagine (N), lysine (K), arginine (R), methionine (M), cysteine (C), histidine (H), and proline (P). In some embodiments, the non-conservative amino acid substitution comprises substituting any of methionine (M) and cysteine (C) for any of glycine (G), alanine (A), isoleucine (I), valine (V), leucine (L), serine (S), threonine (T), aspartic acid (D), glutamic acid (E), glutamine (Q), asparagine (N), lysine (K), arginine (R), phenylalanine (F), tyrosine (Y), tryptophan (W), histidine (H), and proline (P). In some embodiments, the non-conservative amino acid substitution comprises substituting histidine (H) for any of glycine (G), alanine (A), isoleucine (I), valine (V), leucine (L), serine (S), threonine (T), aspartic acid (D), glutamic acid (E), glutamine (Q), asparagine (N), lysine (K), arginine (R), phenylalanine (F), tyrosine (Y), tryptophan (W), methionine (M), cysteine (C), and proline (P). In some embodiments, the non-conservative amino acid substitution comprises substituting proline (P) for any of glycine (G), alanine (A), isoleucine (I), valine (V), leucine (L), serine (S), threonine (T), aspartic acid (D), glutamic acid (E), glutamine (Q), asparagine (N), lysine (K), arginine (R), phenylalanine (F), tyrosine (Y), tryptophan (W), methionine (M), cysteine (C), and histidine (H).

In some embodiments, the anti-C3d or anti-C3dg antibodies described herein comprise an altered or mutated sequence that leads to altered stability or half-life compared to parent antibodies. This includes, for example, an increased stability or half-life for higher affinity or longer clearance time in vitro or in vivo, or a decreased stability or half-life for lower affinity or quicker removal.

In some embodiments, the anti-C3d or anti-C3dg antibodies described herein comprise an altered heavy chain constant region that has reduced (or no) effector function relative to its corresponding unaltered constant region. That is, in some embodiments, an antibody described herein comprises an altered constant region that exhibits approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the effector function of the corresponding unaltered (native) form of the constant region. Effector functions involving the constant region of the anti-C3d or anti-C3dg antibody may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent.

An altered constant region with altered FcR binding affinity and/or ADCC activity and/or altered CDC activity is a polypeptide which has an enhanced or diminished FcR binding activity and/or ADCC activity and/or CDC activity compared to the unaltered form of the constant region. An altered constant region which displays increased binding to an FcR binds at least one FcR with greater affinity than the unaltered polypeptide. An altered constant region which displays decreased binding to an FcR binds at least one FcR with lower affinity than the unaltered form of the constant region. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, an altered constant region that displays modulated ADCC and/or CDC activity may exhibit either increased or reduced ADCC and/or CDC activity compared to the unaltered constant region. For example, in some embodiments, the anti-C3d or -C3dg antibody comprising an altered constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the constant region. An anti-C3d or -C3dg antibody described herein comprising an altered constant region displaying reduced ADCC and/or CDC may exhibit reduced or no ADCC and/or CDC activity as exemplified herein.

In some embodiments, the altered constant region has at least one amino acid substitution, insertion, and/or deletion, compared to a native sequence constant region or to the unaltered constant region, e.g., from about one to about one hundred amino acid substitutions, insertions, and/or deletions in a native sequence constant region or in the constant region of the parent polypeptide. In some embodiments, the altered constant region herein will possess at least about 70% homology (similarity) or identity with the unaltered constant region and in some instances at least about 75% and in other instances at least about 80% homology or identity therewith, and in other embodiments at least about 85%, 90% or 95% homology or identity therewith. The altered constant region may also contain one or more amino acid deletions or insertions. Additionally, the altered constant region may contain one or more amino acid substitutions, deletions, or insertions that result in altered post-translational modifications, including, for example, an altered glycosylation pattern (e.g., the addition of one or more sugar components, the loss of one or more sugar components, or a change in composition of one or more sugar components relative to the unaltered constant region).

Antibodies with altered or no effector functions may be generated by engineering or producing antibodies with variant constant, Fc, or heavy chain regions; recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g., glycosylation patterns, may be achieved by manipulating the cell culture and expression conditions by which the antibody is produced. Suitable methods for introducing one or more substitutions, additions, or deletions into an Fc region of an antibody are well known in the art and include, e.g., standard DNA mutagenesis techniques as described in, e.g., Sambrook et al. (1989) "Molecular Cloning: A Laboratory Manual, 2nd Edition," Cold Spring Harbor Laboratory Press, Cold Spring Harbor, N.Y.; Harlow and Lane (1988), supra; Borrebaek (1992), supra; Johne et al. (1993), supra; PCT publication no. WO 06/53301; and U.S. Pat. No. 7,704,497.

In some embodiments, an anti-C3d or anti-C3dg antibody described herein exhibits reduced or no effector function. In some embodiments, an anti-C3d or anti-C3dg antibody comprises a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):441-452). See above.

In addition to using a G2/G4 construct as described above, an anti-C3d or anti-C3dg antibody described herein having reduced effector function may be produced by introducing other types of changes in the amino acid sequence of certain regions of the antibody. Such amino acid sequence changes include but are not limited to the Ala-Ala mutation described in, e.g., PCT Publication nos. WO 94/28027 and WO 98/47531; and Xu et al. (2000) *Cell Immunol* 200:16-26. Thus, in some embodiments, an anti-C3d or -C3dg antibody with one or more mutations within the constant region including the Ala-Ala mutation has reduced or no effector function. According to these embodiments, the constant region of the antibody can comprise a substitution to an alanine at position 234 or a mutation to an alanine at position 235. Additionally, the altered constant region may contain a double mutation: a mutation to an alanine at position 234 and a second mutation to an alanine at position 235. In some embodiments, an anti-C3d or anti-C3dg antibody comprises an IgG4 framework, wherein the Ala-Ala mutation would describe a mutation(s) from phenylalanine to alanine at position 234 and/or a mutation from leucine to alanine at position 235. In some embodiments, the anti-C3d or anti-C3dg antibody comprises an IgG1 framework, wherein the Ala-Ala mutation would describe a mutation(s) from leucine to alanine at position 234 and/or a mutation from leucine to alanine at position 235. An anti-C3d or anti-C3dg antibody may alternatively or additionally carry other mutations, including the point mutation K322A in the CH2 domain (Hezareh et al. (2001) *J Virol* 75:12161-12168). An antibody with said mutation(s) in the constant region may furthermore be a blocking or non-blocking antibody.

Additional substitutions that, when introduced into a heavy chain constant region, result in decreased effector function are set forth in, e.g., Shields et al. (2001) *J Biol Chem* 276(9):6591-6604. See particularly Table 1 ("Binding of human IgG1 variants to human FcRn and FcγR") of Shields et al., the disclosure of which is incorporated herein by reference in its entirety. By screening a library of anti-IgE antibodies, each antibody of the library differing by one or more substitutions in the heavy chain constant region, for binding to a panel of Fc receptors (including FcRn, FcγRI, FcγRIIA, FcγRIIB, and FcγRIIIA), the authors identified a number of substitutions that modulate specific Fc-Fc receptor interactions. For example, a variant IgG2a heavy chain constant region in which the CH2 domain contains a D265A substitution (heavy chain amino acid numbering according to Kabat et al. (supra)) results in a complete loss of interaction between the variant constant region and IgG Fc receptors FcγRIIB, FcγRIII, FcγRI, and FcγRIV. Shields et al. (2001) at page 6595, Table 1. See also Baudino et al. (2008) *J Immunol* 181:6664-6669 (supra).

Changes within the hinge region also affect effector functions. For example, deletion of the hinge region may reduce affinity for Fc receptors and may reduce complement activation (Klein et al. (1981) *Proc Natl Acad Sci USA* 78: 524-528). The present disclosure therefore also relates to antibodies with alterations in the hinge region.

In some embodiments, an anti-C3d or anti-C3dg antibody may contain an altered constant region exhibiting enhanced or reduced complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See, e.g., Caron et al. (1992) J Exp Med 176:1191-1195 and Shopes (1992) *Immunol* 148:2918-2922; PCT publication nos. WO 99/51642 and WO 94/29351; Duncan and Winter (1988) *Nature* 322:738-40; and U.S. Pat. Nos. 5,648,260 and 5,624, 821.

Another potential means of modulating effector function of antibodies includes changes in glycosylation, which is summarized in, e.g., Raju (2003) *BioProcess International* 1(4):44-53. According to Wright and Morrison, the microheterogeneity of human IgG oligosaccharides can affect biological functions such as CDC and ADCC, binding to various Fc receptors, and binding to C1q protein. (1997) *TIBTECH* 15:26-32. Glycosylation patterns of antibodies can differ depending on the producing cell and the cell culture conditions (Raju, supra). Such differences can lead to changes in both effector function and pharmacokinetics. See, e.g., Israel et al. (1996) Immunology 89(4):573-578; Newkirk et al. (1996) *Clin Exp Immunol* 106(2):259-264. Differences in effector function may be related to the IgG's ability to bind to the Fcy receptors (FcγRs) on the effector cells. Shields et al. have shown that IgG, with alterations in amino acid sequence that have improved binding to FcγR, can exhibit up to 100% enhanced ADCC using human effector cells. (2001) *J Biol Chem* 276(9):6591-6604. While these alterations include changes in amino acids not found at the binding interface, both the nature of the sugar component as well as its structural pattern may also contribute to the differences observed. In addition, the presence or absence of fucose in the oligosaccharide component of an IgG can improve binding and ADCC. See, e.g., Shields et al. (2002) *J Biol Chem* 277(30):26733-26740. An IgG that lacked a fucosylated carbohydrate linked to Asn297 exhibited normal receptor binding to the FcγRI receptor. In contrast, binding to the FcγRIIIA receptor was improved 50-fold and accompanied by enhanced ADCC, especially at lower antibody concentrations.

Shinkawa et al. demonstrated that an antibody to the human IL-5 receptor produced in a rat hybridoma showed more than 50% higher ADCC when compared to the antibody produced in Chinese hamster ovary cells (CHO) (Shinkawa et al. (2003) *J Biol Chem* 278(5):3466-73). Monosaccharide composition and oligosaccharide profiling showed that the rat hybridoma-produced IgG had a lower content of fucose than the CHO-produced protein. The authors concluded that the lack of fucosylation of an IgG1 has a critical role in enhancement of ADCC activity.

A different approach was taken by Umana et al. who changed the glycosylation pattern of chCE7, a chimeric IgG1 anti-neuroblastoma antibody. (1999) *Nat Biotechnol* 17(2):176-180). Using tetracycline, they regulated the activity of a glycosyltransferase enzyme (GnTIII) which bisects oligosaccharides that have been implicated in ADCC activity. The ADCC activity of the parent antibody was barely above background level. Measurement of ADCC activity of the chCE7 produced at different tetracycline levels showed an optimal range of GnTIII expression for maximal chCE7 in vitro ADCC activity. This activity correlated with the level of constant region-associated, bisected complex oligosaccharide. Newly optimized variants exhibited substantial ADCC activity. Similarly, Wright and Morrison produced antibodies in a CHO cell line deficient in glycosylation and showed that antibodies produced in this cell line were incapable of complement-mediated cytolysis. (1994) *J Exp Med* 180:1087-1096. Thus, as known alterations that affect effector function include modifications in the glycosylation pattern or a change in the number of glycosylated residues, the present disclosure relates to an anti-C3d or -C3dg antibody wherein glycosylation is altered to either enhance or decrease effector function(s) including ADCC and CDC. Altered glycosylation includes a decrease or increase in the number of glycosylated residues as well as a change in the pattern or location of glycosylated residues.

Still other approaches exist for altering the effector function of antibodies. For example, antibody-producing cells can be hypermutagenic, thereby generating antibodies with randomly altered polypeptide residues throughout an entire antibody molecule. See, e.g., PCT publication no. WO 05/011735. Hypermutagenic host cells include cells deficient in DNA mismatch repair. Antibodies produced in this manner may be less antigenic and/or have beneficial pharmacokinetic properties. Additionally, such antibodies may be selected for properties such as enhanced or decreased effector function(s). Additional details of molecular biology techniques useful for preparing an antibody or antigen-binding fragment thereof described herein are set forth below.

Fusion Molecules

The present disclosure also provides compositions containing a fusion molecule comprising a targeting moiety and an active prophylactic, therapeutic, or diagnostic moiety.

In some embodiments, the fusion molecules described herein are able to specifically deliver their active prophylactic, therapeutic, or diagnostic moiety or portion to a surface (e.g., cell surface, antigen surface, etc.) through the specific binding of the targeting moiety or portion to a binding partner on such surface. The targeting moiety is preferably one which binds to a binding partner, which is a complement component protein and is preferably selected from the group consisting of C3dg, C3d, and CR2. Suitable targeting moieties can be small molecular compounds, peptides, proteins, or other moieties known in the art. Suitable targeting moieties include antibodies which bind a binding partner selected from the group consisting of C3dg and C3d; or fragments of such antibodies which retain the ability to bind to its respective binding partner. Suitable targeting moieties also include the antibodies of the present invention, or fragments thereof which retain the ability to bind to their respective binding partner. Examples of such targeting moieties or portions are discussed above.

In some embodiments, a fusion molecule is targeted for increased association to tissue that has been injured, damaged or has become inflamed by physical, chemical or other insult or injury. Targeting can be accomplished by tethering, fusing or otherwise associating an active agent to a targeting moiety. In some embodiments, the targeting moiety will bind to tissue-associated complement component 3 (C3) or one or more fragments of C3, including, but not limited to: C3b, iC3b, C3d and C3dg. In some embodiments, the targeting moieties include, for example, monoclonal antibodies to C3, C3b, iC3b, C3d, C3dg, or other fragments of C3, or fragments of such monoclonal antibodies that retain the ability to bind to their respective binding partner. In some embodiments, the targeting moieties can be monoclonal antibodies to iC3b, C3dg and C3d, as illustrated by the 3d9a, 3d29 and 3d8b antibodies. It is also possible to use non-complement regulatory fragments of Factor H that retain the ability to bind to one or more fragments of C3, including C3b, iC3b and C3d or other tissue-associated fragments of C3. These fragments of factor H potentially include fragments comprising SCR domains 5-8 and SCR domains 19-20.

In some embodiments, the fusion molecule described herein is designed to synergize two or more effects in a subject, preferably, a mammal. In some embodiments, the targeting moiety or portion, through its binding to its binding partner, has an in vitro and/or in vivo activity for stabilizing or modulating one target, activity, pathway, or mechanism which is different from the one stabilized or modulated by the active prophylactic, therapeutic, or diagnostic moiety or portion in the same fusion molecule. In some embodiments, the targeting moiety or portion may be fused to more than one active prophylactic, therapeutic, or diagnostic moiety or portion, each of which may have different activity for stabilizing or modulating different targets, activities, pathways, or mechanisms. In any case, the multiple functions of different moieties or portions of the fusion molecule described herein may lead to a synergy or better effect for this fusion molecule.

Active Prophylactic, Therapeutic, or Diagnostic Moiety

In some embodiments, the present disclosure provides an active prophylactic, therapeutic, or diagnostic moiety to be fused to the targeting moiety in the fusion molecule described herein. In some embodiments, an active prophylactic, therapeutic, or diagnostic moiety is targeted or presented to the near space of the binding partner recognized by the targeting moiety. In some embodiments, such targeting moiety is a binding molecule for a complement component protein, as discussed above. In some embodiments, such targeting moiety is an antibody to C3d or C3dg. In some embodiments, such active prophylactic, therapeutic, or diagnostic moiety is a complement modulator. While the disclosure is in no way limited by one particular theory or mechanism of action, the inventors assert that through binding to the complement component protein, e.g., C3d or C3dg, by the targeting moiety, the active prophylactic, therapeutic, or diagnostic moiety, preferably, a complement modulator, is presented closely to the surface of the target, where it can function more effectively because of the increased local concentration of itself and other complement components modulated by it.

As used herein, the term "complement modulator" refers to a compound, composition, or protein that modulates (e.g., inhibits or activates) complement activity. A complement modulator can be a complement inhibitor or a complement activator. As used herein, the term "complement inhibitor" refers to any compound, composition, or protein that reduces or eliminates complement activity. The reduction in complement activity may be incremental (e.g., a 10%, 20%, 30%, 40%, 50%, 60%, 70%, 80%, or 90% reduction in activity) or complete. For example, in some embodiments, a complement inhibitor can inhibit complement activity by at least 10 (e.g., at least 15, 20, 25, 30, 35, 40, 45, 50, 55, 60, 65, 70, 75, 80, 85, 90, or 95 or greater) % in a standard in vitro red blood cell hemolysis assay or an in vitro CH50eq assay. See, e.g., Kabat and Mayer (eds), "Experimental Immunochemistry, $2^{nd}$ Edition," 135-240, Springfield, Ill., CC Thomas (1961), pages 135-139, or a conventional variation of that assay such as the chicken erythrocyte hemolysis method as described in, e.g., Hillmen et al. (2004) N Engl J Med 350(6):552.

The CH50eq assay is a method for measuring the total classical complement activity in serum. This test is a lytic assay, which uses antibody-sensitized erythrocytes as the activator of the classical complement pathway and various dilutions of the test serum to determine the amount required to give 50% lysis (CH50). The percent hemolysis can be determined, for example, using a spectrophotometer. The CH50eq assay provides an indirect measure of terminal complement complex (TCC) formation, since the TCC themselves are directly responsible for the hemolysis that is measured.

The assay is well known and commonly practiced by those of skill in the art. Briefly, to activate the classical complement pathway, undiluted serum samples (e.g., human serum samples) are added to microassay wells containing the antibody-sensitized erythrocytes to thereby generate TCC. Next, the activated sera are diluted in microassay wells, which are coated with a capture reagent (e.g., an antibody that binds to one or more components of the TCC). The TCC present in the activated samples bind to the monoclonal antibodies coating the surface of the microassay wells. The wells are washed and, to each well, is added a detection reagent that is detectably labeled and recognizes the bound TCC. The detectable label can be, e.g., a fluorescent label or an enzymatic label. The assay results are expressed in CH50 unit equivalents per milliliter (CH50 U Eq/mL).

Additional methods for detecting and/or measuring complement activity in vitro are set forth and exemplified in the working examples.

A complement inhibitor may be a soluble or membrane-bound protein such as, for example, membrane cofactor protein (MCP), decay accelerating factor (DAF/CD55), CD59, mouse complement receptor 1-related gene/protein y (Crry), human complement receptor 1 (CR1) or factor H, or an antibody specific for a component of a complement pathway such as, for example, eculizumab (an anti-05 antibody marketed under the trade name Solirie), pexelizumab (the antigen-binding fragment of eculizumab), an anti-factor B antibody (such as the monoclonal antibody 1379 produced by ATCC Deposit No. PTA-6230), an anti-properdin antibody, an anti-factor D antibody, and the like (see below). Alternatively, a complement inhibitor may be a small molecule or a linear or cyclic peptide such as, for example, compstatin, N-acetylaspartylglutamic acid (NAAGA), and the like. As used herein the term "complement activator" refers to any compound, composition, or protein that increases or activates complement activity. The increase in complement activity may be incremental (e.g., a 10%, 20%, 30%, 40%, 50%, 60%, 70%, 80%, or 90% increase in activity). A complement activator may be a soluble or membrane-bound protein such as, for example, human Ig isotype $G_1$ (Ig$G_1$), human Ig isotype M (IgM), mouse Ig isotype $G_3$ (Ig$G_3$), and mouse IgM Fc, as well as cobra venom factor (CVF) and biologically-active fragments thereof, such as the Fc domain of Ig proteins, such as human Ig$G_1$ Fc domain, human IgM Fc domain, mouse Ig$G_3$ Fc domain, and mouse IgM Fc domain. Complement activators may also include, for example, hybrid CVF molecules comprising a CVF portion and a complement component 3 (C3) portion, such as those described in Fritzinger et al., "Functional characterization of human C3/cobra venom factor hybrid proteins for therapeutic complement depletion," Develop. Comp. Immunol. 33(1):105-116 (2009). Those hybrids comprise proteins in which the 113 or 315 C-terminal residues of C3 were replaced with corresponding CVF sequences.

A number of endogenous soluble and membrane-bound proteins that inhibit complement have been identified. These complement inhibitor proteins include, but are not limited to, membrane cofactor protein (MCP), decay accelerating factor (DAF/CD55), CD59, mouse complement receptor 1-related gene/protein y (Crry), human complement receptor 1 (CR1) and factor H.

As used herein, the term "membrane cofactor protein," "MCP," or "CD46" refers to a widely distributed C3b/C4b-binding cell surface glycoprotein which inhibits complement activation on host cells and serves as a cofactor for the factor I-mediated cleavage of C3b and C4b, including homologs thereof. T. J. Oglesby et al., J. Exp. Med. (1992) 175:1547-1551. MCP belongs to a family known as the regulators of complement activation ("RCA"). Family members share certain structural features, comprising varying numbers of short consensus repeat (SCR) domains, which are typically between 60 and 70 amino acids in length. Beginning at its amino-terminus, MCP comprises four SCRs, a serine/threonine/proline-enriched region, an area of undefined function, a transmembrane hydrophobic domain, a cytoplasmic anchor and a cytoplasmic tail. It is understood that species and strain variations exist for the disclosed peptides, polypeptides, and proteins, and that human MCP or biologically active fragments thereof encompass all species and strain variations.

SEQ ID NO:1 represents the full-length human MCP amino acid sequence (see, e.g., UniProtKB/Swiss-Prot. Accession No. P15529). Amino acids 1-34 correspond to the signal peptide, amino acids 35-343 correspond to the extracellular domain, amino acids 344-366 correspond to the transmembrane domain, and amino acids 367-392 correspond to the cytoplasmic domain. In the extracellular domain, amino acids 35-96 correspond to SCR 1, amino acids 97-159 correspond to SCR 2, amino acids 160-225 correspond to SCR 3, amino acids 226-285 correspond to SCR 4, and amino acids 302-326 correspond to the serine/threonine-rich domain. It is understood that species and strain variations exist for the disclosed peptides, polypeptides, and proteins, and that MCP or biologically active fragments thereof encompass all species and strain variations. As used herein, the term "biologically active" fragment of MCP refers to any soluble fragment lacking both the cytoplasmic domain and the transmembrane domain, including fragments comprising, consisting essentially of or consisting of 1, 2, 3, or 4 SCR domains, with or without the serine/threonine-rich domain, having some or all of the complement inhibitory activity of the full-length human MCP protein. In some embodiments, the complement inhibitor portion comprises full-length human MCP (amino acids 35-392 of SEQ ID NO:1), the extracellular domain of human MCP (amino acids 35-343 of SEQ ID NO:1), or SCRs 1-4 of human MCP (amino acids 35-285 of SEQ ID NO:1).

Decay accelerating factor, also referred to as CD55 (DAF/CD55) (SEQ ID NO:2 and SEQ ID NO:3), is an ~70 kiloDalton (kDa) membrane-bound glycoprotein which inhibits complement activation on host cells Like several other complement regulatory proteins, DAF comprises several approximately 60 amino acid repeating motifs termed short consensus repeats (SCR).

As used herein, the term "decay accelerating factor," "DAF," or "CD55" refers to a seventy kilodalton ("kDa") membrane glycoprotein comprising four short consensus repeat (SCR) domains followed by a heavily O-glycosylated serine/threonine-rich domain at the C-terminus that elevates the molecule from the membrane surface, followed by a glycosylphosphatidylinositol ("GPI") anchor. DAF protects the cell surface from complement activation by dissociating membrane-bound C3 convertases that are required to cleave complement protein C3 and to amplify the complement cascade. DAF prevents assembly or accelerates decay of both the C3- and C5-convertases of the alternative and classical complement pathways.

SEQ ID NO:2 represents the full-length human DAF amino acid sequence (see, e.g., UniProtKB/Swiss-Prot. Accession No. P08173); SEQ ID NO:3 represents the full-length mouse DAF amino acid sequence (see, e.g., UniProtKB/Swiss-Prot. Accession No. Q61475). In the human DAF sequence, amino acids 1-34 correspond to the signal peptide, amino acids 35-353 appear in the mature protein, and amino acids 354-381 are removed from the polypeptide after translation. Within the mature protein, amino acids 35-96 correspond to SCR 1, amino acids 96-160 correspond to SCR 2, amino acids 161-222 correspond to SCR 3, amino acids 223-285 correspond to SCR 4, and amino acids 287-353 correspond to the O-glycosylated serine/threonine-rich domain. The GPI anchor is attached to human DAF at a serine at position 353. In the mouse DAF sequence, amino acids 1-34 correspond to the signal peptide, amino acids 35-362 appear in the mature protein, and amino acids 363-390 are removed from the polypeptide after translation. Within the mature protein, amino acids 35-96 correspond to SCR 1, amino acids 97-160 correspond to SCR 2, amino acids 161-222 correspond to SCR 3, amino acids 223-286 correspond to SCR 4, and amino acids 288-362 correspond to the O-glycosylated serine/threonine-rich domain. The GPI anchor is attached to mouse DAF at a serine at position 362. It is understood that species and strain variations exist for the disclosed peptides, polypeptides, and proteins, and that DAF or biologically active fragments thereof encompass all species and strain variations. As used herein, the term "biologically active" fragment of DAF refers to any fragment of DAF lacking a GPI anchor and/or the amino acid to which it is attached (i.e., Ser-353), including any fragments of the full-length DAF protein comprising, consisting essentially of or consisting of 1, 2, 3, or 4 SCR domains, with or without the O-glycosylated serine/threonine-rich domain, having some or all the complement inhibitory activity of the full-length DAF protein.

As used herein, the term "CD59" refers to a membrane-bound 128 amino acid glycoprotein that potently inhibits the membrane attack complex (MAC) of complement. CD59 acts by binding to the C8 and/or C9 components of the MAC during assembly, ultimately preventing incorporation of the multiple copies of C9 required for complete formation of the osmolytic pore at the heart of the MAC. CD59 is both N- and O-glycosylated. The N-glycosylation comprises primarily bi- or tri-antennary structures with and without lactosamine and outer arm fucose residues, with variable sialylation present at some sites. Like DAF, CD59 is anchored in the cell membrane by a glycosylphosphatidylinositol ("GPI") anchor, which is attached to an asparagine at amino acid 102. Soluble forms of CD59 (sCD59) have been produced, but they generally have low functional activity in vitro, particularly in the presence of serum, suggesting that unmodified sCD59 has little or no therapeutic efficacy. See, e.g., S. Meri et al., "Structural composition and functional characterization of soluble CD59: heterogeneity of the oligosaccharide and glycophosphoinositol (GPI) anchor revealed by laser-desorption mass spectrometric analysis," *Biochem. J.*:923-935 (1996).

SEQ ID NO:4 represents the full-length human CD59 amino acid sequence (see, e.g., UniProtKB/Swiss-Prot. Accession No. P13987); SEQ ID NO:5 represents the full-length mouse CD59 sequence, isoform A (see, e.g., UniProtKB/Swiss-Prot. Accession No. O55186); SEQ ID NO:6 represents the full-length mouse CD59 sequence, isoform B (see, e.g., UniProtKB/Swiss-Prot. Accession No. P58019). In the human CD59 sequence, amino acids 1-25 of SEQ ID NO:4 correspond to the leader peptide, amino acids 26-102 of SEQ ID NO:4 correspond to the mature protein, and amino acids 103-128 of SEQ ID NO:4 are removed after translation. The GPI anchor is attached to CD59 at an asparagine at position 102 of SEQ ID NO:4. In isoform A of the mouse CD59 sequence, amino acids 1-23 of SEQ ID NO:5 correspond to the leader peptide, amino acids 24-96 of SEQ ID NO:5 correspond to the mature protein, and amino acids 97-123 of SEQ ID NO:5 are removed after translation. The GPI anchor is attached to CD59 at a serine at position 96 of SEQ ID NO:5. In isoform B of the mouse CD59 sequence, amino acids 1-23 of SEQ ID NO:6 correspond to the leader peptide, amino acids 24-104 of SEQ ID NO:6 correspond to the mature protein, and amino acids 105-129 of SEQ ID NO:6 are removed after translation. The GPI anchor is attached to CD59 at an asparagine at position 104 of SEQ ID NO:6. It is understood that species and strain variations exist for the disclosed peptides, polypeptides, and proteins, and that CD59 or biologically active fragments thereof encompass all species and strain variations.

As used herein, the term "biologically active" fragment of human CD59 refers to any fragment of human CD59 lacking a GPI anchor and/or the amino acid to which it is attached (i.e., Asn-102), including any fragments of the full-length human CD59 protein having some or all the complement inhibitory activity of the full-length CD59 protein; and the term "biologically active" fragment of mouse CD59 refers to any fragment of mouse CD59 isoform A or isoform B lacking a GPI anchor and/or the amino acid to which it is attached (i.e., Ser-96 of isoform A, or Asp-104 of isoform B), including any fragments of either full-length mouse CD59 protein isoform having some or all the complement inhibitory activity of the full-length CD59 protein.

As used herein, the term "mouse complement receptor 1-related gene/protein y" or "Crry" refers to a membrane-bound mouse glycoprotein that regulates complement activation, including homologs thereof. Crry regulates complement activation by serving as a cofactor for complement factor I, a serine protease which cleaves C3b and C4b deposited on host tissue. Crry also acts as a decay-accelerating factor, preventing the formation of C4b2a and C3bBb, the amplification convertases of the complement cascade.

SEQ ID NO:7 represents the full-length mouse Crry protein amino acid sequence. Amino acids 1-40 correspond to the leader peptide, amino acids 41-483 of SEQ ID NO:7 correspond to the mature protein, comprising amino acids 41-405 of SEQ ID NO:7, corresponding to the extracellular domain, amino acids 406-426 of SEQ ID NO:7, corresponding to the transmembrane domain, and amino acids 427-483 of SEQ ID NO:7, corresponding to the cytoplasmic domain. In the extracellular domain, amino acids 83-143 of SEQ ID NO:7 correspond to SCR 1, amino acids 144-205 of SEQ ID NO:7 correspond to SCR 2, amino acids 206-276 of SEQ ID NO:7 correspond to SCR 3, amino acids 277-338 of SEQ ID NO:7 correspond to SCR 4, and amino acids 339-400 of SEQ ID NO:7 correspond to SCR 5. It is understood that species and strain variations exist for the disclosed peptides, polypeptides, and proteins, and that mouse Crry protein or biologically active fragments thereof encompasses all species and strain variations. As used herein, the term "biologically active" fragment of mouse Crry protein refers to any soluble fragment of mouse Crry lacking the transmembrane domain and the cytoplasmic domain, including fragments comprising, consisting essentially of or consisting of 1, 2, 3, 4, or 5 SCR domains, including any fragments of the full-length mouse Crry protein having some or all the complement inhibitory activity of the full-length Crry protein.

As used herein, the term "complement receptor 1," "CR1," or "CD35" refers to a human gene encoding a protein of 2039 amino acids, with a predicted molecular weight of 220 kilodaltons ("kDa"), including homologs thereof. The gene is expressed principally on erythrocytes, monocytes, neutrophils, and B cells, but is also present on some T lymphocytes, mast cells, and glomerular podocytes. CR1 protein is typically expressed at between 100 and 1000 copies per cell. CR1 is the main system for processing and clearance of complement-opsonized immune complexes. CR1 negatively regulates the complement cascade, mediates immune adherence and phagocytosis, and inhibits both the classic and alternative complement pathways. The full-length CR1 protein comprises a 42 amino acid signal peptide, an extracellular domain of 1930 amino acids, a 25 amino acid transmembrane domain, and a 43 amino acid C-terminal cytoplasmic domain. The extracellular domain of CR1 has 25 potential N-glycosylation signal sequences, and comprises 30 short consensus ("SCR") domains, also known as complement control protein (CCP) repeats, or sushi domains, each 60 to 70 amino acids long. The sequence homology between SCRs ranges between 60-99 percent. The 30 SCR domains are further grouped into four longer regions termed long homologous repeats ("LHRs"), each encoding approximately 45 kDa segments of the CR1 protein, designated LHR-A, -B, -C, and -D. The first three comprise seven SCR domains each, while LHR-D comprises 9 SCR domains. The active sites on the extracellular domain of CR1 protein include a C4b-binding site with lower affinity for C3b in SCRs 1-4 comprising amino acids 42-295, a C3b-binding site with lower affinity for C4b in SCRs 8-11 comprising amino acids 490-745, a C3b-binding site with lower affinity for C4b in SCRs 15-18 comprising amino acids 940-1196, and a C1q-binding site in SCRs 22-28 comprising amino acids 1394-1842.

SEQ ID NO:8 represents the full-length human CR1 amino acid sequence (see, e.g., UniProtKB/Swiss-Prot. Accession No. P17927). Amino acids 1-41 correspond to the signal peptide, amino acids 42-2039 correspond to the mature protein, comprising amino acids 42-1971, corresponding to the extracellular domain, amino acids 1972-1996, corresponding to the transmembrane domain, and amino acids 1997-2039, corresponding to the cytoplasmic domain In the extracellular domain, amino acids 42-101 correspond to SCR 1, 102-163 correspond to SCR2, amino acids 164-234 correspond to SCR3, amino acids 236-295 correspond to SCR4, amino acids 295-355 correspond to SCR5, amino acids 356-418 correspond to SCR6, amino acids 419-489 correspond to SCR7, amino acids 491-551 correspond to SCR8, amino acids 552-613 correspond to SCR9, amino acids 614-684 correspond to SCR10, amino acids 686-745 correspond to SCR11, amino acids 745-805 correspond to SCR12, amino acids 806-868 correspond to SCR13, amino acids 869-939 correspond to SCR14, amino acids 941-1001 correspond to SCR15, amino acids 1002-1063 correspond to SCR16, amino acids 1064-1134 correspond to SCR17, amino acids 1136-1195 correspond to SCR18, amino acids 1195-1255 correspond to SCR 19, amino acids 1256-1318 correspond to SCR 20, amino acids 1319-1389 correspond to SCR 21, amino acids 1394-1454 correspond to SCR 22, amino acids 1455-1516 correspond to SCR 23, amino acids 1517-1587 correspond to SCR 24, amino acids 1589-1648 correspond to SCR 25, amino acids 1648-1708 correspond to SCR 26, amino acids 1709-1771 correspond to SCR 27, amino acids 1772-1842 correspond to SCR 28, amino acids 1846-1906 correspond to SCR 29, amino acids 1907-1967 correspond to SCR 30. It is understood that species and strain variations exist for the disclosed peptides, polypeptides, and proteins, and that CR1 protein or biologically active fragments thereof encompass all species and strain variations. As used herein, the term "biologically active" fragment of CR1 protein refers to any soluble fragment of CR1 lacking the transmembrane domain and the cytoplasmic domain, including fragments comprising, consisting essentially of or consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 SCR domains, including any fragments of the full-length CR1 protein having some or all the complement inhibitory activity of the full-length CR1 protein.

As used herein, the term "complement factor H," "factor H," or "FH" refers to complement factor H, a single polypeptide chain plasma glycoprotein, including homologs thereof. The protein is composed of 20 conserved short consensus repeat (SCR) domains of approximately 60 amino acids, arranged in a continuous fashion like a string of beads, separated by short linker sequences of 2-6 amino acids each. Factor H binds to C3b, accelerates the decay of the alternative pathway C3-convertase (C3bBb), and acts as a cofactor for the proteolytic inactivation of C3b. In the presence of factor H, proteolysis by factor I results in the cleavage and inactivation of C3b. Factor H has at least three distinct binding domains for C3b, which are located within SCRs 1-4, SCRs 5-8, and SCRs 19-20. Each domain binds to a distinct region within the C3b protein: the N-terminal sites bind to native C3b; the second site, located in the middle region of factor H, binds to the C3c fragment and the site located within SCR19 and 20 binds to the C3d region. In addition, factor H also contains binding sites for heparin, which are located within SCR 7, SCRs 5-12, and SCR 20 of factor H and overlap with those of the C3b binding sites. Structural and functional analyses have shown that the domains for the complement inhibitory activity of factor H are located within the first four N-terminal SCR domains.

SEQ ID NO:9 represents the full-length human factor H amino acid sequence (see, e.g., UniProtKB/Swiss-Prot. Accession No. P08603); SEQ ID NO:10 represents the full-length mouse factor H amino acid sequence (see, e.g., UniProtKB/Swiss-Prot. Accession No. P06909). In the human factor H sequence, amino acids 1-18 of SEQ ID NO:9 correspond to the signal peptide, and amino acids 19-1231 of SEQ ID NO:9 correspond to the mature protein. Within that protein, amino acids 21-80 of SEQ ID NO:9 correspond to SCR 1, amino acids 85-141 of SEQ ID NO:9 correspond to SCR 2, amino acids 146-205 of SEQ ID NO:9 correspond to SCR 3, amino acids 210-262 of SEQ ID NO:9 correspond to SCR 4, and amino acids 267-320 of SEQ ID NO:9 correspond to SCR 5. In the mouse factor H sequence, amino acids 1-18 of SEQ ID NO:10 correspond to the signal peptide, and amino acids 19-1234 of SEQ ID NO:10 correspond to the mature protein. Within that protein, amino acids 19-82 of SEQ ID NO:10 correspond to SCR 1, amino acids 83-143 of SEQ ID NO:10 correspond to SCR 2, amino acids 144-207 of SEQ ID NO:10 correspond to SCR 3, amino acids 208-264 of SEQ ID NO:10 correspond to SCR 4, and amino acids 265-322 of SEQ ID NO:10 correspond to SCR 5. It is understood that species and strain variations exist for the disclosed peptides, polypeptides, and proteins, and that factor H or biologically active fragments thereof encompass all species and strain variations.

As used herein, the term "biologically active" fragment of factor H refers to any portion of a factor H protein having some or all the complement inhibitory activity of the full-length factor H protein, and includes, but is not limited to, factor H fragments comprising SCRs 1-4, SCRs 1-5, SCRs 1-8, SCRs 1-18, SCRs 19-20, or any homolog of a naturally-occurring factor H or fragment thereof, as described in detail below. In some embodiments, the biologically active fragment of factor H has one or more of the following properties: (1) binding to C-reactive protein (CRP), (2) binding to C3b, (3) binding to heparin, (4) binding to sialic acid, (5) binding to endothelial cell surfaces, (6) binding to cellular integrin receptor, (7) binding to pathogens, (8) C3b co-factor activity, (9) C3b decay-acceleration activity, and (10) inhibiting the alternative complement pathway.

In some embodiments, the complement modulator portion of the construct comprises a complement inhibitor or biologically active fragment thereof. In some embodiments, the complement inhibitor is selected from the group consisting of human MCP, human DAF, mouse DAF, human CD59, mouse CD59 isoform A, mouse CD59 isoform B, mouse Crry protein, human CR1, human factor H, or mouse factor H, or a biologically active fragment thereof.

In some embodiments, the complement inhibitor portion of the construct comprises full-length human MCP (SEQ ID NO:1). In some embodiments, the complement inhibitor portion of the construct comprises a biologically active fragment of human MCP (SEQ ID NO:1). In some embodiments, the biologically active fragment of human MCP is selected from the group consisting of SCRs 1-4 (amino acids 35-285 of SEQ ID NO:1), SCRs 1-4 plus the serine/threonine-rich domain (amino acids 35-326 of SEQ ID NO:1), and the extracellular domain of MCP (amino acids 35-343 of SEQ ID NO:1).

In some embodiments, the complement inhibitor portion of the construct comprises full-length human DAF. In some embodiments, the complement inhibitor portion of the construct comprises a biologically active fragment of human DAF (SEQ ID NO:2). In some embodiments, the biologically active fragment of human DAF is selected from the group consisting of SCRs 1-4 (amino acids 25-285 of SEQ ID NO:2) and SCRs 1-4 plus the O-glycosylated serine/threonine-rich domain (amino acids 25-353 of SEQ ID NO:2). In some embodiments, the complement inhibitor portion of the construct comprises full-length mouse DAF (SEQ ID NO:3). In some embodiments, the complement inhibitor portion of the construct comprises a biologically active fragment of mouse DAF. In some embodiments, the biologically active fragment of mouse DAF is selected from the group consisting of SCRs 1-4 (amino acids 35-286 of SEQ ID NO:3) and SCRs 1-4 plus the O-glycosylated serine/threonine-rich domain (amino acids 35-362 of SEQ ID NO:3).

In some embodiments, the complement inhibitor portion of the construct comprises full-length human CD59 (SEQ ID NO:4). In some embodiments, the complement inhibitor portion of the construct comprises a biologically active fragment of human CD59 (SEQ ID NO:4). In some embodiments, the biologically active fragment of human CD59 comprises the extracellular domain of human CD59 lacking its GPI anchor (amino acids 26-101 of SEQ ID NO:4). In some embodiments, the complement inhibitor portion of the construct comprises full-length mouse CD59, isoform A (SEQ ID NO:5). In some embodiments, the complement inhibitor portion of the construct comprises a biologically active fragment of mouse CD59, isoform A (SEQ ID NO:5). In some embodiments, the biologically active fragment of mouse CD59, isoform A comprises the extracellular domain of mouse CD59, isoform A lacking its GPI anchor (amino acids 24-95 of SEQ ID NO:5). In some embodiments, the complement inhibitor portion of the construct comprises full-length mouse CD59, isoform B (SEQ ID NO:6). In some embodiments, the complement inhibitor portion of the construct comprises a biologically active fragment of mouse CD59, isoform B (SEQ ID NO:6). In some embodiments, the biologically active fragment of mouse CD59, isoform B comprises the extracellular domain of mouse CD59, isoform B lacking its GPI anchor (amino acids 24-103 of SEQ ID NO:6).

In some embodiments, the complement inhibitor portion of the construct comprises full-length mouse Crry protein (SEQ ID NO:7). In some embodiments, the complement inhibitor portion of the construct comprises a biologically active fragment of mouse Crry protein (SEQ ID NO:7). In some embodiments, the biologically active fragment of mouse Crry protein is selected from the group consisting of SCRs 1-5 (amino acids 41-400 of SEQ ID NO:7) and the extracellular domain of mouse Crry protein (amino acids 41-405 of SEQ ID NO:7).

In some embodiments, the complement inhibitor portion of the construct comprises full-length human CR1 protein (SEQ ID NO:8). In some embodiments, the complement inhibitor portion of the construct comprises a biologically active fragment of human CR1 protein (SEQ ID NO:8). In some embodiments, the biologically active fragment of human CR1 protein is selected from the group consisting of SCRs 1-4 (amino acids 42-295 of SEQ ID NO:8), SCRs 1-10 (amino acids 42-684 of SEQ ID NO:8), SCRs 8-11 (amino acids 490-745 of SEQ ID NO:8), SCRs 15-18 (amino acids 940-1196 of SEQ ID NO:8), and SCRs 22-28 (amino acids 1394-1842 of SEQ ID NO:8).

In some embodiments, the complement inhibitor portion of the construct comprises full-length human (SEQ ID NO:9) or mouse (SEQ ID NO:10) factor H. In some embodiments, the complement inhibitor portion of the construct comprises a biologically active fragment of human (SEQ ID NO:9) or mouse (SEQ ID NO:10) factor H. In some embodiments, the biologically active fragment of human factor H (SEQ ID NO:9) is selected from the group consisting of SCRs 1-4 (amino acids 21-262 of SEQ ID NO:9), SCRs 1-5 of factor H (amino acids 21-320 of SEQ ID NO:9), SCRs 1-8 of factor H (amino acids 21-507 of SEQ ID NO:9), and SCRs 1-18 of factor H (amino acids 21-1104 of SEQ ID NO:9). In some embodiments, the biologically active fragment of mouse factor H (SEQ ID NO:10) is selected from the group consisting of SCRs 1-4 (amino acids 19-264 of SEQ ID NO:10), SCRs 1-5 of factor H (amino acids 19-322 of SEQ ID NO:10), SCRs 1-8 of factor H (amino acids 19-507 of SEQ ID NO:10), and SCRs 1-18 of factor H (amino acids 19-1109 of SEQ ID NO:10). In some embodiments, the biologically active fragment of human (SEQ ID NO:9) or mouse (SEQ ID NO:10) factor H comprises (and in some embodiments consists of or consists essentially of) at least the first four N-terminal SCR domains of factor H, including for example, at least any of the first 5, 6, 7, 8, 9, 10, 11, 12, 13, 14, 15, 16, 17, 18, or more N-terminal SCR domains of factor H.

In some embodiments, the complement inhibitor portion is an antibody (or an antigen-binding fragment thereof) that binds to a complement component, e.g., a complement component selected from the group consisting of C1, C1q, C1s, C2, C2a, C3, C3a, C3b, C4, C4b, C5, C5a, C5b, C6, C7, C8, and C9. The complement polypeptides to which the antibodies or antigen-binding fragments thereof bind can be, in some embodiments, human polypeptides, e.g., human C1, C1q, C1s, C2, C2a, C3, C3a, C3b, C4, C4b, C5, C5a, C5b, C6, C7, C8, C9, factor B, factor D, or properdin polypeptides. The amino acid sequences for the foregoing complement proteins are well-known in the art as are methods for preparing the proteins or fragments thereof for use in preparing an antibody (or antigen-binding fragment thereof) specific for one or more of the complement proteins. Suitable methods are also described and exemplified herein.

Exemplary anti-complement protein antibodies, which are suitable for incorporation into the fusion proteins described herein and for subsequent use in any of the methods described herein, are also well known in the art. For example, antibodies that bind to complement component C5 and inhibit the cleavage of C5 into fragments C5a and C5b include, e.g., eculizumab (Soliris®; Alexion Pharmaceuticals, Inc., Cheshire, Conn.) and pexelizumab (Alexion Pharmaceuticals, Inc., Cheshire, Conn.). See, e.g., Kaplan (2002) Curr Opin Investig Drugs 3(7):1017-23; Hill (2005) Clin Adv Hematol Oncol 3(11):849-50; Rother et al. (2007) Nature Biotechnol 25(11):1256-1488; Whiss (2002) Curr Opin Investig Drugs 3(6):870-7; Patel et al. (2005) Drugs Today (Barc) 41(3):165-70; and Thomas et al. (1996) Mol Immunol. 33(17-18):1389-401.

In some embodiments, the anti-05 antibody can bind to an epitope in the alpha chain of the human complement component C5 protein. Antibodies that bind to the alpha chain of C5 are described in, for example, PCT application publication no. WO 2010/136311 and U.S. Pat. No. 6,355,245.

In some embodiments, the anti-05 antibody can bind to an epitope in the beta chain of the human complement component C5 protein. Antibodies that bind to the C5 beta chain are described in, e.g., Moongkarndi et al. (1982) Immunobiol 162:397; Moongkarndi et al. (1983) Immunobiol 165: 323; and Mollnes et al. (1988) Scand J Immunol 28:307-312.

Additional anti-05 antibodies, and antigen-binding fragments thereof, suitable for use in the fusion proteins described herein are described in, e.g., PCT application publication no. WO 2010/015608, the disclosure of which is incorporated herein by reference in its entirety.

Antibodies that bind to C3b and, for example, inhibit the C3b convertase are also well known in the art. For example, PCT application publication nos. WO 2010/136311, WO 2009/056631, and WO 2008/154251, the disclosures of each of which are incorporated herein by reference in their entirety. Antagonistic anti-C6 antibodies and anti-C7 antibodies have been described in, e.g., Brauer et al. (1996) Transplantation 61(4):588-594 and U.S. Pat. No. 5,679,345.

In some embodiments, the complement inhibitor portion is an anti-factor B antibody (such as the monoclonal antibody 1379 produced by ATCC Deposit No. PTA-6230). Anti-factor B antibodies are also described in, e.g., Ueda et al. (1987) J Immunol 138(4):1143-9; Tanhehco et al. (1999) Transplant Proc 31(5):2168-71; U.S. patent application publication nos. 20050260198 and 2008029911; and PCT publication no. WO 09/029,669.

In some embodiments, the complement inhibitor portion is an anti-factor D antibody, e.g., an antibody described in Pascual et al. (1990) J Immunol Methods 127:263-269; Sahu et al. (1993) Mol Immunol 30(7):679-684; Pascual et al. (1993) Eur J Immunol 23:1389-1392; Niemann et al. (1984) J Immunol 132(2):809-815; U.S. Pat. No. 7,439,331; or U.S. patent application publication no. 20080118506.

In some embodiments, the complement inhibitor portion is an anti-properdin antibody. Suitable anti-properdin antibodies are also well-known in the art and include, e.g., U.S. patent application publication nos. 20110014614 and PCT application publication no. WO2009110918.

In some embodiments, the complement inhibitor portion is an antibody (or antigen-binding fragment thereof) that specifically binds to a human complement component protein (e.g., human C5, C6, C7, C8, or C9). The terms "specific binding" or "specifically binds" refer to two molecules forming a complex (e.g., a complex between an antibody and C3b) that is relatively stable under physiologic conditions. Typically, binding is considered specific when the association constant ($K_a$) is higher than $10^6$ $M^{-1}$. Thus, an antibody can specifically bind to a C5 protein with a $K_a$ of at least (or greater than) $10^6$ (e.g., at least or greater than $10^7$, $10^8$, $10^9$, $10^{10}$, $10^{11}$, $10^{12}$, $10^{13}$, $10^{14}$, or $10^{15}$ orhigher) $M^{-1}$. Examples of antibodies that specifically bind to a human complement component C5 protein are described in, e.g., U.S. Pat. No. 6,355,245 and PCT application publication no. WO 2010/015608.

Methods for determining whether an antibody binds to a protein antigen and/or the affinity for an antibody to a protein antigen are known in the art and described herein. For example, the binding of an antibody to a protein antigen can be detected and/or quantified using a variety of techniques such as, but not limited to, Western blot, dot blot, plasmon surface resonance method (e.g., BIAcore system; Pharmacia Biosensor AB, Uppsala, Sweden and Piscataway, N.J.), or enzyme-linked immunosorbent assay (ELISA) assays. See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," 2nd Edition, Oxford University Press, NY, Oxford; Johne et al. (1993) J Immunol Meth. 160: 191-198; Jonsson et al. (1993) Ann Biol Clin 51:19-26; and Jonsson et al. (1991) Biotechniques 11:620-627. See also, U.S. Pat. No. 6,355,245.

A number of endogenous soluble proteins that activate complement have also been identified. These complement activators include, but are not limited to, various immunoglobulin (Ig) proteins, including human Ig isotype $G_1$ (IgG1), human Ig isotype M (IgM), mouse Ig isotype $G_3$ ($IgG_3$), and mouse IgM Fc, as well as cobra venom factor (CVF) and biologically-active fragments thereof. The complement activating activity of Ig proteins has been localized to the Fc domain. Therefore biologically-active fragments of complement-activating human and mouse Ig proteins include the Fc domain, such as human $IgG_1$ Fc domain, human IgM Fc domain, mouse $IgG_3$ Fc domain, and mouse IgM Fc domain.

As used herein, the terms "cobra venom factor," "CVF," and "C3b (Cobra)" refer to the non-toxic, complement-activating component of cobra venom. Like naturally occurring human C3b, CVF (SEQ ID NO:11) forms a complex, or convertase, with complement components Factor B and Factor D. This CVFBbD convertase is capable of activating C3 in a wide variety of species via the alternative complement pathway. CVFBbD convertase is Factor H-resistant and is therefore not blocked through the activity of Factor I or CR1 and can convert nearly 100% of the C3 to C3 fragments and C5 to C5 fragments. Levels of iC3b, C3a, C5b-9, C5a and the Factor B cleavage product Bb are all extremely high in CVF treated sera. The cloning and sequencing of CVF from the monocled cobra (*Naja kaouthia*) was reported in Fritzinger, et al., "Molecular cloning and derived primary structure of cobra venom factor," *Proc. Nat'l Acad. Sci. USA* 91(26):12775-779 (1994); the sequence was deposited in the GenBank database under Accession Number U09969. Both the Fritzinger et al. reference and the sequence deposited in GenBank under Accession Number U09969 are hereby incorporated herein by reference. The terms "cobra venom factor," "CVF," and "C3b (Cobra)" also refer to hybrid CVF molecules comprising a CVF portion and a complement component 3 (C3) portion, such as those described in Fritzinger et al., "Functional characterization of human C3/cobra venom factor hybrid proteins for therapeutic complement depletion," *Develop. Comp. Immunol.* 33(1):105-116 (2009), which is incorporated herein by reference. Those hybrids comprise proteins in which the 113 or 315 C-terminal residues of C3 were replaced with corresponding CVF sequences. Both hybrids formed stable convertases that exhibited C3-cleaving activity, although at different rates. Neither convertase cleaved C5. Both convertases showed partial resistance to inactivation by factors H and I, allowing them to deplete complement in human serum.

In some embodiments, the complement modulator portion of the construct comprises a complement activator or biologically-active fragment thereof. In some embodiments, the complement activator portion of the construct comprises an Ig protein or biologically-active fragment thereof. In some embodiments, the Ig protein or biologically-active fragment thereof comprises human $IgG_1$, human $IgG_1$ Fc domain, human IgM, human IgM Fc domain, mouse $IgG_3$, mouse $IgG_3$ Fc domain, mouse IgM, and mouse IgM Fc domain. In some embodiments, the complement activator portion of the construct comprises a cobra venom factor (CVF) or biologically-active fragment thereof.

In any of the embodiments described herein, the construct comprising a C3d-binding antibody or a biologically active fragment thereof and a complement inhibitor portion comprising human CD59, mouse CD59 isoform A, mouse CD59 isoform B, mouse Crry protein, human factor H, mouse factor H, human CR1, human MCP, human DAF or mouse DAF or a biologically active fragment thereof also includes an amino acid linker sequence linking the anti-C3d or anti-C3dg portion and the complement inhibitor portion (e.g., human CD59, mouse CD59 isoform A, mouse CD59 isoform B, mouse Crry protein, human factor H, mouse factor H, human CR1, human MCP, human DAF or mouse DAF or a biologically active fragment thereof).

In any of the embodiments described herein, the construct comprising a C3d-binding antibody, or a biologically active fragment thereof and a complement activator portion comprising human $IgG_1$, human IgM, mouse $IgG_3$, mouse IgM, and CVF or a biologically-active fragment thereof also includes an amino acid linker sequence linking the anti-C3d or anti-C3dg portion and the complement activator portion (e.g., human $IgG_1$, human IgM, mouse $IgG_3$, mouse IgM, and CVF or a biologically active fragment thereof).

In some embodiments, the targeting portion of the fusion molecule is joined (e.g., directly or by way of a linker) to the amino-terminus of the complement modulator polypeptide (e.g., the complement inhibitor polypeptide). In some embodiments, the targeting portion of the fusion molecule is joined (e.g., directly or by way of a linker) to the carboxy-terminus of the complement modulator polypeptide (e.g., the complement inhibitor polypeptide). For example, the disclosure features an exemplary construct comprising a single chain scFv fragment of an anti-C3d antibody and a complement inhibitor polypeptide (such as soluble CD59, MCP, or DAF), in which the carboxy-terminal end of the complement inhibitor polypeptide (e.g., the soluble CD59 polypeptide) is joined, optionally by way of a linker (e.g., $(GGGGS)_n$ or any other linker described herein), to the amino-terminal end of the heavy or light chain polypeptide portion of the scFv.

In some embodiments, a fusion molecule described herein comprises more than one (e.g., two, three, four, five, six, or seven or more) complement modulators, e.g., more than one complement inhibitor polypeptide. The two or more complement modulators can be the same or different. For example, a fusion protein described herein can comprise, in some embodiments, two or more soluble CD59 portions (e.g., soluble human CD59 portions). In another example, a fusion protein described herein can contain two or more complement inhibitor polypeptide portions, wherein one is a soluble human CD59 and another is soluble human MCP. Thus, e.g., a fusion molecule described herein can comprise: (a) a targeting portion (e.g., an anti-C3d antibody, an anti-C3dg antibody, or an antigen-binding fragment of either of the foregoing); (b) a first complement inhibitor polypeptide (e.g., a soluble form of CD59, e.g., human CD59); and (c) a second complement inhibitor polypeptide (e.g., a soluble form of DAF, e.g., a soluble form of human DAF). The complement inhibitor polypeptides can be, e.g., any of those described herein including variants and biologically active fragments thereof.

In some embodiments, e.g., wherein the targeting portion is an antibody (or an antigen-binding fragment thereof), the light chain of the targeting portion comprises at least one complement modulator (e.g., a complement inhibitor polypeptide) and the heavy chain comprises at least one complement modulator. The two or more complement modulators (e.g., complement inhibitor polypeptides) can be the same or different. For example, in some embodiments, the fusion protein comprises a targeting portion comprising the Fab fragment of anti-C3d (or anti-C3dg) antibody, wherein: (i) the light chain of the Fab fragment comprises (at its C-terminal end) a complement inhibitor polypeptide such as sDAF, sCD59, or any of the complement inhibitor polypeptides described herein and (ii) the heavy chain of the Fab fragment comprises (at its C-terminal end) the same or a different complement inhibitor polypeptide as in (i). Appropriate pairing of the two chains can be expected to occur as an inherent property of the Fab. The complement modulator (e.g., complement inhibitor) portion and the light chain or heavy chain of the Fab can be joined together directly or by way of a linker sequence (such as any of those described herein).

Immunomodulatory Agents

The disclosure also provides fusion molecules that are capable of inhibiting B cell activation or activity, by way of a first portion, and, by way of a second portion, inhibiting complement activity. The constructs are useful for, among other things, treating disorders such as, but not limited to, transplant rejection and autoimmune diseases (e.g., any of those described herein). As used herein, a compound (e.g., a small molecule or a polypeptide such as an antibody) which inhibits B cell activation or activity is one that inhibits any aspect of: (a) antigen-specific production or secretion of an antibody by a B cell or plasma cell; (b) proliferation of a B cell or plasma cell; (c) antigen processing by B cells; (d) antigen presentation by B cells to T cells; (e) upregulation of B cell cell surface markers; and/or (f) differentiation (e.g., antigen-driven) of a B cell into an antibody-producing plasma cell. For example, in some embodiments, the compound (in this case, the first portion of the construct) is one that inhibits one or more signaling or co-signaling events that are associated with the proliferation and/or differentiation of B cells into plasma cells. Exemplary compounds useful in the constructs described herein include, e.g., a molecule that binds to and inhibits the activity, expression, or surface presentation of a B cell receptor by a B cell. For example, the molecule can be an antibody or antigen-binding fragment thereof that binds to a B cell receptor and (a) inhibits its function, e.g., inhibits the interaction between B cell receptor and cognate receptors on T cells and/or (b) promotes the cellular internalization of the bound B cell receptor. In some embodiments, the compound is a molecule (e.g., an antibody or antigen-binding fragment thereof) that inhibits the interaction between a costimulatory molecule binding pair (e.g., a B cell-T cell costimulatory molecule binding pair), e.g., CD40 and CD40L. For example, the first portion can be an antagonist anti-CD40 antibody, an antagonist anti-CD40L antibody, or an antagonist antigen-binding fragment of either of the foregoing. Antagonist anti-CD40 antibodies, useful in conjunction with the constructs described herein, are well known in the art and include, e.g., HCD122 [Luqman et al. (2008) *Blood* 112(3):711-720]. See also the antagonist anti-CD40 antibodies disclosed in U.S. patent application publication no. 20090304706 and PCT application publication no. WO 07/129,895, the disclosures of each of which are incorporated herein by reference in their entirety. Suitable anti-CD40L antibodies are described in, e.g., PCT application publication no. WO 06/030220 and U.S. patent application publication no. 20030180292, the disclosures of which are incorporated herein in their entirety. Additional exemplary molecules that inhibit B cell activation or activity include, e.g., antagonists of CD19 such as an antagonist anti-CD19 antibody or antagonist CD19-binding fragments of such an antibody. Suitable antagonist anti-CD19 antibodies for use in the constructs described herein include, e.g., MDX-1342 (Bristol-Myers Squibb) Kardarelli et al. (2010) *Cancer Immunol Immunother* 59(2):257-2651.

While not bound by any particular theory or mechanism of action, the inventors believe that inhibition of the interaction between C3d or C3dg and CR2 on host B cells reduces B cell activation and/or activity, for example, by reducing antigen presentation by B cells to T cells and thus further inhibiting subsequent T cell activation. Thus, in some embodiments, the first portion, which inhibits B cell activation and/or activity, is, e.g., an antibody or an antigen-binding fragment thereof that: (i) binds to a natural ligand of CR2 such as C3d, C3dg, and iC3b and (ii) inhibits the interaction between CR2 and at least one of its natural ligands. The antibody or antigen-binding fragment thereof can be any of the antibodies described herein. The disclosure also embraces constructs comprising a first portion comprising an antagonist anti-CR2 antibody (or antigen-binding fragment thereof) that inhibits the interaction between CR2 and C3d or C3dg. Suitable anti-CR2 (CD21) antibodies are well known in the art and include, e.g., mAb OKB7 in Rao et al. OKB7, a monoclonal antibody that binds at or near the C3d binding site of human CR2. *Cellular Immunology* 1985; 93(2): 549-555. The amino acid sequence of human CR2 (NCBI accession no. NP_001006659) and mouse CR2 (NCBI accession no. NP_031784.1), for example, are well known in the art, as are methods for producing and isolating the protein (e.g., for use in immunizations associated with antibody production). See, e.g., Moore et al. (1987) *Proc Natl Acad Sci USA* 84:9194-9198; Prota et al. (2002) *Proc Natl Acad Sci USA* 99:10641-10646; and Weis et al. (1984) *Proc Natl Acad Sci USA* 81:881-885. Methods for making (e.g., immunizing mammals and isolating resultant antibodies) and testing such anti-CD21 antibodies are also known in the art and described herein. The second portion, which inhibits complement activity, present in the constructs described herein can be, e.g., any one of the complement inhibitor polypeptides (including variants and functional fragments) described herein.

Methods (e.g., competitive binding studies) for determining whether a molecule (e.g., an antibody or an antigen-binding fragment thereof such as an anti-CR2 antibody or an anti-C3d antibody) inhibits the interaction between two proteins (e.g., CR2 and a natural ligand of CR2 or CD40 and CD40L) are well-known in the art and described herein.

Linkers for Fusion Molecules

The present disclosure provides a fusion molecule described herein that may include two moieties or portions, e.g., the targeting moiety or portion and the active prophylactic, therapeutic, or diagnostic moiety or portion, which are directly fused together by a covalent bond or fused through a linker. Examples of linker sequences are known in the art, and include, for example, $(Gly_4Ser)$, $(Gly_4Ser)_2$, $(Gly_4Ser)_3$, $(Gly_3Ser)_4$, $(SerGly_4)$, $(SerGly_4)_2$, $(SerGly_4)_3$, and $(SerGly_4)_4$. Linking sequences can also comprise "natural" linking sequences found between different domains of complement factors. For example, VSVFPLE or EYFNKYSS, the linking sequence between the first two N-terminal short consensus repeat domains of human CR2, can be used. In some embodiments, the linking sequence between the fourth and the fifth N-terminal short consensus repeat domains of human CR2 (EEIF) is used.

Production Methods

The fusion proteins described herein can be produced using a variety of techniques known in the art of molecular biology and protein chemistry. For example, a nucleic acid encoding a fusion protein described herein can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of fusion proteins from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981)*Proc Natl Acad Sci USA* 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA*, 79:7147), polyoma virus (Deans et al. (1984) *Proc Natl Acad Sci USA* 81:1292), or SV40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include $CaPO_4$ precipitation, liposome fusion, lipofectin, electroporation, viral infection, dextran-mediated transfection, polybrene-mediated transfection, protoplast fusion, and direct microinjection.

Appropriate host cells for the expression of the fusion proteins include yeast, bacteria, insect, plant, and, as described above, mammalian cells. Of interest are bacteria such as *E. coli*, fungi such as *Saccharomyces cerevisiae* and *Pichia pastoris*, insect cells such as SF9, mammalian cell lines (e.g., human cell lines), as well as primary cell lines (e.g., primary mammalian cells). In some embodiments, the fusion proteins can be expressed in Chinese hamster ovary (CHO) cells or in a suitable myeloma cell line such as (NS0). Suitable cell lines also include, for example, BHK-21 (baby hamster kidney) cells; 293 (human embryonic kidney) cells; HMEpC (Human Mammary Epithelial cells; 3T3 (mouse embryonic fibroblast) cells.

The targeting and active prophylactic or therapeutic moieties may optionally be directly joined to each other, or may optionally be joined via a linker moiety. Where the targeting and active moieties are directly joined, the hybrid vector is made where the DNA encoding the targeting and active moieties are themselves directly ligated to each other using known scientific methods. Where a linker moiety is used, the hybrid vector is made where the DNA encoding the targeting moiety is ligated to DNA encoding one end of the linker moiety; and the DNA encoding the active moiety is ligated to the other end of the linker moiety. Methods are known for performing such ligations in proper orientation. Such ligation may be performed either in series, or as a three way ligation. Examples of sequences which may serve as the linker sequence in the present invention include short peptides of about 2 to about 15 amino acids in length. Among the peptide sequences useful as linkers in the present invention are (Gly-Ser)$_n$, where n=1 (SEQ ID NO:12), 2 (SEQ ID NO:13) 3 (SEQ ID NO:14), 4 (SEQ ID NO:15), 5 (SEQ ID NO:16), 6 (SEQ ID NO:17), 7 (SEQ ID NO:18), or 8 (SEQ ID NO:19); (GlyGlyGlySer)$_n$, where n=1 (SEQ ID NO:20), 2 (SEQ ID NO:21), 3 (SEQ ID NO:22), or 4 (SEQ ID NO:23); (GlySerSerGly)$_n$, where n=1 (SEQ ID NO:32), 2 (SEQ ID NO:33), 3 (SEQ ID NO:34), or 4 (SEQ ID NO:35). Other examples of sequences useful as the linker sequence in the present invention include one or more short conserved region (SCR) domains from one or more of the following complement-related proteins: Factor H; complement receptor 1; complement receptor 2; Factor B; DAF; and others.

As will be recognized by the skilled artisan, many active moieties which may be used in the present invention occur in nature as secreted proteins in conjunction with a signal or leader peptide and/or as a pro-peptide which undergoes further intra- or extra-cellular processing. In such cases, the hybrid vectors of the present invention may include one or more DNA sequences encoding such signal or leader peptides and/or one or more DNA sequences encoding such pro-peptide sequence, depending upon whether such secretion and/or processing is desired. Alternatively, the hybrid vectors of the present disclosure may include DNA sequences encoding a different signal or leader peptide and/or pro-peptide sequence chosen to optimize the expression and localization of the fusion protein. In most cases, the signal peptide may be omitted, as the targeting moiety will supply sufficient information for targeting of the active moiety to the desired tissue and cells within the subject's body.

In some embodiments, a fusion protein described herein can be expressed in, and purified from, transgenic animals (e.g., transgenic mammals). For example, a fusion protein described herein can be produced in transgenic non-human mammals (e.g., rodents, sheep or goats) and isolated from milk as described in, e.g., Houdebine (2002) *Curr Opin Biotechnol* 13(6):625-629; van Kuik-Romeijn et al. (2000) *Transgenic Res* 9(2):155-159; and Pollock et al. (1999) *J Immunol Methods* 231(1-2):147-157. Additional methods for producing proteins in mammalian milk products are described in, e.g., U.S. patent application publication nos. 200600105347 and 20040006776 and U.S. Pat. No. 7,045,676.

The fusion proteins described herein can be produced from cells by culturing a host cell transformed with the expression vector containing nucleic acid encoding the antibodies, under conditions, and for an amount of time, sufficient to allow expression of the proteins. Such conditions for protein expression will vary with the choice of the expression vector and the host cell, and will be easily ascertained by one skilled in the art through routine experimentation. For example, polypeptides expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. A fusion protein described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the fusion proteins can be isolated. The term "purified" or "isolated" as applied to any of the proteins described herein (e.g., a fusion protein described herein) refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

A fusion protein described herein can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, a fusion protein can be purified using a standard anti-fusion protein antibody affinity column. Ultrafiltration and diafiltration techniques, in conjunction with protein concentration, are also useful. See, e.g., Scopes (1994) "Protein Purification, $3^{rd}$ edition," Springer-Verlag, New York City, N.Y. The degree of purification necessary will vary depending on the desired use. In some instances, no purification of the expressed polypeptide thereof will be necessary.

Methods for determining the yield or purity of a purified polypeptide are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

In some embodiments, a fusion protein described herein can be synthesized de novo in whole or in part, using chemical methods well known in the art. For example, the component amino acid sequences can be synthesized by solid phase techniques, cleaved from the resin, and purified by preparative high performance liquid chromatography followed by chemical linkage to form a desired polypeptide. The composition of the synthetic peptides may be confirmed by amino acid analysis or sequencing.

Once expressed and/or purified, a fusion protein described herein can be assayed for any one of a numbered of desired properties using in vitro or in vivo assays such as any of those described herein. For example, a fusion protein described herein can be assayed for its ability to inhibit C5 convertase as described in, e.g., Heinen et al. (2009), supra.

In some embodiments, endotoxin can be removed from the fusion protein preparations. Methods for removing endotoxin from a protein sample are known in the art. For example, endotoxin can be removed from a protein sample using a variety of commercially available reagents including, without limitation, the ProteoSpin™ Endotoxin Removal Kits (Norgen Biotek Corporation), Detoxi-Gel Endotoxin Removal Gel (Thermo Scientific; Pierce Protein Research Products), MiraCLEAN® Endotoxin Removal Kit (Mirus), or Acrodisc™-Mustang® E membrane (Pall Corporation).

Methods for detecting and/or measuring the amount of endotoxin present in a sample (both before and after purification) are known in the art and commercial kits are available. For example, the concentration of endotoxin in a protein sample can be determined using the QCL-1000 Chromogenic kit (BioWhittaker), the *limulus amebocyte lysate* (LAL)-based kits such as the Pyrotell®, Pyrotell®-T, Pyrochrome®, Chromo-LAL, and CSE kits available from the Associates of Cape Cod Incorporated.

Following expression and purification, the fusion proteins described herein can be modified. The modifications can be covalent or non-covalent modifications. Such modifications can be introduced into the fusion proteins by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the fusion proteins described herein.

In some embodiments, a fusion protein described herein can be conjugated to a heterologous moiety. In embodiments where the heterologous moiety is a polypeptide, a fusion protein and a corresponding heterologous moiety described herein can be joined by way of fusion protein. The heterologous moiety can be, e.g., a heterologous polypeptide, a therapeutic agent (e.g., a toxin or a drug), or a detectable label such as, but not limited to, a radioactive label, an enzymatic label, a fluorescent label, or a luminescent label. Suitable heterologous polypeptides include, e.g., an antigenic tag (e.g., FLAG, polyhistidine, hemagglutinin (HA), glutathione-S-transferase (GST), or maltose-binding protein (MBP)) for use in purifying the antibodies. Heterologous polypeptides also include polypeptides that are useful as diagnostic or detectable markers, for example, luciferase, green fluorescent protein (GFP), or chloramphenicol acetyl transferase (CAT). Where the heterologous moiety is a polypeptide, the moiety can be incorporated into a fusion protein described herein, resulting in a fusion protein.

Conjugates

In some embodiments, the fusion molecules described herein are created by linkage of two independently produced polypeptide fragments, e.g., an antibody (e.g., a Fab fragment of an anti-C3d antibody) and a complement modulator polypeptide (e.g., a soluble form of CD59). Two proteins (e.g., a fusion protein described herein and a heterologous moiety or the two constituent parts of a fusion protein) can, in some embodiments, be chemically cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio)toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a fusion protein described herein can contain a heterologous moiety which is chemically linked to the fusion protein. For example, in some embodiments, a radioactive label can be directly conjugated to the amino acid backbone of the fusion protein (e.g., for use of the labeled fusion protein for in vivo imaging studies).

In some embodiments, the fusion proteins can be modified, e.g., with a moiety that improves the stabilization and/or retention of the antibodies in circulation, e.g., in blood, serum, or other tissues. For example, a fusion protein described herein can be PEGylated as described in, e.g., Lee et al. (1999) *Bioconjug Chem* 10(6): 973-8; Kinstler et al.

(2002) *Advanced Drug Deliveries Reviews* 54:477-485; and Roberts et al. (2002) *Advanced Drug Delivery Reviews* 54:459-476. The stabilization moiety can improve the stability, or retention of, the polypeptide by at least 1.5 (e.g., at least 2, 5, 10, 15, 20, 25, 30, 40, or 50 or more) fold.

In some embodiments, the fusion proteins described herein can be glycosylated. In some embodiments, a fusion protein described herein can be subjected to enzymatic or chemical treatment, or produced from a cell, such that the antibody has reduced or absent glycosylation. Methods for producing polypeptides with reduced glycosylation are known in the art and described in, e.g., U.S. Pat. No. 6,933,368; Wright et al. (1991) *EMBO J.* 10(10):2717-2723; and Co et al. (1993) *Mol Immunol* 30:1361.

Therapeutic Methods

The above-described constructs (e.g., fusion molecules) and antibodies (and antigen-binding fragments thereof) are useful in, inter alia, methods for treating or preventing a variety of complement-associated disorders in a subject. The compositions can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. An antibody or fusion protein described herein can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

In some embodiments, an antibody or fusion protein described herein is therapeutically delivered to a subject by way of local administration. As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

In some embodiments, an antibody, antigen-binding fragment thereof, or fusion protein described herein can be locally administered to a joint (e.g., an articulated joint). For example, in embodiments where the complement-associated disorder is arthritis, the complement inhibitor can be administered directly to a joint (e.g., into a joint space) or in the vicinity of a joint. Examples of intraarticular joints to which a fusion protein described herein can be locally administered include, e.g., the hip, knee, elbow, wrist, sternoclavicular, temperomandibular, carpal, tarsal, ankle, and any other joint subject to arthritic conditions. An antibody, antigen-binding fragment thereof, or fusion protein described herein can also be administered to bursa such as, e.g., acromial, bicipitoradial, cubitoradial, deltoid, infrapatellar, ischial, and any other bursa known in the art of medicine.

In some embodiments, an antibody, antigen-binding fragment thereof, or fusion protein described herein can be locally administered to the eye. As used herein, the term "eye" refers to any and all anatomical tissues and structures associated with an eye. The eye has a wall composed of three distinct layers: the outer sclera, the middle choroid layer, and the inner retina. The chamber behind the lens is filled with a gelatinous fluid referred to as the vitreous humor. At the back of the eye is the retina, which detects light. The cornea is an optically transparent tissue, which conveys images to the back of the eye. The cornea includes one pathway for the permeation of drugs into the eye. Other anatomical tissue structures associated with the eye include the lacrimal drainage system, which includes a secretory system, a distributive system and an excretory system. The secretory system comprises secretors that are stimulated by blinking and temperature change due to tear evaporation and reflex secretors that have an efferent parasympathetic nerve supply and secrete tears in response to physical or emotional stimulation. The distributive system includes the eyelids and the tear meniscus around the lid edges of an open eye, which spread tears over the ocular surface by blinking, thus reducing dry areas from developing.

In some embodiments, an antibody, antigen-binding fragment thereof, or fusion protein described herein is administered to the posterior chamber of the eye. In some embodiments, an antibody, antigen-binding fragment thereof, or fusion protein described herein is administered intravitreally. In some embodiments, an antibody, antigen-binding fragment thereof, or fusion protein described herein is administered trans-sclerally.

In some embodiments, e.g., in embodiments for treatment or prevention of a complement-associated pulmonary disorder such as COPD or asthma, an antibody, antigen-binding fragment thereof, or fusion protein described herein can be administered to a subject by way of the lung. Pulmonary drug delivery may be achieved by inhalation, and administration by inhalation herein may be oral and/or nasal. Examples of pharmaceutical devices for pulmonary delivery include metered dose inhalers, dry powder inhalers (DPIs), and nebulizers. For example, an antibody, antigen-binding fragment thereof, or fusion protein described herein can be administered to the lungs of a subject by way of a dry powder inhaler. These inhalers are propellant-free devices that deliver dispersible and stable dry powder formulations to the lungs. Dry powder inhalers are well known in the art of medicine and include, without limitation: the Turbo-Haler® (AstraZeneca; London, England) the AIR® inhaler (Alkermes®; Cambridge, Mass.); Rotahaler® (GlaxoSmithKline; London, England); and Eclipse™ (Sanofi-Aventis; Paris, France). See also, e.g., PCT Publication Nos. WO 04/026380, WO 04/024156, and WO 01/78693. DPI devices have been used for pulmonary administration of polypeptides such as insulin and growth hormone. In some embodiments, an antibody, antigen-binding fragment thereof, or fusion protein described herein can be intrapulmonarily administered by way of a metered dose inhaler. These inhalers rely on a propellant to deliver a discrete dose of a compound to the lungs. Examples of compounds administered by metered dose inhalers include, e.g., Astovent® (Boehringer-Ingelheim; Ridgefield, Conn.) and Flovent® (GlaxoSmithKline). See also, e.g., U.S. Pat. Nos. 6,170,717; 5,447,150; and 6,095,141.

In some embodiments, an antibody, antigen-binding fragment thereof, or fusion protein described herein can be administered to the lungs of a subject by way of a nebulizer. Nebulizers use compressed air to deliver a compound as a liquefied aerosol or mist. A nebulizer can be, e.g., a jet nebulizer (e.g., air or liquid-jet nebulizers) or an ultrasonic nebulizer. Additional devices and intrapulmonary administration methods are set forth in, e.g., U.S. Patent Application Publication Nos. 20050271660 and 20090110679, the disclosures of each of which are incorporated herein by reference in their entirety.

In some embodiments, an antibody, antigen-binding fragment thereof, or fusion protein described herein is present in unit dosage form, which can be particularly suitable for self-administration. A formulated product of the present disclosure can be included within a container, typically, for example, a vial, cartridge, prefilled syringe or disposable pen. A doser such as the doser device described in U.S. Pat. No. 6,302,855 may also be used, for example, with an injection system of the present disclosure.

An injection system of the present disclosure may employ a delivery pen as described in U.S. Pat. No. 5,308,341. Pen devices, most commonly used for self-delivery of insulin to patients with diabetes, are well known in the art. Such devices can comprise at least one injection needle (e.g., a 31 gauge needle of about 5 to 8 mm in length), are typically pre-filled with one or more therapeutic unit doses of a therapeutic solution, and are useful for rapidly delivering the solution to a subject with as little pain as possible.

One medication delivery pen includes a vial holder into which a vial of insulin or other medication may be received. The vial holder is an elongate generally tubular structure with proximal and distal ends. The distal end of the vial holder includes mounting means for engaging a double-ended needle cannula. The proximal end also includes mounting means for engaging a pen body which includes a driver and dose setting apparatus. A disposable medication (e.g., a high concentration solution of a fusion protein described herein) containing vial for use with the prior art vial holder includes a distal end having a pierceable elastomeric septum that can be pierced by one end of a double-ended needle cannula. The proximal end of this vial includes a stopper slidably disposed in fluid tight engagement with the cylindrical wall of the vial. This medication delivery pen is used by inserting the vial of medication into the vial holder. A pen body then is connected to the proximal end of the vial holder. The pen body includes a dose setting apparatus for designating a dose of medication to be delivered by the pen and a driving apparatus for urging the stopper of the vial distally for a distance corresponding to the selected dose. The user of the pen mounts a double-ended needle cannula to the distal end of the vial holder such that the proximal point of the needle cannula pierces the septum on the vial. The patient then selects a dose and operates the pen to urge the stopper distally to deliver the selected dose. The dose selecting apparatus returns to zero upon injection of the selected dose. The patient then removes and discards the needle cannula, and keeps the medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above. Accordingly, a medication delivery pen generally has a drive mechanism for accurate dosing and ease of use.

A dosage mechanism such as a rotatable knob allows the user to accurately adjust the amount of medication that will be injected by the pen from a prepackaged vial of medication. To inject the dose of medication, the user inserts the needle under the skin and depresses the knob once as far as it will depress. The pen may be an entirely mechanical device or it may be combined with electronic circuitry to accurately set and/or indicate the dosage of medication that is injected into the user. See, e.g., U.S. Pat. No. 6,192,891.

In some embodiments, the needle of the pen device is disposable and the kits include one or more disposable replacement needles. Pen devices suitable for delivery of the any one of the presently featured antibodies, antigen-binding fragments thereof, or fusion proteins described herein are also described in, e.g., U.S. Pat. Nos. 6,277,099; 6,200,296; and 6,146,361, the disclosures of each of which are incorporated herein by reference in their entirety. A microneedle-based pen device is described in, e.g., U.S. Pat. No. 7,556,615, the disclosure of which is incorporated herein by reference in its entirety. See also the Precision Pen Injector (PPI) device, Molly™, manufactured by Scandinavian Health Ltd.

The present disclosure also presents controlled-release or extended-release formulations suitable for chronic and/or self-administration of a medication such as an antibody, antigen-binding fragment thereof, or fusion protein described herein. The various formulations can be administered to a patient in need of treatment with the medication as a bolus or by continuous infusion over a period of time.

In some embodiments, a high concentration solution of an antibody, antigen-binding fragment thereof, or fusion protein described herein is formulated for sustained-release, extended-release, timed-release, controlled-release, or continuous-release administration. In some embodiments, depot formulations are used to administer the fusion protein to the subject in need thereof. In this method, the antibody, antigen-binding fragment thereof, or fusion protein described herein is formulated with one or more carriers providing a gradual release of active agent over a period of a number of hours or days. Such formulations are often based upon a degrading matrix which gradually disperses in the body to release the active agent.

In some embodiments, an antibody, antigen-binding fragment thereof, or fusion protein described herein is administered by way of intrapulmonary administration to a subject in need thereof. For example, an antibody, antigen-binding fragment thereof, or fusion protein described herein can be delivered by way of a nebulizer or an inhaler to a subject (e.g., a human) afflicted with a complement-associated pulmonary disorder such as asthma or COPD.

A "subject," as used herein, can be any mammal. For example, a subject can be a human, a non-human primate (e.g., orangutan, gorilla, macaque, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant).

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an antibody, antigen-binding fragment thereof, or a fusion protein described herein).

The term "preventing" is art-recognized, and when used in relation to a condition, is well understood in the art, and includes administration of a composition which reduces the frequency of, or delays the onset of, symptoms of a medical condition in a subject relative to a subject which does not receive a fusion protein described herein. Thus, prevention of a complement-associated disorder such as asthma includes, for example, reducing the extent or frequency of coughing, wheezing, or chest pain in a population of patients receiving a prophylactic treatment relative to an untreated control population, and/or delaying the occurrence of coughing or wheezing in a treated population versus an untreated control population, e.g., by a statistically and/or clinically significant amount.

In some embodiments, the present disclosure provides a method of specifically targeting a moiety or portion of a fusion molecule to a pre-defined area or compartment in vivo, thus increasing the local concentration of such moiety or portion in such area or compartment but not in other areas or compartments or increasing the accessibility of such moiety or portion to at least one pre-defined molecule located in such area or compartment, by the specific interaction between a targeting moiety or portion of such fusion molecule and a target molecule located in such area or compartment. In some embodiments, the present disclosure provides a method of specifically targeting an active or therapeutic moiety or portion of a fusion molecule to a surface of complement activation by an antibody or antigen-binding fragment thereof which is fused to such active or therapeutic moiety or portion and is able to specifically bind to a complement component protein. In some embodiments, such complement component protein is C3d or C3dg.

In some embodiments, the present disclosure provides a method of reducing, inhibiting, or preventing host humoral immune response by using a composition comprising an anti-C3d/C3dg antibody, or antigen-binding fragment thereof, or a fusion molecule comprising such antibody or fragment, as described in this application. In some embodiments, the present disclosure provides a method of reducing, inhibiting, or preventing host B cell activation by using a composition comprising an anti-C3d/C3dg antibody, or antigen-binding fragment thereof, or a fusion molecule comprising such antibody or fragment, as described herein.

In some embodiments, the present disclosure provides a method of treating, alleviating, or preventing a disease characterized with upregulated humoral immune response, compared to the normal host immune response without the disease onset, in a subject by using a composition comprising an anti-C3d/C3dg antibody, or antigen-binding fragment thereof, or a fusion molecule comprising such antibody or fragment, as described in this application. In some embodiments, the present disclosure provides a method of treating, alleviating or preventing a disease characterized with upregulated B cell activation, compared to the normal B cell activation level without the disease onset, in a subject by using a composition comprising an anti-C3d/C3dg antibody, or antigen-binding fragment thereof, or a fusion molecule comprising such antibody or fragment, as described herein.

In some embodiments, the present disclosure provides a method of treating a subject having a disease or preventing a subject from developing a disease, wherein the subject has upregulated humoral immune response, compared to the normal immune response level in a subject without such disease, using a composition comprising an anti-C3d/C3dg antibody, or antigen-binding fragment thereof, or a fusion molecule comprising such antibody or fragment, as described herein. In some embodiments, the present disclosure provides a method of treating a subject having a disease or preventing a subject from developing a disease, wherein the subject has upregulated B cell activation, compared to the normal B cell activation level in a subject without such disease, using a composition comprising an anti-C3d/C3dg antibody, or antigen-binding fragment thereof, or a fusion molecule comprising such antibody or fragment, as described herein.

In some embodiments, the present disclosure provides a method of modulating complement activity by using a composition comprising an anti-C3d/C3dg antibody, or antigen-binding fragment thereof, or a fusion molecule comprising such antibody or fragment, as described herein. In some embodiments, such fusion molecule comprises an anti-C3d/C3dg antibody, or antigen-binding fragment thereof, as the targeting moiety and a complement modulator as the active or therapeutic moiety.

In some embodiments, the present disclosure provides a method of increasing or activating complement activity by using a composition comprising an anti-C3d/C3dg antibody, or antigen-binding fragment thereof, or a fusion molecule comprising such antibody or fragment, as described herein. In some embodiments, such fusion molecule comprises an anti-C3d/C3dg antibody, or antigen-binding fragment thereof, as the targeting moiety and a complement activator or agonist as the active or therapeutic moiety.

In some embodiments, the present disclosure provides a method of decreasing or inhibiting complement activity by using a composition comprising an anti-C3d/C3dg antibody, or antigen-binding fragment thereof, or a fusion molecule comprising such antibody or fragment, as described herein. In some embodiments, such fusion molecule comprises an anti-C3d/C3dg antibody, or antigen-binding fragment thereof, as the targeting moiety and a complement inhibitor or antagonist as the active or therapeutic moiety.

In some embodiments, the present disclosure provides a method of treating, alleviating, or preventing a disease characterized with abnormal complement activity, compared to the normal complement activity without the disease onset, in a subject by using a composition comprising an anti-C3d/C3dg antibody, or antigen-binding fragment thereof, or a fusion molecule comprising such antibody or fragment and a complement modulator, as described herein. In some embodiments, the present disclosure provides a method of treating, alleviating or preventing a disease characterized with increased complement activity, compared to the normal complement activity without the disease onset, in a subject by using a composition comprising an anti-C3d/C3dg antibody, or antigen-binding fragment thereof, or a fusion molecule comprising such antibody or fragment and a complement inhibitor or antagonist, as described herein. In some embodiments, the present disclosure provides a method of treating, alleviating or preventing a disease characterized with decreased complement activity, compared to the normal complement activity without the disease onset, in a subject by using a composition comprising an anti-C3d/C3dg antibody, or antigen-binding fragment thereof, or a fusion molecule comprising such antibody or fragment and a complement activator or agonist, as described herein.

In some embodiments, the present disclosure provides a method of treating a subject having a disease or preventing a subject from developing a disease, wherein the subject has abnormal complement activity, compared to the normal complement activity in a subject without such disease, using a composition comprising an anti-C3d/C3dg antibody, or antigen-binding fragment thereof, or a fusion molecule comprising such antibody or fragment and a complement modulator, as described herein. In some embodiments, the present disclosure provides a method of treating a subject having a disease or preventing a subject from developing a disease, wherein the subject has increased complement activity, compared to the normal complement activity in a subject without such disease, using a composition comprising an anti-C3d/C3dg antibody, or antigen-binding fragment thereof, or a fusion molecule comprising such antibody or fragment and a complement inhibitor or antagonist, as described herein. In some embodiments, the present disclosure provides a method of treating a subject having a disease or preventing a subject from developing a disease, wherein the subject has decreased complement activity, compared to the normal complement activity in a subject without such disease, using a composition comprising an anti-C3d/C3dg antibody, or antigen-binding fragment thereof, or a fusion molecule comprising such antibody or fragment and a complement activator or agonist, as described herein.

In some embodiments, the present disclosure provides a method of synergizing the modulation of complement activity and at least one other in vivo function using a composition comprising a fusion molecule comprising an anti-C3d/C3dg antibody, or antigen-binding fragment thereof, and at least one another active or functional moiety or portion, as described herein. In some embodiments, such fusion molecule comprises an anti-C3d/C3dg antibody, or antigen-binding fragment thereof, as the targeting moiety and a complement inhibitor or antagonist as the active or therapeutic moiety, leading to a synergy of inhibiting both complement activation and humoral immune response. In some embodiments, the present disclosure provides a method of synergizing the inhibition of complement activity and humoral immune response by using a composition comprising a fusion molecule comprising an anti-CR2 antibody, or antigen-binding fragment thereof, and a complement inhibitor or antagonist.

In some embodiments, the present disclosure provides a method of treating, alleviating, or preventing a disease characterized with both increased complement activity and humoral immune response, compared to the normal complement activity and immune response without the disease onset, in a subject by using a composition comprising a fusion molecule comprising an anti-C3d/C3dg antibody, or antigen-binding fragment thereof, and a complement inhibitor or antagonist. In other embodiments, an anti-CR2 antibody, or antigen-binding fragment thereof, is fused to such complement inhibitor or antagonist for the method.

In some embodiments, the present disclosure provides a method of treating a subject having a disease or preventing a subject from developing a disease, wherein the subject has both increased complement activity and humoral immune response, compared to the normal complement activity and immune response in a subject without the disease, using a composition comprising a fusion molecule comprising an anti-C3d/C3dg antibody, or antigen-binding fragment thereof, and a complement inhibitor or antagonist. In other embodiments, an anti-CR2 antibody, or antigen-binding fragment thereof, is fused to such complement inhibitor or antagonist for the method.

In some embodiments, the present disclosure provides a method of synergizing at least two modulator functions using a composition comprising a fusion molecule comprising an anti-C3d/C3dg antibody, or antigen-binding fragment thereof, and at least two active or functional moieties or portions, as described herein. In some embodiments, such two active or functional moieties or portions are fused to the heavy and light chain of such antibody or fragment, respectively. Both the N-terminus and the C-terminus of the anti-C3d/C3dg antibody or antigen-binding fragment thereof can be used for the fusion to the active or functional moieties or portions in either direction. Generally the C-terminus of the antibody or antigen-binding fragment thereof is used for fusion since it may not disturb the antigen-binding activity. One example of the fusion molecule is an anti-C3d/C3dg antibody or Fab linked to both CD59 and DAF, each of which is on one of its heavy/light chains. Such a fusion protein will have an improved inhibitory function towards complement activation. Indications include, e.g., PNH patients. Another example is an anti-C3d/C3dg antibody or Fab fused to factor H (or equivalent) and to an anti-angiogenic peptide/protein (e.g. endostatin, angiostatin, and others reported in literature) for AMD patients.

As described above, the antibodies and biologically-active fragments or fusion molecules comprising such antibodies or fragments as the targeting moiety described herein can be used to treat a variety of complement-associated disorders such as, but not limited to: rheumatoid arthritis (RA); lupus nephritis; ischemia-reperfusion injury; atypical hemolytic uremic syndrome (aHUS); typical or infectious hemolytic uremic syndrome (tHUS); dense deposit disease (DDD); paroxysmal nocturnal hemoglobinuria (PNH); multiple sclerosis (MS); macular degeneration (e.g., age-related macular degeneration (AMD)); hemolysis, elevated liver enzymes, and low platelets (HELLP) syndrome; sepsis; dermatomyositis; diabetic retinopathy; thrombotic thrombocytopenic purpura (TTP); spontaneous fetal loss; Pauci-immune vasculitis; epidermolysis bullosa; recurrent fetal loss; multiple sclerosis (MS); and traumatic brain injury. See, e.g., Holers (2008) *Immunological Reviews* 223:300-316 and Holers and Thurman (2004) *Molecular Immunology* 41:147-152. In some embodiments, the complement-mediated disorder is a complement-mediated vascular disorder such as, but not limited to, a cardiovascular disorder, myocarditis, a cerebrovascular disorder, a peripheral (e.g., musculoskeletal) vascular disorder, a renovascular disorder, a mesenteric/enteric vascular disorder, revascularization to transplants and/or replants, vasculitis, Henoch-Schönlein purpura nephritis, systemic lupus erythematosus-associated vasculitis, vasculitis associated with rheumatoid arthritis, immune complex vasculitis, Takayasu's disease, capillary leak syndrome, dilated cardiomyopathy, diabetic angiopathy, thoracic-abdominal aortic aneurysm, Kawasaki's disease (arteritis), venous gas embolus (VGE), and restenosis following stent placement, rotational atherectomy, and percutaneous transluminal coronary angioplasty (PTCA). See, e.g., U.S. patent application publication no. 20070172483. In some embodiments, the complement-associated disorder is myasthenia gravis, cold-agglutinin disease (CAD), paroxysmal cold hemoglobinuria (PCH), dermatomyositis, scleroderma, warm autoimmune hemolytic anemia, Graves' disease, Hashimoto's thyroiditis, type I diabetes, psoriasis, pemphigus, autoimmune hemolytic anemia (AIHA), idiopathic thrombocytopenic purpura (ITP), Goodpasture's syndrome, antiphospholipid syndrome (APS), Degos disease, and catastrophic APS (CAPS).

In some embodiments, an anti-C3d/C3dg antibody or antigen-binding fragment thereof or a fusion molecule comprising such antibody or fragment thereof as the targeting moiety described herein, alone or in combination with a second anti-inflammatory agent, can be used to treat an inflammatory disorder such as, but not limited to, RA (above), inflammatory bowel disease, sepsis (above), septic shock, acute lung injury, disseminated intravascular coagulation (DIC), or Crohn's disease. In some embodiments, the second anti-inflammatory agent can be one selected from the group consisting of NSAIDs, corticosteroids, methotrexate, hydroxychloroquine, anti-TNF agents such as etanercept and infliximab, a B cell depleting agent such as rituximab, an interleukin-1 antagonist, or a T cell costimulatory blocking agent such as abatacept.

In some embodiments, the complement-associated disorder is a complement-associated neurological disorder such as, but not limited to, amyotrophic lateral sclerosis (ALS), brain injury, Alzheimer's disease, and chronic inflammatory demyelinating neuropathy.

Complement-associated disorders also include complement-associated pulmonary disorders such as, but not limited to, asthma, bronchitis, a chronic obstructive pulmonary disease (COPD), an interstitial lung disease, $\alpha$-1 anti-trypsin deficiency, emphysema, bronchiectasis, bronchiolitis obliterans, alveolitis, sarcoidosis, pulmonary fibrosis, and collagen vascular disorders.

In some embodiments, an anti-C3d/C3dg antibody or an antigen-binding fragment thereof described herein can be administered to a subject as a monotherapy. Alternatively, as described above, the antibody or fragment thereof can be administered to a subject as a combination therapy with another treatment, e.g., another treatment for a complement-associated disorder or a complement-associated inflammatory response. For example, the combination therapy can include administering to the subject (e.g., a human patient) one or more additional agents (e.g., anti-coagulants, anti-hypertensives, or anti-inflammatory drugs (e.g., steroids)) that provide a therapeutic benefit to a subject who has, or is at risk of developing, sepsis. In another example, the combination therapy can include administering to the subject one or more additional agents (e.g., an anti-IgE antibody, an anti-IL-4 antibody, an anti-IL-5 antibody, or an anti-histamine antibody) that provide therapeutic benefit to a subject who has, is at risk of developing, or is suspected of having a complement-associated pulmonary disorder such as COPD or asthma. In some embodiments, an anti-C3d/C3dg antibody and the one or more additional active agents are administered at the same time. In other embodiments, the anti-C3d/C3dg antibody is administered first in time and the one or more additional active agents are administered second in time. In some embodiments, the one or more additional active agents are administered first in time and the anti-C3d/C3dg antibody is administered second in time.

An anti-C3d/C3dg antibody or an antigen-binding fragment thereof described herein can replace or augment a previously or currently administered therapy. For example, upon treating with an anti-C3d/C3dg antibody or antigen-binding fragment thereof, administration of the one or more additional active agents can cease or diminish, e.g., be administered at lower levels. In some embodiments, administration of the previous therapy can be maintained. In some embodiments, a previous therapy will be maintained until the level of the anti-C3d/C3dg antibody reaches a level sufficient to provide a therapeutic effect. The two therapies can be administered in combination.

Monitoring a subject (e.g., a human patient) for an improvement in a complement-associated disorder (e.g., sepsis, severe burn, RA, lupus nephritis, Goodpasture's syndrome, or asthma), as defined herein, means evaluating the subject for a change in a disease parameter, e.g., an improvement in one or more symptoms of a given disorder. The symptoms of complement-associated disorders are well known in the art of medicine. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a complement-associated disorder described herein.

Pharmaceutical Compositions

In another aspect, provided herein are pharmaceutical compositions comprising any of the constructs and/or fusion proteins described herein. Pharmaceutical compositions comprising any of the constructs and/or fusion proteins described herein are generally formulated as sterile, substantially isotonic pharmaceutical solutions in full compliance with all Good Manufacturing Practice (GMP) regulations of the U.S. Food and Drug Administration. In some embodiments, the composition is free of pathogen. For injection, the pharmaceutical compositions can be in the form of liquid solutions, for example in physiologically compatible buffers such as Hank's Balanced Salt Solution, Phosphate-Buffered Saline or Ringer's solution. In addition, the pharmaceutical compositions provided herein can be in solid form and redissolved or resuspended immediately prior to use. Lyophilized compositions are also contemplated.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

In some embodiments, the compositions are formulated in accordance with routine procedures as a pharmaceutical composition adapted for injection. In some embodiments, the pharmaceutical compositions provided herein are formulated for intravenous, intraperitoneal, or intraocular injection. Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions may further comprise additional ingredients, for example preservatives, buffers, tonicity agents, antioxidants and stabilizers, nonionic wetting or clarifying agents, viscosity-increasing agents, and the like.

Suitable preservatives for use in a solution include polyquaternium-1, benzalkonium chloride, thimerosal, chlorobutanol, methyl paraben, propyl paraben, phenylethyl alcohol, disodium-EDTA, sorbic acid, benzethonium chloride, and the like. Typically (but not necessarily) such preservatives are employed at a level of from 0.001% to 1.0% by weight.

Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5.

Suitable tonicity agents include dextran 40, dextran 70, dextrose, glycerin, potassium chloride, propylene glycol, sodium chloride, and the like, such that the sodium chloride equivalent of the injectable solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like.

As described above, the antibodies, antigen-binding fragments thereof, or fusion proteins described herein can be formulated as relatively high concentrations in aqueous pharmaceutical solutions. For example, an antibody or a fusion protein described herein can be formulated in solution at a concentration of between about 10 mg/mL to 100 mg/mL (e.g., between about 9 mg/mL and 90 mg/mL; between about 9 mg/mL and 50 mg/mL; between about 10 mg/mL and 50 mg/mL; between about 15 mg/mL and 50 mg/mL; between about 15 mg/mL and 110 mg/mL; between about 15 mg/mL and 100 mg/mL; between about 20 mg/mL and 100 mg/mL; between about 20 mg/mL and 80 mg/mL; between about 25 mg/mL and 100 mg/mL; between about 25 mg/mL and 85 mg/mL; between about 20 mg/mL and 50 mg/mL; between about 25 mg/mL and 50 mg/mL; between about 30 mg/mL and 100 mg/mL; between about 30 mg/mL and 50 mg/mL; between about 40 mg/mL and 100 mg/mL; between about 50 mg/mL and 100 mg/mL; or between about 20 mg/mL and 50 mg/mL). In some embodiments, a fusion protein described herein can be formulated in an aqueous solution at a concentration of greater than 5 mg/mL and less than 50 mg/mL. Methods for formulating a protein in an aqueous solution are known in the art and are described in, e.g., U.S. Pat. No. 7,390,786; McNally and Hastedt (2007), "Protein Formulation and Delivery," Second Edition, *Drugs and the Pharmaceutical Sciences*, Volume 175, CRC Press; and Banga (1995), "Therapeutic peptides and proteins: formulation, processing, and delivery systems," CRC Press. In some embodiments, the aqueous solution has a neutral pH, e.g., a pH between, e.g., 6.5 and 8 (e.g., between and inclusive of 7 and 8). In some embodiments, the aqueous solution has a pH of about 6.6, 6.7, 6.8, 6.9, 7, 7.1, 7.2, 7.3, 7.4, 7.5, 7.6, 7.7, 7.8, 7.9, or 8.0. In some embodiments, the aqueous solution has a pH of greater than (or equal to) 6 (e.g., greater than or equal to 6.1, 6.2, 6.3, 6.4, 6.5, 6.6, 6.7, 6.8, 6.9, 7, 7.1, 7.2, 7.3, 7.4, 7.5, 7.6, 7.7, 7.8, or 7.9), but less than pH 8.

In some embodiments, a therapeutic composition described herein (e.g., an antibody, an antigen-binding fragment thereof, or a fusion protein described herein) can be formulated with one or more additional active agents useful for treating or preventing a complement-associated disorder (e.g., an AP-associated disorder or a CP-associated disorder) in a subject. Additional agents for treating a complement-associated disorder in a subject will vary depending on the particular disorder being treated, but can include, without limitation, an antihypertensive (e.g., an angiotensin-converting enzyme inhibitor) [for use in treating, e.g., HELLP syndrome], an anticoagulant, a corticosteroid (e.g., prednisone), or an immunosuppressive agent (e.g., vincristine or cyclosporine A). Examples of anticoagulants include, e.g., warfarin (Coumadin), aspirin, heparin, phenindione, fondaparinux, idraparinux, and thrombin inhibitors (e.g., argatroban, lepirudin, bivalirudin, or dabigatran). A fusion protein described herein can also be formulated with a fibrinolytic agent (e.g., ancrod, ε-aminocaproic acid, anti-plasmin-$a_1$, prostacyclin, and defibrotide) for the treatment of a complement-associated disorder. In some embodiments, a fusion protein can be formulated with a lipid-lowering agent such as an inhibitor of hydroxymethylglutaryl CoA reductase. In some embodiments, a fusion protein can be formulated with, or for use with, an anti-CD20 agent such as rituximab (Rituxan™; Biogen Idec, Cambridge, Mass.). In some embodiments, e.g., for the treatment of RA, the fusion protein can be formulated with one or both of infliximab (Remicade®; Centocor, Inc.) and methotrexate (Rheumatrex®, Trexall®). In some embodiments, a fusion protein described herein can be formulated with a non-steroidal anti-inflammatory drug (NSAID). Many different NSAIDS are available, some over the counter including ibuprofen (Advil®, Motrin®, Nuprin®) and naproxen (Alleve®) and many others are available by prescription including meloxicam (Mobic®), etodolac (Lodine®), nabumetone (Relafen®), sulindac (Clinoril®), tolementin (Tolectin®), choline magnesium salicylate (Trilasate®), diclofenac (Cataflam®, Voltaren®, Arthrotec®), Diflusinal (Dolobid®), indomethicin (Indocin®), Ketoprofen (Orudis®, Oruvail®), Oxaprozin (Daypro®), and piroxicam (Feldene®). In some embodiments a fusion protein can be formulated for use with an anti-hypertensive, an anti-seizure agent (e.g., magnesium sulfate), or an anti-thrombotic agent. Anti-hypertensives include, e.g., labetalol, hydralazine, nifedipine, calcium channel antagonists, nitroglycerin, or sodium nitroprussiate. (See, e.g., Mihu et al. (2007) *J Gastrointestin Liver Dis* 16(4):419-424.) Anti-thrombotic agents include, e.g., heparin, antithrombin, prostacyclin, or low dose aspirin.

In some embodiments, a therapeutic composition described herein (e.g., an antibody, an antigen-binding fragment thereof, or a fusion protein described herein) can be formulated for administration (e.g., intrapulmonary administration) with at least one additional active agent for treating a pulmonary disorder. The at least one active agent can be, e.g., an anti-IgE antibody (e.g., omalizumab), an anti-IL-4 antibody or an anti-IL-5 antibody, an anti-IgE inhibitor (e.g., montelukast sodium), a sympathomimetic (e.g., albuterol), an antibiotic (e.g., tobramycin), a deoxyribonuclease (e.g., pulmozyme), an anticholinergic drug (e.g., ipratropium bromide), a corticosteroid (e.g., dexamethasone), a β-adrenoreceptor agonist, a leukotriene inhibitor (e.g., zileuton), a 5-lipoxygenase inhibitor, a PDE inhibitor, a CD23 antagonist, an IL-13 antagonist, a cytokine release inhibitor, a histamine H1 receptor antagonist, an anti-histamine, an anti-inflammatory agent (e.g., cromolyn sodium), or a histamine release inhibitor.

In some embodiments, a therapeutic composition described herein (e.g., an antibody, an antigen-binding fragment thereof, or a fusion protein described herein) can be formulated for administration with one or more additional therapeutic agents for use in treating a complement-associated disorder of the eye. Such additional therapeutic agents can be, e.g., bevacizumab or the Fab fragment of bevacizumab or ranibizumab, both sold by Roche Pharmaceuticals, Inc., and pegaptanib sodium (Mucogen®; Pfizer, Inc.). Such a kit can also, optionally, include instructions for administering the fusion protein to a subject.

In some embodiments, a therapeutic composition described herein (e.g., an antibody, an antigen-binding fragment thereof, or a fusion protein described herein) can be formulated for administration to a subject along with intravenous gamma globulin therapy (IVIG), plasmapheresis, plasma replacement, or plasma exchange. In some embodiments, a therapeutic composition described herein (e.g., an antibody, an antigen-binding fragment thereof, or a fusion protein described herein) can be formulated for use before, during, or after, a kidney transplant.

When a therapeutic composition described herein (e.g., an antibody, an antigen-binding fragment thereof, or a fusion protein described herein) is to be used in combination with a second active agent, the agents can be formulated separately or together. For example, the respective pharmaceutical compositions can be mixed, e.g., just prior to administration, and administered together or can be administered separately, e.g., at the same or different times (see below).

As described above, a pharmaceutical composition can be formulated such that it includes a therapeutically effective amount of an antibody, an antigen-binding fragment thereof, or a fusion protein described herein. In some embodiments, a composition can be formulated to include a sub-therapeutic amount of a fusion protein and a sub-therapeutic amount of one or more additional active agents such that the components in total are therapeutically effective for treating or preventing a complement-associated disorder (e.g., an alternative complement pathway-associated complement disorder or a classical complement pathway-associated disorder) in a subject. Methods for determining a therapeutically effective dose of an agent such as a therapeutic fusion protein, antibody, or antigen-binding fragment thereof are known in the art and described herein.

Methods for Administration

The pharmaceutical compositions may be suitable for a variety of modes of administration described herein, including for example systemic or localized administration. The pharmaceutical compositions can be in the form of injectable solutions or in a form suitable for oral administration. The pharmaceutical compositions described herein can be packaged in single unit dosages or in multidosage forms. In some embodiments, the pharmaceutical compositions are suitable for administration to an individual, a vertebrate, a mammal, or a human by any route of administration described herein, including oral administration or intravenous injection.

The compositions described herein can be administered to an individual via any route, including, but not limited to, intravenous (e.g., by infusion pumps), intraperitoneal, intraocular, intra-arterial, intrapulmonary, oral, inhalation, intravesicular, intramuscular, intra-tracheal, subcutaneous, intrathecal, transdermal, transpleural, topical, inhalational (e.g., as mists of sprays), mucosal (such as via nasal mucosa), subcutaneous, gastrointestinal, intraarticular, intracisternal, intraventricular, rectal (i.e., via suppository), vaginal (i.e., via pessary), intracranial, intraurethral, intrahepatic, and intratumoral. In some embodiments, the compositions are administered systemically (for example by intravenous injection). In some embodiments, the compositions are administered locally (for example by intraarterial or intraocular injection).

In some embodiments, the compositions are administered intravascularly, such as intravenously or intraarterially. In some embodiments (for example for the treatment of renal diseases), the compositions are administered directly into arteries (such as renal arteries). In some embodiments, the compositions are administered subcutaneously.

In some embodiments, the compositions are administered directly to the eye or the eye tissue. In some embodiments, the compositions are administered topically to the eye, for example, in eye drops. In some embodiments, the compositions are administered by injection to the eye (intraocular injection) or to the tissues associated with the eye. The compositions can be administered, for example, by intraocular injection, periocular injection, subretinal injection, intravitreal injection, trans-septal injection, subscleral injection, intrachoroidal injection, intracameral injection, subconjunctival injection, sub-Tenon's injection, retrobulbar injection, peribulbar injection, or posterior juxtascleral delivery. These methods are known in the art. For example, for a description of exemplary periocular routes for retinal drug delivery, see Periocular routes for retinal drug delivery, Raghava et al. (2004), Expert Opin. Drug Deliv. 1(1):99-114. The compositions may be administered, for example, to the vitreous, aqueous humor, sclera, conjunctiva, the area between the sclera and conjunctiva, the retina choroids tissues, macula, or other area in or proximate to the eye of an individual.

The compositions can also be administered to the individual as an implant. Preferred implants are biocompatible and/or biodegradable sustained release formulations which gradually release the compounds over a period of time. Ocular implants for drug delivery are well-known in the art. See, e.g., U.S. Pat. Nos. 5,501,856, 5,476,511, and 6,331,313. The compositions can also be administered to the individual using iontophoresis, including, but are not limited to, the ionophoretic methods described in U.S. Pat. No. 4,454,151 and US 2003/0181531 and 2004/0058313.

Dosage

A suitable dose of an antibody, antigen-binding fragment thereof, or fusion protein described herein, which dose is capable of treating or preventing a complement-associated disorder in a subject, can depend on a variety of factors including, e.g., the age, sex, and weight of a subject to be treated and the particular inhibitor compound used. For example, a different dose of one fusion may be required to treat a subject with RA as compared to the dose of a different fusion required to treat the same subject. Other factors affecting the dose administered to the subject include, e.g., the type or severity of the complement-mediated disorder. For example, a subject having RA may require administration of a different dosage of a fusion protein described herein than a subject with AMD. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will also depend upon the judgment of the treating medical practitioner (e.g., doctor or nurse).

An antibody, antigen-binding fragment thereof, or fusion protein described herein can be administered as a fixed dose, or in a milligram per kilogram (mg/kg) dose. In some embodiments, the dose can also be chosen to reduce or avoid production of antibodies or other host immune responses against one or more of the active fusion proteins in the composition. While in no way intended to be limiting, exemplary dosages of an antibody, such as a fusion protein described herein include, e.g., 1-1000 mg/kg, 1-100 mg/kg, 0.5-50 mg/kg, 0.1-100 mg/kg, 0.5-25 mg/kg, 1-20 mg/kg, and 1-10 mg/kg, 1-100 mg/kg, 0.5-50 mg/kg, 0.1-100 mg/kg, 0.5-25 mg/kg, 1-20 mg/kg, 0.100 mg/kg to 1 mg/kg, and 1-10 mg/kg. Exemplary dosages of an fusion protein described herein include, without limitation, 0.1 mg/kg, 0.5 mg/kg, 1.0 mg/kg, 2.0 mg/kg, 4 mg/kg, and 8 mg/kg, 0.1 mg/kg, 0.5 mg/kg, 1.0 mg/kg, 2.0 mg/kg, 4 mg/kg, 8 mg/kg, and 20 mg/kg. In some embodiments, the amount of composition administered to an individual is about 10 µg to about 500 mg per dose, including for example any of about 10 µg to about 50 µg, about 50 µg to about 100 µg, about 100 µg to about 200 µg, about 200 µg to about 300 µg, about 300 µg to about 500 µg, about 500 µg to about 1 mg, about 1 mg to about 10 mg, about 10 mg to about 50 mg, about 50 mg to about 100 mg, about 100 mg to about 200 mg, about 200 mg to about 300 mg, about 300 mg to about 400 mg, or about 400 mg to about 500 mg per dose.

A pharmaceutical composition can include a therapeutically effective amount of an antibody, antigen-binding fragment thereof, or fusion protein described herein. Such effective amounts can be readily determined by one of ordinary skill in the art based, in part, on the effect of the administered antibody, fragment, or fusion protein, or the combinatorial effect of the compound (e.g., antibody, fragment, or fusion protein) and one or more additional active agents, if more than one agent is used. A therapeutically effective amount of an antibody, antigen-binding fragment thereof, or fusion protein described herein can also vary according to factors such as the disease state, age, sex, and weight of the individual, and the ability of the primary agent (and one or more additional active agents) to elicit a desired response in the individual, e.g., amelioration of at least one condition parameter, e.g., amelioration of at least one symptom of the complement-mediated disorder. For example, a therapeutically effective amount of an antibody, antigen-binding fragment thereof, or fusion protein described herein can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of the fusion proteins described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

The terms "therapeutically effective amount" or "therapeutically effective dose," or similar terms used herein are intended to mean an amount of an agent that will elicit the desired biological or medical response (e.g., an improvement in one or more symptoms of a complement-associated disorder). In some embodiments, a pharmaceutical composition described herein contains a therapeutically effective amount of at least one of said antibodies, antigen-binding fragments thereof, or fusion proteins described herein. In some embodiments, the composition contains any of the antibodies, antigen-binding fragments thereof, or fusion proteins described herein and one or more (e.g., two, three, four, five, six, seven, eight, nine, 10, or 11 or more) additional therapeutic agents such that the composition as a whole is therapeutically effective. For example, a composition can contain a fusion protein described herein and an immunosuppressive agent, wherein the fusion protein and agent are each at a concentration that when combined are therapeutically effective for treating or preventing a complement-associated disorder (e.g., a complement-associated inflammatory disorder such as COPD, asthma, sepsis, or RA) in a subject.

Toxicity and therapeutic efficacy of such compositions can be determined by known pharmaceutical procedures in cell cultures or experimental animals (e.g., animal models of any of the complement-mediated disorders described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$, A fusion protein described herein that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of the antibodies, antigen-binding fragments thereof, or fusion proteins described herein lies generally within a range of circulating concentrations of the fusion proteins that include the $ED_{50}$ with little or no toxicity. The dosage may vary within this range depending upon the dosage form employed and the route of administration utilized. For a fusion protein described herein, the therapeutically effective dose can be estimated initially from cell culture assays. A dose can be formulated in animal models to achieve a circulating plasma concentration range that includes the $IC_{50}$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

In some embodiments, the methods can be performed in conjunction with other therapies for complement-associated disorders. For example, the composition can be administered to a subject at the same time, prior to, or after, plasmapheresis, IVIG therapy, or plasma exchange. See, e.g., Appel et al. (2005) *J Am Soc Nephrol* 16:1392-1404. In some embodiments, the composition can be administered to a subject at the same time, prior to, or after, a kidney transplant.

Compositions including an antibody, antigen-binding fragment thereof, or construct (e.g., fusion molecule) described herein may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgically implanted in various locations in the body.

Gene Therapy

The molecules can also be delivered by expression of the fusion protein in vivo, which is often referred to as "gene therapy." For example, cells may be engineered with a polynucleotide (DNA or RNA) encoding the fusion protein ex vivo, and the engineered cells are then provided to an individual to be treated with the fusion protein. Such methods are well-known in the art. For example, cells may be engineered by procedures known in the art by use of a retroviral particle containing RNA encoding the fusion protein of the present disclosure. Local delivery of the fusion proteins of the present disclosure using gene therapy may provide the therapeutic agent to a localized target area.

Methods of gene delivery are known in the art. These methods include, but are not limited to, 1) direct DNA transfer, see, e.g., Wolff et al. (1990) Science 247: 1465-1468; 2) Liposome-mediated DNA transfer, see, e.g., Caplen et al. (1995) Nature Med. 3:39-46; Crystal (1995) Nature Med. 1:15-17; Gao and Huang (1991) Biochem. Biophys. Res. Comm 179:280-285; 3) Retrovirus-mediated DNA transfer, see, e.g., Kay et al. (1993) Science 262:117-119; Anderson (1992) Science 256:808-813; and 4) DNA Virus-mediated DNA transfer. Such DNA viruses include adenoviruses (preferably Ad2 or Ad5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al. (1994) Gene Therapy 1:367-384; U.S. Pat. No. 4,797,368, incorporated herein by reference, and U.S. Pat. No. 5,139,941.

Retroviruses from which the retroviral plasmid vectors hereinabove mentioned may be derived include, but are not limited to, Moloney Mouse Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In some embodiments, the retroviral plasmid vector is derived from Moloney Mouse Leukemia Virus.

Adenoviruses have the advantage that they have a broad host range, can infect quiescent or terminally differentiated cells, such as neurons or hepatocytes, and appear essentially non-oncogenic. See, e.g., Ali et al. (1994), supra, p. 367. Adenoviruses do not appear to integrate into the host genome. Because they exist extrachromosomally, the risk of insertional mutagenesis is greatly reduced. Ali et al. (1994), supra, p. 373.

Adeno-associated viruses exhibit similar advantages as adenoviral-based vectors. However, AAVs exhibit site-specific integration on human chromosome 19 (Ali et al. (1994), supra, p. 377).

The gene therapy vectors may include one or more promoters. In some embodiments, the vector has a promoter that drives expression in multiple cell types. In some embodiments, the vector has a promoter that drives expression in specific cell types (such as cells of retina or cells in the kidney). Suitable promoters which may be employed include, but are not limited to, the retroviral LTR; the SV40 promoter; and the human cytomegalovirus (CMV) promoter described in Miller et al. (1989) Biotechniques 7(9):980-990, or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding a fusion protein is preferably under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoter.

Retroviral plasmid vectors can be employed to transduce packaging cell lines to form producer cell lines. Examples of packaging cells which may be transfected are described in Miller (1990) Human Gene Therapy 1:5-14. The vectors may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host. The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

In some embodiments, the complement activation is inhibited by contacting a body fluid with a composition comprising a molecule ex vivo under conditions that permit the molecule to function to inhibit complement activation. Suitable body fluids include those that can be returned to the individual, such as blood, plasma, or lymph. Affinity adsorption apheresis is described generally in Nilsson et al. (1988) Blood 58(1):38-44; Christie et al. (1993) Transfusion 33:234-242; Richter et al. (1997) ASAIO J. 43(1):53-59; Suzuki et al. (1994) Autoimmunity 19: 105-112; U.S. Pat.

No. 5,733,254; Richter et al. (1993) Metabol. Clin. Exp. 42:888-894; and Wallukat et al. (1996) Int'l J. Card. 54:1910195.

Accordingly, the disclosure includes methods of treating one or more diseases described herein in an individual comprising treating the individual's blood extracorporeally (i.e., outside the body or ex vivo) with a composition comprising a molecule under conditions that permit the molecule to function to inhibit complement activation, and returning the blood to the individual.

Unit Dosages, Articles of Manufacture, and Kits

Also provided are unit dosage forms of compositions, each dosage containing from about 0.01 mg to about 50 mg, including for example any of about 0.1 mg to about 50 mg, about 1 mg to about 50 mg, about 5 mg to about 40 mg, about 10 mg to about 20 mg, or about 15 mg of the molecule. In some embodiments, the unit dosage forms of molecule composition comprises about any of 0.01 mg-0.1 mg, 0.1 mg-0.2 mg, 0.2 mg-0.25 mg, 0.25 mg-0.3 mg, 0.3 mg-0.35 mg, 0.35 mg-0.4 mg, 0.4 mg-0.5 mg, 0.5 mg-1.0 mg, 1.0 mg-10 mg, 10 mg-20 mg, 20 mg-50 mg, 50 mg-80 mg, 80 mg-100 mg, 100 mg-150 mg, 150 mg-200 mg, 200 mg-250 mg, 250 mg-300 mg, 300 mg-400 mg, or 400 mg-500 mg molecule. In some embodiments, the unit dosage form comprises about 0.25 mg molecule. The term "unit dosage form" refers to a physically discrete unit suitable as unitary dosages for an individual, each unit containing a predetermined quantity of active material calculated to produce the desired therapeutic effect, in association with a suitable pharmaceutical carrier, diluent, or excipient. These unit dosage forms can be stored in a suitable packaging in single or multiple unit dosages and may also be further sterilized and sealed.

Also provided are articles of manufacture comprising the compositions described herein in suitable packaging. Suitable packaging for compositions (such as ophthalmic compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present disclosure also provides kits comprising compositions (or unit dosage forms and/or articles of manufacture) described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein.

The compositions and formulations of the present disclosure are useful for the treatment of conditions associated with complement activation, preferably those which involve the complement alternative pathway, which is largely unaffected by terminal complement inhibitors [e.g., inhibitors of steps of the complement pathway subsequent to the activation of C3].

EXAMPLES

Anti-C3d Antibodies:

Recombinant human C3d was generated using the pGEX expression system in *E. coli* as has been described (Hannan, J. P., et al. (2005) *J. Mol. Biol.* 346, 845-858). Briefly, ampicillin-resistant colonies were used to start overnight cultures that were expanded to 1 liter and grown at 37° C. until an $A_{600}$ of 0.3 was achieved. Cultures were induced with 0.3 mM isopropyl-β-D-thiogalactoside at 30° C. overnight before harvesting by centrifugation. Harvested pellets were resuspended in glutathione S-transferase column buffer (50 mM Tris-HCl, pH 8.0, 250 mM NaCl, 1 mM EDTA) and lysed by sonication. Lysate was clarified by centrifugation and applied to a GStrap column (GE Biosciences). C3d was cleaved from the column by digesting with 50 units of thrombin overnight at 4° C. and subsequently purified by size exclusion chromatography. Purity of C3d was monitored via SDS-PAGE.

A $C3^{-/-}$ mouse was immunized with 60 μg of recombinant C3d emulsified in complete Freund's adjuvant. Two months later the mouse received a booster injection of 80 μg of C3d in incomplete Freund's adjuvant. It received two more immunizations of 100 μg of C3d in PBS at two-month intervals. The mouse was then sacrificed, and a single cell suspension of splenocytes was made. The splenocytes were fused with Sp2/0 mouse myeloma cell line.

The fused cells were grown in Hypoxanthine Aminopterin Thymidine (HAT)-DMEM medium containing 10% fetal calf serum for seven days. The cells were then changed to HAT medium that did not contain fetal calf serum and the medium was changed twice weekly. Peritoneal macrophages were obtained from $C3^{-/-}$ mice by peritoneal lavage and were used as feeder cells for the cultures. Serum-free medium and feeder cells from $C3^{-/-}$ mice were used in order to avoid exposure of the hybridomas to homologous C3d. The resulting clones were screened for anti-C3d antibodies using an anti-C3d ELISA protocol. Briefly, 100 μl/well of 5 μg/ml recombinant C3d was bound to the wells of a polyvinyl chloride 96-well plate (Falcon). Polyclonal supernatants of the hybridomas were incubated on the plates, and anti-C3d reactivity was detected using secondary antibodies to mouse IgM, mouse IgG, mouse IgG1, mouse IgG2a, and mouse IgG2b. Wells that displayed reactivity against C3d underwent further cloning by limiting dilution in serum-free medium, and the resulting clones were again screened for reactivity against recombinant C3d.

Cell cultures of hybridomas with anti-C3d reactivity were expanded. Serum containing and serum-free medium formulations were tested for each clone, and the formulation that yielded better growth characteristics for each clone was used. Antibody was then purified from the supernatants using protein G columns (GE Biosciences). Briefly, the supernatants were passed over the column. The column was washed with 20 mM sodium phosphate, pH 7. The bound antibody was then eluted with 0.1 M Glycine-HCl, pH 2.7. The eluent was neutralized in 1 M Tris-HCl, pH 9 and the buffer exchanged with PBS.

Binding Affinity of Anti-C3D Antibodies

The ability of the purified antibodies to bind several forms of C3d was tested. Direct binding of the purified antibodies to recombinant human C3d was tested as described above. In another protocol, a polyclonal rabbit anti-human C3d antibody was used to capture the recombinant human C3d to ELISA plates and binding of the hybridomas to the captured C3d was then tested. Commercially available human C3d (Complement Technology, Inc.) was also bound to ELISA plates and used as the target. In another ELISA-type assay, the antibodies were bound to the plates, and reactivity to C3d was detected using biotinylated recombinant human C3d generated as described above, and also using a another construct for biotinylated, His-tagged C3d. To test the reactivity of these antibodies to C3d of other species, murine and cynomolgus recombinant C3d was produced. The ability of the purified antibodies to bind murine and cynomolgus C3d was tested using protocols where the C3d was directly bound to the ELISA plate or where it was captured with the rabbit anti-human C3d antibody. The cross-species activity of 3d8b, 3d9a, 3d29, 3d11, and 3d31 is shown in FIG. 8.

The binding affinity of the anti-C3d/C3dg antibodies to C3d was further tested by BIAcore analysis. As shown in FIG. 6, 10, 30, and 90 nM of free antibodies were floated through bound C3d and their bindings were recorded respectively. mAb 3d8b binds to C3d with a $K_D=4.65\times10^{-10}$ M. mAb 3d9a binds to C3d with a $K_D=3.67\times10^{-10}$ M. mAb 3d29 binds to C3d with a $K_D=1.06\times10^{-9}$ M.

Testing for Binding Discrimination
C3d and Intact C3 by Western Blot Analysis

One μg of unreduced, purified intact C3 (Complement Technology, Inc.) or recombinant C3d was separated by SDS-PAGE and transferred to nitrocellulose membranes. The membranes were incubated with purified anti-C3d antibodies, washed, and then incubated with HRP conjugated anti-mouse IgG. The antibodies demonstrated four patterns of reactivity: 1) they reacted weakly with intact C3 and very strongly with C3d (clones 3d8b, 3d9a, and 3d29), 2) they reacted strongly with both the intact C3 and the C3d (clones 3d11 and 3d31), or 3-4) they did not bind either protein (clones 3d10 and 3d16), or they reacted weakly with C3d (clones 3d3 and 3d15).

C3 Fragments on Zymosan Particles

Figure 4:
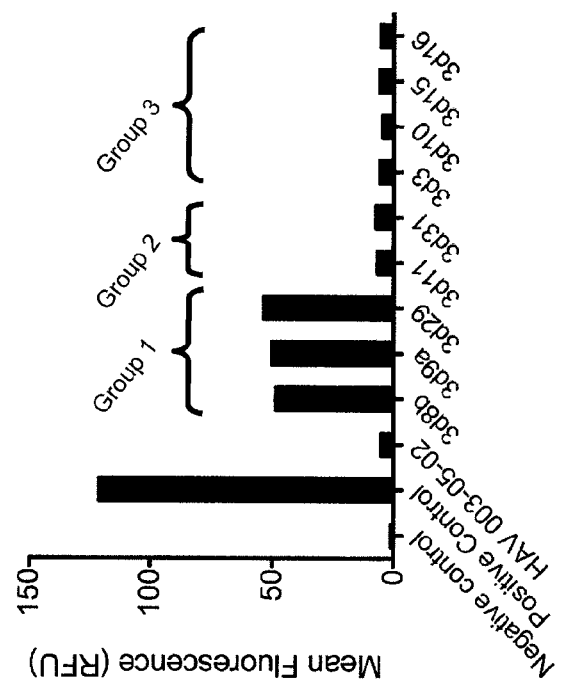
FIG. 4 illustrates the binding of monoclonal antibodies to C3-opsonized zymosan particles derived from incubation of mouse serum with zymosan and generation of C3 fragments iC3b and C3dg/C3d by using only endogenously available mechanisms. Notably, only Group 1 antibodies recognize C3 fragments bound to this target.
Figure 5:
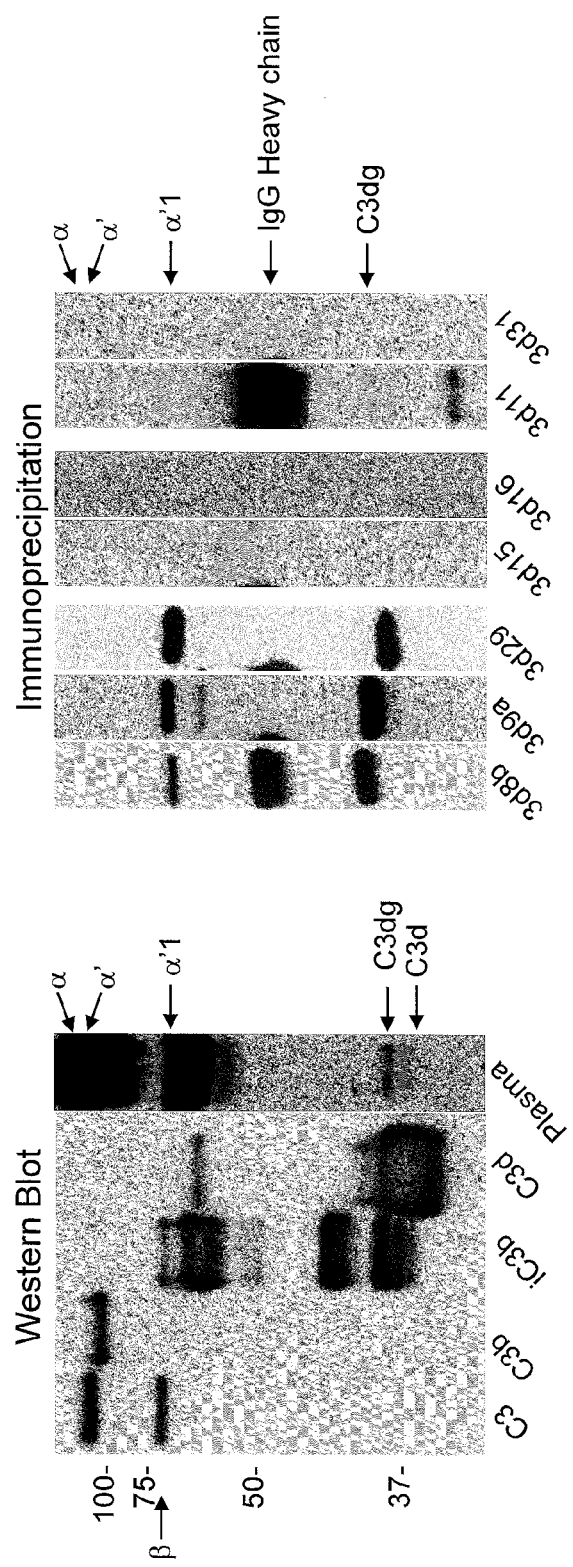
FIG. 5 illustrates the immunoprecipitation by Group 1 monoclonal antibodies only, but not by members of Group 2 or 3 antibodies, of the α'1 and C3dg bands from zymosan-activated plasma. This result demonstrates that Group 1 antibodies recognize exposed epitopes on iC3b and C3dg but not C3 or C3b.
Figure 6:
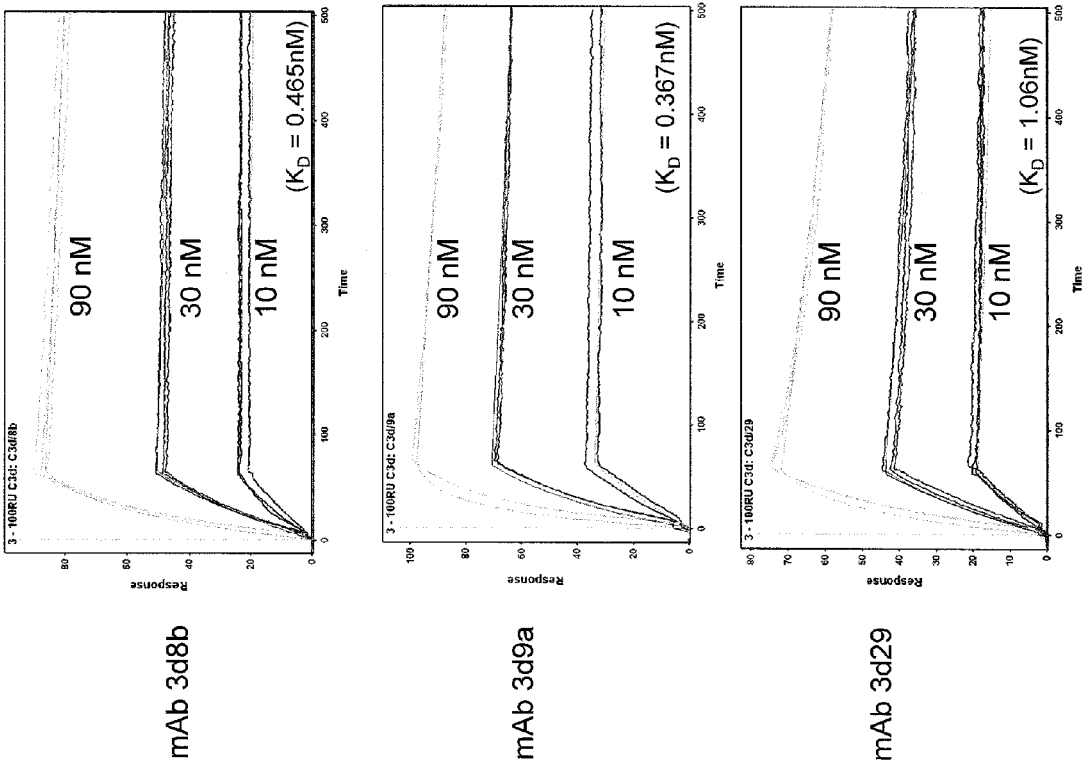
FIG. 6 illustrates the kinetics data revealing high affinity binding of clones 3d8b, 3d9a and 3d29 to C3d immobilized on a Biacore chip at increasing antibody concentrations. Lines representing injections of 90, 30 and 10 nM of antibody are shown. The data fit a simple 1:1 Langmuir binding model. $K_D$s of the individual monoclonal antibodies are included in the sensograms.

To test whether the antibodies bind to surface-bound C3 fragments generated physiologically, zymosan particles were incubated with 10% mouse serum at 37° C. for 30 minutes in a reaction containing 5 mM $MgCl_2$ and 10 mM EGTA. The zymosan particles were washed and were then incubated with one μg of the purified antibodies at 4° C. for an hour. The particles were washed, incubated with a FITC-conjugated antibody to mouse IgG, washed, and analyzed by flow cytometry. Binding of antibody to the particles was assessed by comparing fluorescence of the particles to negative controls (no primary antibody) and positive controls (a commercial polyclonal antibody to mouse C3). Clones that bound to the opsonized zymosan particles were 3d8b, 3d9a, and 3d29 (FIG. 4).

C3 Fragments on Tissue Sections.

Factor H deficient mice ($fH^{-/-}$ mice) are known to have heavy deposits of C3b/iC3b/C3d in the renal glomeruli (Paixao-Cavalcante, D., S. Hanson, M. Botto, H. T. Cook, and M. C. Pickering. 2009. Factor H facilitates the clearance of GBM bound iC3b by controlling C3 activation in fluid phase. *Mol Immunol* 46:1942-1950). To test the ability of the purified anti-C3d antibodies to bind to the tissue deposits of C3 fragments, 5 μm sections of kidneys from $fH^{-/-}$ mice were fixed with acetone and incubated with approximately 5 ng of purified antibody. The tissue sections were washed and then incubate with a FITC-conjugated antibody to mouse IgG. The sections were examined using a fluorescent microscope, and glomeruli were examined in order to detect IgG bound to the glomerular capillary loops. Clones 3d8b, 3d9a, and 3d29 demonstrated IgG bound to the glomeruli in a pattern identical to the pattern of C3 fragment deposition.

Targeting C3 Fragments In Vivo—Discrimination Between Tissue Bound Fragments and Circulating C3/C3b.

To test whether the purified anti-C3d antibodies could target to tissue bound C3d fragments in vivo, the antibodies were injected into $fH^{-/-}$ mice. $fH^{-/-}$ mice were chosen because they have discrete deposits of C3b/iC3b/C3d in the renal glomeruli, and a large proportion of the C3 in the circulation is in the cleaved C3b form. Mice were injected via the tail-vein with 0.5 mg of purified antibody. As a control, another mouse was injected with 0.5 mg of a chimeric protein comprised of the iC3b/C3d binding region of human CR2 linked to the Fc region of mouse IgG1 (CR2-Fc). After 24 hours the mice were sacrificed and the kidneys were harvested. Five μm sections of kidneys were cut, fixed with acetone, and incubated with a FITC-conjugated antibody to mouse IgG. The sections were examined using a fluorescent microscope, and glomeruli were examined in order to detect IgG that had bound to the glomerular capillary loops. Clones 3d8b, 3d9a, and 3d29 demonstrated IgG bound to the glomeruli in a pattern identical to the pattern of C3 fragment deposition (FIGS. 9A-B) and identical to the pattern of deposition seen with CR2-Fc.

Competition with CR2Binding to C3d

Figure 7:
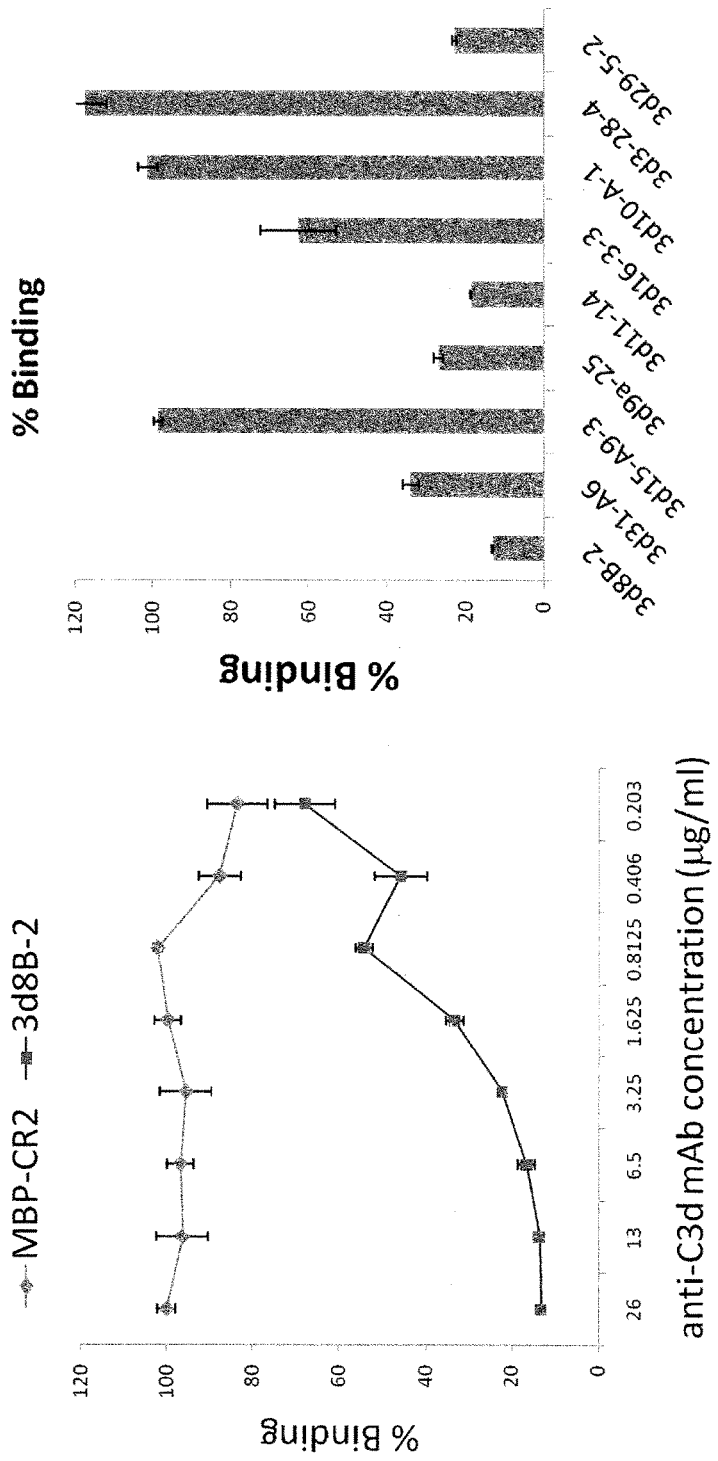
FIG. 7 illustrates the effect of anti-C3d monoclonal antibodies on the binding of human CR2-MBP to human C3d by ELISA. The top line (diamonds) illustrates one example of the binding in the absence, and bottom line (squares) the presence, of anti-C3d monoclonal antibody 3d8b. Summary histogram at right demonstrates percent binding of CR2 and C3d in the presence of the indicated monoclonal antibodies.

To determine whether the purified antibodies compete with CR2 for binding to C3d, polyvinyl chloride plates were coated with 100 microliters of recombinant C3d at a concentration of 5 micrograms/ml in 1/3 PBS. The plates were washed three times in 1/3 PBS-Tween 20 (0.01%), and then blocked for 1 hour with PBS/1% BSA at 100 microliters per well at room temperature. The plates were again washed three times as above. Serial dilutions of the purified anti-C3d antibodies (concentrations ranging from 1.8-15 μg/ml) were added to recombinant maltose binding protein (MBP)-CR2 SCRs 1-2 (10 micrograms/ml in PBS). This solution of anti-C3d+MBP-CR2 SCRs 1-2 was added to the plate and incubated for 1 hour at room temperature. The plates were washed three times in 1/3 PBS-Tween 20(0.01%). Following this 100 microliters per well of HRP-conjugated anti-MBP mAb (New England Biolabs) were added, and the plate was wrapped in foil and stored in darkness for 1 hour. The plates were then washed three times in 1/3 PBS-Tween 20(0.01%), following which 100 microliters of ABTS (prepared by dissolving 22 mg of azino-bis(3-ethylbenzothiazole sulfonic acid) diammonium salt in 100 ml of 50 mM sodium citrate, pH 4.0)+1/1000 35% hydrogen peroxide were added into each well. The plates were incubated in darkness for 10-20 minutes, and then read at 405 nm FIG. 7 illustrates exemplary data of the competition with CR2 for binding to C3d, in varied degrees, by the anti-C3d mAb clones 3d8b, 3d31, 3d9a, 3d11, and 3d29.

Effects on CR2 and FH Binding to C3d

For analysis of the binding of CR2 and factor H to C3d, Costar IIA/RIA plates are coated overnight at 4° C. with 50 microliters of wild-type or mutant C3d at a concentration of 5 micrograms/ml in 50 mM sodium bicarbonate buffer, pH 8.8. Then plates are washed three times in 100 microliters per well of PBS-Tween 20 (0.01%). Plates are then blocked for 1 hour with 100 microliters per well of PBS/1% BSA at room temperature, and washed three times as above. Serial dilutions of MBP-CR2 SCRs 1-2 are made up using a stock solution of 10 micrograms/ml (in PBS). Either monoclonal antibodies to C3d, or factor H (wild type or the factor H SCR19-20 or other fragments) are added to the solution of MBP-CR2 SCRs 1-2. This solution of MBP-CR2 SCRs 1-2 is added to the plate and incubated for 1 hour at room temperature. A stock of Horseradish peroxidase-conjugated anti-MBP monoclonal antibody (1/1000 dilution in PBS) (New England Biolabs: Anti-MBP Monoclonal Antibody HRP Conjugated, product number E8038L or E8038S) is prepared. The plates are washed three times in PBS-Tween 20(0.01%). Following this 50 microliters per well of HRP-conjugated anti-MBP mAb are added, and the plate is wrapped in foil and stored in darkness for 1 hour. The plates are then washed three times in PBS-Tween 20(0.01%), following which 50 microliters of ABTS+1/1000 35% hydrogen peroxide are added into each well (add $H_2O_2$ immediately before developing color). The plates are incubated in darkness for 10-20 minutes, and then read at 405 nm.

Effects on CR1, CR3 Binding to iC3b/C3dg

For analysis of the effects of anti-C3d monoclonal antibodies on CR1 function, fresh sheep erythrocytes (SRBCs) are conjugated with purified C3b using standard protocols. The cells are then incubated with human polymorphonuclear cells expressing CR1 Inhibition and confirmation of CR1-dependent binding and rosette formation is measured using anti-CR1 monoclonal antibody, such as anti-CD35 mAb 3E11 (Edberg et al., Quantitative analyses of the binding of soluble complement-fixing antibody/dsDNA immune complexes to CR1 on human red blood cells. *J Immunol* (1987) 139:3739-3747) Inhibition of binding of C3fragment coated cells to polymorphonuclear cells is assessed by pre-incubation of the C3b-coated erythrocytes with anti-C3d monoclonal antibodies for 60 minutes.

To measure CR3-dependent binding, fresh sheep erythrocytes (SRBCs) are sensitized with a predetermined sub-agglutinating amount of rabbit anti-SRBC IgM for 30 minutes at 37° C. in gelatin veronal buffer (GVB) (Advanced Research Technologies). After washing twice, C3b-opsonized SRBCs are prepared by incubating IgM-sensitized SRBCs with an equal volume of a 1:2 dilution of C6-deficient human serum in GVB$^{++}$ (120 minutes at 37° C.). Cells are washed twice and pellets are resuspended in GVB. Most of the C3 bound to erythrocytes after this treatment is in the form of iC3b or C3d degradation products (CR2 ligands). U937 cells are then added to 50 microliters of C3-fragment-opsonized SRBCs ($2 \times 10^6$ cells), and the mixture is minimally centrifuged and left at room temperature for 90 minutes. Cells are then examined by phase-contrast microscopy, and the number of U937 cells adherent to erythrocytes are determined. At least 100 erythrocytes are scored per sample, and the average number of U937 cells bound per erythrocyte is calculated. Triplicate determinations are made for each experiment performed. To increase CR3 levels, U937 cells are cultured for 3 days in the presence of 50 ng/ml PMA before harvest. Cells incubated with IgM-coated SRBCs alone or SRBCs incubated directly with C6-deficient human serum are used as controls.

Function Studies for Anti-C3d Monoclonal Antibodies

Effects on (Non-Stabilization of) CAP.

Figure 10:
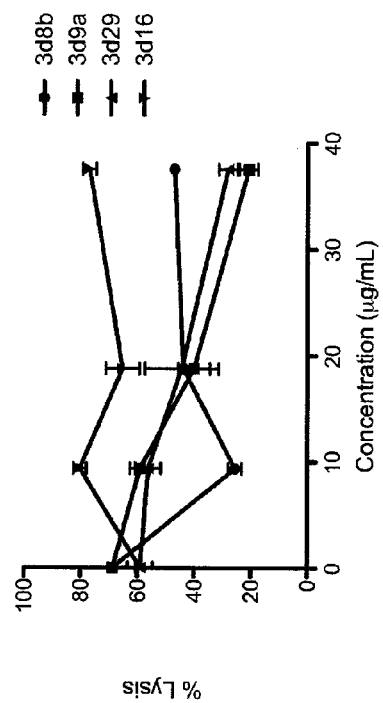
FIG. 10 illustrates the effect of monoclonal antibodies against C3d on complement activation (AH50) and the lack of enhancement by Group 1 monoclonal antibodies. The lysis of cells in serum supplemented with 10, 20 and 40 μg of each antibody is measured and compared with the lysis of cells in serum alone. The Y axis shows the percent change in lysis in serum with antibody compared with lysis in serum alone.
Figure 11:
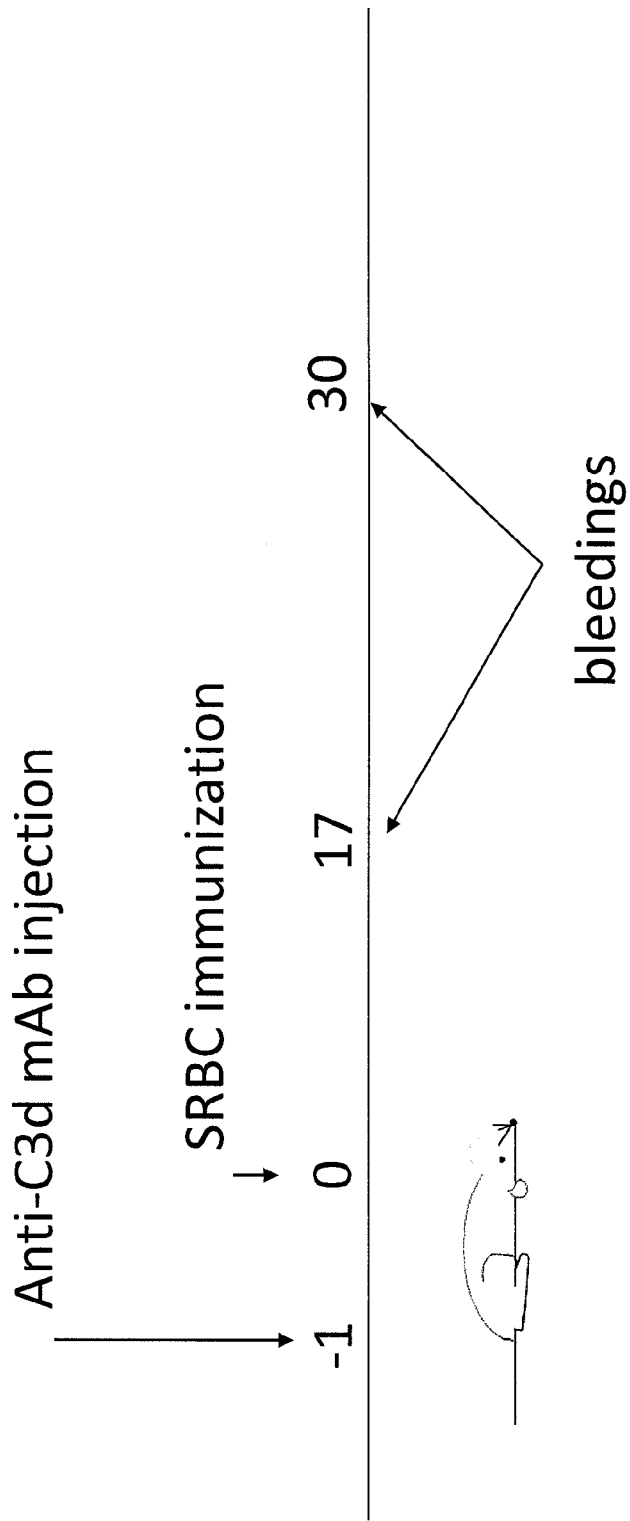
FIG. 11 illustrates the protocol utilized to assess the effect of anti-C3d monoclonal antibodies on the humoral immune response to a model complement-dependent antigen, sheep red blood cells.

To verify that the antibodies do not stabilize the CAP C3-convertase and amplify complement activation on surfaces, an AH50 assay was employed. To perform this assay, 5 ml of whole rabbit blood was washed in GVB-Mg$^{++}$-EGTA and resuspended in a volume of 20 ml. Fifty μl of the erythrocytes were then added to 15 μl of human serum. Purified antibody (0-150 μg/reaction) was added, and the volume was brought to 150 ml with GVB-Mg++-EGTA. The mixture was incubated at 37° C. for 30 minutes with periodic shaking of the tubes. As a negative control, 10 mM EDTA was added to the reaction. As a positive control (full lysis), 100 μl of water was added to the erythrocytes. The mixture was incubated at 37° C. for 30 minutes with periodic shaking of the tubes. To stop the reaction, 1.2 ml of cold PBS was added to the tubes. The tubes were then centrifuged at 1000×g for five minutes and the supernatants were transferred to new tubes. The O.D. at 415 nm was read, and the percent lysis for each sample was determined relative to the negative and positive control values. One clone (3d16) showed higher lysis than serum alone (FIG. 10). Clones 3d8b, 3d9a, and 3d29 did not demonstrate increased lysis with increasing concentrations of the antibodies.

As an exemplary experiment to further demonstrate whether the mAbs described herein bind to the same, or overlapping, epitopes on C3d or C3dg as those for CR2 binding, mutations are introduced into the CR2 binding site on C3d using standard methods. These C3d mutants will be tested for binding to both CR2 and the mAbs described herein. Finding any mutant which binds to only CR2 but not any one of the anti-C3d/C3dg antibodies described herein, or vice versa, demonstrates that the mutated amino acid residue is crucial for binding for the antibodi(es) but not CR2, or vice versa, and that CR2 and the antibodi(es) bind to different epitopes. Similarly, different profiles of binding to these mutants among the anti-C3d/C3dg antibodies will help to determine different binding epitopes or crucial amino acid residue(s) for binding on C3d for these antibodies. The binding between C3d mutants and CR2 or the anti-C3d/C3dg antibodies can be tested by many standard methods well known in the art. One exemplary ELISA assay is illustrated herein. Following purification of C3d mutant proteins, ELISA plates are coated with wild-type or mutant C3d at a concentration of 5 micrograms/ml in 50 mM sodium bicarbonate buffer, pH 8.8. Plates are then washed three times in with PBS-Tween 20 (0.01%); 100 microliters per well. Plates are then blocked for 1 hour with PBS/1% BSA; 100 microliters per well at room temperature and washed three times as above. Serial dilutions of anti-C3d monoclonal antibodies are made up using a stock solution of 10 micrograms/ml (in PBS). Monoclonal antibodies are added to the plate and incubate for 1 hour at room temperature. A stock of Horseradish peroxidase-conjugated anti-mouse IgG antibody is prepared. The plates are washed three times in PBS-Tween 20(0.01%). Following this 50 microliters per well of HRP-conjugated anti-mouse antibody are added, and the plate is wrapped in foil and stored in darkness for 1 hour. The plates are then washed three times in PBS-Tween 20(0.01%), following which 50 microliters of ABTS+1/1000 35% hydrogen peroxide are added into each well (add $H_2O_2$ immediately before developing color). The plates are incubated in darkness for 10-20 minutes, and then read at 405 nm Effects on Antigen Immune Response.

To assess the effect of anti-C3d monoclonal antibodies on host humoral immune responses, which is hypothesized based on the role of C3d in enhancing B cell responses, a model complement-dependent antigen, sheep red blood cells (SRBCs), was utilized to induce host immune response. In one exemplary experiment, as illustrated in FIG. 11, one day after the injection of anti-C3d monoclonal antibodies, mice were immunized with SRBCs as a foreign antigen. Blood samples were collected 17 and 30 days post immunization and analyzed for their antigen-specific IgG1 concentration. As shown in FIG. 12, SRBC induced a host humoral immune response, which led to an increase of SRBC-specific IgG1 concentration. Both mAb 3d8b and 3d29 of Group 1, with their inhibitory activity towards CR2-C3d binding, were able to decrease significantly the host IgG1 production, while a Group 3 C3d antibody, 3d10, did not decrease the IgG1 production, probably due to its inability to inhibit CR2-C3d interaction (FIG. 12, FIG. 7, and FIG. 8). Interestingly, a Group 2 C3d antibody, 3d11, which competed with CR2 for binding recombinant C3d (FIG. 7), did not decrease the SRBC-specific IgG1 production in mice (FIG. 12). However, this is consistent with its lack of ability to bind native C3d or iC3b fragments on opsonized zymosan particles (FIG. 4), which may suggest that 3d11 is not, at least, a strong C3d binding partner under physiological settings of complement activation.

Preparation and Testing of Fusion Proteins of Anti-C3d Monoclonal Antibody with Complement Modulatory Moieties The hybridoma cell lines producing the various anti-C3d monoclonal antibodies described herein have been deposited with the American Type Culture Collection (ATCC),10801 University Boulevard, Manassas, VA 20108 U.S.A. as follows: (1) hybridoma cell line 3d-9a/25, deposited on May 26, 2010, and designated as ATCC Patent Deposit PTA-10998; (2) hybridoma cell line 3d-8b/2, deposited on May 26, 2010, and designated as ATCC Patent Deposit PTA-10999; (3) hybridoma cell line 3d-29/5/2, deposited on May 26, 2010, and designated as ATCC Patent Deposit PTA-11000; (4) hybridoma cell line 3d-10/14/1, deposited on Jun. 2, 2010, and designated as ATCC Patent Deposit PTA-11010; (5) hybridoma cell line 3d-11/14, deposited on Jun. 2, 2010, and designated as ATCC Patent Deposit PTA-11011; (6) hybridoma cell line 3d-15A9, deposited on Jun. 2, 2010, and designated as ATCC Patent Deposit PTA-11012; (7) hybridoma cell line 3d-3/28/4, deposited on Jun. 9, 2010, and designated as ATCC Patent Deposit PTA-11025; (8) hybridoma cell line 3d-16/3/3, deposited on Jun. 9, 2010, and designated as ATCC Patent Deposit PTA-11026; and (9) hybridoma cell line 3d-31/A6/9, deposited on Jun. 9, 2010, and designated as ATCC Patent Deposit PTA-11027. The complete nucleotide and amino acid sequences of the monoclonal antibodies produced by those hybridoma cell lines can easily be determined with standard methods such as, for example, the polymerase chain reaction (PCR) and automated sequencing.

Conversion of Anti-C3d Monoclonal Antibodies into Single-chain Variable Fragments (scFvs).

Single chain Fvs of the present disclosure preferably comprise $V_H$ and $V_L$ domains joined by a flexible peptide linker that prevents dissociation. The scFvs usually retain the specificity of the parental antibody and bind the target antigen in a monovalent manner. Conversion of antibodies to scFvs is a well-known process (see Nat. Biotechnol. 23:1126 (2005); Biomol Eng. 24:201 (2007); J Immunol Methods., 168:149 (1994); Arch Virol. 148:497 (2003)). ScFvs can be constructed by either de novo gene synthesis, overlap extension polymerase chain reaction (PCR) or sequential ligation of the individual heavy ($V_H$) and light ($V_L$) chain variable gene segments. Sequential cloning of the individual $V_H$ and $V_L$ genes into a vector containing a synthetic linker sequence (e.g., $(Gly_4Ser)_3$) can be performed as well. The sequence can be either $V_H$-linker-$V_L$ or $V_L$-linker-$V_H$.

Attachment of Complement Modulator to scFvs Specific for C3d.

An ScFv generated according to the previous paragraph can be linked to the complement modulator protein, e.g. factor H SCRs 1-5 (SEQ ID NO: 5). A series of linkers can be used to identify the optimal distance between scFv and the complement modulator protein, ranging from no linker to linkers of 40 amino acids or more, and the sequence chosen for the linker can be, for example, $(GlyGlyGlyGlySer)_n$ where n=0-8. The construction of the scFv linked to the complement modulator can be done by de novo gene synthesis, overlap PCR, sequential cloning or ligation. The N-terminal moiety of the final construct can be either the complement modulator or the scFv.

In Vitro Inhibition of Alternative Pathway by Anti-C3d scFv-FH.

Human or mouse fusion proteins containing the anti-C3d scFv and the first five SCR domains of human or murine FH without linker (antiC3dFv-FH) or with linker (antiC3dFv-L-FH) are made by recombinant DNA cloning and gene expression methods. The sequence for FH to be used in one of the antiC3dFv-FH fusion proteins is provided in SEQ ID NO: 5 (human) or SEQ ID NO: 8 (murine). Note that, because the anti-C3d antibodies cross react with human and mouse C3d, the same antibody fragments can be used in in vitro assays and in vivo in both humans and mice. For use with human cells or in humans, the Factor H component of the fusion molecules is preferably of human origin. For use with murine cells or in mice, the Factor H component of the fusion molecules is preferably of murine origin.

A mouse antiC3dFv-FH fusion protein (designated as antiC3dFv-FHFH) containing the [antiC3dFv] and two tandemly linked FH portions (each containing the first five SCR domains of FH) is also made. The antiC3dFv portion and the first FH portion are linked by a linker sequence.

In vitro assays for activation of the alternative pathway are conducted as essentially described in Quigg et al., J. Immunol. 1998, 160(9):4553-60. Factor H (1H) or anti-C3d antibody are used as controls in the experiment. Specifically, 50 mg of zymosan beads in 10 ml of 0.15M NaCl are activated by boiling for 60 minutes, and washed twice in PBS. In each reaction mixture add: 1) 10 mM EGTA and 5 mM $MgCl_2$ (final concentration); 2) $1\times10^7$ beads; 3) 10 mM EDTA (negative control 1) or heat-inactivated serum (negative control 2) or increasing concentration of one of the antiC3dFab-FH fusion proteins or control proteins; 4) 10 μl of serum; and 5) PBS to bring the total volume to 100 μl. The mixtures are incubated at 37° C. for 20 minutes, and the reactions are stopped by addition of 10 mM EDTA (final concentration). The beads are washed twice with cold PBSB (PBS with 1% BSA), and incubated with FTIC-conjugated goat-anti-C3 antibody for one hour on ice. The sample is then washed twice in PBSB, resuspended with 1% paraformaldehyde and analyzed under flow cytometry.

Inhibition of complement activation by antiC3dFab-FH and antiC3dFab-FHFH, with and without the linker, is compared to that of FH alone; FH—FH; antiC3dFab alone and anti-C3d antibody alone. The effects of antiC3dFab-FH and antiC3dFab-FHFH proteins are measured relative to the independent function of each portion.

Treatment of Intestinal Ischemia and Reperfusion Injury by AntiC3dFab-FH.

This experiment is designed to illustrate the effects of treatment of intestinal ischemia and reperfusion injury in a mouse model.

Intestinal ischemia reperfusion injury.

For a detailed description of exemplary methods, see, e.g., Huang et al. "A novel targeted inhibitor of the alternative pathway of complement and its therapeutic application in ischemia/reperfusion injury." *The Journal of Immunology* (2008), 181:11:8068-76, the disclosure of which is hereby incorporated by reference in its entirety. Briefly, three adult male mice aged 8 weeks and weighing 20-25 g are anesthetized with 10 mg/kg ketamine and 6 mg/kg xylazine by i.p. injection. Animals are breathing spontaneously and body temperature is maintained using a heat mat for the entire experiment. A medial laparotomy is performed and the intestines are carefully moved allowing access to the superior mesenteric artery. The superior mesenteric artery is clamped using a microsurgical clamp (Fine Instruments, USA). Ischemia is confirmed by pallor of the small intestine. Sham treated mice undergo laparotomy without clamping of superior mesenteric artery. After 30 min ischemia, the arterial clamp is removed, allowing reperfusion of the mesenteric vasculature. Animals are sutured using 6.0 ethicon suture and allowed to reperfuse for 2 hours. Then 0.1 mg or 0.05 mg antiC3dFab-FH, or control (PBS) are administered through i.v. 30 minutes post reperfusion and animals are sacrificed 90 minutes later following a total of 2 hours of reperfusion.

Histology.

Tissue samples for histological staining are taken from the intestine and either fixed in 10% formalin at 4° C. overnight and subsequently processed to paraffin, or frozen in liquid nitrogen for immunofluorescence analysis. Sections of intestine from each animal are stained with hematoxylin and eosin and scored for mucosal damage and villi height as previously described. See, e.g., Rehrig et al. Complement Inhibitor, Complement Receptor 1-Related Gene/Protein y-Ig Attenuates Intestinal Damage After the Onset of Mesenteric Ischemia/Reperfusion Injury in Mice. *J Immunol* (2001) 167:5921-5927. Briefly, a score of 0 is assigned to a normal villus; villi with tip distortion are scored as 1; villi lacking goblet cells and containing Gugenheims' spaces are scored as 2; villi with patchy disruption of the epithelial cells are scored as 3; villi exposed but intact lamina propria and epithelial cell sloughing are assigned as 4; villi in which lamina propria were exuding are scored as 5, and finally, villi displaying hemorrhage or denuded villi are scored as 6. All histological evaluations are carried out in a blinded fashion.

The effect of antiC3dFab-FH is measured relative to the control animal, which is expected to have normal levels of circulating endogenous factor H in excess of the amounts of antiC3dFab-FH to be administered.

Treatment of Renal Ischemia Reperfusion by Mouse antiC3dFab-FH

This example is designed to illustrate the effects of antiC3dFab-FH on renal ischemia reperfusion.

Protocol for Induction of Ischemic Acute Renal Failure (ARF).

For a detailed description of exemplary methods, see, e.g., Thurman et al. Lack of a Functional Alternative Complement Pathway Ameliorates Ischemic Acute Renal Failure in Mice. *J Immunol* (2003) 170:1517-1523, the disclosure of which is hereby incorporated by reference in its entirety. Briefly, mice weighing 20-25 grams are anesthetized with 300 µl of 2,2,2-Tribromoethanol (Sigma-Aldrich) injected intra-peritoneally. After the mice are anesthetized, they are placed on a heating pad to maintain their body temperature during surgery. Laparotomies are then performed, and the renal pedicles are located and isolated by blunt dissection. The pedicles are clamped with surgical clips (Miltex Instrument Company, Inc.), and occlusion of blood flow is confirmed by visual inspection of the kidneys. The clamps are left in place for 24 minutes and then released. The time of ischemia is chosen to obtain a reversible model of ischemic ARF with a minimum of vascular thrombosis, and to avoid animal mortality. The kidneys are observed for approximately one minute to ensure blood re-flow. After 15 minutes of reperfusion the mice receive 0.25 mg of the mouse antiC3dFab-FH intra-peritoneally. Fascia and skin are sutured with 4-0 silk (United States Surgical). The mice are volume resuscitated with 0.5 ml of normal saline and kept in an incubator at 29° C. to maintain body temperature.

After 24 hours of reperfusion the mice are anesthetized, and blood is obtained by cardiac puncture. Laparotomy is performed and the kidneys are harvested. All animal studies are performed in compliance with standard humane laboratory practice.

Serum Urea Nitrogen Measurements.

Serum urea nitrogen is determined for each mouse using a Beckman Autoanalyzer (Beckman). The effect of antiC3dFab-FH on kidney function is measured using the serum urea nitrogen determination.

Renal Morphology.

After the kidneys are removed from the mice, sagittal sections are fixed in 4% paraformaldehyde. After being embedded in paraffin, four µm sections are cut and stained with periodic acid Schiff. The sections are evaluated by a renal pathologist in a blinded fashion. The cortex and outer stripe of the outer medulla are assessed for epithelial necrosis, loss of brush border, tubular dilatation and cast formation. At least ten fields (400×) are reviewed for each slide, and the percentage of tubules displaying these findings is determined. The kidney sections are scored as follows based on the percentage of affected tubules: 0, none; 1, <10%; 2, 11-25%; 3, 26-45%; 4, 46-75%; 5, >75%. The effects of antiC3dFab-FH are measured relative to the control animal.

Immunofluorescence.

For immunofluorescence, sagittal sections of the kidneys are snap frozen in OCT compound (Sakura Finetek). Four µm sections are cut with a cryostat and stored at −70° C. The slides are later fixed with acetone and incubated with the FITC conjugated antibody to mouse C3 (Cappel). After hybridization with the antibody for one hour at room temperature, the slides are counterstained with hematoxylin (Vector Laboratories, Inc.). The effects of antiC3dFab-FH on the level of C3 deposited into kidneys of sham treated mice are measured relative to untreated control mice.

Treatment of Age-Related Macular Degeneration by antiC3dFab-FH.

For a detailed description of exemplary methods, see, e.g., Rohrer et al. Eliminating complement factor D reduces photoreceptor susceptibility to light-induced damage. *Investigative Ophthalmology & Visual Science* (2007) 48(11): 5282-9, the disclosure of which is hereby incorporated by reference in its entirety. Briefly, constant light exposed albino rats are used as animal models for age-related macular degeneration (dry AMD). Five to eight animals are injected intraocularly under anesthesia every other day with an antiC3dFab-FH fusion protein (1 µl of 4.3 mg/ml stock solution), starting with the first injection the day prior to the onset of continuous light exposure (days −1, 1, 3, 5, 7). One eye serves as the experimental, while the other eye serves as the PBS-injected control eye. Animals are tested with electroretinography (ERG) on day 8 and then euthanized for histology and PCR analysis. Number of rows of photoreceptors in eyes injected with antiC3dFab-FH is compared with those of the PBS control eyes.

The effects of anti-C3dFab-FH are measured using three parameters: functional activity (ERG) potentials, i.e., photoreceptor and retinal pigment epithelium (RPE) responses), histology and measures of inflammation (e.g., gene expression by RT-PCR and protein expression by immunohistochemistry).

Reduction in CNV Volume by AntiC3d-Murine FH.

For a detailed description of exemplary methods, see, e.g., Rohrer et al. "A targeted inhibitor of the alternative complement pathway reduces angiogenesis in a mouse model of age-related macular degeneration." *Invest Ophthalmol V is Sci.* (2009) 50:3056-3064, the disclosure of which is hereby incorporated by reference in its entirety. Briefly, for generation of CNV, 3-month-old mice are anesthetized using xylazine and ketamine (20 and 80 mg/kg, respectively) and pupils are dilated with a drop of phenylephrine HCl (2.5%) and atropine sulfate (1%). Argon laser photocoagulation (532 nm, 50 µm spot size, 0.05 s duration, 250 mW) is used to generate four laser spots in each eye surrounding the optic nerve, using a handheld coverslip as a contact lens. A bubble formed at a laser spot indicates the rupture of Bruch's membrane. Nozaki et al., *Proc. Natl. Acad. Sci.* (2006) 103:2328-33.

The effects of antiC3dFab-FH are measured using four parameters: functional activity (ERG potentials, i.e., photoreceptor and RPE responses), histology, vascular integrity (choroidal flatmounts after fluorescein injections) and measures of inflammation (e.g., gene expression by RT-PCR and protein expression by immunohistochemistry).

For assessment of CNV lesions, CNV size is determined in flat-mount preparations of RPE/choroids stained with isolectin B (which binds to terminal beta-D-galactose residues on the surface of endothelial cells and selectively labels the mouse vasculature). Fluorescence measurements taken in 2 μm sections using confocal microscopy are used for size determination. In short, a Z-stack of images through the CNV lesion is obtained, using the same laser intensity setting for all experiments. For each slice the overall fluorescence is determined and plotted against depth.

For electroretinography, animals are anesthetized using xylazine (20 mg/kg bodyweight) and ketamine (80 mg/kg bodyweight). Pupils are dilated with a drop of phenylephrine HCl (2.5%) and tropicamide (1%). Body temperature is stabilized via a DC-powered heating pad held at 37° C. The ERG setup used is previously described by Rohrer et al., *J. Neurosci.*, 1999, 19(20): 8919-30 and is built according to Lyubarsky and Pugh Lyubarsky et al., *J. Neurosci.*, 1996, 16:563-571. Stimulus light intensity was controlled using neutral density filters.

Stimulus Paradigms.

Animals are dark-adapted overnight and ERGs will be recorded. Rods are analyzed in response to single-flash stimuli of increasing light intensity. The single-flash responses are an average of at least 3 flashes with an inter-stimulus interval (ISI) of 15 s to 2 min (lowest intensity to highest, respectively). The different ISIs ensures that ERG amplitudes at a given intensity are identical between the first and the last flash.

Data Analysis.

For all ERG recordings, a-wave amplitude are measured from baseline to trough; b-wave amplitude are measured from a-wave trough or baseline to peak of b-wave, and implicit times are measured from onset of stimulus to a-wave trough or b-wave peak.

In one experiment, mice are treated with intravenous mouse antiC3dFabFH (250 μg) at 30 minutes post laser burn, 48 hours post laser burn, or 6 hours post laser burn. After 6 days post laser burn, retinal function is assessed, and then mice are sacrificed for histology.

The effects of antiC3dFab-FH on a- and b-wave retinal responses in mice are measured relative to controls. Quantification of isolectin-b stained lesions is assessed for both antiC3dFab-FH and controls.

In a separate experiment, 1 μg mouse antiC3dFab-FH is administered intraoptically immediately after laser burn, 48 hours post burn, or 96 hours post burn. Eyes are collected at day 6 for histology. Lesions are visualized by isolectin-b staining. The effects on lesion size of antiC3dFab-FH delivered directly to the eye are measured relative to controls.

Delay of Onset of Antibody-Mediated Rejection in a Mouse Heterotopic Heart Transplant Model by Mouse AntiC3dFab-FH.

For a detailed description of exemplary methods, see, e.g., Atkinson et al. "Targeted Complement Inhibitors Protect against Posttransplant Cardiac Ischemia and Reperfusion Injury and Reveal an Important Role for the Alternative Pathway of Complement Activation." *J Immunol* (2010) 185:7007-7013, the disclosure of which is hereby incorporated by reference by its entirety. Briefly in this experiment, hearts are heterotopically transplanted from C3H donor mice into Balb/c recipient mice. This strain combination promotes a TH2 immune phenotype which promotes acute vascular rejection, and is characterized by anti-graft antibody production and graft deposition of complement activation fragments.

Recipient mice are treated with 1) PBS, i.v., 2) a single 0.25 mg dose of mouse antiC3dFab-FH, i.v. 30 minutes post reperfusion, and 3) multiple doses of 0.25 mg mouse antiC3dFab-FH, i.v., starting 30 minutes post reperfusion and then every three days thereafter.

Hearts are harvested 24 hours post reperfusion for analysis. The effects of mouse antiC3dFab-FH on ischemia and reperfusion injury are assessed by histology, and measurements of C3, neutrophil infiltration, and inflammatory cytokines, compared to control animals. The effects of mouse antiC3dFab-FH on acute vascular rejection are also assessed by time of survival in mice treated with mouse antiC3dFab-FH when compared to controls.

Inhibition of Alternative Complement Pathway by Human AntiC3dFab-FH.

The protein sequence of the FH component present in human antiC3dFab-FH, also designated as antiC3dFH, and human antiC3dFab-FHFH, also designated as antiC3dFH2, are provided in SEQ ID NO: 9. The protein sequence of the FH present in murine antiC3dFH and murine antiC3dFH2, is shown in SEQ ID NO: 10.

Human antiC3dFH and human antiC3dFH2 are purified from transfected 293 cell supernatants by affinity chromatography using HB5-separose, which contains anti-FH antibody linked to CNBr-activated sepharose (Amersham Biosciences). Crude antiC3dFH or antiC3dFH2 supernatants are passed over the matrix, washed with PBS, and eluted in 0.1M glycine-HCl, pH 3.0. The eluted fraction is immediately neutralized by the addition of 1M Tris-Cl, pH 9.0, followed by exchange into PBS using centricon columns (Millipore). Three hundred nanograms of nonreduced, purified antiC3dFH and antiC3dFH2 are resolved on SDS-PAGE and visualized by Coomassie staining.

The effects of human antiC3dFH and human antiC3dFH2 on alternative pathway specific C3b deposition onto zymosan particles are assessed as follows. Briefly, Zymosan particles are incubated in PBS containing 5 mM $Mg^{2+}$, 10 mM EGTA, 10% human serum, and increasing concentrations of antiC3dFH and antiC3dFH2 for 30 minutes at room temperature with a FITC conjugated goat anti-human C3 antibody. Zymosan is pelleted and washed, followed by FACS analysis. Endogenous FH levels can be measured and the effects of the targeted FH are compared with untargeted endogenous FH.

The effects of human antiC3dFH and human antiC3dFH2 on alternative pathway-mediated erythrocyte lysis are assessed as follows. Briefly, rabbit erythrocytes ($1 \times 10^8$) are incubated with various concentrations of antiC3dFH or antiC3dFH2 in $1 \times GVB^{++}$ (Boston BioProducts) and 17% human serum for 30 minutes at 37° C. The reaction is stopped with the addition of one tenth volume cold PBS followed by centrifugation to pellet unlysed erythrocytes. Hemolysis is quantified by measuring $OD_{415}$ nm Endogenous FH levels can be measured and the effects of the targeted FH are compared with untargeted endogenous FH.

Inhibition of the Alternative Complement Pathway by antiC3d-muFH.

This example shows inhibition of the alternative complement pathway by mouse antiC3d-muFH using serum from mice deficient in the classical pathway.

ELISA assay with immune complexes of collagen-anticollagen antibodies on the plates are used. C3 deposition/activation is measured by using anti-C3b antibody in the presence of serum from wild-type or from $C4^-/C4^-$ mice. Different amounts of full length mouse FH (2 μg/10 μl), the first four SCR domains of mouse CR2 (2 μg/10 μl), and antiC3d-muFH (2 μg/10 μl) are added to the serum.

To further demonstrate that the inhibition of C3b deposition observed with antiC3dFH is due to inhibition of the alternative pathway, the effects of antiC3dFH on C3b deposition are studied in the absence of the classical pathway ($C4^-/C4^-$ mice). Calcium inhibits the lectin complement pathway.

SEQUENCES

SEQ ID NO: 1
[amino acid sequence of human membrane cofactor protein (MCP)]:
MEPPGRRECPFPSWRFPGLLLAAMVLLLYSFSDACEEPPTFEAMELIGKPKPYYEIGERV

DYKCKKGYFYIPPLATHTICDRNHTWLPVSDDACYRETCPYIRDPLNGQAVPANGTYEF

GYQMHFICNEGYYLIGEEILYCELKGSVAIWSGKPPICEKVLCTPPPKIKNGKHTFSEVEV

FEYLDAVTYSCDPAPGPDPFSLIGESTIYCGDNSVWSRAAPECKVVKCRFPVVENGKQIS

GEGKKFYYKATVMFECDKGFYLDGSDTIVCDSNSTWDPPVPKCLKVLPPSSTKPPALSH

SVSTSSTTKSPASSASGPRPTYKPPVSNYPGYPKPEEGILDSLDVWVIAVIVIAIVVGVAVI

CVVPYRYLQRRKKKGTYLTDETHREVKFTSL

SEQ ID NO: 2
[amino acid sequence of human decay accelerating factor (DAF/CD55)]:
MTVARPSVPAALPLLGELPRLLLLVLLCLPAVWGDCGLPPDVPNAQPALEGRTSFPEDT

VITYKCEESFVKIPGEKDSVICLKGSQWSDIEEFCNRSCEVPTRLNSASLKQPYITQNYFP

VGTVVEYECRPGYRREPSLSPKLTCLQNLKWSTAVEFCKKKSCPNPGEIRNGQIDVPGGI

LFGATISFSCNTGYKLFGSTSSFCLISGSSVQWSDPLPECREIYCPAPPQIDNGIIQGERDHY

GYRQSVTYACNKGFTMIGEHSIYCTVNNDEGEWSGPPPECRGKSLTSKVPPTVQKPTTV

NVPTTEVSPTSQKTTTKTTTPNAQATRSTPVSRTTKHFHETTPNKGSGTTSGTTRLLSGH

TCFTLTGLLGTLVTMGLLT

SEQ ID NO: 3
[amino acid sequence of mouse decay accelerating factor (DAF/CD55)]:
MIRGRAPRTRPSPPPPLLPLLSLLLLLSPTVRGDCGPPPDIPNARPILGRHSKFAEQSKVA

YSCNNGFKQVPDKSNIVVCLENGQWSSHETFCEKSCVAPERLSFASLKKEYLNMNFFPV

GTIVEYECRPGFRKQPPLPGKATCLEDLVWSPVAQFCKKKSCPNPKDLDNGHINIPTGIL

FGSEINESCNPGYRLVGVSSTFCSVTGNTVDWDDEFPVCTEIHCPEPPKINNGIMRGESDS

YTYSQVVTYSCDKGFILVGNASIYCTVSKSDVGQWSSPPPRCIEKSKVPTKKPTINVPSTG

TPSTPQKPTTESVPNPGDQPTPQKPSTVKVSATQHVPVTKTTVRHPIRTSTDKGEPNTGG

DRYIYGHTCLITLTVLHVMLSLIGYLT

SEQ ID NO: 4
[amino acid sequence of human CD59 protein]:
MGIQGGSVLEGLLLVLAVFCHSGHSLQCYNCPNPTADCKTAVNCSSDFDACLITKAGLQ

VYNKCWKFEHCNFNDVTTRLRENELTYYCCKKDLCNFNEQLENGGTSLSEKTVLLLVT

PFLAAAWSLHP

SEQ ID NO: 5
[amino acid sequence of mouse CD59A protein]:
MRAQRGLILLLLLLAVFCSTAVSLTCYHCFQPVVSSCNMNSTCSPDQDSCLYAVAGMQ

VYQRCWKQSDCHGEIIMDQLEETKLKFRCCQFNLCNKSDGSLGKTPLLGTSVLVAILNL

CFLSHL

SEQ ID NO: 6
[amino acid sequence of mouse CD59B protein]:
MRAQRGLILLLLLLAVFCSTAVSLKCYNCFQFVSSCKINTTCSPNLDSCLYAVAGRQVY

QQCWKLSDCNSNYIMSRLDVAGIQSKCCQWGLCNKNLDGLEEPNNAETSSLRKTALLG

TSVLVAILKFCF

-continued

SEQ ID NO: 7
[amino acid sequence of mouse complement receptor 1-related gene/protein y (Crry)]:
MEVSSRSSEPLDPVWLLVAFGRGGVKLEVLLLFLLPFTLGELRGGLGKHGHTVHREPAV

NRLCADSKRWSGLPVSAQRPFPMGHCPAPSQLPSAKPINLTDESMFPIGTYLLYECLPGY

IKRQFSITCKQDSTWTSAEDKCIRKQCKTPSDPENGLVHVHTGIQFGSRINYTCNQGYRLI

GSSSAVCVITDQSVDWDTEAPICEWIPCEIPPGIPNGDFFSSTREDFHYGMVVTYRCNTD

ARGKALFNLVGEPSLYCTSNDGEIGVWSGPPPQCIELNKCTPPPYVENAVMLSENRSLFS

LRDIVEFRCHPGFIMKGASSVHCQSLNKWEPELPSCFKGVICRLPQEMSGFQKGLGMKK

EYYYGENVTLECEDGYTLEGSSQSQCQSDGSWNPLLAKCVSRSISGLIVGIFIGIIVFILVII

VFIWMILKYKKRNTTDEKYKEVGIHLNYKEDSCVRLQSLLTSQENSSTTSPARNSLTQEV

S

SEQ ID NO: 8
[amino acid sequence of human complement receptor 1 (CR1)]:
MGASSPRSPEPVGPPAPGLPFCCGGSLLAVVVLLALPVAWGQCNAPEWLPFARPTNLTD

EFEFPIGTYLNYECRPGYSGRPFSIICLKNSVWTGAKDRCRRKSCRNPPDPVNGMVHVIK

GIQFGSQIKYSCTKGYRLIGSSSATCIISGDTVIWDNETPICDRIPCGLPPTITNGDFISTNRE

NFHYGSVVTYRCNPGSGGRKVFELVGEPSIYCTSNDDQVGIWSGPAPQCIIPNKCTPPNV

ENGILVSDNRSLFSLNEVVEFRCQPGFVMKGPRRVKCQALNKWEPELPSCSRVCQPPPD

VLHAERTQRDKDNFSPGQEVFYSCEPGYDLRGAASMRCTPQGDWSPAAPTCEVKSCDD

FMGQLLNGRVLFPVNLQLGAKVDFVCDEGFQLKGSSASYCVLAGMESLWNSSVPVCE

QIFCPSPPVIPNGRHTGKPLEVFPPFGKAVNYTCDPHPDRGTSFDLIGESTIRCTSDPQGNG

VWSSPAPRCGILGHCQAPDHFLFAKLKTQTNASDFPIGTSLKYECRPEYYGRPFSITCLD

NLVWSSPKDVCKRKSCKTPPDPVNGMVHVITDIQVGSRINYSCTTGHRLIGHSSAECILS

GNAAHWSTKPPICQRIPCGLPPTIANGDFISTNRENFHYGSVVTYRCNPGSGGRKVFELV

GEPSIYCTSNDDQVGIWSGPAPQCIIPNKCTPPNVENGILVSDNRSLFSLNEVVEFRCQPG

FVMKGPRRVKCQALNKWEPELPSCSRVCQPPPDVLHAERTQRDKDNFSPGQEVFYSCE

PGYDLRGAASMRCTPQGDWSPAAPTCEVKSCDDFMGQLLNGRVLFPVNLQLGAKVDF

VCDEGFQLKGSSASYCVLAGMESLWNSSVPVCEQIFCPSPPVIPNGRHTGKPLEVFPPFGK

AVNYTCDPHPDRGTSFDLIGESTIRCTSDPQGNGVWSSPAPRCGILGHCQAPDHFLFAKL

KTQTNASDFPIGTSLKYECRPEYYGRPFSITCLDNLVWSSPKDVCKRKSCKTPPDPVNGM

VHVITDIQVGSRINYSCTTGHRLIGHSSAECILSGNTAHWSTKPPICQRIPCGLPPTIANGD

FISTNRENFHYGSVVTYRCNLGSRGRKVFELVGEPSIYCTSNDDQVGIWSGPAPQCIIPNK

CTPPNVENGILVSDNRSLFSLNEVVEFRCQPGFVMKGPRRVKCQALNKWEPELPSCSRV

CQPPPEILHGEHTPSHQDNFSPGQEVFYSCEPGYDLRGAASLHCTPQGDWSPEAPRCAV

KSCDDFLGQLPHGRVLFPLNLQLGAKVSFVCDEGFRLKGSSVSHCVLVGMRSLWNNSV

PVCEHIFCPNPPAILNGRHTGTPSGDIPYGKEISYTCDPHPDRGMTFNLIGESTIRCTSDPH

GNGVWSSPAPRCELSVRAGHCKTPEQFPFASPTIPINDFEFPVGTSLNYECRPGYFGKMF

SISCLENLVWSSVEDNCRRKSCGPPPEPFNGMVHINTDTQFGSTVNYSCNEGFRLIGSPST

TCLVSGNNVTWDKKAPICEIISCEPPPTISNGDFYSNNRTSFHNGTVVTYQCHTGPDGEQ

LFELVGERSIYCTSKDDQVGVWSSPPPRCISTNKCTAPEVENAIRVPGNRSFFSLTEIIRFR

CQPGFVMVGSHTVQCQTNGRWGPKLPHCSRVCQPPPEILHGEHTLSHQDNFSPGQEVFY

SCEPSYDLRGAASLHCTPQGDWSPEAPRCTVKSCDDFLGQLPHGRVLLPLNLQLGAKVS

```
FVCDEGFRLKGRSASHCVLAGMKALWNSSVPVCEQIFCPNPPAILNGRHTGTPFGDIPYG

KEISYACDTHPDRGMTFNLIGESSIRCTSDPQGNGVWSSPAPRCELSVPAACPHPPKIQNG

HYIGGHVSLYLPGMTISYTCDPGYLLVGKGFIFCTDQGIWSQLDHYCKEVNCSFPLFMN

GISKELEMKKVYHYGDYVTLKCEDGYTLEGSPWSQCQADDRWDPPLAKCTSRAHDALI

VGTLSGTIFFILLIIFLSWIILKHRKGNNAHENPKEVAIHLHSQGGSSVHPRTLQTNEENSR

VLP
```

SEQ ID NO: 9
[amino acid sequence of human factor H]:
```
MRLLAKIICLMLWAICVAEDCNELPPRRNTEILTGSWSDQTYPEGTQAIYKCRPGYRSLG

NVIMVCRKGEWVALNPLRKCQKRPCGHPGDTPFGTFTLTGGNVFEYGVKAVYTCNEG

YQLLGEINYRECDTDGWTNDIPICEVVKCLPVTAPENGKIVSSAMEPDREYHFGQAVRF

VCNSGYKIEGDEEMHCSDDGFWSKEKPKCVEISCKSPDVINGSPISQKIIYKENERFQYK

CNMGYEYSERGDAVCTESGWRPLPSCEEKSCDNPYIPNGDYSPLRIKHRTGDEITYQCR

NGFYPATRGNTAKCTSTGWIPAPRCTLKPCDYPDIKHGGLYHENMRRPYFPVAVGKYY

SYYCDEHFETPSGSYWDHIHCTQDGWSPAVPCLRKCYFPYLENGYNQNYGRKFVQGKS

IDVACHPGYALPKAQTTVTCMENGWSPTPRCIRVKTCSKSSIDIENGFISESQYTYALKE

KAKYQCKLGYVTADGETSGSITCGKDGWSAQPTCIKSCDIPVFMNARTKNDFTWFKLN

DTLDYECHDGYESNTGSTTGSIVCGYNGWSDLPICYERECELPKIDVHLVPDRKKDQYK

VGEVLKFSCKPGFTIVGPNSVQCYHFGLSPDLPICKEQVQSCGPPPELLNGNVKEKTKEE

YGHSEVVEYYCNPRFLMKGPNKIQCVDGEWTTLPVCIVEESTCGDIPELEHGWAQLSSP

PYYYGDSVEFNCSESFTMIGHRSITCIHGVWTQLPQCVAIDKLKKCKSSNLIILEEHLKNK

KEFDHNSNIRYRCRGKEGWIHTVCINGRWDPEVNCSMAQIQLCPPPPQIPNSHNMTTTL

NYRDGEKVSVLCQENYLIQEGEEITCKDGRWQSIPLCVEKIPCSQPPQIEHGTINSSRSSQ

ESYAHGTKLSYTCEGGFRISEENETTCYMGKWSSPPQCEGLPCKSPPEISHGVVAHMSDS

YQYGEEVTYKCFEGFGIDGPAIAKCLGEKWSHPPSCIKTDCLSLPSFENAIPMGEKKDVY

KAGEQVTYTCATYYKMDGASNVTCINSRWTGRPTCRDTSCVNPPTVQNAYIVSRQMSK

YPSGERVRYQCRSPYEMFGDEEVMCLNGNWTEPPQCKDSTGKCGPPPPIDNGDITSFPLS

VYAPASSVEYQCQNLYQLEGNKRITCRNGQWSEPPKCLHPCVISREIMENYNIALRWTA

KQKLYSRTGESVEFVCKRGYRLSSRSHTLRTTCWDGKLEYPTCAKR
```

SEQ ID NO: 10
[amino acid sequence of mouse factor H]:
```
MRLSARIIWLILWTVCAAEDCKGPPPRENSEILSGSWSEQLYPEGTQATYKCRPGYRTLG

TIVKVCKNGKWVASNPSRICRKKPCGHPGDTPFGSFRLAVGSQFEFGAKVVYTCDDGY

QLLGEIDYRECGADGWINDIPLCEVVKCLPVTELENGRIVSGAAETDQEYYFGQVVRFE

CNSGFKIEGHKEIHCSENGLWSNEKPRCVEILCTPPRVENGDGINVKPVYKENERYHYK

CKHGYVPKERGDAVCTGSGWSSQPFCEEKRCSPPYILNGIYTPHRIIHRSDDEIRYECNY

GFYPVTGSTVSKCTPTGWIPVPRCTLKPCEFPQFKYGRLYYEESLRPNFPVSIGNKYSYK

CDNGFSPPSGYSWDYLRCTAQGWEPEVPCVRKCVFHYVENGDSAYWEKVYVQGQSLK

VQCYNGYSLQNGQDTMTCTENGWSPPPKCIRIKTCSASDIHIDNGFLSESSSIYALNRETS

YRCKQGYVTNTGEISGSITCLQNGWSPQPSCIKSCDMPVFENSITKNTRTWFKLNDKLD

YECLVGFENEYKHTKGSITCTYYGWSDTPSCYERECSVPTLDRKLVVSPRKEKYRVGDL

LEFSCHSGHRVGPDSVQCYHFGWSPGFPTCKGQVASCAPPLEILNGEINGAKKVEYSHG
```

-continued

EVVKYDCKPRFLLKGPNKIQCVDGNWTTLPVCIEEERTCGDIPELEHGSAKCSVPPYHH

GDSVEFICEENFTMIGHGSVSCISGKWTQLPKCVATDQLEKCRVLKSTGIEAIKPKLTEFT

HNSTMDYKCRDKQEYERSICINGKWDPEPNCTSKTSCPPPPQIPNTQVIETTVKYLDGEK

LSVLCQDNYLTQDSEEMVCKDGRWQSLPRCIEKIPCSQPPTIEHGSINLPRSSEERRDSIES

SSHEHGTTFSYVCDDGFRIPEENRITCYMGKWSTPPRCVGLPCGPPPSIPLGTVSLELESY

QHGEEVTYHCSTGFGIDGPAFIICEGGKWSDPPKCIKTDCDVLPTVKNAIIRGKSKKSYRT

GEQVTFRCQSPYQMNGSDTVTCVNSRWIGQPVCKDNSCVDPPHVPNATIVTRTKNKYL

HGDRVRYECNKPLELFGQVEVMCENGIWTEKPKCRDSTGKCGPPPPIDNGDITSLSLPV

YEPLSSVEYQCQKYYLLKGKKTITCTNGKWSEPPTCLHACVIPENIMESHNIILKWRHTE

KIYSHSGEDIEFGCKYGYYKARDSPPFRTKCINGTINYPTCV

SEQ ID NO: 11
[amino acid sequence of CVF from *Naja kaouthia*]:
MERMALYLVAALLIGFPGSSHGALYTLITPAVLRTDTEEQILVEAHGDSTPKQLDIFVHD

FPRKQKTLFQTRVDMNPAGGMLVTPTIEIPAKEVSTDSRQNQYVVVQVTGPQVRLEKV

VLLSYQSSFLFIQTDKGIYTPGSPVLYRVFSMDHNTSKMNKTVIVEFQTPEGILVSSNSVD

LNFFWPYNLPDLVSLGTWRIVAKYEHSPENYTAYFDVRKYVLPSFEVRLQPSEKFFYID

GNENFHVSITARYLYGEEVEGVAFVLFGVKIDDAKKSIPDSLTRIPIIDGDGKATLKRDTF

RSRFPNLNELVGHTLYASVTVMTESGSDMVVTEQSGIHIVASPYQIHFTKTPKYFKPGMP

YELTVYVTNPDGSPAAHVPVVSEAFHSMGTTLSDGTAKLILNIPLNAQSLPITVRTNHGD

LPRERQATKSMTAIAYQTQGGSGNYLHVAITSTEIKPGDNLPVNFNVKGNANSLKQIKY

FTYLILNKGKIFKVGRQPRRDGQNLVTMNLHITPDLIPSFRFVAYYQVGNNEIVADSVW

VDVKDTCMGTLVVKGDNLIQMPGAAMKIKLEGDPGARVGLVAVDKAVYVLNDKYKIS

QAKIWDTIEKSDFGCTAGSGQNNLGVFEDAGLALTTSTNLNTKQRSAAKCPQPANRRR

RSSVLLLDSNASKAAEFQDQDLRKCCEDVMHENPMGYTCEKRAKYIQEGDACKAAFLE

CCRYIKGVRDENQRESELFLARDDNEDGFIADSDIISRSDFPKSWLWLTKDLTEEPNSQGI

SSKTMSFYLRDSITTWVVLAVSFTPTKGICVAEPYEIRVMKVFFIDLQMPYSVVKNEQVE

IRAILHNYVNEDIYVRVELLYNPAFCSASTKGQRYRQQFPIKALSSRAVPFVIVPLEQGLH

DVEIKASVQEALWSDGVRKKLKVVPEGVQKSIVTIVKLDPRAKGVGGTQLEVIKARKL

DDRVPDTEIETKIIIQGDPVAQIIENSIDGSKLNHLIITPSGCGEQNMIRMAAPVIATYYLDT

TEQWETLGINRRTEAVNQIVTGYAQQMVYKKADHSYAAFTNRASSSWLTAYVVKVFA

MAAKMVAGISHEIICGGVRWLILNRQQPDGAFKENAPVLSGTMQGGIQGAEEEVYLTAF

ILVALLESKTICNDYVNSLDSSIKKATNYLLKKYEKLQRPYTTALTAYALAAADQLNDD

RVLMAASTGRDHWEEYNAHTHNIEGTSYALLALLKMKKFDQTGPIVRWLTDQNFYGE

TYGQTQATVMAFQALAEYEIQMPTHKDLNLDITIELPDREVPIRYRINYENALLARTVET

KLNQDITVTASGDGKATMTILTFYNAQLQEKANVCNKFHLNVSVENIHLNAMGAKGAL

MLKICTRYLGEVDSTMTIIDISMLTGFLPDAEDLTRLSKGVDRYISRYEVDNNMAQKVA

VIIYLNKVSHSEDECLHFKILKHFEVGFIQPGSVKVYSYYNLDEKCTKFYHPDKGTGLLN

KICIGNVCRCAGETCSSLNHQERIDVPLQIEKACETNVDYVYKTKLLRIEEQDGNDIYVM

DVLEVIKQGTDENPRAKTHQYISQRKCQEALNLKVNDDYLIWGSRSDLLPTKDKISYIIT

KNTWIERWPHEDECQEEEFQKLCDDFAQFSYTLTEFGCPT

In the foregoing specification and in the examples below, the invention has been described with specific embodiments thereof. However, it will be evident to those skilled in the art that various modifications and changes may be made thereto without departing from the broader scope of the invention.

All publications that are cited herein are hereby specifically incorporated herein by reference into the disclosure for the teachings for which they are cited.

---

What we claim is:

1. An isolated antibody or antigen-binding fragment thereof, comprising the complementarity determining regions of an antibody selected from the group consisting of:
   i) 3db8 produced by hybridoma cell line 3d-8b/2 (ATCC Deposit PTA-10999);
   ii) 3d9a produced by hybridoma cell line 3d-9a/25 (ATCC Deposit PTA-10998);
   iii) 3d29 produced by hybridoma cell line 3d-29/5/2 (ATCC Deposit PTA-11000)
   iv) 3d11 produced by hybridoma cell line 3d-11/14 (ATCC Deposit PTA-10011);
   v) 3d31 produced by hybridoma cell line 3d-31/A6/9 (ATCC Deposit PTA-11027);
   vi) 3d3 produced by hybridoma cell line 3d-3/28/4 (ATCC Deposit PTA-11025)
   vii) 3d15 produced by hybridoma cell line 3d-15A9 (ATCC Deposit PTA-11012);
   viii) 3d10 produced by hybridoma cell line 3d-10/14/1 (ATCC Deposit PTA-11010); and
   ix) 3d16 produced by hybridoma cell line 3d-16/3/3 (ATCC Deposit PTA-11026);
   wherein said isolated antibody or antigen-binding fragment thereof is capable of specifically binding to a mammalian complement component C3d protein.

2. The isolated antibody or antigen-binding fragment thereof of claim 1, wherein said antibody or antigen-binding fragment thereof is a humanized, primatized, or chimerized antibody or antigen-binding fragment thereof.

3. The isolated antibody or antigen-binding fragment thereof of claim 1, wherein said antibody or antigen-binding fragment thereof is selected from the group consisting of: a monoclonal antibody or antibody fragment, a single chain antibody, an Fv, an Fab, an Fab', and an F(ab')$_2$.

4. The isolated antibody of claim 3, wherein said antibody is a monoclonal antibody.

5. The isolated antibody of claim 4, wherein said antibody is selected from the group consisting of:
   i) 3db8 produced by hybridoma cell line 3d-8b/2 (ATCC Deposit PTA-10999);
   ii) 3d9a produced by hybridoma cell line 3d-9a/25 (ATCC Deposit PTA-10998);
   iii) 3d29 produced by hybridoma cell line 3d-29/5/2 (ATCC Deposit PTA-11000)
   iv) 3d11 produced by hybridoma cell line 3d-11/14 (ATCC Deposit PTA-10011);
   v) 3d31 produced by hybridoma cell line 3d-31/A6/9 (ATCC Deposit PTA-11027);
   vi) 3d3 produced by hybridoma cell line 3d-3/28/4 (ATCC Deposit PTA-11025)
   vii) 3d15 produced by hybridoma cell line 3d-15A9 (ATCC Deposit PTA-11012);
   viii) 3d10 produced by hybridoma cell line 3d-10/14/1 (ATCC Deposit PTA-11010); and
   ix) 3d16 produced by hybridoma cell line 3d-16/3/3 (ATCC Deposit PTA-11026).

6. A hybridoma cell selected from the group consisting of: 3d-8b/2 (ATCC Deposit PTA-10999), 3d-9a/25 (ATCC Deposit number: PTA-10998), 3d-29/5/2 (ATCC Deposit number: PTA-11000), 3d-11/14 (ATCC Deposit number: PTA-11011), 3d-31/A6/9 (ATCC Deposit number: PTA-11027), 3d-3/28/4 (ATCC Deposit number: PTA-11025), 3d-15A9 (ATCC Deposit number: PTA-11012), 3d-10/14/1 (ATCC Deposit number: PTA-11010), and 3d-16/3/3 (ATCC Deposit number: PTA-11026).

7. A pharmaceutical composition comprising the isolated antibody or antigen-binding fragment thereof of claim 1 and a pharmaceutically-acceptable excipient.

8. A therapeutic kit comprising:
   (i) the antibody or antigen-binding fragment of claim 1, and
   (ii) means for delivering the antibody or antigen-binding fragment to a human.

9. A pre-filled syringe comprising the antibody or antigen-binding fragment thereof of claim 1.

10. The isolated antibody or antigen-binding fragment thereof of claim 1, comprising the complementarity determining regions of the antibody 3db8 produced by hybridoma cell line 3d-8b/2 (ATCC Deposit PTA-10999).

11. The isolated antibody or antigen-binding fragment thereof of claim 1, comprising the complementarity determining regions of the antibody 3d9a produced by hybridoma cell line 3d-9a/25 (ATCC Deposit PTA-10998).

12. The isolated antibody or antigen-binding fragment thereof of claim 1, comprising the complementarity determining regions of the antibody 3d29 produced by hybridoma cell line 3d-29/5/2 (ATCC Deposit PTA-11000).

13. The isolated antibody or antigen-binding fragment thereof of claim 1, comprising the complementarity determining regions of the antibody 3d11 produced by hybridoma cell line 3d-11/14 (ATCC Deposit PTA-10011).

14. The isolated antibody or antigen-binding fragment thereof of claim 1, comprising the complementarity determining regions of the antibody 3d31 produced by hybridoma cell line 3d-31/A6/9 (ATCC Deposit PTA-11027).

15. The isolated antibody or antigen-binding fragment thereof of claim 1, comprising the complementarity determining regions of the antibody 3d3 produced by hybridoma cell line 3d-3/28/4 (ATCC Deposit PTA-11025).

16. The isolated antibody or antigen-binding fragment thereof of claim 1, comprising the complementarity determining regions of the antibody 3d15 produced by hybridoma cell line 3d-15A9 (ATCC Deposit PTA-11012).

17. The isolated antibody or antigen-binding fragment thereof of claim 1, comprising the complementarity determining regions of the antibody 3d10 produced by hybridoma cell line 3d-10/14/1 (ATCC Deposit PTA-11010).

18. The isolated antibody or antigen-binding fragment thereof of claim 1, comprising the complementarity determining regions of the antibody 3d16 produced by hybridoma cell line 3d-16/3/3 (ATCC Deposit PTA-11026).

* * * * *